(12) United States Patent
Cappuccilli et al.

(10) Patent No.: US 9,376,483 B2
(45) Date of Patent: Jun. 28, 2016

(54) UNIVERSAL FIBRONECTIN TYPE III BINDING-DOMAIN LIBRARIES

(71) Applicants: Guido Cappuccilli, San Mateo, CA (US); Roberto Crea, San Mateo, CA (US); Randy Shen, Sunnyvale, CA (US); Craig A. Hokanson, Pleasanton, CA (US); Peter B. Kirk, San Mateo, CA (US); David R. Liston, San Mateo, CA (US)

(72) Inventors: Guido Cappuccilli, San Mateo, CA (US); Roberto Crea, San Mateo, CA (US); Randy Shen, Sunnyvale, CA (US); Craig A. Hokanson, Pleasanton, CA (US); Peter B. Kirk, San Mateo, CA (US); David R. Liston, San Mateo, CA (US)

(73) Assignee: Protelica, Inc., Hayward, CA (US)

( * ) Notice: Subject to any disclaimer, the term of this patent is extended or adjusted under 35 U.S.C. 154(b) by 160 days.

(21) Appl. No.: 13/899,698

(22) Filed: May 22, 2013

(65) Prior Publication Data
US 2014/0135474 A1 May 15, 2014

Related U.S. Application Data

(60) Division of application No. 12/820,018, filed on Jun. 21, 2010, now Pat. No. 8,470,966, which is a continuation-in-part of application No. 12/562,992, filed on Sep. 18, 2009, now Pat. No. 8,680,019, which is a continuation-in-part of application No. 12/228,404, filed on Aug. 11, 2008, now abandoned.

(60) Provisional application No. 61/075,107, filed on Jun. 24, 2008, provisional application No. 60/955,334, filed on Aug. 10, 2007.

(51) Int. Cl.
| | | |
|---|---|---|
| C40B 40/10 | (2006.01) |
| C07K 14/78 | (2006.01) |
| C07K 16/18 | (2006.01) |
| C07K 16/22 | (2006.01) |
| C07K 16/24 | (2006.01) |
| C12N 15/10 | (2006.01) |

(52) U.S. Cl.
CPC ............ *C07K 14/78* (2013.01); *C07K 16/18* (2013.01); *C07K 16/22* (2013.01); *C07K 16/241* (2013.01); *C12N 15/1044* (2013.01); *C07K 2317/21* (2013.01); *C07K 2317/52* (2013.01); *C07K 2318/20* (2013.01); *C40B 40/10* (2013.01)

(58) Field of Classification Search
None
See application file for complete search history.

(56) References Cited

U.S. PATENT DOCUMENTS

| | | | |
|---|---|---|---|
| 4,725,677 A | 2/1988 | Koster et al. |
| 4,888,286 A | 12/1989 | Crea |
| 5,324,637 A | 6/1994 | Thompson et al. |
| 5,492,817 A | 2/1996 | Thompson et al. |

(Continued)

FOREIGN PATENT DOCUMENTS

| | | |
|---|---|---|
| WO | 0232925 A2 | 4/2002 |
| WO | 03089671 A1 | 10/2003 |
| WO | 2008031098 A1 | 3/2008 |

OTHER PUBLICATIONS

Bloom et al. 'FN3: A New Protein Scaffold Reaches the Clinic'. Drug Discovery Today. 2009, vol. 14, No. 19-20, pp. 949-955.

(Continued)

*Primary Examiner* — Christian Boesen
(74) *Attorney, Agent, or Firm* — Lathrop & Gage LLP; James H. Velema, Esq.

(57) ABSTRACT

Fibronectin Type III (FN3) polypeptide libraries are described, along with their use in identifying fibronectin-type binding peptides having high binding affinities, e.g., greater than 300 nM, for VEGFR2 or Axl proteins.

6 Claims, 60 Drawing Sheets

(56) References Cited

U.S. PATENT DOCUMENTS

| | | |
|---|---|---|
| 5,665,563 A | 9/1997 | Beckler |
| 5,798,208 A | 8/1998 | Crea |
| 5,830,650 A | 11/1998 | Crea |
| 6,214,553 B1 | 4/2001 | Szoostak et al. |
| 6,258,558 B1 | 7/2001 | Szoostak et al. |
| 6,261,804 B1 | 7/2001 | Szoostak et al. |
| 6,300,065 B1 | 10/2001 | Kieke et al. |
| 6,348,315 B1 | 2/2002 | Pluckthun et al. |
| 6,423,538 B1 | 7/2002 | Wittrup et al. |
| 6,462,189 B1 | 10/2002 | Koide |
| 6,649,340 B1 | 11/2003 | Crea |
| 6,818,418 B1 | 11/2004 | Lipovsek et al. |
| 7,022,479 B2 | 4/2006 | Wagner |
| 7,078,490 B2 | 7/2006 | Koide |
| 7,115,396 B2 | 10/2006 | Lipovsek et al. |
| 7,119,171 B2 | 10/2006 | Koide |
| 7,153,661 B2 | 12/2006 | Koide |
| 7,357,928 B2 | 4/2008 | Bates et al. |
| 7,442,573 B2 | 10/2008 | Hutchison et al. |
| 7,521,542 B2 | 4/2009 | Johnson et al. |
| 7,541,150 B2 | 6/2009 | Miller et al. |
| 7,556,925 B2 | 7/2009 | Koide |
| 7,598,352 B2 | 10/2009 | Koide |
| 7,626,192 B2 | 12/2009 | Hutchison et al. |
| 7,700,729 B2 | 4/2010 | Scholl et al. |
| 7,732,586 B2 | 6/2010 | Martin, Jr. et al. |
| 7,749,694 B2 | 7/2010 | Ghosh et al. |
| 7,754,213 B2 | 7/2010 | Nash et al. |
| 7,786,270 B2 | 8/2010 | Johnson et al. |
| 2003/0036092 A1 | 2/2003 | Iverson et al. |
| 2003/0100023 A1 | 5/2003 | Iverson et al. |
| 2003/0215914 A1 | 11/2003 | Houtzager et al. |
| 2004/0033569 A1 | 2/2004 | Crea et al. |
| 2004/0058403 A1 | 3/2004 | Harvey et al. |
| 2004/0072740 A1 | 4/2004 | Iverson et al. |
| 2005/0037427 A1 | 2/2005 | Houtzager et al. |
| 2005/0038229 A1 | 2/2005 | Lipovsek et al. |
| 2005/0053607 A1 | 3/2005 | Bates et al. |
| 2005/0074865 A1 | 4/2005 | Afeyan et al. |
| 2005/0136428 A1 | 6/2005 | Crea |
| 2005/0215764 A1 | 9/2005 | Tuszynski et al. |
| 2005/0227354 A1* | 10/2005 | Sagawa ............... C12N 5/0636 435/372 |
| 2005/0249667 A1 | 11/2005 | Tuszynski et al. |
| 2005/0255548 A1 | 11/2005 | Lipovsek et al. |
| 2005/0260213 A1 | 11/2005 | Koenig et al. |
| 2005/0260680 A1 | 11/2005 | Yeaman et al. |
| 2006/0013810 A1 | 1/2006 | Johnson et al. |
| 2006/0140889 A1 | 6/2006 | Houtzager et al. |
| 2006/0147371 A1 | 7/2006 | Tuszynski et al. |
| 2006/0182783 A1 | 8/2006 | Hughes et al. |
| 2006/0246059 A1 | 11/2006 | Lipovsek et al. |
| 2006/0270604 A1 | 11/2006 | Lipovsek et al. |
| 2006/0292604 A1 | 12/2006 | Houtzager et al. |
| 2007/0027129 A1 | 2/2007 | Tuszynski et al. |
| 2007/0065447 A1 | 3/2007 | Tryggvason et al. |
| 2007/0082365 A1 | 4/2007 | Lipovsek et al. |
| 2007/0092549 A1 | 4/2007 | Tuszynski et al. |
| 2007/0149496 A1 | 6/2007 | Tuszynski et al. |
| 2007/0249518 A1 | 10/2007 | Chumakov et al. |
| 2007/0275367 A1 | 11/2007 | Ghosh et al. |
| 2008/0015339 A1 | 1/2008 | Lipovsek et al. |
| 2008/0025947 A1 | 1/2008 | Gillies et al. |
| 2008/0044417 A1 | 2/2008 | Johnson et al. |
| 2008/0044424 A1 | 2/2008 | Cohen et al. |
| 2008/0044429 A1 | 2/2008 | Johnson et al. |
| 2008/0063651 A1 | 3/2008 | Lipovsek et al. |
| 2008/0108798 A1 | 5/2008 | Lipovsek et al. |
| 2008/0119421 A1 | 5/2008 | Tuszynski et al. |
| 2008/0124309 A1 | 5/2008 | Fitzgerald et al. |
| 2008/0139791 A1 | 6/2008 | Lipovsek et al. |
| 2008/0166343 A1 | 7/2008 | Nash et al. |
| 2008/0171038 A1 | 7/2008 | Bebbington et al. |
| 2008/0196113 A1 | 8/2008 | Fitzgerald et al. |
| 2008/0206241 A1 | 8/2008 | Bebbington et al. |
| 2008/0213286 A1 | 9/2008 | Fitzgerald et al. |
| 2008/0213814 A1 | 9/2008 | Gerion et al. |
| 2008/0226640 A1 | 9/2008 | Fitzgerald et al. |
| 2008/0254035 A1 | 10/2008 | Yorke-Smith et al. |
| 2008/0254451 A1 | 10/2008 | Chumakov et al. |
| 2008/0268051 A1 | 10/2008 | Hughes et al. |
| 2008/0286272 A1 | 11/2008 | Lackmann et al. |
| 2008/0299137 A1 | 12/2008 | Svendsen et al. |
| 2008/0305486 A1 | 12/2008 | Tan et al. |
| 2009/0017009 A1 | 1/2009 | Bates et al. |
| 2009/0053218 A1 | 2/2009 | Koenig et al. |
| 2009/0053232 A1 | 2/2009 | Eroglu |
| 2009/0074747 A1 | 3/2009 | Dong et al. |
| 2009/0074771 A1 | 3/2009 | Koenig et al. |
| 2009/0076251 A1 | 3/2009 | Koenig et al. |
| 2009/0104197 A1 | 4/2009 | Davies et al. |
| 2009/0130113 A1 | 5/2009 | Kneissel et al. |
| 2009/0175875 A1 | 7/2009 | Eremad-Gilbertson et al. |
| 2009/0176654 A1 | 7/2009 | Cappuccilli et al. |
| 2009/0181020 A1 | 7/2009 | Bebbington et al. |
| 2009/0186022 A1 | 7/2009 | Bardoff et al. |
| 2009/0191195 A1 | 7/2009 | Tuaillon et al. |
| 2009/0202537 A1 | 8/2009 | Johnson et al. |
| 2009/0214548 A1 | 8/2009 | Michalovich et al. |
| 2009/0215672 A1 | 8/2009 | Power et al. |
| 2009/0232795 A1 | 9/2009 | Condra et al. |
| 2009/0246192 A1 | 10/2009 | Condra et al. |
| 2009/0263387 A1 | 10/2009 | Bebbington et al. |
| 2009/0285799 A1 | 11/2009 | Nash et al. |
| 2009/0286312 A1 | 11/2009 | Dong et al. |
| 2009/0299040 A1 | 12/2009 | Camphausen et al. |
| 2009/0311727 A1 | 12/2009 | Watkins et al. |
| 2010/0021452 A1 | 1/2010 | Heusser et al. |
| 2010/0028335 A1 | 2/2010 | Lu et al. |
| 2010/0034809 A1 | 2/2010 | Diefenbach-Streiber et al. |
| 2010/0040610 A1 | 2/2010 | Sitlani et al. |
| 2010/0040611 A1 | 2/2010 | Sparrow et al. |
| 2010/0041102 A1 | 2/2010 | Sitlani et al. |
| 2010/0048467 A1 | 2/2010 | Davies et al. |
| 2010/0069300 A1 | 3/2010 | Ghosh et al. |
| 2010/0121033 A1 | 5/2010 | Camphausen et al. |
| 2010/0136028 A1 | 6/2010 | Sparrow et al. |
| 2010/0143954 A1 | 6/2010 | Muntendam et al. |
| 2010/0144599 A1 | 6/2010 | Mendlin et al. |
| 2010/0150937 A1 | 6/2010 | Sparrow et al. |
| 2010/0166748 A1 | 7/2010 | Guild et al. |
| 2010/0183613 A1 | 7/2010 | Borowski et al. |
| 2010/0196349 A1 | 8/2010 | Power et al. |
| 2010/0215650 A1 | 8/2010 | Bebbington et al. |
| 2010/0226928 A1 | 9/2010 | Dani |
| 2010/0226930 A1 | 9/2010 | Bebbington et al. |
| 2010/0233177 A1 | 9/2010 | Yowe et al. |

OTHER PUBLICATIONS

Parker et al. 'Antibody Mimics Based on Human Fibronectin type three Binding to Vascular Andothelial Domain Engineered for Thermostability and High-affinity Binding to Vascular Endothelial Growth Factor Receptor two'. Protein Engineering. 2005, vol. 18, No. 9, pp. 435-444.

International Search Report for PCT/US2010049391, dated Jul. 9, 2013, 9 pages.

Better et al. 'Expression of Engineered Antibodies and Antibody Fragments in Microoganisms'. Methods in Enzymology. 1989, vol. 178, pp. 476-496.

Boder et al. 'Yeast Surface Display for Directed Evolution of Protein Expression, Affinity, and Stability'. Methods in Enzymology. 2000, vol. 328, pp. 430-444.

Boder et al. 'Yeast Surface Display for Screening Combinatorial Polypeptide Libraries'. Nature Biotechnology. 1997, vol. 15, No. 6, pp. 553-557.

Johnson et al. 'SEQHUNT. A Program to Screen Aligned Nucleotide and Amino Acid Sequences'. Methods in Enzymology. 1995, vol. 51, pp. 1-15.

Knappik et al. 'Fully Synthetic Human Combinatorial Antibody Libraries (HuCAL) Based on Modular Consensus Frameworks and CDRs Randomized with Nucleotides'. Journal of Molecular Biology. 2007, vol. 296, No. 1, pp. 57-86.

(56) References Cited

OTHER PUBLICATIONS

Lei et al. 'Characterization of the Erwinia carotovora pelB Gene and its product pectate lyase'. Journal of Bacteriology. 1987, vol. 169, pp. 4379-4383.

Li et al. 'Clustering of Highly Homologous Sequences to Reduce the Size of Large Protein Databases'. Bioinformatics. 2001, vol. 17, No. 3, pp. 282-283.

Lipovsek et al. 'Evolution of an Interloop Disulfide Bond in High-affinity Antibody Mimics Based on Fibronectin Type III Domain and Selected by Yeast Surface Display: Molecule convergence with Single-Domain Camelid and Shark Antibodies'. Journal of Molecular Biology. 2007, vol. 368, No. 4, pp. 1024-1041.

Peters et al. 'Membrane Insertion Defects Caused by Positive Charges in the Early Mature Region of Protein pIII of Filamentous Phage fd Can be Corrected by prlA Suppressors'. Journal of Bacteriology. 1994, vol. 176, No. 14, pp. 4296-4305.

Skerra et al. 'The Functional Expression of Antibody Fv Fragments in *Escherichia coli*: Improved Vectors and a Generally Applicable Purification Technique'. Biotechnology. 1991, vol. 9, No. 3, pp. 273-278.

Skerra et al. 'Alternative non-antibody Scaffolds for Molecular Recognition'. Current Opinion in Biotechnology. 2007, vol. 18, pp. 295-304.

Binz et al. 'Designed Repeat Proteins: Well-expressed, Soluble and Stable Proteins from Combinatorial Libraries of Consensus Ankyrin Repeat Proteinn'. Journal of Molecular Biology. 2003, vol. 332, pp. 489-503.

Karatan et al. 'Molecular Recognition Properties of FN3 Monobodies that Bind to the Src SH3Domain'. Chemistry & Biology. 2004, vol. 11, pp. 835-844.

Rajpal et al. 'A General Method for Greatly Improving the Affinity of Antibodies by using Combinatorial Libraries'. PNAS, 2005, vol. 102, No. 24, pp. 8466-8471.

Shimaoka et al. 'Therapeutic Antagonists and Conformational Regulation of Integrin Function'. Nature Reviews. 2003, vol. 2, pp. 703-716.

\* cited by examiner

FN3 modules 1-14 domain alignment

```
         W22           Y/F32              V50  A57            A74         I/L88
          ↓             ↓                  ↓    ↓              ↓           ↓
 1fn3   ---SGPVEVFITETPSQPNSHPIQWNAPQPSHISKYILRWRPKNSV-GRWKEATIPGHLNSYTIKGLKPGVVYEGQLISIQQYGHQ----EVTRFDFTTT------
 2fn3   -SPLVATSESVTEITAS--SFVVSWVSA-SDTVSGFRVEYELSEEG-DEPQYLDLPSTATSVNIPDLLPGRKYIVNVYQISEDGEQ----SLILSTSQTT------
 3fn3   -APDAPPDPTVDQVDDT--SIVVRWSRP-QAPITGYRIVYSPSVEG-S-STELNLPETANSVTLSDLQPGVQYNITIYAVEENQES----TPVVIQETTGTPR----
 4fn3   -TVPSPRDLQFVEVTDV--KVTIMWTPP-ESAVTGYRVDVIPVNLP-GEHGQRLPISRNTFAEVTGLSPGVTYYFKVFAVSHGRES----KPLTAQQTT-------
 5fn3   -KLDAPTNLQFVNETDS--TVLVRWTPP-RAQITGYRLTVGLITR-R-GQPRQYNVGPSVSKYPLRNLQPASEYTVSLVAIKGNQES----PKATGVFTTL------
 6fn3   -QPGSSIPPYNTEVTET--TIVITWTPA---PRIGFKLGVRPSQGG---EAPREVTSDSGSIVVSGLTPGVEYVYTIQVLRDGQER----DAPIVNKVVT------
 7fn3   -PLSPPTNLHLEANPDTG-VLTVSWERSTTPDIITGYRITTTPTNGQQGNSLEEVVHADQSSCTFDNLSPGLEYNVSVYTVKDDKES----VPISDTIIP-------
 8fn3   -AVPPPTDLRFTNIGPD--TMRVTWAPPPSIDLTNFLVRYSPVKNE-EDVAELSISPSDNAVVLTNLLPGTEYVVSVSSVYEQHES----TPLRGRQKT------
 9fn3   -GLDSPTGIDFSDITAN--SFTVHWIAP-RATITGYRIRHPEHFS-GRPREDRVPHSRNSITLTNLTPGTEYVVSIVALNGREES----PLLIGQQST-------
10fn3   -VSDVPRDLEVVAATPT--SLLISWDAP-AVTVRYRITYGETGGN-SPVQEFTVPGSKSTATISGLKPGVDYTITVYAVTGRGDSPASSKPISINYRT----
11fn3   -EIDKPSQMQVTDVQDN--SISVKWLPSSSP-VTGYRVTTTPKNGP-GPTKTKTAGPDQTEMTIEGLQPTVEYVVSVYAQNPSGES----QPLVQTAVT------
12fn3   -NIDRPKGLAFTDVDVD--SIKIAWESP-QGQVSRYRVTYSSPEDG-IHELFPAPDGEEDTAELQGLRPGSEYTVSVVALHDDMES----QPLIGTQST------
13fn3   -AIPAPTDLKFTQVTPT--SLSAQWTPP-NVQLTGYRVRVTPKEKT-GPMKEINLAPDSSSVVVSGLMVATKYEVSVYALKDTLTS----RPAQGVVTTLE-----
14fn3   -NVSPPRRARVTDATET--TITISWRTKTET-ITGFQVDAVPANGQ--TPIQRTIKPDVRSYTITGLQPGTDYKIYLYTLNDNARS----SPVVIDAST------
15fn3   -AIDAPSNLRFLATTPN--SLLVSWQPP-RARITGYILRYEKPGSP-PREVVPRPRPGVTEATITGLEPGTEYTIYVIALKNNQKS----EPLIGRKKT------
16fn3   PGLNPNASTGQEALSQT---TISWAPF--QDTSEYIISCHPVGTD-EEPLQFRVPGTSTSATLGLTRGATYNIIVEALKDQQRH----KVREEVTV-------

━━━━━━━                        ━━━━━━━                                           ━━━━━━━━━━
          BC LOOP                        DE LOOP                                           FG LOOP
```

Figure 5

K-WTM (SEQ ID NO.: 82)

| 21 | 22 | 23 | 24 | 25 | 26 | 27 | 28 | 29 | 30 | 31 |
|---|---|---|---|---|---|---|---|---|---|---|
| S | W | X/T | X/P | X/P | X/P | X/G | X/P | X/V | X/D | G |
| AGC | TGG | AMA | MMA | MMA | MMA | RRA | MMA | RWG | RAW | GGC |
| 1 | 1 | 2 | 4 | 4 | 4 | 4 | 4 | 4 | 4 | 1 |
| S | W | T | T | T | T | R | T | E | E | G |
|  |  | K | K | K | K | E | K | K | N |  |
|  |  | Q | Q | Q | Q | G | Q | V | K |  |
|  |  |  | P | P | P | K | P | M | D |  |

Figure 15A

Q-WTM (SEQ ID NO.: 85)

| 21 | 22 | 23 | 24 | 25 | 26 | 27 | 28 | 29 | 30 | 31 |
|---|---|---|---|---|---|---|---|---|---|---|
| S | W | X/T | X/P | X/P | X/P | X/G | X/P | X/V | X/D | G |
| AGC | TGG | MMG | CMG | CMG | CMG | SRG | CMG | SWG | SAK | GGC |
| 1 | 1 | 4 | 2 | 2 | 2 | 4 | 2 | 4 | 4 | 1 |
| S | W | K | P | P | P | E | P | L | E | G |
|  |  | T | Q | Q | Q | G | Q | E | D |  |
|  |  | P |  |  |  | R |  | V | Q |  |
|  |  | Q |  |  |  | Q |  | Q | H |  |

Figure 15B

D-WTM (SEQ ID NO.: 84)

| 21 | 22 | 23 | 24 | 25 | 26 | 27 | 28 | 29 | 30 | 31 |
|---|---|---|---|---|---|---|---|---|---|---|
| S | W | X/T | X/P | X/P | X/P | X/G | X/P | X/V | X/D | G |
| AGC | TGG | RMC | SMT | SMT | SMT | GRT | SMT | GWT | GAT | GGC |
| 1 | 1 | 4 | 4 | 4 | 4 | 2 | 4 | 2 | 1 | 1 |
| S | W | N | P | P | P | G | P | V | D | G |
|  |  | T | D | D | D | D | D | D |  |  |
|  |  | D | A | A | A |  | A |  |  |  |
|  |  | A | H | H | H |  | H |  |  |  |

Figure 15C

Y-WTM (SEQ ID NO.: 88)

| 21 | 22 | 23 | 24 | 25 | 26 | 27 | 28 | 29 | 30 | 31 |
|---|---|---|---|---|---|---|---|---|---|---|
| S | W | X/T | X/P | X/P | X/P | X/G | X/P | X/V | X/D | G |
| AGC | TGG | WMC | YMT | YMT | YMT | KRT | YMT | KWT | KAT | GGC |
| 1 | 1 | 4 | 4 | 4 | 4 | 4 | 4 | 4 | 2 | 1 |
| S | W | N | S | S | S | G | S | V | D | G |
|  |  | S | P | P | P | D | P | D | Y |  |
|  |  | T | Y | Y | Y | Y | Y | F |  |  |
|  |  | Y | H | H | H | C | H | Y |  |  |

Figure 15D

L-WTM (SEQ ID NO.: 89)

| 21 | 22 | 23 | 24 | 25 | 26 | 27 | 28 | 29 | 30 | 31 |
|---|---|---|---|---|---|---|---|---|---|---|
| S | W | X/T | X/P | X/P | X/P | X/G | X/P | X/V | X/D | G |
| AGC | TGG | MYG | CYG | CYG | CYG | SKG | CYG | STG | SWT | GGC |
| 1 | 1 | 4 | 2 | 2 | 2 | 4 | 2 | 2 | 4 | 1 |
| S | W | L | L | L | L | L | L | L | L | G |
|  |  | T | P | P | P | G | P | V | V |  |
|  |  | P |  |  |  | R |  |  | D |  |
|  |  | M |  |  |  | V |  |  | H |  |

Figure 15E

P-WTM (SEQ ID NO.: 90)

| 21 | 22 | 23 | 24 | 25 | 26 | 27 | 28 | 29 | 30 | 31 |
|---|---|---|---|---|---|---|---|---|---|---|
| S | W | X/T | X/P | X/P | X/P | X/G | X/P | X/V | X/D | G |
| AGC | TGG | MCG | CCG | CCG | CCG | SSG | CCG | SYG | SMT | GGC |
| 1 | 1 | 2 | 1 | 1 | 1 | 4 | 1 | 4 | 4 | 1 |
| S | W | T | P | P | P | G | P | L | P | G |
|  |  | P |  |  |  | R |  | V | D |  |
|  |  |  |  |  |  | P |  | P | A |  |
|  |  |  |  |  |  | A |  | A | H |  |

Figure 15F

S-WTM (SEQ ID NO.: 86)

| 21 | 22 | 23 | 24 | 25 | 26 | 27 | 28 | 29 | 30 | 31 |
|---|---|---|---|---|---|---|---|---|---|---|
| S | W | X/T | X/P | X/P | X/P | X/G | X/P | X/V | X/D | G |
| AGC | TGG | ASC | YCT | YCT | YCT | RGC | YCT | RKC | RRC | GGC |
| 1 | 1 | 2 | 2 | 2 | 2 | 2 | 2 | 4 | 4 | 1 |
| S | W | S | S | S | S | G | S | G | N | G |
|  |  | T | P | P | P | S | P | I | G |  |
|  |  |  |  |  |  |  |  | S | S |  |
|  |  |  |  |  |  |  |  | V | D |  |

Figure 15G

H-WTM (SEQ ID NO.: 87)

| 21 | 22 | 23 | 24 | 25 | 26 | 27 | 28 | 29 | 30 | 31 |
|---|---|---|---|---|---|---|---|---|---|---|
| S | W | X/T | X/P | X/P | X/P | X/G | X/P | X/V | X/D | G |
| AGC | TGG | MMC | CMT | CMT | CMT | SRT | CMT | SWT | SAT | GGC |
| 1 | 1 | 4 | 2 | 2 | 2 | 4 | 2 | 4 | 2 | 1 |
| S | W | N | P | P | P | G | P | L | D | G |
|  |  | T | H | H | H | R | H | V | H |  |
|  |  | P |  |  |  | D |  | D |  |  |
|  |  | H |  |  |  | H |  | H |  |  |

Figure 15H

G-WTM (SEQ ID NO.: 83)

| 21  | 22  | 23  | 24  | 25  | 26  | 27  | 28  | 29  | 30  | 31  |
|-----|-----|-----|-----|-----|-----|-----|-----|-----|-----|-----|
| S   | W   | X/T | X/P | X/P | X/P | X/G | X/P | X/V | X/D | G   |
| AGC | TGG | RSC | SSC | SSC | SSC | GGC | SSC | GKC | GRC | GGC |
| 1   | 1   | 4   | 4   | 4   | 4   | 1   | 4   | 2   | 2   | 1   |
| S   | W   | G   | G   | G   | G   | G   | G   | G   | G   | G   |
|     |     | S   | R   | R   | R   |     | R   | V   | D   |     |
|     |     | T   | P   | P   | P   |     | P   |     |     |     |
|     |     | A   | A   | A   | A   |     | A   |     |     |     |

Figure 15I

K-WTM (SEQ ID NO.: 100)

| 21  | 22  | 23  | 24  | 25  | 26  | 26a | 26b | 25c | 26d | 27  | 28  | 29  | 30  | 31  |
|-----|-----|-----|-----|-----|-----|-----|-----|-----|-----|-----|-----|-----|-----|-----|
| S   | W   | X/E | X/P | X/P | X/E | X/D | X/D | X/G | X/G | X/S | X/P | X/I | X/T | X/G |
| AGC | TGG | RAA | MMA | MMA | RAA | RAW | RAW | RRA | RRA | ARM | MMA | AWA | AMA | RRA |
| 1   | 1   | 2   | 4   | 4   | 2   | 4   | 4   | 4   | 4   | 4   | 4   | 2   | 2   | 4   |
| S   | W   | E   | T   | T   | E   | N   | N   | R   | R   | T   | I   | T   | R   |
|     |     | K   | K   | K   | K   | E   | E   | E   | E   | N   | K   | K   | K   | E   |
|     |     |     | Q   | Q   |     | K   | K   | G   | G   | K   | Q   |     |     | G   |
|     |     |     | P   | P   |     | D   | D   | K   | K   | S   | P   |     |     | K   |

Figure 16A

Q-WTM (SEQ ID NO.: 103)

| 21 | 22 | 23 | 24 | 25 | 26 | 26a | 26b | 25c | 26d | 27 | 28 | 29 | 30 | 31 |
|---|---|---|---|---|---|---|---|---|---|---|---|---|---|---|
| S | W | X/E | X/P | X/P | X/E | X/D | X/D | X/G | X/G | X/S | X/P | X/I | X/T | X/G |
| AGC | TGG | SAG | CMG | CMG | SAG | SAK | SAK | SRG | SRG | MRS | CMG | MWA | MMG | SRG |
| 1 | 1 | 2 | 2 | 2 | 2 | 4 | 4 | 4 | 4 | 6 | 2 | 4 | 4 | 4 |
| S | W | E | Q | Q | E | H | H | R | R | H | Q | I | T | R |
|  |  | Q | P | P | Q | E | E | E | E | R | P | Q | K | E |
|  |  |  |  |  |  | D | D | G | G | N |  | L | Q | G |
|  |  |  |  |  |  | Q | Q | Q | Q | K |  | K | P | Q |
|  |  |  |  |  |  |  |  |  |  | S |  |  |  |  |
|  |  |  |  |  |  |  |  |  |  | Q |  |  |  |  |

Figure 16B

D-WTM (SEQ ID NO.: 102)

| 21 | 22 | 23 | 24 | 25 | 26 | 26a | 26b | 25c | 26d | 27 | 28 | 29 | 30 | 31 |
|---|---|---|---|---|---|---|---|---|---|---|---|---|---|---|
| S | W | X/E | X/P | X/P | X/E | X/D | X/D | X/G | X/G | X/S | X/P | X/I | X/T | X/G |
| AGC | TGG | GAW | SMT | SMT | GAW | GAT | GAT | GRT | GRT | KMT | SMT | RWT | RMC | GRT |
| 1 | 1 | 2 | 4 | 4 | 2 | 1 | 1 | 2 | 2 | 4 | 4 | 4 | 4 | 2 |
| S | W | E | H | H | E | D | D | G | G | A | H | I | A | G |
|  |  | D | A | A | D |  |  | D | D | Y | A | D | T | D |
|  |  |  | D | D |  |  |  |  |  | S | D | N | N |  |
|  |  |  | P | P |  |  |  |  |  | D | P | V | D |  |

Figure 16C

Y-WTM (SEQ ID NO.: 106)

| 21 | 22 | 23 | 24 | 25 | 26 | 26a | 26b | 25c | 26d | 27 | 28 | 29 | 30 | 31 |
|---|---|---|---|---|---|---|---|---|---|---|---|---|---|---|
| S | W | X/E | X/P | X/P | X/E | X/D | X/D | X/G | X/G | X/S | X/P | X/I | X/T | X/G |
| AGC | TGG | TAT GAA | YMT | YMT | TAT GAA | KAT | KAT | KRT | KRT | TMT | YMT | WWT | WMC | KRT |
| 1 | 1 | 2 | 4 | 4 | 2 | 2 | 2 | 4 | 4 | 2 | 4 | 4 | 4 | 4 |
| S | W | E | H | H | E | Y | Y | G | G | Y | H | I | T | G |
|  |  | Y | Y | Y | Y | D | D | Y | Y | S | Y | Y | N | Y |
|  |  | S | S |  |  | D | D |  |  |  | S | F | Y | D |
|  |  | P | P |  |  |  |  | C | C |  | P | N | S | C |

Figure 16D

L-WTM (SEQ ID NO.: 107)

| 21 | 22 | 23 | 24 | 25 | 26 | 26a | 26b | 25c | 26d | 27 | 28 | 29 | 30 | 31 |
|---|---|---|---|---|---|---|---|---|---|---|---|---|---|---|
| S | W | X/E | X/P | X/P | X/E | X/D | X/D | X/G | X/G | X/S | X/P | X/I | X/T | X/G |
| AGC | TGG | SWG | CYG | CYG | SWG | SWT | SWT | SKG | SKG | TYA | CYG | WTA | MYG | SKG |
| 1 | 1 | 4 | 2 | 2 | 4 | 4 | 4 | 4 | 4 | 2 | 2 | 2 | 4 | 4 |
| S | W | E | P | P | E | H | H | R | R | S | P | I | T | R |
|  |  | Q | L | L | Q | D | D | G | G | L | L | L | P | G |
|  |  | V |  |  | V | V | V | V | V |  |  |  | L | V |
|  |  | L |  |  | L | L | L | L | L |  |  |  | M | L |

Figure 16E

P-WTM (SEQ ID NO.: 108)

| 21 | 22 | 23 | 24 | 25 | 26 | 26a | 26b | 25c | 26d | 27 | 28 | 29 | 30 | 31 |
|----|----|----|----|----|----|-----|-----|-----|-----|----|----|----|----|----|
| S | W | X/E | X/P | X/P | X/E | X/D | X/D | X/G | X/G | X/S | X/P | X/I | X/T | X/G |
| AGC | TGG | SMG | CCG | CCG | SMG | SMT | SMT | SSG | SSG | YCT | CCG | MYT | MCG | SSG |
| 1 | 1 | 4 | 1 | 1 | 4 | 4 | 4 | 4 | 4 | 2 | 1 | 4 | 2 | 4 |
| S | W | A | P | P | A | H | H | R | R | S | P | I | T | R |
|   |   | E |   |   | E | A | A | A | A | P |   | P | P | A |
|   |   | Q |   |   | Q | D | D | G | G |   |   | L |   | G |
|   |   | P |   |   | P | P | P | P | P |   |   | T |   | P |

Figure 16F

S-WTM (SEQ ID NO.: 104)

| 21 | 22 | 23 | 24 | 25 | 26 | 26a | 26b | 25c | 26d | 27 | 28 | 29 | 30 | 31 |
|----|----|----|----|----|----|-----|-----|-----|-----|----|----|----|----|----|
| S | W | X/E | X/P | X/P | X/E | X/D | X/D | X/G | X/G | X/S | X/P | X/I | X/T | X/G |
| AGC | TGG | RRM | YCT | YCT | RRM | RRC | RRC | RGC | RGC | AGC | YCT | AKC | ASC | RGC |
| 1 | 1 | 7 | 2 | 2 | 7 | 4 | 4 | 2 | 2 | 1 | 2 | 2 | 2 | 2 |
| S | W | R | S | S | R | N | N | G | G | S | S | I | T | G |
|   |   | E | P | P | E | G | G | S | S |   | P | S | S | S |
|   |   | N |   |   | N | S | S |   |   |   |   |   |   |   |
|   |   | G |   |   | G | D | D |   |   |   |   |   |   |   |
|   |   | K |   |   | K |   |   |   |   |   |   |   |   |   |
|   |   | S |   |   | S |   |   |   |   |   |   |   |   |   |
|   |   | D |   |   | D |   |   |   |   |   |   |   |   |   |

Figure 16G

H-WTM (SEQ ID NO.: 105)

| 21 | 22 | 23 | 24 | 25 | 26 | 26a | 26b | 25c | 26d | 27 | 28 | 29 | 30 | 31 |
|---|---|---|---|---|---|---|---|---|---|---|---|---|---|---|
| S | W | X/E | X/P | X/P | X/E | X/D | X/D | X/G | X/G | X/S | X/P | X/I | X/T | X/G |
| AGC | TGG | SAW | CMT | CMT | SAW | SAT | SAT | SRT | SRT | YMT | CMT | MWT | MMC | SRT |
| 1 | 1 | 4 | 2 | 2 | 4 | 2 | 2 | 4 | 4 | 4 | 2 | 4 | 4 | 4 |
| S | W | H | H | H | H | H | H | H | H | H | H | I | H | H |
|   |   | E | P | P | E | D | D | R | R | Y | P | H | T | R |
|   |   | D |   |   | D |   |   | G | G | S |   | L | N | G |
|   |   | Q |   |   | Q |   |   | D | D | P |   | N | P | D |

Figure 16H

G-WTM (SEQ ID NO.: 101)

| 21 | 22 | 23 | 24 | 25 | 26 | 26a | 26b | 25c | 26d | 27 | 28 | 29 | 30 | 31 |
|---|---|---|---|---|---|---|---|---|---|---|---|---|---|---|
| S | W | X/E | X/P | X/P | X/E | X/D | X/D | X/G | X/G | X/S | X/P | X/I | X/T | X/G |
| AGC | TGG | GRA | SSC | SSC | GRA | GRC | GRC | GGC | GGC | RGC | SSC | RKC | RSC | GGC |
| 1 | 1 | 2 | 4 | 4 | 2 | 2 | 2 | 1 | 1 | 2 | 4 | 4 | 4 | 1 |
| S | W | E | R | R | E | G | G | G | G | R | I | A | G |   |
| S |   | G | A | A | G | D | D |   |   | S | A | G | T |   |
|   |   | G | G |   |   |   |   |   |   |   | G | S | G |   |
|   |   | P | P |   |   |   |   |   |   |   | P | V | S |   |

Figure 16I

K-WTM (SEQ ID NO.: 109)

| 51 | 52 | 53 | 54 | 55 | 56 |
|---|---|---|---|---|---|
| X/P | X/G | X/T | X/E | X/T | X/S |
| MMA | RRA | AMA | RAA | AMA | ARM |
| 4 | 4 | 2 | 2 | 2 | 4 |
| T | R | T | E | T | R |
| K | E | K | K | K | N |
| Q | G |   |   |   | K |
| P | K |   |   |   | S |

Figure 17A

Q-WTM (SEQ ID NO.: 112)

| 51 | 52 | 53 | 54 | 55 | 56 |
|---|---|---|---|---|---|
| X/P | X/G | X/T | X/E | X/T | X/S |
| CMG | SRG | MMG | SAG | MMG | MRS |
| 2 | 4 | 4 | 2 | 4 | 6 |
| Q | R | T | E | T | H |
| P | E | K | Q | K | R |
|   | G | Q |   | Q | N |
|   | Q | P |   | P | K |
|   |   |   |   |   | S |
|   |   |   |   |   | Q |

Figure 17B

D-WTM (SEQ ID NO.: 111)

| 51 | 52 | 53 | 54 | 55 | 56 |
|---|---|---|---|---|---|
| X/P | X/G | X/T | X/E | X/T | X/S |
| SMT | GRT | RMC | GAW | RMC | KMT |
| 4 | 2 | 4 | 2 | 4 | 4 |
| H | G | A | E | A | A |
| A | D | T | D | T | Y |
| D |   | N |   | N | S |
| P |   | D |   | D | D |

Figure 17C

Y-WTM (SEQ ID NO.: 115)

| 51 | 52 | 53 | 54 | 55 | 56 |
|---|---|---|---|---|---|
| X/P | X/G | X/T | X/E | X/T | X/S |
| YMT | KRT | WMC | TAT GAA | WMC | TMT |
| 4 | 4 | 4 | 2 | 4 | 2 |
| H | G | T | E | T | Y |
| Y | Y | N | Y | N | S |
| S | D | Y |   | Y |   |
| P | C | S |   | S |   |

Figure 17D

L-WTM (SEQ ID NO.: 116)

| 51 | 52 | 53 | 54 | 55 | 56 |
|---|---|---|---|---|---|
| X/P | X/G | X/T | X/E | X/T | X/S |
| CYG | SKG | MYG | SWG | MYG | TYA |
| 2 | 4 | 4 | 4 | 4 | 2 |
| P | R | T | E | T | S |
| L | G | P | Q | P | L |
|   | V | L | V | L |   |
|   | L | M | L | M |   |

Figure 17E

P-WTM (SEQ ID NO.: 117)

| 51 | 52 | 53 | 54 | 55 | 56 |
|---|---|---|---|---|---|
| X/P | X/G | X/T | X/E | X/T | X/S |
| CCG | SSG | MCG | SMG | MCG | YCT |
| 1 | 4 | 2 | 4 | 2 | 2 |
| P | R | T | A | T | S |
|   | A | P | E | P | P |
|   | G |   | Q |   |   |
|   | P |   | P |   |   |

Figure 17F

S-WTM (SEQ ID NO.: 113)

| 51 | 52 | 53 | 54 | 55 | 56 |
|---|---|---|---|---|---|
| X/P | X/G | X/T | X/E | X/T | X/S |
| YCT | RGC | ASC | RRM | ASC | AGC |
| 2 | 2 | 2 | 7 | 2 | 1 |
| S | G | T | R | T | S |
| P | S | S | E | S |  |
|  |  |  | N |  |  |
|  |  |  | G |  |  |
|  |  |  | K |  |  |
|  |  |  | S |  |  |
|  |  |  | D |  |  |

Figure 17G

H-WTM (SEQ ID NO.: 114)

| 51 | 52 | 53 | 54 | 55 | 56 |
|---|---|---|---|---|---|
| X/P | X/G | X/T | X/E | X/T | X/S |
| CMT | SRT | MMC | SAW | MMC | YMT |
| 2 | 4 | 4 | 4 | 4 | 4 |
| H | H | H | H | H | H |
| P | R | T | E | T | Y |
|  | G | N | D | N | S |
|  | D | P | Q | P | P |

Figure 17H

G-WTM (SEQ ID NO.: 110)

| 51 | 52 | 53 | 54 | 55 | 56 |
|---|---|---|---|---|---|
| X/P | X/G | X/T | X/E | X/T | X/S |
| SSC | GGC | RSC | GRA | RSC | RGC |
| 4 | 1 | 4 | 2 | 4 | 2 |
| R | G | A | E | A | G |
| A |   | T | G | T | S |
| G |   | G |   | G |   |
| P |   | S |   | S |   |

Figure 17I

K-WTM (SEQ ID NO.: 118)

| 76 | 77 | 78 | 79 | 80 | 81 | 82 | 83 | 84 | 85 | 86 |
|---|---|---|---|---|---|---|---|---|---|---|
| N | X/A | X/A | X/G | X/V | X/G | X/P | X/P | X/S | X/S | X/K |
| AAT | RMG | RMG | RRA | RWG | RRA | MMA | MMA | ARM | ARM | AAA |
| 1 | 4 | 4 | 4 | 4 | 4 | 4 | 4 | 4 | 4 | 1 |
| N | E | E | G | E | G | K | K | N | N | K |
|   | K | K | E | K | E | T | T | R | R |   |
|   | T | T | R | V | R | P | P | S | S |   |
|   | A | A | K | M | K | Q | Q | K | K |   |

Figure 18A

O-WTM (SEQ ID NO.: 121)

| 76 | 77 | 78 | 79 | 80 | 81 | 82 | 83 | 84 | 85 | 86 |
|---|---|---|---|---|---|---|---|---|---|---|
| N | X/A | X/A | X/G | X/V | X/G | X/P | X/P | X/S | X/S | X/K |
| AAT | SMG | SMG | SRG | SWG | SRG | CMG | CMG | MRS | MRS | MAG |
| 1 | 4 | 4 | 4 | 4 | 4 | 2 | 2 | 6 | 6 | 2 |
| N | E | E | G | L | G | P | P | N | N | K |
|  | P | P | E | E | E | Q | Q | R | R | Q |
|  | Q | Q | R | V | R |  |  | K | K |  |
|  | A | A | Q | Q | Q |  |  | S | S |  |
|  |  |  |  |  |  |  |  | Q | Q |  |
|  |  |  |  |  |  |  |  | H | H |  |

Figure 18B

D-WTM (SEQ ID NO.: 120)

| 76 | 77 | 78 | 79 | 80 | 81 | 82 | 83 | 84 | 85 | 86 |
|---|---|---|---|---|---|---|---|---|---|---|
| N | X/A | X/A | X/G | X/V | X/G | X/P | X/P | X/S | X/S | X/K |
| AAT | GMC | GMC | GRT | GWT | GRT | SMT | SMT | KMT | KMT | RAW |
| 1 | 2 | 2 | 2 | 2 | 2 | 4 | 4 | 4 | 4 | 4 |
| N | D | D | G | V | G | P | P | S | S | N |
|  | A | A | D | D | D | D | D | D | D | E |
|  |  |  |  |  |  | A | A | A | A | K |
|  |  |  |  |  |  | H | H | Y | Y | D |

Figure 18C

Y-WTM (SEQ ID NO.: 124)

| 76 | 77 | 78 | 79 | 80 | 81 | 82 | 83 | 84 | 85 | 86 |
|---|---|---|---|---|---|---|---|---|---|---|
| N | X/A | X/A | X/G | X/V | X/G | X/P | X/P | X/S | X/S | X/K |
| AAT | KMC | KMC | KRT | KWT | KRT | YMT | YMT | TMT | TMT | AAA TAT |
| 1 | 4 | 4 | 4 | 4 | 4 | 4 | 4 | 2 | 2 | 2 |
| N | S | S | G | V | G | S | S | S | S | K |
|  | D | D | D | D | D | P | P | Y | Y | Y |
|  | A | A | Y | F | Y | Y | Y |  |  |  |
|  | Y | Y | C | Y | C | H | H |  |  |  |

Figure 18D

L-WTM (SEQ ID NO.: 125)

| 76 | 77 | 78 | 79 | 80 | 81 | 82 | 83 | 84 | 85 | 86 |
|---|---|---|---|---|---|---|---|---|---|---|
| N | X/A | X/A | X/G | X/V | X/G | X/P | X/P | X/S | X/S | X/K |
| AAT | SYG | SYG | SKG | STG | SKG | CYG | CYG | TYA | TYA | MWG |
| 1 | 4 | 4 | 4 | 2 | 4 | 2 | 2 | 2 | 2 | 4 |
| N | L | L | L | L | L | L | L | L | L | L |
|  | V | V | G | V | G | P | P | S | S | K |
|  | P | P | R |  | R |  |  |  |  | M |
|  | A | A | V |  | V |  |  |  |  | Q |

Figure 18E

P-WTM (SEQ ID NO.: 126)

| 76 | 77 | 78 | 79 | 80 | 81 | 82 | 83 | 84 | 85 | 86 |
|---|---|---|---|---|---|---|---|---|---|---|
| N | X/A | X/A | X/G | X/V | X/G | X/P | X/P | X/S | X/S | X/K |
| AAT | SCG | SCG | SSG | SYG | SSG | CCG | CCG | YCT | YCT | MMG |
| 1 | 2 | 2 | 4 | 4 | 4 | 1 | 1 | 2 | 2 | 4 |
| N | P | P | G | L | G | P | P | S | S | K |
|   | A | A | R | V | R |   |   | P | P | T |
|   |   |   |   | P | P | P |   |   |   | P |
|   |   |   |   | A | A | A |   |   |   | Q |

Figure 18F

S-WTM (SEQ ID NO.: 122)

| 76 | 77 | 78 | 79 | 80 | 81 | 82 | 83 | 84 | 85 | 86 |
|---|---|---|---|---|---|---|---|---|---|---|
| N | X/A | X/A | X/G | X/V | X/G | X/P | X/P | X/S | X/S | X/K |
| AAT | KCT | KCT | RGC | RKC | RGC | YCT | YCT | AGC | AGC | ARM |
| 1 | 2 | 2 | 2 | 4 | 2 | 2 | 2 | 1 | 1 | 4 |
| N | S | S | G | G | G | S | S | S | S | N |
|   | A | A | S | I | S | P | P |   |   | R |
|   |   |   |   | S |   |   |   |   |   | S |
|   |   |   |   | V |   |   |   |   |   | K |

Figure 18G

H-WTM (SEQ ID NO.: 123)

| 76 | 77 | 78 | 79 | 80 | 81 | 82 | 83 | 84 | 85 | 86 |
|---|---|---|---|---|---|---|---|---|---|---|
| N | X/A | X/A | X/G | X/V | X/G | X/P | X/P | X/S | X/S | X/K |
| AAT | SMC | SMC | SRT | SWT | SRT | CMT | CMT | YMT | YMT | MAW |
| 1 | 4 | 4 | 4 | 4 | 4 | 2 | 2 | 4 | 4 | 4 |
| N | P | P | G | L | G | P | P | S | S | N |
|  | D | D | R | V | R | H | H | P | P | K |
|  | A | A | D | D | D |  |  | Y | Y | Q |
|  | H | H | H | H | H |  |  | H | H | H |

Figure 18H

G-WTM (SEQ ID NO.: 119)

| 76 | 77 | 78 | 79 | 80 | 81 | 82 | 83 | 84 | 85 | 86 |
|---|---|---|---|---|---|---|---|---|---|---|
| N | X/A | X/A | X/G | X/V | X/G | X/P | X/P | X/S | X/S | X/K |
| AAT | GSC | GSC | GGC | GKC | GGC | SSC | SSC | RGC | RGC | RRA |
| 1 | 2 | 2 | 1 | 2 | 1 | 4 | 4 | 2 | 2 | 4 |
| N | G | G | G | G | G | G | G | G | G | G |
|  | A | A |  | V |  | R | R | S | S | E |
|  |  |  |  |  |  | P | P |  |  | R |
|  |  |  |  |  |  | A | A |  |  | K |

Figure 18I

| | 21 | 22 | 23 | 24 | 25 | 26 | 26A | 26B | 26C | 26D | 27 | 28 | 29 | 30 | 31 |
|---|---|---|---|---|---|---|---|---|---|---|---|---|---|---|---|
| WTM Degenerate DNA Sequence | arm | tgg | raa | mma | ccg | raa | raw | gat | ggc | ggc | arm | mma | att | ama | rra |
| Mixed DNA Bases | a<sup>a</sup>g<sup>a</sup>c | tgg | g<sup>a</sup>aa | a<sup>a</sup>c<sup>a</sup>c | ccg | g<sup>a</sup>aa | a<sup>a</sup>g<sup>t</sup>a | gat | ggc | ggc | a<sup>a</sup>g<sup>a</sup>c | a<sup>a</sup>c<sup>a</sup>c | att | a<sup>a</sup>c<sup>a</sup>c | a<sup>a</sup>g<sup>a</sup>g |
| WILD TYPE AMINO ACIDS | S | W | E | P | P | E | D | D | G | G | S | P | I | T | G |
| WTM-TARGET AMINO ACID | K | | K | K | | K | K | | | | K | K | | K | K |
| WTM-COPRODUCT AMINO ACIDS | R N | | | T Q | | | N E | | | | R N | T Q | | | R E |

Figure 19

| BC (11) | 21 | 22 | 23 | 24 | 25 | 26 | 27 | 28 | 29 | 30 | 31 |
|---|---|---|---|---|---|---|---|---|---|---|---|
| | S | W | T | P | P | P | G | P | F | D | G |
| | T | | K | A | A | E | S | A | I | A | S |
| | P | | R | L | S | Q | | E | V | V | R |
| | R | | A | L | | R | | Q | | I | |
| | | | E | R | | A | | T | | N | |
| | | | G | G | | G | | K | | T | |

Fig. 23A

| DE (6) | | | | | |
|---|---|---|---|---|---|
| 51 | 52 | 53 | 54 | 55 | 56 |
| P | G | T | E | T | S |
| A | P | D | K | R | T |
| H | A | S | T | N | I |
| K | S | N | A | S | V |
| N | R | G | Y | H | A |
| Q | T | A | I | P | G |
| T | | | | | |
| D | | | | | |
| E | | | | | |

| 76 | 77 | 78 | 79 | 80 | 81 | 82 | 83 | 84 | 85 | 86 |
|----|----|----|----|----|----|----|----|----|----|----|
| N  | R  | Y  | G  | I  | G  | T  | S  | R  | S  | S  |
| T  | S  | S  |    | V  | S  | Q  | Y  | S  |    |    |
|    | T  | F  |    | T  |    | N  | L  | T  |    |    |
|    | N  | V  |    | A  |    | D  | D  | A  |    |    |
|    | D  | A  |    | N  |    | P  | P  | G  |    |    |
|    | E  | D  |    | D  |    | E  | H  |    |    |    |
|    | A  | K  |    | K  |    | H  | A  |    |    |    |
|    | G  | I  |    | E  |    | A  | V  |    |    |    |
|    | K  | T  |    | S  |    | H  | F  |    |    |    |
|    | I  | R  |    | G  |    |    |    |    |    |    |
|    | V  |    |    | R  |    |    |    |    |    |    |
|    | M  |    |    |    |    |    |    |    |    |    |

| Clone | Copies |
|---|---|
| R1D4 | 29 |
| R1F1 | 1 |
| R1G1 | 1 |

BC

| 21 | 22 | 23 | 24 | 25 | 26 | 27 | 28 | 29 | 30 | 31 |
|---|---|---|---|---|---|---|---|---|---|---|
| S | W | T | K | A | P | P | G | P | F | G |
| T |   | K | R | Y | S | Q | S | E | I | S |
| R |   |   | V |   | Q | R | Q | V | N | R |
| P |   |   | L |   | R | A | A | T | A |   |
|   |   | E | G |   | A | G | K |   | D |   |
|   |   | G | G |   | G |   |   |   |   |   |

| 21 | 22 | 23 | 24 | 25 | 26 | 27 | 28 | 29 | 30 | 31 |
|---|---|---|---|---|---|---|---|---|---|---|
| P | W | E | V | A | G | G | P | I | I | S |
| P | W | A | L | G | G | G | P | I | I | S |
| R | W | A | G | S | P | G | P | V | D | S |

DE

| 51 | 52 | 53 | 54 | 55 | 56 |
|---|---|---|---|---|---|
| P | G | T | E | T | S |
| T | P | D | K | R | T |
| A | A | S | N | N | I |
| H | S | N | A | S | V |
| N | R | G | V | H | A |
| D | T | A | I | P | G |
| Q |   |   |   |   |   |
| K |   |   |   |   |   |
| E |   |   |   |   |   |

| 51 | 52 | 53 | 54 | 55 | 56 |
|---|---|---|---|---|---|
| T | P | D | A | T | G |
| T | P | D | I | R | G |
| Q | T | S | E | T | G |

Fig. 25B

| | BC | | | | | | | | | | | DE | | | | | |
|---|---|---|---|---|---|---|---|---|---|---|---|---|---|---|---|---|---|
| | 21 | 22 | 23 | 24 | 25 | 26 | 27 | 28 | 29 | 30 | 31 | 51 | 52 | 53 | 54 | 55 | 56 |
| | S | W | T | P | P | P | G | P | F | T | G | P | G | T | E | T | S |
| | T | | K | A | A | E | S | E | I | I | S | T | P | D | K | R | T |
| | R | | R | V | S | Q | | Q | V | N | R | A | A | S | T | N | I |
| | P | | A | L | | R | | A | | V | | H | S | N | A | S | V |
| | | | E | R | | A | | T | | A | | N | R | G | V | H | A |
| | | | G | G | | G | | K | | D | | D | T | A | I | P | G |
| | | | | | | | | | | | | Q | | | | | |
| | | | | | | | | | | | | K | | | | | |
| | | | | | | | | | | | | E | | | | | |

| Clone | Copies | 21 | 22 | 23 | 24 | 25 | 26 | 27 | 28 | 29 | 30 | 31 | 51 | 52 | 53 | 54 | 55 | 56 |
|---|---|---|---|---|---|---|---|---|---|---|---|---|---|---|---|---|---|---|
| R2E6 | 22 | R | W | G | V | A | Q | S | Q | V | A | R | K | R | S | V | H | T |
| P2F3 | 8 | R | W | G | V | P | H | S | - | - | - | - | K | R | G | V | R | S |
| R2G2 | 2 | S | W | R | A | A | E | S | A | I | A | R | K | R | T | K | H | T |
| R2D4 | 2 | S | W | G | V | A | E | S | E | V | T | R | K | R | S | K | H | A |
| P1E8 | 2 | S | W | R | A | A | E | S | A | I | A | R | K | R | T | K | H | T |
| R2F8 | 1 | R | W | A | R | S | A | S | E | I | A | R | K | R | S | A | N | I |
| R2G9 | 1 | R | W | G | V | S | E | S | E | V | I | R | K | R | S | K | H | A |
| R2F4 | 1 | R | W | G | V | S | P | S | E | V | V | R | K | R | S | V | H | G |
| R2B5 | 1 | R | W | T | V | A | E | S | K | I | A | R | K | R | S | K | H | S |
| R2E5 | 1 | S | W | G | V | A | P | S | E | I | N | R | K | R | S | K | H | A |
| R2F5 | 1 | R | W | G | V | S | E | G | Q | I | V | R | K | R | S | K | H | A |
| P2F6 | 1 | R | W | T | V | P | A | S | P | I | A | R | K | R | T | T | R | T |
| P2C6 | 1 | R | W | G | V | A | P | S | Q | V | I | R | K | R | S | V | H | A |
| P2F5 | 1 | R | W | G | V | P | G | S | P | V | V | R | K | R | G | A | R | I |
| P2F7 | 1 | R | W | G | A | P | A | S | E | I | I | R | K | R | T | I | H | T |

Fig. 26A

| | | BC | DE | FG |
|---|---|---|---|---|
| 1637115 | VGR2B10 | SWRTK----TKTITG | IERNAHGY | YG---LGEASS |
| 1637102 | VGR2E11 | SWRTK----TETITG | IETGANGY | NEDGGSAYTEL |
| 1637114 | VGR2C07 | SWRTK----TETITG | IDTSANSY | NEYGDSNFTQL |
| 1637114 | VGR2C11 | SWRTK----TETITG | ITANERGY | NDFGDSKYAQL |
| 1637102 | VGR2E05 | RWNQPAYDGGRAIPG | INADVSTY | N----DNARSS |
| 1637102 | VGR2C08 | RWETPEYNGGTAIPG | INADISTY | N----DNARSS |
| 1637102 | VGR2H05 | RWGQPRYNGGSTVPS | INADISTY | N----DNARSS |
| 1637114 | VGR2E05 | RWGQPAYDGGSEVPG | INADISTY | N----DNARSS |
| 1637102 | VGR2H07 | RWGAPELDGGSGIPS | INADISTY | N----DNARSS |
| 1637102 | VGR2E08 | RWGAPEDDGGGTVPG | INADTSTY | N----DNARSS |
| 1637114 | VGR2D05 | RWGAPEDDGGGEVPG | INADVSTY | N----DNARSS |
| 1637102 | VGR2A05 | RWNTPENDGGGTVPG | INADVSTY | N----DNARSS |
| 1637114 | VGR2C02 | RWQAP-DDGDGVVPG | INADTNTY | N----DNARSS |
| 1637114 | VGR2F06 | RWQQGE-EGGGVVPG | INADTSTY | N----DNARSS |
| 1637114 | VGR2H04 | RWNTPGDAGGSTVPG | INADISTY | N----DNARSS |
| 1637102 | VGR2D04 | RWRAPEANGGSAVPG | INADTSTY | N----DNARSS |
| 1637114 | VGR2A06 | RWKAPIDNGGSTVPG | INADTSTY | N----DNARSS |
| 1637102 | VGR2F04 | RWKAPEYTGGAEVLG | INADTSTY | N----DNARSS |
| 1637102 | VGR2A08 | RWKVPI-QRDSIVPG | INADTSTY | N----DNARSS |
| 1637114 | VGR2H02 | RWTVPE-GGDSIVPS | INADVSTY | N----DNARSS |
| 1637114 | VGR2A04 | RWTVPEERDG-VIPG | INADISTY | N----DNARSS |
| 1637102 | VGR2A04 | RWTQGVSRNG-TIPG | INADTSTY | N----DNARSS |
| 1637102 | VGR2D08 | RWTL-----AG-PIAG | INADTSTY | N----DNARSS |
| 1637114 | VGR2D06 | RWQLGVGPGG-TIPG | INADISTY | N----DNARSS |
| 1637102 | VGR2B01 | RWTR----APS-QDG | INADTTVY | N----DNARSS |
| 1637115 | VGR2C06 | RWTV----SGSPFDG | INADTTVY | N----DNARSS |
| 1637102 | VGR2F09 | RWTLGI-SGNSIVPG | INADTTTY | N----DNARSS |
| 1637114 | VGR2B04 | RWRAAR-----SQFG | INADASTY | N----DNARSS |
| 1637114 | VGR2B01 | RWAQGGNGSG-VIPS | INADVSTY | N----DNARSS |
| 1637114 | VGR2G01 | RWAPGE-ERGSVVPS | INADTSTY | N----DNARSS |
| 1637102 | VGR2D01 | RWEAGV-EADGEVPS | INADTSTY | N----DNARSS |
| 1637114 | VGR2B02 | RWELGS-DRDSEVPS | INADISTY | N----DNARSS |
| 1637114 | VGR2C06 | RWEQPVHPNS-LIPS | INADVSTY | N----DNARSS |
| 1637114 | VGR2H03 | RWTVPVHGSS-VIPS | INADVSTY | N----DNARSS |
| 1637102 | VGR2H01 | RWTVPVSANG-QIPS | INADVSTY | N----DNARSS |
| 1637102 | VGR2E01 | RWKQPIKPDS-VIPS | INADISTY | N----DNARSS |
| 1637114 | VGR2B05 | RWQLPIRADS-AIPS | INADISTY | N----DNARSS |
| 1637102 | VGR2C07 | RWELPINRNS-TIPS | INADISTY | N----DNARSS |
| 1637102 | VGR2A09 | RWELPIKASS-IIPS | IQADVSTY | N----DNARSS |
| 1637102 | VGR2C03 | RWKLPIKPNS-TIPS | INADVSTY | N----DNARSS |
| 1637102 | VGR2G05 | RWKLPI-EADGIVPS | IQADVSTY | N----DNARSS |

Fig 29A

| | | BC | DE | FG |
|---|---|---|---|---|
| 1637102 | VGR2F07 | RWTLGDQVSS-AIPG | INADVSTY | N----DNARSS |
| 1637102 | VGR2H02 | RWALGVDASS-VIPG | INADVSTY | N----DNARSS |
| 1637102 | VGR2B07 | RWKLPIGRGS-EIPG | INADVSTY | N----DNARSS |
| 1637114 | VGR2A02 | RWELPIQRSS-LIPG | INADVSTY | N----DNARSS |
| 1637102 | VGR2E04 | RWELPI-EASGLVPG | INADTSTY | N----DNARSS |
| 1637102 | VGR2C01 | RWQLPG-DANGEVPG | INADVSTY | N----DNARSS |
| 1637102 | VGR2A07 | RWQLPI-KASSEVPG | INADVSTY | N----DNARSS |
| 1637102 | VGR2H03 | RWTLPV-QANGIVPG | IHADVSTY | N----DNARSS |
| 1637102 | VGR2C10 | RWKLPV-SADGVVPG | INADISTY | N----DNARSS |
| 1637114 | VGR2A05 | RWKLPSEPSS-VVLG | INATVSTY | N----DNARSS |
| 1637102 | VGR2B03 | RWQQPVEADG-IIPS | IHADISTY | N----DNARSS |
| 1637102 | VGR2F05 | RWQVGVDADS-PIPS | IHADISTY | N----DNARSS |
| 1637102 | VGR2D05 | RWRTPADNGGGIPS | INADISTY | N----DNARSS |
| 1637114 | VGR2E04 | RWRTPADTGGAGIPS | IHADVSTY | N----DNARSS |
| 1637102 | VGR2F03 | RWDTPGDAGGSGIPS | INADVSTY | N----DNARSS |
| 1637102 | VGR2C04 | RWRTPIDAGGGQVPS | INADVSTY | N----DNARSS |
| 1637114 | VGR2G05 | RWSTPAYAGGGEVPS | INADVSTY | N----DNARSS |
| 1637102 | VGR2D07 | RWALPI-DPGSLVPS | IHADTSTY | N----DNARSS |
| 1637102 | VGR2B04 | RWKQPK-EAESQVLS | INASTNVY | N----DNARSS |
| 1637102 | VGR2B05 | RWKQPK-EADSQVLS | INASTNVY | N----DNARSS |
| 1637114 | VGR2F02 | RWKQPI-HADSILLS | INASTNIY | N----DNARSS |
| 1637102 | VGR2F01 | RWKVPV-HRNSTLIS | INATTNVY | N----DNARSS |
| 1637102 | VGR2D03 | RWTVPV-HRDSEIIS | INATTNVY | N----DNARSS |
| 1637114 | VGR2C10 | RWEVPN-KGGSQLLS | INATTNVY | N----DNARSS |
| 1637102 | VGR2D12 | RWER----SGGPVDG | INADTNIY | N----DNARSS |
| 1637114 | VGR2A08 | RWER----SGGPVDG | INADTNIY | N----DNARNT |
| 1637104 | VGR2D03 | RWAR----APGPFDG | INADTNIY | N----DNARSS |
| 1637102 | VGR2E03 | RWER----APSEVDG | IHADTNIY | N----DNARSS |
| 1637102 | VGR2G09 | RWER----APGEVDG | INADTNIY | N----DNARSS |
| 1637102 | VGR2C09 | RWER----AQGEVDG | IHADTNVY | N----DNARSS |
| 1637102 | VGR2D09 | RWTR----AGSEVDG | INADTNVY | N----DNARSS |
| 1637104 | VGR2C09 | RWER----ARSEVDG | INADTNVY | N----DNARSS |
| 1637104 | VGR2F11 | RWTR----AAGEVDG | INADTNTY | N----DNARSS |
| 1637104 | VGR2C05 | RWTR----AAGEVDG | INADTNTY | N----DNARSS |
| 1637102 | VGR2F11 | RWTR----AAGEVDG | INADTNTY | N----DNARSS |
| 1637102 | VGR2F02 | RWTR----ARSEVIG | INADTNIY | N----DNARSS |
| 1637102 | VGR2G08 | RWER----AAGEFAG | IHADTNIY | N----DNARSS |
| 1637102 | VGR2C05 | RWQQPI-RASGELPG | INADTNIY | N----DNARSS |
| 1637115 | VGR2F06 | RWER----SQGQFDG | INADTNVY | N----DNARSS |
| 1637104 | VGR2H04 | RWER----SIGQFDG | INADTNVY | N----DNARSS |
| 1637115 | VGR2G11 | RWER----SQGQFDG | INADTNVY | TAPGAGDVTSS |

Fig 29B

|  |  |  | BC | DE | FG |
|---|---|---|---|---|---|
| 1637103 | VGR2H03 | | RWRVA-----GSEFDS | IHAATTTY | N----DNARSS |
| 1637104 | VGR2H12 | | RWRVA-----GSEFDS | IHAATTTY | N----DNARSS |
| 1637115 | VGR2H09 | | RWRVA-----GSEFDS | IHAATTTY | N----DNARSS |
| 1637103 | VGR2F12 | | RWRVA-----GSEFDS | IHAATTTY | N----DNARSS |
| 1637103 | VGR2B09 | | RWRVA-----GSEFDS | IHAATTTY | N----DNARSS |
| 1637104 | VGR2G12 | | RWRVA-----GSEFDS | IHAATTTY | N----DNARXS |
| 1637104 | VGR2B11 | | RWAVA-----GSEFDS | IHAATTTY | N----DNARSS |
| 1637103 | VGR2H11 | | RWKVA-----GSEFDS | IHAATTTY | N----DNARSS |
| 1637104 | VGR2E02 | | RWKVA-----GGEFDS | IHAATTTY | N----DNARSS |
| 1637115 | VGR2E01 | | RWRVA-----GSEFDS | IHAATTTY | N----DNARTS |
| 1637104 | VGR2C12 | | RWRVA-----GSEFDS | IHAATTTY | N----DNARSX |
| 1637104 | VGR2H06 | | RWIGA-----RSEFDX | IHAATTTY | N----DNARSS |
| 1637103 | VGR2D06 | | RWTVA-----ESTFDS | IHAATTTY | N----DNARSS |
| 1637115 | VGR2C02 | | RWEVA-----ESAFDS | INAATTTY | N----DNARSS |
| 1637103 | VGR2E12 | | RWKVA-----GGTFDS | INAATTTY | N----DNARSS |
| 1637115 | VGR2G01 | | RWKVA-----GGTFDS | INAATTTY | N----DNARSI |
| 1637103 | VGR2H07 | | RWKVA-----GGTFDS | INAATTTY | N----DNARSS |
| 1637104 | VGR2G07 | | RWKVA-----GGTFDS | INAATTTY | N----DNARSS |
| 1637114 | VGR2D02 | | RWKVA-----GSQFTS | INAATTTY | N----DNARSS |
| 1637104 | VGR2D07 | | RWTVS-----ASEFDS | IHATTTTY | N----DNARSS |
| 1637115 | VGR2F04 | | RWTVS-----ASEFDS | IHATTTTY | N----DNARSS |
| 1637102 | VGR2E07 | | RWAVS-----QSAFDS | IHATTSTY | N----DNARSS |
| 1637115 | VGR2A08 | | RWRVG-----GSEFDS | IHAATTTY | N----DNARXT |
| 1637102 | VGR2G07 | | RWGEPTHNGGTEIPS | INADTHTY | N----DNARSS |
| 1637115 | VGR2D10 | | XWTR-----AGGEFDG | INADTNTY | N----DTARSP |
| 1637104 | VGR2A06 | | SWRLP-----AGAVAG | IKPDVRSY | TR----GRGGSS |
| 1637115_VGR2C03 | | | RWGVP-----EGKVVS | IKPDVRSY | NNTGGSTYTEL |

Fig 29C

| | BC | DE | FG |
|---|---|---|---|
| 1637111_AXLC02 | TWTV----PRSKFVG | KPDVRS | YGYVSG---SS |
| 1637117_AXLE05 | TWTG----SRGKFVG | KPDVRS | YGYVSG---SS |
| 1637111_AXLG09 | SWGL----PRSKVVG | KPDVRS | YGYVSG---SS |
| 1637111_AXLF09 | RWER----APSKFVG | KPDVRS | YGYVSG---SS |
| 1637113_AXLB06 | TW----------PLG | KRGVSS | NDN----ARSS |
| 1637117_AXLA04 | TWGLAES----KVVG | KPDVRS | N--GN---VGGL |
| 1637113_AXLE06 | TW----------RVS | KRGVSS | NDN----ARSS |
| 1637113_AXLA08 | RWGVL---------G | NRSVRA | NDN----ARSS |
| 1637113_AXLF05 | RWPVN---------G | NRGVRT | NDN----ARSS |
| 1637116_AXLC09 | RWSIT---------G | NRGVRS | NDN----ARSS |
| 1637118_AXLB09 | RWAVPG--------- | QRGVRA | NDN----ARSS |
| 1637110_AXLH04 | RWSI----------G | KRDAPS | NDN----ARSS |
| 1637119_AXLE06 | RWGV---------TG | KRNARS | NDN----ARSS |
| 1637113_AXLB05 | TWTLPH--------- | DRGTRA | NDN----ARSS |
| 1637110_AXLE01 | SWK----------VR | TSSVRS | NDN----ARSS |
| 1637110_AXLC04 | RWAVP---------G | KRNVSV | NDN----ARSS |
| 1637116_AXLC06 | RWPVL---------G | KRTVSV | NDN----ARSS |
| 1637111_AXLE04 | SWEGSPS----TFIG | KPDVRS | PDSG---RSSS |
| 1637118_AXLD11 | SWAV----------G | KRDVRA | NDNAR----SS |
| 1637110_AXLF08 | SWPVP---------G | KRDVNS | NDNAR----SS |
| 1637113_AXLA06 | RWKVP---------G | TRGVRG | NDN----ARSS |
| 1637118_AXLB06 | RWKVP---------G | ARGVRV | NDN----ARSS |
| 1637118_AXLE08 | RWKVN---------G | HRAVRV | NDN----ARSS |
| 1637113_AXLG10 | RWKVD---------G | TRGVRV | NDN----ARSS |
| 1637116_AXLA09 | RWKVP---------G | HRGIRS | NDN----ARSS |
| 1637111_AXLF11 | TWTRARS----TVVG | KPDVRS | TVIGDSAYSSS |
| 1637113_AXLG09 | RWE---------AVG | KRNVTV | NDN----ARSS |
| 1637119_AXLC02 | RW----------AAG | KRNINS | NDN----ARSS |
| 1637112_AXLE12 | RWAEP---------G | KRTARV | NDN----ARSS |
| 1637113_AXLD08 | RWKVP---------G | TRGTRV | NDN----ARSS |
| 1637117_AXLC05 | TWARSQS----TVVG | KPDVRS | TVVGGSAYGSS |
| 1637110_AXLF04 | RWTLG--------LG | KRDAHV | NDN----ARSS |
| 1637110_AXLF09 | RWKIA---------G | HRGVRA | NDN----ARSS |
| 1637110_AXLH03 | RWIP---------PG | KRNVNV | NDN----ARSS |
| 1637118_AXLA07 | RWKV---------LG | KRNISS | NDN----ARSS |
| 1637110_AXLB11 | SWQ----------QG | KRSISS | NDN----ARSS |
| 1637112_AXLA04 | SWR----------TS | KRGVTS | NDN----ARSS |
| 1637110_AXLH10 | TWR---------PPG | KRNASS | NDN----ARSS |
| 1637113_AXLH02 | RWGV---------LG | KRAINS | NDN----ARSS |

Fig 30A

| | BC | DE | FG |
|---|---|---|---|
| 1637110_AXLF11 | RWG----------TG | KRSITS | NDN----ARSS |
| 1637110_AXLC08 | RWAPPE--------G | HRSARS | NDN----ARSS |
| 1637110_AXLD11 | SWP----------AG | KRGKRT | NDN----ARSS |
| 1637111_AXLH12 | SWG----------VG | KRGKTV | NDN----ARSS |
| 1637113_AXLB04 | SWKVAPS-----TVVG | KPDVRS | NVFGGSAYSSS |
| 1637113_AXLA04 | RWRVL---------G | HRGVNV | NDN----ARSS |
| 1637116_AXLB02 | RWPVP---------G | HRAVTV | NDN----ARSS |
| 1637116_AXLD03 | RWAVP---------G | HRGVSV | NDN----ARSS |
| 1637111_AXLE06 | RWAVSPS-----TVVG | KPDVRS | NVKGGSASASS |
| 1637116_AXLB05 | RWKVD---------G | HRAVNV | NDN----ARSS |
| 1637111_AXLA09 | SWAPAAS-----TVVG | KPDVRS | IMVGAGAVGSS |
| 1637117_AXLH04 | RWSN----------G | KRTAPS | NDN----ARSS |
| 1637110_AXLA06 | RWKVL---------G | ARGART | NDN----ARSS |
| 1637110_AXLH01 | RWKVD---------G | TRNTRT | NDN----ARSS |
| 1637118_AXLG03 | RWA---------QVLR | KRDVHS | NDN----ARSS |
| 1637111_AXLB07 | RWEGRG-------VIG | KPDVRS | TVVGNSAFASS |
| 1637113_AXLH03 | RWRGPR-------- | DAGTRG | NDN----ARSS |
| 1637111_AXLE11 | SWGL-----APSQFAR | KPDVRS | NGYGRGQVASS |
| 1637113_AXLF01 | RWAIPG-------- | TRGARA | NDN----ARSS |
| 1637110_AXLD12 | TWAGP---------E | HRGITS | NDN----ARSS |
| 1637113_AXLD03 | RWGIPG-------- | KRAISA | NDN----ARSS |
| 1637113_AXLH01 | RWAAP---------G | HRTAPS | NDN----ARSS |
| 1637111_AXLC06 | SWRRAES-----TVVG | KPDVRS | NIRGGSAAASS |
| 1637111_AXLG12 | RWALPAS-----TVVG | KPDVRS | NIRGNSASASS |
| 1637116_AXLG07 | RWKGA---------D | TRGVRT | NDN----ARSS |
| 1637110_AXLB10 | RWPA---------PG | KRTVNV | NDN----ARSS |
| 1637110_AXLF07 | RWG--------QFDR | KRTVHS | NDN----ARSS |
| 1637110_AXLB03 | RWKVP---------G | HRGATV | NDN----ARSS |
| 1637110_AXLA12 | RWKVD---------G | HRGITV | NDN----ARSS |
| 1637111_AXLE12 | RWKLAGS-----QVVG | KPDVRS | TIRGGSAVGSS |
| 1637111_AXLB09 | SWERSES-----TVVG | KPDVRS | TVVGKSAHGSS |
| 1637119_AXLH10 | RWGQ---------TG | KRAATS | NDN----ARSS |
| 1637111_AXLB01 | SWKKPKHNGGSKLTG | KPDVRS | YRRLG----ASS |
| 1637113_AXLE04 | RWG--------APTG | KSDIHG | NDN----ARSS |
| 1637116_AXLG10 | RWS---------LLG | KRNVNA | NDN----ARSS |
| 1637113_AXLC05 | RWTL---------TG | KRSANV | NDN----ARSS |
| 1637117_AXLD04 | SWKRSES-----QVVG | KPDVRS | NVVGRSAYGSS |
| 1637113_AXLC02 | RWG---------ALG | KRSVTT | NDN----ARSS |
| 1637117_AXLD12 | SWR----------TS | KRGVTX | NDN----ARSS |

Fig 30B

| | BC | DE | FG |
|---|---|---|---|
| 1637110_AXLE11 | RWA----------QVLS | KRDVHS | NDN----ARSS |
| 1637117_AXLC10 | SWR-----------TS | KRGVTS | NDN----ARSX |
| 1637110_AXLC10 | RWP----------ILG | KRSTHA | NDN----ARSS |
| 1637111_AXLC01 | RWKKPKHDGGAKLTG | KPDVRS | NTRGSGHVRSS |
| 1637116_AXLF09 | RWK----------AAG | KRNANI | NDN----ARSS |
| 1637110_AXLA04 | RW----------SQVPG | TSDIHI | NDN----ARSS |
| 1637113_AXLF06 | RWQL-----------PG | KRAANV | NDN----ARSS |
| 1637113_AXLB01 | RWS----------QIDR | KSDVHI | NDN----ARSS |
| 1637119_AXLE11 | RWKVD-----------G | HRAVNV | NDN----ARNN |
| 1637112_AXLE11 | RWTLAGS----QFIG | DGSVHV | SKR---LETSS |
| 1637113_AXLB11 | SWRTKTE----TITG | TASVSS | SEY---EETSS |
| 1637113_AXLD11 | RWKIPG---------- | NRGITT | NDN----ARSS |
| 1637110_AXLH08 | RWAGSG---------- | NRGISA | NDN----ARSS |
| 1637110_AXLB04 | RWELSRG----TITG | KGAKRS | NDN----ARSS |
| 1637119_AXLF04 | RWR----------VAG | ARNTHS | NDN----ARSS |
| 1637119_AXLB04 | RWGE-----------LG | KRAANT | NDN----ARSS |
| 1637116_AXLB12 | PWTLGVE-ASGVITG | KPDVRS | YGGGKT---SS |
| 1637110_AXLE03 | RWS----------QPG | ARATRA | NDN----ARSS |
| 1637111_AXLF03 | TWEAPVR-ANSILIS | KPDVRS | KNYESS---SS |
| 1637110_AXLA05 | RWELPAG----TVNG | KGAKRG | NDN----ARSS |
| 1637113_AXLE08 | RWASQ--------ING | KRTIHV | NDN----ARSS |
| 1637111_AXLG02 | PWAAGIE-ANGEITG | KPDVRS | YGAGKT---SS |
| 1637111_AXLE01 | RWG----------VPG | HRATNI | NDN----ARSS |
| 1637113_AXLG12 | RWQA-----------LG | ARNAPA | NDN----ARSS |
| 1637113_AXLG07 | RWQQY--------ING | ARDAPT | NDN----ARSS |
| 1637110_AXLE06 | RWKGA-----------Q | ARGANV | NDN----ARSS |
| 1637116_AXLB10 | RWG---------QVIS | KSDIHT | NDN----ARSS |
| 1637110_AXLG07 | RWTVGGRAN-STIPG | TRDIHI | NDN----ARSS |
| 1637112_AXLG06 | SWRTKTE----TITG | AAATRS | IKYR---AASS |
| 1637116_AXLG05 | RWKG-----------DR | TSGVTG | NDN----ARSS |
| 1637119_AXLD01 | RW----------TGQR | KTTIHG | NDN----ARSS |
| 1637113_AXLE03 | SWRTKTE----TITG | NSGARS | TGYGVGQDASS |
| 1637112_AXLA11 | SWRTKTE----TITG | NSGARS | NGYGVGTLASS |
| 1637111_AXLD11 | SWGLPRG----TVNG | KGAKRV | NDN----ARSS |
| 1637117_AXLB08 | RWELPRG----EVTG | KGAKRG | NDN----ARSS |
| 1637119_AXLB01 | RWA----------QVLS | KXXVXX | NDN----ARSS |
| 1637118_AXLF10 | RWALPRG----TVVG | HRTATS | NDN----ARSS |
| 1637112_AXLA05 | SWRTKTE----TITG | ATGARV | TGYGVGTYSSS |
| 1637112_AXLD08 | SWRTKTE----TITG | ATAKRV | TGYGVGEYRSS |

Fig 30C

|  | BC | DE | FG |
|---|---|---|---|
| 1637117_AXLF06 | SWRTKTE----TITG | ATGIRV | TGYGVGTLSSS |
| 1637112_AXLB09 | SWRTKTE----TITG | ATGARV | TGYGVGTHASS |
| 1637113_AXLF09 | RWALPRS----EFTR | TSNIRG | NDN----ARSS |
| 1637113_AXLB03 | RWALPQS----TFTR | TTNIRG | NDN----ARSS |
| 1637112_AXLE07 | SWRTKTE----TITG | ATGARV | TGYGVGQAASS |
| 1637110_AXLE08 | RWALPRS----EFTR | TSNIRT | NDN----ARSS |
| 1637118_AXLC11 | SWAVPQS----PIVS | DTGASG | NDN----ARSS |
| 1637113_AXLH06 | SWRTKTE----TITG | NSAAHS | NGYGVGTLASS |
| 1637112_AXLH05 | SWRTKTE----TITG | NAGART | TGYGVGTFGSS |
| 1637117_AXLE11 | SWRLAES----KVVG | HTDTSS | NTVGKSAVASS |
| 1637117_AXLD09 | SWRTKTE----TITG | ATAIRV | TGYGVGESRSS |
| 1637112_AXLD02 | SWRTKTE----TITG | ATAKRV | TGYGVGEVRSS |
| 1637112_AXLC05 | SWRTKTE----TITG | NSGARV | NGYGVGTHASS |
| 1637112_AXLG05 | SWRTKTE----TITG | ASTVNT | YKVR----ATSS |
| 1637117_AXLG08 | SWRTKTE----TITG | ATNENS | NGRG----ATSS |
| 1637113_AXLE10 | RWKAP------QSD | KRSATI | NDN----ARSS |
| 1637113_AXLD05 | RWKLP------EGD | KRNAST | NDN----ARSS |
| 1637110_AXLD03 | RWALPRS----AFDR | TTNIRA | NDN----ARSS |
| 1637118_AXLA01 | SWRTKTE----TITG | ASNIHS | TGYGVGAVGSS |
| 1637113_AXLH09 | SWRTKTE----TITG | NSAAHS | TGYGVGAVGSS |
| 1637113_AXLC08 | RWELPAG----TVNG | KGAKRG | NDN----ARST |
| 1637112_AXLA10 | SWRTKTE----TITG | ASNIHS | TGYGVGTHGSS |
| 1637112_AXLH07 | SWRTKTE----TITG | NRNAHS | TGYGVGTLGSS |
| 1637117_AXLH09 | SWRVKXE----TITG | NRNAHX | TGYGVGTLGSS |
| 1637112_AXLA08 | SWRTKTE----TITG | ATGARV | TGYGVGASASS |
| 1637112_AXLF12 | SWRTKTE----TITG | AAAVHT | TGYGVGQVGSS |
| 1637117_AXLC11 | SWRTKTE----TITG | ATGARV | TGYGVGAVASS |
| 1637110_AXLG03 | RWALPRS----EFTR | TANIRG | NDN----ARSS |
| 1637112_AXLD03 | SWRTKTE----TITG | ASNIHS | NGYGVGTVSSS |
| 1637119_AXLA12 | RWALPRS----AFDR | TTSIRT | NDN----ARSS |
| 1637116_AXLE07 | RWALPQS----AFDR | TTAIRT | NDN----ARSS |
| 1637112_AXLA06 | SWRTKTE----TITG | NSAAHA | NGYGVGTLASS |
| 1637112_AXLE08 | SWRTKTE----TITG | NRNAHA | TGYGVGTFASS |
| 1637112_AXLF08 | SWRTKTE----TITG | ATNVHS | TKRGT----GSS |
| 1637112_AXLF11 | SWRTKTE----TITG | AASIHV | NGYGVGESRSS |
| 1637112_AXLE04 | SWRTKTE----TITG | NSAAHV | TGYGVGTDASS |
| 1637112_AXLG12 | SWRTKTE----TITG | TATISG | NGYGVGTVRSS |
| 1637112_AXLE03 | SWRTKTE----TITG | NSGAHS | IMYGVGEVRSS |
| 1637112_AXLC01 | SWRTKTE----TITG | NSNAHI | NGYGVGTVTSS |

Fig 30D

|  | BC | DE | FG |
|---|---|---|---|
| 1637110_AXLC11 | RWGPSQG-----TVTR | KRAIHT | NDN----ARSS |
| 1637118_AXLB01 | SWRTKTE-----TITG | ATNVHV | TGRGD---SSS |
| 1637113_AXLC12 | SWKKPKHNGGTGVTS | KPDVRS | NKRRN---SSS |
| 1637112_AXLB11 | SWRTKTE-----TITG | NRNAHT | NGYGVGTVSSS |
| 1637117_AXLE07 | SWRTKTE-----TITG | NRNAHA | TGYGVGTVASS |
| 1637113_AXLG03 | SWRRSGS-----EVTR | ARSITV | NDN----ARSS |
| 1637112_AXLD06 | SWRTKTE-----TITG | TPTASG | NDREK---ASS |
| 1637112_AXLB10 | SWLTKTE-----TITG | HAGAHI | NGFGNGEPTSS |
| 1637112_AXLF07 | SWRTKTE-----TITG | DPSKSG | KSGGR---ASS |
| 1637112_AXLA12 | SWRTKTE-----TITG | DADIHT | NEIGDSKYRSS |

Fig 30E

|  | BC | DE | FG |
|---|---|---|---|
| 1637110_AXLD03 | RWALPRS---AFDR | TTNIRA | NDNAR----SS |
| 1637111_AXLE06 | RWAVSPS---TVVG | KPDVRS | NVKGGSASASS |
| 1637111_AXLB09 | SWERSES---TVVG | KPDVRS | TVVGKSAHGSS |
| 1637116_AXLB12 | PWTLGVEASGVITG | KPDVRS | YGGGK---TSS |
| 1637112_AXLB09 | SWRTKTE---TITG | ATGARV | TGYGVGTHASS |
| 1637112_AXLG12 | SWRTKTE---TITG | TATISG | NGYGVGTVRSS |
| 1637117_AXLE11 | SWRLAES---KVVG | HTDTSS | NTVGKSAVASS |

Fig 30F

SEQUENCE LISTING

<160> NUMBER OF SEQ ID NOS: 498

<210> SEQ ID NO 1
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 1

Ser Gly Pro Val Glu Val Phe Ile Thr Glu Thr Pro Ser Gln Pro Asn
1               5                   10                  15

Ser His Pro Ile Gln Trp Asn Ala Pro Gln Pro Ser His Ile Ser Lys
            20                  25                  30

Tyr Ile Leu Arg Trp Arg Pro Lys Asn Ser Val Gly Arg Trp Lys Glu
        35                  40                  45

Ala Thr Ile Pro Gly His Leu Asn Ser Tyr Thr Ile Lys Gly Leu Lys
    50                  55                  60

Pro Gly Val Val Tyr Glu Gly Gln Leu Ile Ser Ile Gln Gln Tyr Gly
65                  70                  75                  80

His Gln Glu Val Thr Arg Phe Asp Phe Thr Thr Thr
                85                  90

<210> SEQ ID NO 2
<211> LENGTH: 91
<212> TYPE: PRT
<213> ORGANISM: Artificial Sequence
<220> FEATURE:
<223> OTHER INFORMATION: Synthetic polypeptide

<400> SEQUENCE: 2

Ser Pro Leu Val Ala Thr Ser Glu Ser Val Thr Glu Ile Thr Ala Ser
1               5                   10                  15

Ser Phe Val Val Ser Trp Val Ser Ala Ser Asp Thr Val Ser Gly Phe
            20                  25                  30

Arg Val Glu Tyr Glu Leu Ser Glu Glu Gly Asp Glu Pro Gln Tyr Leu
        35                  40                  45

Asp Leu Pro Ser Thr Ala Thr Ser Val Asn Ile Pro Asp Leu Leu Pro

```
                    50                  55                  60

Gly Arg Lys Tyr Ile Val Asn Val Tyr Gln Ile Ser Glu Asp Gly Glu
 65                  70                  75                  80

Gln Ser Leu Ile Leu Ser Thr Ser Gln Thr Thr
                 85                  90
```

<210> SEQ ID NO 3
<211> LENGTH: 94
<212> TYPE: PRT
<213> ORGANISM: Artificial Sequence
<220> FEATURE:
<223> OTHER INFORMATION: Synthetic polypeptide

<400> SEQUENCE: 3

```
Ala Pro Asp Ala Pro Pro Asp Pro Thr Val Asp Gln Val Asp Thr
  1               5                  10                  15

Ser Ile Val Val Arg Trp Ser Arg Pro Gln Ala Pro Ile Thr Gly Tyr
                 20                  25                  30

Arg Ile Val Tyr Ser Pro Ser Val Glu Gly Ser Ser Thr Glu Leu Asn
             35                  40                  45

Leu Pro Glu Thr Ala Asn Ser Val Thr Leu Ser Asp Leu Gln Pro Gly
         50                  55                  60

Val Gln Tyr Asn Ile Thr Ile Tyr Ala Val Glu Glu Asn Gln Glu Ser
 65                  70                  75                  80

Thr Pro Val Val Ile Gln Gln Glu Thr Thr Gly Thr Pro Arg
                 85                  90
```

<210> SEQ ID NO 4
<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 4

```
Thr Val Pro Ser Pro Arg Asp Leu Gln Phe Val Glu Val Thr Asp Val
  1               5                  10                  15

Lys Val Thr Ile Met Trp Thr Pro Pro Glu Ser Ala Val Thr Gly Tyr
                 20                  25                  30

Arg Val Asp Val Ile Pro Val Asn Leu Pro Gly Glu His Gly Gln Arg
             35                  40                  45

Leu Pro Ile Ser Arg Asn Thr Phe Ala Glu Val Thr Gly Leu Ser Pro
         50                  55                  60

Gly Val Thr Tyr Tyr Phe Lys Val Phe Ala Val Ser His Gly Arg Glu
 65                  70                  75                  80

Ser Lys Pro Leu Thr Ala Gln Gln Thr Thr
                 85                  90
```

<210> SEQ ID NO 5
<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 5

```
Lys Leu Asp Ala Pro Thr Asn Leu Gln Phe Val Asn Glu Thr Asp Ser
  1               5                  10                  15

Thr Val Leu Val Arg Trp Thr Pro Pro Arg Ala Gln Ile Thr Gly Tyr
                 20                  25                  30
```

-continued

Arg Leu Thr Val Gly Leu Thr Arg Arg Gly Gln Pro Arg Gln Tyr Asn
                35                  40                  45

Val Gly Pro Ser Val Ser Lys Tyr Pro Leu Arg Asn Leu Gln Pro Ala
 50                  55                  60

Ser Glu Tyr Thr Val Ser Leu Val Ala Ile Lys Gly Asn Gln Glu Ser
 65                  70                  75                  80

Pro Lys Ala Thr Gly Val Phe Thr Thr Leu
                85                  90

<210> SEQ ID NO 6
<211> LENGTH: 87
<212> TYPE: PRT
<213> ORGANISM: Artificial Sequence
<220> FEATURE:
<223> OTHER INFORMATION: Synthetic polypeptide

<400> SEQUENCE: 6

Gln Pro Gly Ser Ser Ile Pro Pro Tyr Asn Thr Glu Val Thr Glu Thr
 1                   5                  10                  15

Thr Ile Val Ile Thr Trp Thr Pro Ala Pro Arg Ile Gly Phe Lys Leu
                20                  25                  30

Gly Val Arg Pro Ser Gln Gly Gly Glu Ala Pro Arg Glu Val Thr Ser
                35                  40                  45

Asp Ser Gly Ser Ile Val Val Ser Gly Leu Thr Pro Gly Val Glu Tyr
 50                  55                  60

Val Tyr Thr Ile Gln Val Leu Arg Asp Gly Gln Glu Arg Asp Ala Pro
 65                  70                  75                  80

Ile Val Asn Lys Val Val Thr
                85

<210> SEQ ID NO 7
<211> LENGTH: 93
<212> TYPE: PRT
<213> ORGANISM: Artificial Sequence
<220> FEATURE:
<223> OTHER INFORMATION: Synthetic polypeptide

<400> SEQUENCE: 7

Pro Leu Ser Pro Thr Asn Leu His Leu Glu Ala Asn Pro Asp Thr
 1                   5                  10                  15

Gly Val Leu Thr Val Ser Trp Glu Arg Ser Thr Thr Pro Asp Ile Thr
                20                  25                  30

Gly Tyr Arg Ile Thr Thr Thr Pro Thr Asn Gly Gln Gln Gly Asn Ser
                35                  40                  45

Leu Glu Glu Val Val His Ala Asp Gln Ser Ser Cys Thr Phe Asp Asn
 50                  55                  60

Leu Ser Pro Gly Leu Glu Tyr Asn Val Ser Val Tyr Thr Val Lys Asp
 65                  70                  75                  80

Asp Lys Glu Ser Val Pro Ile Ser Asp Thr Ile Ile Pro
                85                  90

<210> SEQ ID NO 8
<211> LENGTH: 91
<212> TYPE: PRT
<213> ORGANISM: Artificial Sequence
<220> FEATURE:
<223> OTHER INFORMATION: Synthetic polypeptide

<400> SEQUENCE: 8

```
Ala Val Pro Pro Thr Asp Leu Arg Phe Thr Asn Ile Gly Pro Asp
 1               5                  10                  15

Thr Met Arg Val Thr Trp Ala Pro Pro Ser Ile Asp Leu Thr Asn
                20                  25                  30

Phe Leu Val Arg Tyr Ser Pro Val Lys Asn Glu Glu Asp Val Ala Glu
            35                  40                  45

Leu Ser Ile Ser Pro Ser Asp Asn Ala Val Val Leu Thr Asn Leu Leu
 50                  55                  60

Pro Gly Thr Glu Tyr Val Val Ser Val Ser Ser Val Tyr Glu Gln His
 65                  70                  75                  80

Glu Ser Thr Pro Leu Arg Gly Arg Gln Lys Thr
                85                  90
```

<210> SEQ ID NO 9
<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 9

```
Gly Leu Asp Ser Pro Thr Gly Ile Asp Phe Ser Asp Ile Thr Ala Asn
 1               5                  10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
            35                  40                  45

Arg Val Pro His Ser Arg Asn Ser Ile Thr Leu Thr Asn Leu Thr Pro
 50                  55                  60

Gly Thr Glu Tyr Val Val Ser Ile Val Ala Leu Asn Gly Arg Glu Glu
 65                  70                  75                  80

Ser Pro Leu Leu Ile Gly Gln Gln Ser Thr
                85                  90
```

<210> SEQ ID NO 10
<211> LENGTH: 94
<212> TYPE: PRT
<213> ORGANISM: Artificial Sequence
<220> FEATURE:
<223> OTHER INFORMATION: Synthetic polypeptide

<400> SEQUENCE: 10

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr
                85                  90
```

<210> SEQ ID NO 11
<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 11

Glu Ile Asp Lys Pro Ser Gln Met Gln Val Thr Asp Val Gln Asp Asn
1               5                   10                  15

Ser Ile Ser Val Lys Trp Leu Pro Ser Ser Pro Val Thr Gly Tyr
            20                  25                  30

Arg Val Thr Thr Thr Pro Lys Asn Gly Pro Gly Pro Thr Lys Thr Lys
            35                  40                  45

Thr Ala Gly Pro Asp Gln Thr Glu Met Thr Ile Glu Gly Leu Gln Pro
    50                  55                  60

Thr Val Glu Tyr Val Val Ser Val Tyr Ala Gln Asn Pro Ser Gly Glu
65                  70                  75                  80

Ser Gln Pro Leu Val Gln Thr Ala Val Thr
                85                  90

<210> SEQ ID NO 12
<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 12

Asn Ile Asp Arg Pro Lys Gly Leu Ala Phe Thr Asp Val Asp Val Asp
1               5                   10                  15

Ser Ile Lys Ile Ala Trp Glu Ser Pro Gln Gly Gln Val Ser Arg Tyr
            20                  25                  30

Arg Val Thr Tyr Ser Ser Pro Glu Asp Gly Ile His Glu Leu Phe Pro
            35                  40                  45

Ala Pro Asp Gly Glu Glu Asp Thr Ala Glu Leu Gln Gly Leu Arg Pro
    50                  55                  60

Gly Ser Glu Tyr Thr Val Ser Val Val Ala Leu His Asp Asp Met Glu
65                  70                  75                  80

Ser Gln Pro Leu Ile Gly Thr Gln Ser Thr
                85                  90

<210> SEQ ID NO 13
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 13

Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
            35                  40                  45

Asn Leu Ala Pro Asp Ser Ser Ser Val Val Val Ser Gly Leu Met Val
    50                  55                  60

Ala Thr Lys Tyr Glu Val Ser Val Tyr Ala Leu Lys Asp Thr Leu Thr
65                  70                  75                  80

Ser Arg Pro Ala Gln Gly Val Val Thr Thr Leu Glu
                85                  90

<210> SEQ ID NO 14
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 14

```
Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85
```

<210> SEQ ID NO 15
<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 15

```
Ala Ile Asp Ala Pro Ser Asn Leu Arg Phe Leu Ala Thr Thr Pro Asn
 1               5                  10                  15

Ser Leu Leu Val Ser Trp Gln Pro Pro Arg Ala Arg Ile Thr Gly Tyr
            20                  25                  30

Ile Ile Lys Tyr Glu Lys Pro Gly Ser Pro Pro Arg Glu Val Val Pro
        35                  40                  45

Arg Pro Arg Pro Gly Val Thr Glu Ala Thr Ile Thr Gly Leu Glu Pro
    50                  55                  60

Gly Thr Glu Tyr Thr Ile Tyr Val Ile Ala Leu Lys Asn Asn Gln Lys
65                  70                  75                  80

Ser Glu Pro Leu Ile Gly Arg Lys Lys Thr
                85                  90
```

<210> SEQ ID NO 16
<211> LENGTH: 88
<212> TYPE: PRT
<213> ORGANISM: Artificial Sequence
<220> FEATURE:
<223> OTHER INFORMATION: Synthetic polypeptide

<400> SEQUENCE: 16

```
Pro Gly Leu Asn Pro Asn Ala Ser Thr Gly Gln Glu Ala Leu Ser Gln
 1               5                  10                  15

Thr Thr Ile Ser Trp Ala Pro Phe Gln Asp Thr Ser Glu Tyr Ile Ile
            20                  25                  30

Ser Cys His Pro Val Gly Thr Asp Glu Glu Pro Leu Gln Phe Arg Val
        35                  40                  45

Pro Gly Thr Ser Thr Ser Ala Thr Leu Thr Gly Leu Thr Arg Gly Ala
    50                  55                  60

Thr Tyr Asn Ile Ile Val Glu Ala Leu Lys Asp Gln Gln Arg His Lys
```

```
                65                  70                  75                  80
Val Arg Glu Glu Val Val Thr Val
                85

<210> SEQ ID NO 17
<211> LENGTH: 14
<212> TYPE: PRT
<213> ORGANISM: Artificial Sequence
<220> FEATURE:
<223> OTHER INFORMATION: Synthetic peptide

<400> SEQUENCE: 17

Val Ser Asp Val Pro Arg Asp Leu Glu Val Val Ala Ala Thr
1               5                   10

<210> SEQ ID NO 18
<211> LENGTH: 2
<212> TYPE: PRT
<213> ORGANISM: Artificial Sequence
<220> FEATURE:
<223> OTHER INFORMATION: Synthetic peptide

<400> SEQUENCE: 18

Pro Thr
1

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide

<400> SEQUENCE: 19

Ser Leu Leu Ile
1

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

<400> SEQUENCE: 20

Tyr Arg Ile Thr Tyr Gly Glu Thr
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide

<400> SEQUENCE: 21

Gly Gly Asn Ser Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22
```

```
Val Gln Glu Phe Thr Val
 1               5

<210> SEQ ID NO 23
<211> LENGTH: 3
<212> TYPE: PRT
<213> ORGANISM: Artificial Sequence
<220> FEATURE:
<223> OTHER INFORMATION: Synthetic peptide

<400> SEQUENCE: 23

Ala Thr Ile
 1

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Ser Gly Leu Lys Pro Gly Val Asp
 1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

Tyr Thr Ile Thr Val Tyr Ala Val
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26

Pro Ile Ser Ile Asn Tyr Arg Thr
 1               5

<210> SEQ ID NO 27
<211> LENGTH: 14
<212> TYPE: PRT
<213> ORGANISM: Artificial Sequence
<220> FEATURE:
<223> OTHER INFORMATION: Synthetic peptide

<400> SEQUENCE: 27

Asn Val Ser Pro Pro Arg Arg Ala Arg Val Thr Asp Ala Thr
 1               5                   10

<210> SEQ ID NO 28
<211> LENGTH: 2
<212> TYPE: PRT
<213> ORGANISM: Artificial Sequence
<220> FEATURE:
<223> OTHER INFORMATION: Synthetic peptide

<400> SEQUENCE: 28
```

Glu Thr
1

<210> SEQ ID NO 29
<211> LENGTH: 4
<212> TYPE: PRT
<213> ORGANISM: Artificial Sequence
<220> FEATURE:
<223> OTHER INFORMATION: Synthetic peptide

<400> SEQUENCE: 29

Thr Ile Thr Ile
1

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide

<400> SEQUENCE: 30

Phe Gln Val Asp Ala Val Pro Ala
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide

<400> SEQUENCE: 31

Asn Gly Gln Thr Pro
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic peptide

<400> SEQUENCE: 32

Ile Gln Arg Thr Ile
1               5

<210> SEQ ID NO 33
<211> LENGTH: 3
<212> TYPE: PRT
<213> ORGANISM: Artificial Sequence
<220> FEATURE:
<223> OTHER INFORMATION: Synthetic peptide

<400> SEQUENCE: 33

Tyr Thr Ile
1

<210> SEQ ID NO 34
<211> LENGTH: 8
<212> TYPE: PRT
<213> ORGANISM: Artificial Sequence
<220> FEATURE:
<223> OTHER INFORMATION: Synthetic peptide

<400> SEQUENCE: 34

Thr Gly Leu Gln Pro Gly Thr Asp

```
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic peptide

<400> SEQUENCE: 35

Tyr Lys Ile Tyr Leu Tyr Thr Leu
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Pro Val Val Ile Asp Ala Ser Thr
1               5

<210> SEQ ID NO 37
<211> LENGTH: 11
<212> TYPE: PRT
<213> ORGANISM: Artificial Sequence
<220> FEATURE:
<223> OTHER INFORMATION: Synthetic peptide

<400> SEQUENCE: 37

Ser Trp Thr Pro Pro Gly Pro Val Asp Gly
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic peptide

<400> SEQUENCE: 38

Ser Trp Lys Pro Pro Asp Asp Pro Asn Gly Pro Ile Thr Gly
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Synthetic peptide

<400> SEQUENCE: 39

Ser Trp Glu Pro Pro Glu Asp Asp Gly Gly Ser Pro Ile Thr Gly
1               5                   10                  15

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide

<400> SEQUENCE: 40

Pro Gly Thr Glu Thr Ser
1               5
```

<210> SEQ ID NO 41
<211> LENGTH: 8
<212> TYPE: PRT
<213> ORGANISM: Artificial Sequence
<220> FEATURE:
<223> OTHER INFORMATION: Synthetic peptide

<400> SEQUENCE: 41

Asn Gly Gly Gly Glu Ser Ser Lys
 1               5

<210> SEQ ID NO 42
<211> LENGTH: 11
<212> TYPE: PRT
<213> ORGANISM: Artificial Sequence
<220> FEATURE:
<223> OTHER INFORMATION: Synthetic peptide

<400> SEQUENCE: 42

Asn Ala Ala Gly Val Gly Pro Pro Ser Ser Ser
 1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(1)
<223> OTHER INFORMATION: Xaa = R, N, K, S
<220> FEATURE:
<221> NAME/KEY: VARIANT
<222> LOCATION: (3)...(3)
<223> OTHER INFORMATION: Xaa = T, K
<220> FEATURE:
<221> NAME/KEY: VARIANT
<222> LOCATION: (4)...(4)
<223> OTHER INFORMATION: Xaa = T, Q, K, P
<220> FEATURE:
<221> NAME/KEY: VARIANT
<222> LOCATION: (6)...(6)
<223> OTHER INFORMATION: Xaa = T, Q, K, P
<220> FEATURE:
<221> NAME/KEY: VARIANT
<222> LOCATION: (7)...(7)
<223> OTHER INFORMATION: Xaa = R, E, K, G
<220> FEATURE:
<221> NAME/KEY: VARIANT
<222> LOCATION: (8)...(8)
<223> OTHER INFORMATION: Xaa = T, Q, K, P
<220> FEATURE:
<221> NAME/KEY: VARIANT
<222> LOCATION: (9)...(9)
<223> OTHER INFORMATION: Xaa = E, N, D, M
<220> FEATURE:
<221> NAME/KEY: VARIANT
<222> LOCATION: (10)...(10)
<223> OTHER INFORMATION: Xaa = E, N, K, D
<220> FEATURE:
<221> NAME/KEY: VARIANT
<222> LOCATION: (11)...(11)
<223> OTHER INFORMATION: Xaa = R, E, K, G

<400> SEQUENCE: 43

Xaa Trp Xaa Xaa Pro Xaa Xaa Xaa Xaa Xaa Xaa
 1               5                   10

<210> SEQ ID NO 44
<211> LENGTH: 14

```
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(1)
<223> OTHER INFORMATION: Xaa = R, N, K, S
<220> FEATURE:
<221> NAME/KEY: VARIANT
<222> LOCATION: (3)...(3)
<223> OTHER INFORMATION: Xaa = Q, K, E, P T, A
<220> FEATURE:
<221> NAME/KEY: VARIANT
<222> LOCATION: (4)...(4)
<223> OTHER INFORMATION: Xaa = T, Q, K, P
<220> FEATURE:
<221> NAME/KEY: VARIANT
<222> LOCATION: (6)...(6)
<223> OTHER INFORMATION: Xaa = E, N, K, D
<220> FEATURE:
<221> NAME/KEY: VARIANT
<222> LOCATION: (7)...(7)
<223> OTHER INFORMATION: Xaa = E, N, K, D
<220> FEATURE:
<221> NAME/KEY: VARIANT
<222> LOCATION: (8)...(8)
<223> OTHER INFORMATION: Xaa = T, Q, K, P
<220> FEATURE:
<221> NAME/KEY: VARIANT
<222> LOCATION: (9)...(9)
<223> OTHER INFORMATION: Xaa = N, K
<220> FEATURE:
<221> NAME/KEY: VARIANT
<222> LOCATION: (10)...(10)
<223> OTHER INFORMATION: Xaa = R, E, K, G
<220> FEATURE:
<221> NAME/KEY: VARIANT
<222> LOCATION: (11)...(11)
<223> OTHER INFORMATION: Xaa = T, K, Q, P
<220> FEATURE:
<221> NAME/KEY: VARIANT
<222> LOCATION: (13)...(13)
<223> OTHER INFORMATION: Xaa = K, T
<220> FEATURE:
<221> NAME/KEY: VARIANT
<222> LOCATION: (14)...(14)
<223> OTHER INFORMATION: Xaa = R, E, K, G

<400> SEQUENCE: 44

Xaa Trp Xaa Xaa Pro Xaa Xaa Xaa Xaa Xaa Xaa Ile Xaa Xaa
 1               5                   10

<210> SEQ ID NO 45
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(1)
<223> OTHER INFORMATION: Xaa = R, N, K, S
<220> FEATURE:
<221> NAME/KEY: VARIANT
<222> LOCATION: (3)...(3)
<223> OTHER INFORMATION: Xaa = E, K
<220> FEATURE:
<221> NAME/KEY: VARIANT
<222> LOCATION: (4)...(4)
<223> OTHER INFORMATION: Xaa = T, K, Q, P
<220> FEATURE:
<221> NAME/KEY: VARIANT
<222> LOCATION: (6)...(6)
<223> OTHER INFORMATION: Xaa = E, K
<220> FEATURE:
<221> NAME/KEY: VARIANT
```

```
<222> LOCATION: (7)...(7)
<223> OTHER INFORMATION: Xaa = E, N, K, D
<220> FEATURE:
<221> NAME/KEY: VARIANT
<222> LOCATION: (11)...(11)
<223> OTHER INFORMATION: Xaa = R, N, K, S
<220> FEATURE:
<221> NAME/KEY: VARIANT
<222> LOCATION: (12)...(12)
<223> OTHER INFORMATION: Xaa = T, K, Q, P
<220> FEATURE:
<221> NAME/KEY: VARIANT
<222> LOCATION: (14)...(14)
<223> OTHER INFORMATION: Xaa = K, T
<220> FEATURE:
<221> NAME/KEY: VARIANT
<222> LOCATION: (15)...(15)
<223> OTHER INFORMATION: Xaa = R, E, K, G

<400> SEQUENCE: 45

Xaa Trp Xaa Xaa Pro Xaa Xaa Asp Gly Gly Xaa Xaa Ile Xaa Xaa
 1               5                  10                  15

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide
      220>
<221> NAME/KEY: VARIANT
<222> LOCATION: (1)...(1)
<223> OTHER INFORMATION: Xaa = T, K, Q, P
<220> FEATURE:
<221> NAME/KEY: VARIANT
<222> LOCATION: (2)...(2)
<223> OTHER INFORMATION: Xaa = R, E, K, G
<220> FEATURE:
<221> NAME/KEY: VARIANT
<222> LOCATION: (3)...(3)
<223> OTHER INFORMATION: Xaa = T. K
<220> FEATURE:
<221> NAME/KEY: VARIANT
<222> LOCATION: (4)...(4)
<223> OTHER INFORMATION: Xaa = E, K
<220> FEATURE:
<221> NAME/KEY: VARIANT
<222> LOCATION: (5)...(5)
<223> OTHER INFORMATION: Xaa = T, K

<400> SEQUENCE: 46

Xaa Xaa Xaa Xaa Xaa
 1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic peptide
      220>
<221> NAME/KEY: VARIANT
<222> LOCATION: (1)...(1)
<223> OTHER INFORMATION: Xaa = N, K
<220> FEATURE:
<221> NAME/KEY: VARIANT
<222> LOCATION: (2)...(2)
<223> OTHER INFORMATION: Xaa = R, E, K, G
<220> FEATURE:
<221> NAME/KEY: VARIANT
<222> LOCATION: (3)...(3)
<223> OTHER INFORMATION: Xaa = R, E, K, G
<220> FEATURE:
<221> NAME/KEY: VARIANT
<222> LOCATION: (4)...(4)
```

```
<223> OTHER INFORMATION: Xaa = R, E, K, G
<220> FEATURE:
<221> NAME/KEY: VARIANT
<222> LOCATION: (5)...(5)
<223> OTHER INFORMATION: Xaa = E, K

<400> SEQUENCE: 47

Xaa Xaa Xaa Xaa Xaa Ser
 1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide
      220>
<221> NAME/KEY: VARIANT
<222> LOCATION: (2)...(2)
<223> OTHER INFORMATION: Xaa = A, T, E, K
<220> FEATURE:
<221> NAME/KEY: VARIANT
<222> LOCATION: (3)...(3)
<223> OTHER INFORMATION: Xaa = A, T
<220> FEATURE:
<221> NAME/KEY: VARIANT
<222> LOCATION: (5)...(5)
<223> OTHER INFORMATION: Xaa = E, K, V, M
<220> FEATURE:
<221> NAME/KEY: VARIANT
<222> LOCATION: (6)...(6)
<223> OTHER INFORMATION: Xaa = G, S
<220> FEATURE:
<221> NAME/KEY: VARIANT
<222> LOCATION: (7)...(7)
<223> OTHER INFORMATION: Xaa = T, K, Q, P
<220> FEATURE:
<221> NAME/KEY: VARIANT
<222> LOCATION: (8)...(8)
<223> OTHER INFORMATION: Xaa = T, K, Q, P

<400> SEQUENCE: 48

Asn Xaa Xaa Gly Xaa Xaa Xaa Xaa Ser
 1               5

<210> SEQ ID NO 49
<211> LENGTH: 11
<212> TYPE: PRT
<213> ORGANISM: Artificial Sequence
<220> FEATURE:
<223> OTHER INFORMATION: Synthetic peptide
      220>
<221> NAME/KEY: VARIANT
<222> LOCATION: (1)...(1)
<223> OTHER INFORMATION: Xaa = S, T, R, P
<220> FEATURE:
<221> NAME/KEY: VARIANT
<222> LOCATION: (3)...(3)
<223> OTHER INFORMATION: Xaa = T, K, R, A, E, G
<220> FEATURE:
<221> NAME/KEY: VARIANT
<222> LOCATION: (4)...(4)
<223> OTHER INFORMATION: Xaa = P, A, V, L, R, G
<220> FEATURE:
<221> NAME/KEY: VARIANT
<222> LOCATION: (5)...(5)
<223> OTHER INFORMATION: Xaa = P, A, S
<220> FEATURE:
<221> NAME/KEY: VARIANT
<222> LOCATION: (6)...(6)
<223> OTHER INFORMATION: Xaa = P, E, Q, R, A, G
<220> FEATURE:
<221> NAME/KEY: VARIANT
<222> LOCATION: (7)...(7)
<223> OTHER INFORMATION: Xaa = G, S
```

```
<220> FEATURE:
<221> NAME/KEY: VARIANT
<222> LOCATION: (8)...(8)
<223> OTHER INFORMATION: Xaa = P, E, Q, A, T, K
<220> FEATURE:
<221> NAME/KEY: VARIANT
<222> LOCATION: (9)...(9)
<223> OTHER INFORMATION: Xaa = F, I, V
<220> FEATURE:
<221> NAME/KEY: VARIANT
<222> LOCATION: (10)...(10)
<223> OTHER INFORMATION: Xaa = T, I, N, V, A, D
<220> FEATURE:
<221> NAME/KEY: VARIANT
<222> LOCATION: (11)...(11)
<223> OTHER INFORMATION: Xaa = G, S, R

<400> SEQUENCE: 49

Xaa Trp Xaa Xaa Xaa Xaa Xaa Xaa Xaa Xaa Xaa
 1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic peptide
      220>
<221> NAME/KEY: VARIANT
<222> LOCATION: (1)...(1)
<223> OTHER INFORMATION: Xaa = S, T, R, P
<220> FEATURE:
<221> NAME/KEY: VARIANT
<222> LOCATION: (3)...(3)
<223> OTHER INFORMATION: Xaa = Q, K, E, P, T, A
<220> FEATURE:
<221> NAME/KEY: VARIANT
<222> LOCATION: (4)...(4)
<223> OTHER INFORMATION: Xaa = P, E, A, Q
<220> FEATURE:
<221> NAME/KEY: VARIANT
<222> LOCATION: (5)...(5)
<223> OTHER INFORMATION: Xaa = P, G
<220> FEATURE:
<221> NAME/KEY: VARIANT
<222> LOCATION: (6)...(6)
<223> OTHER INFORMATION: Xaa = T, K, R, A, E, G
<220> FEATURE:
<221> NAME/KEY: VARIANT
<222> LOCATION: (7)...(7)
<223> OTHER INFORMATION: Xaa = D, E, K, N
<220> FEATURE:
<221> NAME/KEY: VARIANT
<222> LOCATION: (8)...(8)
<223> OTHER INFORMATION: Xaa = P, T, A, R, S, G
<220> FEATURE:
<221> NAME/KEY: VARIANT
<222> LOCATION: (9)...(9)
<223> OTHER INFORMATION: Xaa = N, G, S, D
<220> FEATURE:
<221> NAME/KEY: VARIANT
<222> LOCATION: (10)...(10)
<223> OTHER INFORMATION: Xaa = G, S, A, T
<220> FEATURE:
<221> NAME/KEY: VARIANT
<222> LOCATION: (11)...(11)
<223> OTHER INFORMATION: Xaa = P, T, A, L, I, V
<220> FEATURE:
<221> NAME/KEY: VARIANT
<222> LOCATION: (12)...(12)
<223> OTHER INFORMATION: Xaa = I, V, L
<220> FEATURE:
<221> NAME/KEY: VARIANT
<222> LOCATION: (13)...(13)
<223> OTHER INFORMATION: Xaa = T, L, P, I
<220> FEATURE:
<221> NAME/KEY: VARIANT
```

```
<222> LOCATION: (14)...(14)
<223> OTHER INFORMATION: Xaa = G, S, H, R, N, D

<400> SEQUENCE: 50

Xaa Trp Xaa Xaa Xaa Xaa Xaa Xaa Xaa Xaa Xaa Xaa Xaa Xaa
 1               5                  10

<210> SEQ ID NO 51
<211> LENGTH: 15
<212> TYPE: PRT
<213> ORGANISM: Artificial Sequence
<220> FEATURE:
<223> OTHER INFORMATION: Synthetic peptide
      220>
<221> NAME/KEY: VARIANT
<222> LOCATION: (1)...(1)
<223> OTHER INFORMATION: Xaa = S, T, R, P
<220> FEATURE:
<221> NAME/KEY: VARIANT
<222> LOCATION: (3)...(3)
<223> OTHER INFORMATION: Xaa = Q, K, E, P, T, A
<220> FEATURE:
<221> NAME/KEY: VARIANT
<222> LOCATION: (4)...(4)
<223> OTHER INFORMATION: Xaa = P, E, A, Q
<220> FEATURE:
<221> NAME/KEY: VARIANT
<222> LOCATION: (6)...(6)
<223> OTHER INFORMATION: Xaa = Q, K, E, L, I, V,
<220> FEATURE:
<221> NAME/KEY: VARIANT
<222> LOCATION: (7)...(7)
<223> OTHER INFORMATION: Xaa = Y, N, D, S, T, A
<220> FEATURE:
<221> NAME/KEY: VARIANT
<222> LOCATION: (8)...(8)
<223> OTHER INFORMATION: Xaa = D, N,, S, G
<220> FEATURE:
<221> NAME/KEY: VARIANT
<222> LOCATION: (10)...(10)
<223> OTHER INFORMATION: Xaa = G, N
<220> FEATURE:
<221> NAME/KEY: VARIANT
<222> LOCATION: (11)...(11)
<223> OTHER INFORMATION: Xaa = S, R, G, P, T, A
<220> FEATURE:
<221> NAME/KEY: VARIANT
<222> LOCATION: (12)...(12)
<223> OTHER INFORMATION: Xaa = P, Q, A, E
<220> FEATURE:
<221> NAME/KEY: VARIANT
<222> LOCATION: (13)...(13)
<223> OTHER INFORMATION: Xaa = I, V, L
<220> FEATURE:
<221> NAME/KEY: VARIANT
<222> LOCATION: (14)...(14)
<223> OTHER INFORMATION: Xaa = I, T, L, P
<220> FEATURE:
<221> NAME/KEY: VARIANT
<222> LOCATION: (15)...(15)
<223> OTHER INFORMATION: Xaa = G, N, S, D

<400> SEQUENCE: 51

Xaa Trp Xaa Xaa Pro Xaa Xaa Xaa Gly Xaa Xaa Xaa Xaa Xaa Xaa
 1               5                  10                  15

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide
      220>
<221> NAME/KEY: VARIANT
<222> LOCATION: (1)...(1)
```

<223> OTHER INFORMATION: Xaa = P, T, A, H, N, D, Q, K, E
<220> FEATURE:
<221> NAME/KEY: VARIANT
<222> LOCATION: (2)...(2)
<223> OTHER INFORMATION: Xaa = G, P, A, S, R, T
<220> FEATURE:
<221> NAME/KEY: VARIANT
<222> LOCATION: (3)...(3)
<223> OTHER INFORMATION: Xaa = T. D, S, N, G, A
<220> FEATURE:
<221> NAME/KEY: VARIANT
<222> LOCATION: (4)...(4)
<223> OTHER INFORMATION: Xaa = E, K, T, A, V, I
<220> FEATURE:
<221> NAME/KEY: VARIANT
<222> LOCATION: (5)...(5)
<223> OTHER INFORMATION: Xaa = T, R, N, S, H, P
<220> FEATURE:
<221> NAME/KEY: VARIANT
<222> LOCATION: (6)...(6)
<223> OTHER INFORMATION: Xaa = S, T, I, V, A, G

<400> SEQUENCE: 52

Xaa Xaa Xaa Xaa Xaa Xaa
 1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic peptide
      220>
<221> NAME/KEY: VARIANT
<222> LOCATION: (1)...(1)
<223> OTHER INFORMATION: Xaa = N, K, S, R
<220> FEATURE:
<221> NAME/KEY: VARIANT
<222> LOCATION: (2)...(2)
<223> OTHER INFORMATION: Xaa = N, S, D, G, R, K, E
<220> FEATURE:
<221> NAME/KEY: VARIANT
<222> LOCATION: (3)...(3)
<223> OTHER INFORMATION: Xaa = N, S, D, G, R, K, E
<220> FEATURE:
<221> NAME/KEY: VARIANT
<222> LOCATION: (4)...(4)
<223> OTHER INFORMATION: Xaa = G, Q, R, E
<220> FEATURE:
<221> NAME/KEY: VARIANT
<222> LOCATION: (5)...(5)
<223> OTHER INFORMATION: Xaa = E, K, Q, P, T, A
<220> FEATURE:
<221> NAME/KEY: VARIANT
<222> LOCATION: (6)...(6)
<223> OTHER INFORMATION: Xaa = S, T

<400> SEQUENCE: 53

Xaa Xaa Xaa Xaa Xaa Xaa Ser Lys
 1               5

<210> SEQ ID NO 54
<211> LENGTH: 11
<212> TYPE: PRT
<213> ORGANISM: Artificial Sequence
<220> FEATURE:
<223> OTHER INFORMATION: Synthetic peptide
      220>
<221> NAME/KEY: VARIANT
<222> LOCATION: (1)...(1)
<223> OTHER INFORMATION: Xaa = N, T
<220> FEATURE:
<221> NAME/KEY: VARIANT
<222> LOCATION: (2)...(2)
<223> OTHER INFORMATION: Xaa = T, A, I, V, K, E, N, D

```
<220> FEATURE:
<221> NAME/KEY: VARIANT
<222> LOCATION: (3)...(3)
<223> OTHER INFORMATION: Xaa = T, A, I, V, K, E, N, D
<220> FEATURE:
<221> NAME/KEY: VARIANT
<222> LOCATION: (5)...(5)
<223> OTHER INFORMATION: Xaa = T, A, I, V, K, E, N, D
<220> FEATURE:
<221> NAME/KEY: VARIANT
<222> LOCATION: (6)...(6)
<223> OTHER INFORMATION: Xaa = G, S
<220> FEATURE:
<221> NAME/KEY: VARIANT
<222> LOCATION: (7)...(7)
<223> OTHER INFORMATION: Xaa = P, E, K, A, Q, T
<220> FEATURE:
<221> NAME/KEY: VARIANT
<222> LOCATION: (8)...(8)
<223> OTHER INFORMATION: Xaa = P, F, V, S, L, A
<220> FEATURE:
<221> NAME/KEY: VARIANT
<222> LOCATION: (9)...(9)
<223> OTHER INFORMATION: Xaa = S, T, A

<400> SEQUENCE: 54

Xaa Xaa Xaa Gly Xaa Xaa Xaa Xaa Xaa Ser Ser
 1               5                   10

<210> SEQ ID NO 55
<211> LENGTH: 97
<212> TYPE: PRT
<213> ORGANISM: Artificial Sequence
<220> FEATURE:
<223> OTHER INFORMATION: Synthetic polypeptide

<400> SEQUENCE: 55

Asn Val Ser Pro Pro Arg Arg Ala Arg Val Thr Asp Ala Thr Glu Thr
 1               5                  10                  15

Thr Ile Thr Ile Ser Trp Glu His Ser Glu Asp Cys Tyr Ser Tyr
                20                  25                  30

Ile Tyr Tyr Phe Gln Val Asp Ala Val Pro Ala Asn Gly Gln Thr Pro
             35                  40                  45

Ile Gln Arg Thr Ile Ser Gly Tyr Glu Thr Tyr Tyr Thr Ile Thr Gly
         50                  55                  60

Leu Gln Pro Gly Thr Asp Tyr Lys Ile Tyr Leu Tyr Thr Leu Asn Ser
 65                  70                  75                  80

Ala Gly Phe Cys Pro Pro Tyr Ser Lys Pro Val Val Ile Asp Ala Ser
                 85                  90                  95

Thr

<210> SEQ ID NO 56
<211> LENGTH: 97
<212> TYPE: PRT
<213> ORGANISM: Artificial Sequence
<220> FEATURE:
<223> OTHER INFORMATION: Synthetic polypeptide

<400> SEQUENCE: 56

Asn Val Ser Pro Pro Arg Arg Ala Arg Val Thr Asp Ala Thr Glu Thr
 1               5                  10                  15

Thr Ile Thr Ile Ser Trp Glu Pro Ser Glu Tyr Asp Cys Tyr Tyr Ser
                20                  25                  30

Ile Tyr Tyr Phe Gln Val Asp Ala Val Pro Ala Asn Gly Gln Thr Pro
             35                  40                  45
```

Ile Gln Arg Thr Ile His Asp Ser Tyr Asn Tyr Tyr Thr Ile Thr Gly
            50                  55                  60

Leu Gln Pro Gly Thr Asp Tyr Lys Ile Tyr Leu Tyr Thr Leu Asn Ser
 65                  70                  75                  80

Ala Gly Phe Cys Pro Pro Tyr Ser Lys Pro Val Val Ile Asp Ala Ser
                 85                  90                  95

Thr

<210> SEQ ID NO 57
<211> LENGTH: 97
<212> TYPE: PRT
<213> ORGANISM: Artificial Sequence
<220> FEATURE:
<223> OTHER INFORMATION: Synthetic polypeptide

<400> SEQUENCE: 57

Asn Val Ser Pro Pro Arg Arg Ala Arg Val Thr Asp Ala Thr Glu Thr
 1               5                  10                  15

Thr Ile Thr Ile Ser Trp Glu Ser Tyr Tyr Asp Cys Cys Tyr Tyr
                 20                  25                  30

Ile Tyr Tyr Phe Gln Val Asp Ala Val Pro Ala Asn Gly Gln Thr Pro
             35                  40                  45

Ile Gln Arg Thr Ile Tyr Tyr Pro Tyr Thr Ser Tyr Thr Ile Thr Gly
            50                  55                  60

Leu Gln Pro Gly Thr Asp Tyr Lys Ile Tyr Leu Tyr Thr Leu Asn Ser
 65                  70                  75                  80

Tyr Gly Tyr Gly Tyr His Tyr Tyr Lys Pro Val Val Ile Asp Ala Ser
                 85                  90                  95

Thr

<210> SEQ ID NO 58
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 58

Asn Val Ser Pro Pro Arg Arg Ala Arg Val Thr Asp Ala Thr Glu Thr
 1               5                  10                  15

Thr Ile Thr Ile Ser Trp Tyr Pro Tyr Glu Tyr Asp Asp Cys Tyr Tyr
                 20                  25                  30

Tyr Ile Tyr Tyr Phe Gln Val Asp Ala Val Pro Ala Asn Gly Gln Thr
             35                  40                  45

Pro Ile Gln Arg Thr Ile Pro Asp Tyr Glu Ser Tyr Tyr Thr Ile Thr
            50                  55                  60

Gly Leu Gln Pro Gly Thr Asp Tyr Lys Ile Tyr Leu Tyr Thr Leu Asn
 65                  70                  75                  80

Ser Tyr Gly Phe Cys Pro Pro Tyr Lys Pro Val Val Ile Asp Ala
                 85                  90                  95

Ser Thr

<210> SEQ ID NO 59
<211> LENGTH: 97
<212> TYPE: PRT
<213> ORGANISM: Artificial Sequence
<220> FEATURE:
<223> OTHER INFORMATION: Synthetic polypeptide -continued

```
<400> SEQUENCE: 59

Asn Val Ser Pro Pro Arg Arg Ala Arg Val Thr Asp Ala Thr Glu Thr
1               5                   10                  15

Thr Ile Thr Ile Ser Trp Tyr Pro Ser Glu Asp Tyr Cys Gly Ser Ser
            20                  25                  30

Ile Tyr Gly Phe Gln Val Asp Ala Val Pro Ala Asn Gly Gln Thr Pro
        35                  40                  45

Ile Gln Arg Thr Ile His Gly Asn Glu Thr Ser Tyr Thr Ile Thr Gly
    50                  55                  60

Leu Gln Pro Gly Thr Asp Tyr Lys Ile Tyr Leu Tyr Thr Leu Asn Ser
65                  70                  75                  80

Ala Gly Phe Cys Pro Pro Tyr Ser Lys Pro Val Val Ile Asp Ala Ser
                85                  90                  95

Thr

<210> SEQ ID NO 60
<211> LENGTH: 97
<212> TYPE: PRT
<213> ORGANISM: Artificial Sequence
<220> FEATURE:
<223> OTHER INFORMATION: Synthetic polypeptide

<400> SEQUENCE: 60

Asn Val Ser Pro Pro Arg Arg Ala Arg Val Thr Asp Ala Thr Glu Thr
1               5                   10                  15

Thr Ile Thr Ile Ser Trp Tyr Pro Tyr Tyr Asp Asp Cys Gly Tyr Tyr
            20                  25                  30

Ile Ser Tyr Phe Gln Val Asp Ala Val Pro Ala Asn Gly Gln Thr Pro
        35                  40                  45

Ile Gln Arg Thr Ile Pro Asp Ser Tyr Ser Ser Tyr Thr Ile Thr Gly
    50                  55                  60

Leu Gln Pro Gly Thr Asp Tyr Lys Ile Tyr Leu Tyr Thr Leu Asn Asp
65                  70                  75                  80

Ala Asp Asp Gly His Pro Tyr Ser Lys Pro Val Val Ile Asp Ala Ser
                85                  90                  95

Thr

<210> SEQ ID NO 61
<211> LENGTH: 97
<212> TYPE: PRT
<213> ORGANISM: Artificial Sequence
<220> FEATURE:
<223> OTHER INFORMATION: Synthetic polypeptide

<400> SEQUENCE: 61

Asn Val Ser Pro Pro Arg Arg Ala Arg Val Thr Asp Ala Thr Glu Thr
1               5                   10                  15

Thr Ile Thr Ile Ser Trp Tyr Pro Tyr Tyr Tyr Cys Gly Tyr His
            20                  25                  30

Tyr Ser Tyr Phe Gln Val Asp Ala Val Pro Ala Asn Gly Gln Thr Pro
        35                  40                  45

Ile Gln Arg Thr Ile Tyr Gly Tyr Tyr Thr Tyr Tyr Thr Ile Thr Gly
    50                  55                  60

Leu Gln Pro Gly Thr Asp Tyr Lys Ile Tyr Leu Tyr Thr Leu Asn Ser
65                  70                  75                  80

Ser Asp Tyr Cys Tyr Tyr Ser Tyr Tyr Pro Val Val Ile Asp Ala Ser
                85                  90                  95
```

Thr

<210> SEQ ID NO 62
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 62

Asn Val Ser Pro Pro Arg Arg Ala Arg Val Thr Asp Ala Thr Glu Thr
1               5                   10                  15

Thr Ile Thr Ile Ser Trp Tyr His His Glu Asp Asp Cys Tyr Tyr His
            20                  25                  30

Phe Tyr Tyr Phe Gln Val Asp Ala Val Pro Ala Asn Gly Gln Thr Pro
        35                  40                  45

Ile Gln Arg Thr Ile Leu His Gly Thr Tyr Thr Ser Tyr Thr Ile Thr
    50                  55                  60

Gly Leu Gln Pro Gly Thr Asp Tyr Lys Ile Tyr Leu Tyr Thr Leu Asn
65                  70                  75                  80

Ala Ser Gly Phe Cys Ser His Ser Tyr Lys Pro Val Val Ile Asp Ala
                85                  90                  95

Ser Thr

<210> SEQ ID NO 63
<211> LENGTH: 93
<212> TYPE: PRT
<213> ORGANISM: Artificial Sequence
<220> FEATURE:
<223> OTHER INFORMATION: Synthetic polypeptide

<400> SEQUENCE: 63

Asn Val Ser Pro Pro Arg Arg Ala Arg Val Thr Asp Ala Thr Glu Thr
1               5                   10                  15

Thr Ile Thr Ile Ser Trp Asn Ser Ser Tyr Cys His Phe Tyr Gly Phe
            20                  25                  30

Gln Val Asp Ala Val Pro Ala Asn Gly Gln Thr Pro Ile Gln Arg Thr
        35                  40                  45

Ile Ser Asp Tyr Glu Tyr Ser Tyr Thr Ile Thr Gly Leu Gln Pro Gly
    50                  55                  60

Thr Asp Tyr Lys Ile Tyr Leu Tyr Leu Asn Ala Ser Cys Tyr Gly
65                  70                  75                  80

Tyr His Tyr Tyr Lys Pro Val Val Ile Asp Ala Ser Thr
                85                  90

<210> SEQ ID NO 64
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 64

Asn Val Ser Pro Pro Arg Arg Ala Arg Val Thr Asp Ala Thr Glu Thr
1               5                   10                  15

Thr Ile Thr Ile Pro Trp Glu Val Ala Gly Gly Pro Ile Ile Ser Phe
            20                  25                  30

Gln Val Asp Ala Val Pro Ala Asn Gly Gln Thr Pro Ile Gln Arg Thr
        35                  40                  45

```
Ile Thr Pro Asp Ala Thr Gly Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                85

<210> SEQ ID NO 65
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 65

Asn Val Ser Pro Pro Arg Arg Ala Arg Val Thr Asp Ala Thr Glu Thr
  1               5                  10                  15

Thr Ile Thr Ile Pro Trp Ala Leu Ala Gly Gly Pro Ile Ile Ser Phe
                20                  25                  30

Gln Val Asp Ala Val Pro Ala Asn Gly Gln Thr Pro Ile Gln Arg Thr
            35                  40                  45

Ile Thr Pro Asp Ile Arg Gly Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                85

<210> SEQ ID NO 66
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 66

Asn Val Ser Pro Pro Arg Arg Ala Arg Val Thr Asp Ala Thr Glu Thr
  1               5                  10                  15

Thr Ile Thr Ile Arg Trp Ala Gly Ser Pro Gly Pro Val Asp Ser Phe
                20                  25                  30

Gln Val Asp Ala Val Pro Ala Asn Gly Gln Thr Pro Ile Gln Arg Thr
            35                  40                  45

Ile Gln Thr Ser Glu Thr Gly Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                85

<210> SEQ ID NO 67
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 67

Asn Val Ser Pro Pro Arg Arg Ala Arg Val Thr Asp Ala Thr Glu Thr
  1               5                  10                  15
```

Thr Ile Thr Ile Arg Trp Gly Val Ala Gln Ser Gln Val Ala Arg Phe
           20                  25                  30

Gln Val Asp Ala Val Pro Ala Asn Gly Gln Thr Pro Ile Gln Arg Thr
        35                  40                  45

Ile Lys Arg Ser Val His Thr Tyr Thr Ile Thr Gly Leu Gln Pro Gly
50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 68
<211> LENGTH: 85
<212> TYPE: PRT
<213> ORGANISM: Artificial Sequence
<220> FEATURE:
<223> OTHER INFORMATION: Synthetic polypeptide

<400> SEQUENCE: 68

Asn Val Ser Pro Pro Arg Arg Ala Arg Val Thr Asp Ala Thr Glu Thr
1               5                   10                  15

Thr Ile Thr Ile Arg Trp Gly Val Pro His Ser Phe Gln Val Asp Ala
           20                  25                  30

Val Pro Ala Asn Gly Gln Thr Pro Ile Gln Arg Thr Ile Lys Arg Gly
        35                  40                  45

Val Arg Ser Tyr Thr Ile Thr Gly Leu Gln Pro Gly Thr Asp Tyr Lys
    50                  55                  60

Ile Tyr Leu Tyr Thr Leu Asn Asp Asn Ala Arg Ser Ser Pro Val Val
65                  70                  75                  80

Ile Asp Ala Ser Thr
                85

<210> SEQ ID NO 69
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 69

Asn Val Ser Pro Pro Arg Arg Ala Arg Val Thr Asp Ala Thr Glu Thr
1               5                   10                  15

Thr Ile Thr Ile Ser Trp Arg Ala Ala Glu Ser Ala Ile Ala Arg Phe
           20                  25                  30

Gln Val Asp Ala Val Pro Ala Asn Gly Gln Thr Pro Ile Gln Arg Thr
        35                  40                  45

Ile Lys Arg Thr Lys His Thr Tyr Thr Ile Thr Gly Leu Gln Pro Gly
50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 70
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 70

Asn Val Ser Pro Pro Arg Arg Ala Arg Val Thr Asp Ala Thr Glu Thr
1               5                   10                  15

Thr Ile Thr Ile Ser Trp Gly Val Ala Glu Ser Glu Val Thr Arg Phe
            20                  25                  30

Gln Val Asp Ala Val Pro Ala Asn Gly Gln Thr Pro Ile Gln Arg Thr
        35                  40                  45

Ile Lys Arg Ser Lys His Ala Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 71
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 71

Asn Val Ser Pro Pro Arg Arg Ala Arg Val Thr Asp Ala Thr Glu Thr
1               5                   10                  15

Thr Ile Thr Ile Ser Trp Arg Ala Ala Glu Ser Ala Ile Ala Arg Phe
            20                  25                  30

Gln Val Asp Ala Val Pro Ala Asn Gly Gln Thr Pro Ile Gln Arg Thr
        35                  40                  45

Ile Lys Arg Thr Lys His Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 72
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 72

Asn Val Ser Pro Pro Arg Arg Ala Arg Val Thr Asp Ala Thr Glu Thr
1               5                   10                  15

Thr Ile Thr Ile Arg Trp Ala Arg Ser Ala Ser Glu Ile Ala Arg Phe
            20                  25                  30

Gln Val Asp Ala Val Pro Ala Asn Gly Gln Thr Pro Ile Gln Arg Thr
        35                  40                  45

Ile Lys Arg Ser Ala Asn Ile Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 73
<211> LENGTH: 89

```
<212> TYPE: PRT
<213> ORGANISM: Artificial Sequence
<220> FEATURE:
<223> OTHER INFORMATION: Synthetic polypeptide

<400> SEQUENCE: 73

Asn Val Ser Pro Pro Arg Arg Ala Arg Val Thr Asp Ala Thr Glu Thr
 1               5                  10                  15

Thr Ile Thr Ile Arg Trp Gly Val Ser Glu Ser Glu Val Ile Arg Phe
             20                  25                  30

Gln Val Asp Ala Val Pro Ala Asn Gly Gln Thr Pro Ile Gln Arg Thr
         35                  40                  45

Ile Lys Arg Ser Lys His Ala Tyr Thr Ile Thr Gly Leu Gln Pro Gly
     50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                 85

<210> SEQ ID NO 74
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 74

Asn Val Ser Pro Pro Arg Arg Ala Arg Val Thr Asp Ala Thr Glu Thr
 1               5                  10                  15

Thr Ile Thr Ile Arg Trp Gly Val Ser Pro Ser Glu Val Val Arg Phe
             20                  25                  30

Gln Val Asp Ala Val Pro Ala Asn Gly Gln Thr Pro Ile Gln Arg Thr
         35                  40                  45

Ile Lys Arg Ser Val His Gly Tyr Thr Ile Thr Gly Leu Gln Pro Gly
     50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                 85

<210> SEQ ID NO 75
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 75

Asn Val Ser Pro Pro Arg Arg Ala Arg Val Thr Asp Ala Thr Glu Thr
 1               5                  10                  15

Thr Ile Thr Ile Arg Trp Thr Val Ala Glu Ser Lys Ile Ala Arg Phe
             20                  25                  30

Gln Val Asp Ala Val Pro Ala Asn Gly Gln Thr Pro Ile Gln Arg Thr
         35                  40                  45

Ile Lys Arg Ser Lys His Ser Tyr Thr Ile Thr Gly Leu Gln Pro Gly
     50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
```

<210> SEQ ID NO 76
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 76

Asn Val Ser Pro Pro Arg Arg Ala Arg Val Thr Asp Ala Thr Glu Thr
1               5                   10                  15
Thr Ile Thr Ile Ser Trp Gly Val Ala Pro Ser Glu Ile Asn Arg Phe
            20                  25                  30
Gln Val Asp Ala Val Pro Ala Asn Gly Gln Thr Pro Ile Gln Arg Thr
        35                  40                  45
Ile Lys Arg Ser Lys His Ala Tyr Thr Ile Thr Gly Leu Gln Pro Gly
    50                  55                  60
Thr Asp Tyr Lys Ile Tyr Leu Tyr Thr Leu Asn Asp Asn Ala Arg Ser
65                  70                  75                  80
Ser Pro Val Val Ile Asp Ala Ser Thr
                85

<210> SEQ ID NO 77
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 77

Asn Val Ser Pro Pro Arg Arg Ala Arg Val Thr Asp Ala Thr Glu Thr
1               5                   10                  15
Thr Ile Thr Ile Arg Trp Gly Val Ser Glu Gly Gln Ile Val Arg Phe
            20                  25                  30
Gln Val Asp Ala Val Pro Ala Asn Gly Gln Thr Pro Ile Gln Arg Thr
        35                  40                  45
Ile Lys Arg Ser Lys His Ala Tyr Thr Ile Thr Gly Leu Gln Pro Gly
    50                  55                  60
Thr Asp Tyr Lys Ile Tyr Leu Tyr Thr Leu Asn Asp Asn Ala Arg Ser
65                  70                  75                  80
Ser Pro Val Val Ile Asp Ala Ser Thr
                85

<210> SEQ ID NO 78
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 78

Asn Val Ser Pro Pro Arg Arg Ala Arg Val Thr Asp Ala Thr Glu Thr
1               5                   10                  15
Thr Ile Thr Ile Arg Trp Thr Val Pro Ala Ser Pro Ile Ala Arg Phe
            20                  25                  30
Gln Val Asp Ala Val Pro Ala Asn Gly Gln Thr Pro Ile Gln Arg Thr
        35                  40                  45
Ile Lys Arg Thr Thr Arg Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 79
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 79

Asn Val Ser Pro Pro Arg Arg Ala Arg Val Thr Asp Ala Thr Glu Thr
1               5                   10                  15

Thr Ile Thr Ile Arg Trp Gly Val Ala Pro Ser Gln Val Ile Arg Phe
            20                  25                  30

Gln Val Asp Ala Val Pro Ala Asn Gly Gln Thr Pro Ile Gln Arg Thr
        35                  40                  45

Ile Lys Arg Ser Val His Ala Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 80
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 80

Asn Val Ser Pro Pro Arg Arg Ala Arg Val Thr Asp Ala Thr Glu Thr
1               5                   10                  15

Thr Ile Thr Ile Arg Trp Gly Val Pro Gly Ser Pro Val Val Arg Phe
            20                  25                  30

Gln Val Asp Ala Val Pro Ala Asn Gly Gln Thr Pro Ile Gln Arg Thr
        35                  40                  45

Ile Lys Arg Gly Ala Arg Ile Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 81
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 81

Asn Val Ser Pro Pro Arg Arg Ala Arg Val Thr Asp Ala Thr Glu Thr
1               5                   10                  15

Thr Ile Thr Ile Arg Trp Gly Ala Pro Ala Ser Glu Ile Ile Arg Phe
            20                  25                  30

Gln Val Asp Ala Val Pro Ala Asn Gly Gln Thr Pro Ile Gln Arg Thr
 35                  40                  45

Ile Lys Arg Thr Ile His Thr Tyr Thr Ile Thr Gly Leu Gln Pro Gly
 50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                 85

<210> SEQ ID NO 82
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 82
armtggraam maccgraara wgatggcggc armmmaatta marra          45

<210> SEQ ID NO 83
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 83
rgctgggras scccggragr cgatggcggc rgcsscattr scggc          45

<210> SEQ ID NO 84
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 84
kmttgggaws mtccggawga tgatggcggc kmtsmtattr mcgrt          45

<210> SEQ ID NO 85
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 85
mrstggsagc mgccgsagsa kgatggcggc mrscmgattm mgsrg          45

<210> SEQ ID NO 86
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 86
agctggrrmy ctccgrrmrr cgatggcggc agcyctatta scrgc          45

<210> SEQ ID NO 87
<211> LENGTH: 45
<212> TYPE: DNA
<213> ORGANISM: Artificial Sequence
<220> FEATURE:
<223> OTHER INFORMATION: Synthetic polynucleotide

```
<400> SEQUENCE: 87
ymttggsawc mtccgsawsa tgatggcggc ymtcmtattm mcsrt            45

<210> SEQ ID NO 88
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 88
tmttggtatg aaymtccgta tgaakatgat ggcggctmty mtattwmckr t     51

<210> SEQ ID NO 89
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 89
tyatggswgc ygccgswgsw tgatggcggc tyacygattm ygskg            45

<210> SEQ ID NO 90
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 90
ycttggsmgc cgccgsmgsm tgatggcggc yctccgattm cgssg            45

<210> SEQ ID NO 91
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 91
armtggaaam maccgrawra wmmaaawrra mmaattamar ra               42

<210> SEQ ID NO 92
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 92
rgctggrras scccggrcgr csscrrcggc sscattrscg gc               42

<210> SEQ ID NO 93
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 93
kmttggraws mtccggatga tsmtratgrt smtattrmcg rt               42

<210> SEQ ID NO 94
```

<211> LENGTH: 42
<212> TYPE: PRT
<213> ORGANISM: Artificial Sequence
<220> FEATURE:
<223> OTHER INFORMATION: Synthetic polynucleotide

<400> SEQUENCE: 94

```
Met Arg Ser Thr Gly Gly Met Ala Gly Cys Met Gly Cys Cys Gly Ser
1               5                   10                  15
Ala Lys Ser Ala Lys Cys Met Gly Met Ala Lys Ser Arg Gly Cys Met
            20                  25                  30
Gly Ala Thr Thr Met Met Gly Ser Arg Gly
        35                  40
```

<210> SEQ ID NO 95
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 95
agctggarmy ctccgrrcrr cycyarcrgc ycyattascr gc                              42

<210> SEQ ID NO 96
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 96
ymttggmawc mtccgsatsa tcmtmatsrt cmtattmmcs rt                              42

<210> SEQ ID NO 97
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 97
tmttggaaat atymtccgka tkatymtwat krtymtattw mckrt                           45

<210> SEQ ID NO 98
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 98
tyatggmwgc ygccgswtsw tcygmwtskg cygattmygs kg                              42

<210> SEQ ID NO 99
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 99
ycttggmmgc cgccgsmtsm tccgmmtssg ccgattmcgs sg                              42

<210> SEQ ID NO 100

<210> SEQ ID NO 100
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 100
armtggamam maccgmmarr ammarwgraw rra                33

<210> SEQ ID NO 101
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 101
rgctggrscs scccgsscgg csscgkcgrc ggc                33

<210> SEQ ID NO 102
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 102
kmttggrmcs mtccgsmtgr tsmtgwtgat grt                33

<210> SEQ ID NO 103
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 103
mrstggmmgc mgccgcmgsr gcmgswgsak srg                33

<210> SEQ ID NO 104
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 104
agctggascy ctccgyctrg cyctrkcrrc rgc                33

<210> SEQ ID NO 105
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 105
ymttggmmcc mtccgcmtsr tcmtswtsat srt                33

<210> SEQ ID NO 106
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 106

```
tmttggwmcy mtccgymtkr tymtkwtkat krt                                 33

<210> SEQ ID NO 107
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 107
tyatggmygc ygccgcygsk gcygstgswt skg                                 33

<210> SEQ ID NO 108
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 108
ycttggmcgc cgccgccgss gccgsygsmt ssg                                 33

<210> SEQ ID NO 109
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 109
mmarraamar aaamaarm                                                  18

<210> SEQ ID NO 110
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 110
sscggcrscg rarscrgc                                                  18

<210> SEQ ID NO 111
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 111
smtgrtrmcg awrmckmt                                                  18

<210> SEQ ID NO 112
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 112
cmgsrgmmgs agmmgmrs                                                  18

<210> SEQ ID NO 113
<211> LENGTH: 18
<212> TYPE: DNA
```

```
<213> ORGANISM: Artificial Sequence
<220> FEATURE:
<223> OTHER INFORMATION: Synthetic polynucleotide

<400> SEQUENCE: 113
yctrgcascr rmascagc                                                 18

<210> SEQ ID NO 114
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 114
cmtsrtmmcs awmmcymt                                                 18

<210> SEQ ID NO 115
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 115
ymtkrtwmck awwmctmt                                                 18

<210> SEQ ID NO 116
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 116
cygskgmygs wgmygtya                                                 18

<210> SEQ ID NO 117
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 117
ccgssgmcgs mgmcgyct                                                 18

<210> SEQ ID NO 118
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 118
aawrmgrmgg gcrwgrgcmm ammaagc                                       27

<210> SEQ ID NO 119
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 119
rrcgscgscg gcgkcrgcss csscagc                                       27
```

<210> SEQ ID NO 120
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 120
ratgmcgmcg gcgwtrgcsm tsmtagc                                              27

<210> SEQ ID NO 121
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 121
maksmgsmgg gcswgrgccm gcmgagc                                              27

<210> SEQ ID NO 122
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 122
arckctkctg gcrkcrgcyc tyctagc                                              27

<210> SEQ ID NO 123
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 123
matsmcsmcg gcswtrgccm tcmtagc                                              27

<210> SEQ ID NO 124
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 124
watkmckmcg gckwtrgcym tymtagc                                              27

<210> SEQ ID NO 125
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 125
mwtsygsygg gcstgrgccy gcygagc                                              27

<210> SEQ ID NO 126
<211> LENGTH: 27
<212> TYPE: DNA
<213> ORGANISM: Artificial Sequence
<220> FEATURE:

```
<223> OTHER INFORMATION: Synthetic polynucleotide

<400> SEQUENCE: 126
mmtscgscgg gcsygrgccc gccgagc                                              27

<210> SEQ ID NO 127
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 127
aawrrarrar raraaarm                                                        18

<210> SEQ ID NO 128
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 128
rrcggcggcg gcgrargc                                                        18

<210> SEQ ID NO 129
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 129
ratgrtgrtg rtgawkmt                                                        18

<210> SEQ ID NO 130
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 130
maksrgsrgs rgsagmrs                                                        18

<210> SEQ ID NO 131
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 131
arcrgcrgcr gcrrmagc                                                        18

<210> SEQ ID NO 132
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 132
matsrtsrts rtsawymt                                                        18
```

```
<210> SEQ ID NO 133
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 133
watkrtkrtk rttatgaatm t                                              21

<210> SEQ ID NO 134
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 134
mwtskgskgs kgswgtya                                                  18

<210> SEQ ID NO 135
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 135
mmtssgssgs sgsmgyct                                                  18

<210> SEQ ID NO 136
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 136
armtggaaam aaccgraara wgatggcarm mmaattamar ra                       42

<210> SEQ ID NO 137
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 137
armtggaaam aaccgraara wmcarrmarm mmaattamar ra                       42

<210> SEQ ID NO 138
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 138
armtggaaam aaccgraara agatarmmma attamarra                           39

<210> SEQ ID NO 139
<211> LENGTH: 45
<212> TYPE: DNA
<213> ORGANISM: Artificial Sequence
<220> FEATURE:
<223> OTHER INFORMATION: Synthetic polynucleotide
```

<400> SEQUENCE: 139
agctggraam mammaraara wrawrrarra armmmaawaa marra        45

<210> SEQ ID NO 140
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 140
agctgggras scsscgragr cgrcggcggc rgcsscrkcr scggc        45

<210> SEQ ID NO 141
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 141
agctgggaws mtsmtgawga tgatgrtgrt kmtsmtrwtr mcgrt        45

<210> SEQ ID NO 142
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 142
agctggsagc mgcmgsagsa ksaksrgsrg mrscmgmwam mgsrg        45

<210> SEQ ID NO 143
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 143
agctggrrmy ctyctrrmrr crrcrgcrgc agcyctakca scrgc        45

<210> SEQ ID NO 144
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 144
agctggsawc mtcmtsawsa tsatsrtsrt ymtcmtmwtm mcsrt        45

<210> SEQ ID NO 145
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 145
agctggtatg aaymtymtta tgaakatkat krtkrttmty mtwwtwmckr t        51

<210> SEQ ID NO 146
<211> LENGTH: 45

<210> SEQ ID NO 146
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 146
agctggswgc ygcygswgsw tswtskgskg tyacygwtam ygskg    45

<210> SEQ ID NO 147
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 147
agctggsmgc cgccgsmgsm tsmtssgssg yctccgmytm cgssg    45

<210> SEQ ID NO 148
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 148
agctggaaam mammarawra wmmaaasrra mmaawaamar ra    42

<210> SEQ ID NO 149
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 149
agctggrras scsscgrcgr csscrrtggc sscrkcrscg gc    42

<210> SEQ ID NO 150
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 150
agctggraws mtsmtgatga tsmtratgrt smtrwtrmcg rt    42

<210> SEQ ID NO 151
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 151
agctggmagc mgcmgsaksa kcmgmcwsrg cmgmwammgs rg    42

<210> SEQ ID NO 152
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 152
agctggarmy ctyctrrcrr cyctarcrgc yctakcascr gc                              42

<210> SEQ ID NO 153
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 153
agctggmawc mtcmtsatsa tcmtmatsrt cmtmwtmmcs rt                              42

<210> SEQ ID NO 154
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 154
agctggaaat atymtymtka tkatymtwat krtymtwwtw mckrt                           45

<210> SEQ ID NO 155
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 155
agctggmwgc ygcygswtsw tcygmwcskg cygwtamygs kg                              42

<210> SEQ ID NO 156
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 156
agctggmmgc cgccgsmtsm tccgmmtssg ccgmytmcgs sg                              42

<210> SEQ ID NO 157
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 157
agctggamam mammammarr ammarwgraw ggc                                        33

<210> SEQ ID NO 158
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 158
agctggrscs scsscsscgg csscgkcgrc ggc                                        33

<210> SEQ ID NO 159
<211> LENGTH: 33
<212> TYPE: DNA
<213> ORGANISM: Artificial Sequence

```
<220> FEATURE:
<223> OTHER INFORMATION: Synthetic polynucleotide

<400> SEQUENCE: 159
agctggrmcs mtsmtsmtgr tsmtgwtgat ggc                                    33

<210> SEQ ID NO 160
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 160
agctggmmgc mgcmgcmgsr gcmgswgsak ggc                                    33

<210> SEQ ID NO 161
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 161
agctggascy ctyctyctrg cyctrkcrrc ggc                                    33

<210> SEQ ID NO 162
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 162
agctggmmcc mtcmtcmtsr tcmtswtsat ggc                                    33

<210> SEQ ID NO 163
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 163
agctggwmcy mtymtymtkr tymtkwtkat ggc                                    33

<210> SEQ ID NO 164
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 164
agctggmygc ygcygcygsk gcygstgswt ggc                                    33

<210> SEQ ID NO 165
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 165
agctggmcgc cgccgccgss gccgsygsmt ggc                                    33
```

<210> SEQ ID NO 166
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 166
mmarraamar aaamaarm                                                 18

<210> SEQ ID NO 167
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 167
sscggcrscg rarscrgc                                                 18

<210> SEQ ID NO 168
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 168
smtgrtrmcg awrmckmt                                                 18

<210> SEQ ID NO 169
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 169
cmgsrgmmgs agmmgmrs                                                 18

<210> SEQ ID NO 170
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 170
yctrgcascr rmascagc                                                 18

<210> SEQ ID NO 171
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 171
cmtsrtmmcs awmmcymt                                                 18

<210> SEQ ID NO 172
<211> LENGTH: 18
<212> TYPE: DNA
<213> ORGANISM: Artificial Sequence
<220> FEATURE:
<223> OTHER INFORMATION: Synthetic polynucleotide

```
<400> SEQUENCE: 172
ymtkrtwmck awwmctmt                                                 18

<210> SEQ ID NO 173
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 173
cygskgmygs wgmygtya                                                 18

<210> SEQ ID NO 174
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 174
ccgssgmcgs mgmcgyct                                                 18

<210> SEQ ID NO 175
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 175
aatrmgrmgr rarwgrramm ammaarmarm aaa                                33

<210> SEQ ID NO 176
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 176
aatgscgscg gcgkcggcss csscrgcrgc rra                                33

<210> SEQ ID NO 177
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 177
aatgmcgmcg rtgwtgrtsm tsmtkmtkmt raw                                33

<210> SEQ ID NO 178
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 178
aatsmgsmgs rgswgsrgcm gcmgmrsmrs mag                                33

<210> SEQ ID NO 179
```

```
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 179
aatkctkctr gcrkcrgcyc tyctagcagc arm                            33

<210> SEQ ID NO 180
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 180
aatsmcsmcs rtswtsrtcm tcmtymtymt maw                            33

<210> SEQ ID NO 181
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 181
aatkmckmck rtkwtkrtym tymttmttmt aaatat                         36

<210> SEQ ID NO 182
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 182
aatsygsygs kgstgskgcy gcygtyatya mwg                            33

<210> SEQ ID NO 183
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 183
aatscgscgs sgsygssgcc gccgyctyct mmg                            33

<210> SEQ ID NO 184
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 184
aatrrarrar raraaarmar maaa                                      24

<210> SEQ ID NO 185
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 185
```
aatggcggcg gcgrargcrg crra                                    24

<210> SEQ ID NO 186
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 186
aatgrtgrtg rtgawkmtkm traw                                    24

<210> SEQ ID NO 187
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 187
aatsrgsrgs rgsagmrsmr smag                                    24

<210> SEQ ID NO 188
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 188
aatrgcrgcr gcrrmagcag carm                                    24

<210> SEQ ID NO 189
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 189
aatsrtsrts rtsawymtym tmaw                                    24

<210> SEQ ID NO 190
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 190
aatkrtkrtk rttatgaatm ttmtaaatat                              30

<210> SEQ ID NO 191
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 191
aatskgskgs kgswgtyaty amwg                                    24

<210> SEQ ID NO 192
<211> LENGTH: 24
<212> TYPE: DNA

<213> ORGANISM: Artificial Sequence
<220> FEATURE:
<223> OTHER INFORMATION: Synthetic polynucleotide

<400> SEQUENCE: 192
aatssgssgs sgsmgyctyc tmmg                                    24

<210> SEQ ID NO 193
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 193
accaccatca caattarmtg graammaccg raarawgatg gcggcarmmm aattamarra    60
ttccaagtcg acgca                                              75

<210> SEQ ID NO 194
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 194
acctctttgc ttatatcgga tcacgtac                                28

<210> SEQ ID NO 195
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 195
accaccatca caattagctg graammamma raarawrawr rarraarmmm aawaamarra    60
ttccaagtcg acgca                                              75

<210> SEQ ID NO 196
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 196
catattgctg gtactcaggg atccgttagt gacgtccca                    39

<210> SEQ ID NO 197
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 197
tataagcaaa gaggtaggag tcgctgcaac cacttccaga tcccgtggga cgtcactaac    60

<210> SEQ ID NO 198
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 198
aactgtgaat tcttgaactg gtgagttgcc acctgtctct ccgtacgtga tccgata        57

<210> SEQ ID NO 199
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 199
cactgcatag acagtaatgg tatagtcgac accgggctta agtccagaga tagttgc        57

<210> SEQ ID NO 200
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 200
atgaactggg tatactctct cgagcgtccg atagttgatg ga        42

<210> SEQ ID NO 201
<211> LENGTH: 15
<212> TYPE: PRT
<213> ORGANISM: Artificial Sequence
<220> FEATURE:
<223> OTHER INFORMATION: Synthetic peptide

<400> SEQUENCE: 201

Gly Gly Gly Gly Ser Gly Gly Gly Gly Ser Gly Gly Gly Gly Ser
1               5                   10                  15

<210> SEQ ID NO 202
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 202
catattgctg gtactcaggg atccaacgtt agtccgcct        39

<210> SEQ ID NO 203
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 203
aattgtgatg gtggtctcgg tggcgtctgt gacgcgggca cgccgaggcg gactaacgtt        60

<210> SEQ ID NO 204
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 204
accaccatca caattagctg gcgcactaaa acggaaacaa tcaccggttt ccaagtcgac        60
gca        63

<210> SEQ ID NO 205
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 205
gattgtccgc tgaatgggag tttggccgtt ggctgggact gcgtcgactt ggaa    54

<210> SEQ ID NO 206
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 206
attcagcgga caatcaagcc tgacgttcgt tcttatacca ttaccggg    48

<210> SEQ ID NO 207
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 207
caaagtatac aggtagattt tataatcagt tcctggctgt aacccggtaa tggtata    57

<210> SEQ ID NO 208
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 208
tacctgtata ctttgaatga caacgcgcgt agcagtccgg tggttataga tgccagc    57

<210> SEQ ID NO 209
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 209
tgaactgggt atactctctc gagcgtgctg gcatctataa c    41

<210> SEQ ID NO 210
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 210
accaccatca caattagctg gwmcymtymt ymtkrtymtk wtkatggctt ccaagtcgac    60
gca    63

<210> SEQ ID NO 211
<211> LENGTH: 48
<212> TYPE: DNA

```
<213> ORGANISM: Artificial Sequence
<220> FEATURE:
<223> OTHER INFORMATION: Synthetic polynucleotide

<400> SEQUENCE: 211
attcagcgga caatcymtkr twmctatwmc tmttatacca ttaccggg            48

<210> SEQ ID NO 212
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 212
attcagcgga caatcymtkr twmcgaawmc tmttatacca ttaccggg            48

<210> SEQ ID NO 213
<211> LENGTH: 69
<212> TYPE: DNA
<213> ORGANISM: Artificial Sequence
<220> FEATURE:
<223> OTHER INFORMATION: Synthetic polynucleotide

<400> SEQUENCE: 213
tacctgtata ctttgaatkm ckmckrtkwt krtymtymtt mttmtaaacc ggtggttata    60
gatgccagc                                                           69

<210> SEQ ID NO 214
<211> LENGTH: 69
<212> TYPE: DNA
<213> ORGANISM: Artificial Sequence
<220> FEATURE:
<223> OTHER INFORMATION: Synthetic polynucleotide

<400> SEQUENCE: 214
tacctgtata ctttgaatkm ckmckrtkwt krtymtymtt mttmttatcc ggtggttata    60
gatgccagc                                                           69

<210> SEQ ID NO 215
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 215
accaccatca caattagctg gtatymtymt tatkatkatk rtkrttmtym twwtwmckrt    60
ttccaagtcg acgca                                                    75

<210> SEQ ID NO 216
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 216
accaccatca caattagctg gtatymtymt gaakatkatk rtkrttmtym twwtwmckrt    60
ttccaagtcg acgca                                                    75

<210> SEQ ID NO 217
<211> LENGTH: 75
```

<212> TYPE: DNA
<213> ORGANISM: Artificial Sequence
<220> FEATURE:
<223> OTHER INFORMATION: Synthetic polynucleotide

<400> SEQUENCE: 217
accaccatca caattagctg ggaaymtymt tatkatkatk rtkrttmtym twwtwmckrt    60
ttccaagtcg acgca                                                    75

<210> SEQ ID NO 218
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 218
accaccatca caattagctg ggaaymtymt gagkatkatk rtkrttmtym twwtwmckrt    60
ttccaagtcg acgca                                                    75

<210> SEQ ID NO 219
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 219
atcgccatgg aaaacgttag tccgcctcgg cgt                                33

<210> SEQ ID NO 220
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 220
atgaactggg tatactctct cgagcgtgct ggcatctata ac                      42

<210> SEQ ID NO 221
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 221
atcgctcgag cccaaatctt gtgacaaaac                                    30

<210> SEQ ID NO 222
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 222
cgatctcgag tttacccgga gacagggaga                                    30

<210> SEQ ID NO 223
<211> LENGTH: 92
<212> TYPE: PRT
<213> ORGANISM: Artificial Sequence
<220> FEATURE:

<223> OTHER INFORMATION: Synthetic polypeptide 1637102_VGR2C10

<400> SEQUENCE: 223

Asn Val Ser Pro Pro Arg Arg Ala Arg Val Thr Asp Ala Thr Glu Thr
1               5                   10                  15

Thr Ile Thr Ile Arg Trp Lys Leu Pro Val Ser Ala Asp Gly Val Val
            20                  25                  30

Pro Gly Phe Gln Val Asp Ala Val Pro Ala Asn Gly Gln Thr Pro Ile
        35                  40                  45

Gln Arg Thr Ile Asn Ala Asp Ile Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 224
<211> LENGTH: 92
<212> TYPE: PRT
<213> ORGANISM: Artificial Sequence
<220> FEATURE:
<223> OTHER INFORMATION: Synthetic polypeptide 1637102_VGR2B04

<400> SEQUENCE: 224

Asn Val Ser Pro Pro Arg Arg Ala Arg Val Thr Asp Ala Thr Glu Thr
1               5                   10                  15

Thr Ile Thr Ile Arg Trp Lys Gln Pro Lys Glu Ala Glu Ser Gln Val
            20                  25                  30

Leu Ser Phe Gln Val Asp Ala Val Pro Ala Asn Gly Gln Thr Pro Ile
        35                  40                  45

Gln Arg Thr Ile Asn Ala Ser Thr Asn Val Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 225
<211> LENGTH: 92
<212> TYPE: PRT
<213> ORGANISM: Artificial Sequence
<220> FEATURE:
<223> OTHER INFORMATION: Synthetic polypeptide 1637102_VGR2D07

<400> SEQUENCE: 225

Asn Val Ser Pro Pro Arg Leu Ala Arg Val Thr Asp Ala Thr Glu Thr
1               5                   10                  15

Thr Ile Thr Ile Arg Trp Ala Leu Pro Ile Asp Pro Gly Ser Leu Val
            20                  25                  30

Pro Ser Phe Gln Val Asp Ala Val Pro Ala Asn Gly Gln Thr Pro Ile
        35                  40                  45

Gln Arg Thr Ile His Ala Asp Thr Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 226
<211> LENGTH: 89
<212> TYPE: PRT
<213> ORGANISM: Artificial Sequence
<220> FEATURE:
<223> OTHER INFORMATION: Synthetic polypeptide 1637102_VGR2D12

<400> SEQUENCE: 226

Asn Val Ser Pro Pro Arg Arg Ala Arg Val Thr Asp Ala Thr Glu Thr
1               5                   10                  15

Thr Ile Thr Ile Arg Trp Glu Arg Ser Gly Gly Pro Val Asp Gly Phe
            20                  25                  30

Gln Val Asp Ala Val Pro Ala Asn Gly Gln Thr Pro Ile Gln Arg Thr
        35                  40                  45

Ile Asn Ala Asp Thr Asn Ile Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 227
<211> LENGTH: 92
<212> TYPE: PRT
<213> ORGANISM: Artificial Sequence
<220> FEATURE:
<223> OTHER INFORMATION: Synthetic polypeptide  1637102_VGR2B05

<400> SEQUENCE: 227

Asn Val Ser Pro Pro Arg Arg Ala Arg Val Thr Asp Ala Thr Glu Thr
1               5                   10                  15

Thr Ile Thr Ile Arg Trp Lys Gln Pro Lys Glu Ala Asp Ser Gln Val
            20                  25                  30

Leu Ser Phe Gln Val Asp Ala Val Pro Ala Asn Gly Gln Thr Pro Ile
        35                  40                  45

Gln Arg Thr Ile Asn Ala Ser Thr Asn Val Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 228
<211> LENGTH: 93
<212> TYPE: PRT
<213> ORGANISM: Artificial Sequence
<220> FEATURE:
<223> OTHER INFORMATION: Synthetic polypeptide 1637102_VGR2E05

<400> SEQUENCE: 228

Asn Val Ser Pro Pro Arg Arg Ala Arg Val Thr Asp Ala Thr Glu Thr
1               5                   10                  15

Thr Ile Thr Ile Arg Trp Asn Gln Pro Ala Tyr Asp Gly Gly Arg Ala
            20                  25                  30

Ile Pro Gly Phe Gln Val Asp Ala Val Pro Ala Asn Gly Gln Thr Pro
        35                  40                  45

Ile Gln Arg Thr Ile Asn Ala Asp Val Ser Thr Tyr Thr Ile Thr Gly
    50                  55                  60

Leu Gln Pro Gly Thr Asp Tyr Lys Ile Tyr Leu Tyr Thr Leu Asn Asp
65                  70                  75                  80

```
Asn Ala Arg Ser Ser Pro Val Val Ile Asp Ala Ser Thr
                85                  90
```

<210> SEQ ID NO 229
<211> LENGTH: 93
<212> TYPE: PRT
<213> ORGANISM: Artificial Sequence
<220> FEATURE:
<223> OTHER INFORMATION: Synthetic polypeptide 1637102_VGR2F04

<400> SEQUENCE: 229

```
Asn Val Ser Pro Pro Arg Arg Ala Arg Val Thr Asp Ala Thr Glu Thr
1               5                   10                  15

Thr Ile Thr Ile Arg Trp Lys Ala Pro Glu Tyr Thr Gly Gly Ala Glu
                20                  25                  30

Val Leu Gly Phe Gln Val Asp Ala Val Pro Ala Asn Gly Gln Thr Pro
            35                  40                  45

Ile Gln Arg Thr Ile Asn Ala Asp Thr Ser Tyr Thr Ile Thr Gly
        50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90
```

<210> SEQ ID NO 230
<211> LENGTH: 93
<212> TYPE: PRT
<213> ORGANISM: Artificial Sequence
<220> FEATURE:
<223> OTHER INFORMATION: Synthetic polypeptide 1637102_VGR2G07

<400> SEQUENCE: 230

```
Asn Val Ser Pro Pro Arg Ser Ala Arg Val Thr Asp Ala Thr Glu Thr
1               5                   10                  15

Thr Ile Thr Ile Arg Trp Gly Glu Pro Thr His Asn Gly Gly Thr Glu
                20                  25                  30

Ile Pro Ser Phe Gln Val Asp Ala Val Pro Ala Asn Gly Gln Thr Pro
            35                  40                  45

Ile Lys Arg Thr Ile Asn Ala Asp Thr His Tyr Thr Ile Thr Gly
        50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90
```

<210> SEQ ID NO 231
<211> LENGTH: 92
<212> TYPE: PRT
<213> ORGANISM: Artificial Sequence
<220> FEATURE:
<223> OTHER INFORMATION: Synthetic polypeptide 1637102_VGR2F09

<400> SEQUENCE: 231

```
Asn Val Ser Pro Pro Arg Arg Ala Arg Val Thr Asp Ala Thr Glu Thr
1               5                   10                  15

Thr Ile Thr Ile Arg Trp Thr Leu Gly Ile Ser Gly Asn Ser Ile Val
                20                  25                  30

Pro Gly Phe Gln Val Asp Ala Val Pro Ala Asn Gly Gln Thr Pro Ile
            35                  40                  45
```

Gln Arg Thr Ile Asn Ala Asp Thr Thr Thr Tyr Thr Ile Thr Gly Leu
            50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 232
<211> LENGTH: 92
<212> TYPE: PRT
<213> ORGANISM: Artificial Sequence
<220> FEATURE:
<223> OTHER INFORMATION: Synthetic polypeptide 1637102_VGR2H01

<400> SEQUENCE: 232

Asn Val Ser Pro Pro Arg Arg Ala Arg Val Thr Asp Ala Thr Glu Thr
1               5                   10                  15

Thr Ile Thr Ile Arg Trp Thr Val Pro Val Ser Ala Asn Gly Gln Ile
            20                  25                  30

Pro Ser Phe Gln Val Asp Ala Val Pro Ala Asn Gly Gln Thr Pro Ile
            35                  40                  45

Gln Arg Thr Ile Asn Ala Asp Val Ser Thr Tyr Thr Ile Thr Gly Leu
            50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 233
<211> LENGTH: 93
<212> TYPE: PRT
<213> ORGANISM: Artificial Sequence
<220> FEATURE:
<223> OTHER INFORMATION: Synthetic polypeptide 1637102_VGR22E11

<400> SEQUENCE: 233

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
            35                  40                  45

Ile Glu Thr Gly Ala Arg Gly Tyr Thr Ile Thr Gly Leu Gln Pro Gly
            50                  55                  60

Thr Asp Tyr Lys Ile Tyr Leu Tyr Thr Leu Asn Glu Asp Gly Gly Ser
65                  70                  75                  80

Ala Tyr Thr Glu Leu Thr Gly Val Ile Asp Ala Ser Thr
                85                  90

<210> SEQ ID NO 234
<211> LENGTH: 92
<212> TYPE: PRT
<213> ORGANISM: Artificial Sequence
<220> FEATURE:
<223> OTHER INFORMATION: Synthetic polypeptide 1637102_VGR2A04

<400> SEQUENCE: 234

Asn Val Ser Pro Pro Arg Arg Ala Arg Val Thr Asp Ala Thr Glu Thr
1               5                   10                  15

Thr Ile Thr Ile Arg Trp Thr Gln Gly Val Ser Arg Asn Gly Thr Ile 20                  25                  30

Pro Gly Phe Gln Val Asp Ala Val Pro Ala Asn Gly Gln Thr Pro Ile
            35                  40                  45

Gln Arg Thr Ile Asn Ala Asp Thr Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 235
<211> LENGTH: 92
<212> TYPE: PRT
<213> ORGANISM: Artificial Sequence
<220> FEATURE:
<223> OTHER INFORMATION: Synthetic polypeptide 1637102_VGR2E01

<400> SEQUENCE: 235

Asn Val Ser Pro Pro Arg Arg Ala Arg Val Thr Asp Ala Thr Glu Thr
1               5                   10                  15

Thr Ile Thr Ile Arg Trp Lys Gln Pro Ile Lys Pro Asp Ser Val Ile
                20                  25                  30

Pro Ser Phe Gln Val Asp Ala Val Pro Ala Asn Gly Gln Thr Pro Ile
            35                  40                  45

Gln Arg Thr Ile Asn Ala Asp Ile Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 236
<211> LENGTH: 92
<212> TYPE: PRT
<213> ORGANISM: Artificial Sequence
<220> FEATURE:
<223> OTHER INFORMATION: Synthetic polypeptide 1637102_VGR2D01

<400> SEQUENCE: 236

Asn Val Ser Pro Pro Arg Arg Ala Arg Val Thr Asp Ala Thr Glu Thr
1               5                   10                  15

Thr Ile Thr Ile Arg Trp Glu Ala Gly Val Glu Ala Asp Gly Glu Val
                20                  25                  30

Pro Ser Phe Gln Val Asp Ala Val Pro Ala Asn Gly Gln Thr Pro Ile
            35                  40                  45

Gln Arg Thr Ile Asn Ala Asp Thr Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 237
<211> LENGTH: 89
<212> TYPE: PRT
<213> ORGANISM: Artificial Sequence
<220> FEATURE:
<223> OTHER INFORMATION: Synthetic polypeptide 1637102_VGR2D09

<400> SEQUENCE: 237

```
Asn Val Ser Pro Pro Arg Arg Ala Arg Val Thr Asp Ala Thr Glu Thr
1               5                   10                  15

Thr Ile Thr Ile Arg Trp Thr Arg Ala Gly Ser Glu Val Asp Gly Phe
            20                  25                  30

Gln Val Asp Ala Val Pro Ala Asn Gly Gln Thr Pro Ile Gln Arg Thr
        35                  40                  45

Ile Asn Ala Asp Thr Asn Val Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85
```

<210> SEQ ID NO 238
<211> LENGTH: 92
<212> TYPE: PRT
<213> ORGANISM: Artificial Sequence
<220> FEATURE:
<223> OTHER INFORMATION: Synthetic polypeptide 1637102_VGR2B03

<400> SEQUENCE: 238

```
Asn Val Ser Pro Pro Arg Arg Ala Arg Val Thr Asp Ala Thr Glu Thr
1               5                   10                  15

Thr Ile Thr Ile Arg Trp Gln Gln Pro Val Glu Ala Asp Gly Ile Ile
            20                  25                  30

Pro Ser Phe Gln Val Asp Ala Val Pro Ala Asn Gly Gln Thr Pro Ile
        35                  40                  45

Gln Arg Thr Ile His Ala Asp Ile Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90
```

<210> SEQ ID NO 239
<211> LENGTH: 92
<212> TYPE: PRT
<213> ORGANISM: Artificial Sequence
<220> FEATURE:
<223> OTHER INFORMATION: Synthetic polypeptide 1637102_VGR2C07

<400> SEQUENCE: 239

```
Asn Val Ser Pro Pro Arg Arg Ala Arg Val Thr Asp Ala Thr Glu Thr
1               5                   10                  15

Thr Ile Thr Ile Arg Trp Glu Leu Pro Ile Asn Arg Asn Ser Thr Ile
            20                  25                  30

Pro Ser Phe Gln Val Asp Ala Val Pro Ala Asn Gly Gln Thr Pro Ile
        35                  40                  45

Gln Arg Thr Ile Asn Ala Asp Ile Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90
```

<210> SEQ ID NO 240
<211> LENGTH: 89
<212> TYPE: PRT

```
<213> ORGANISM: Artificial Sequence
<220> FEATURE:
<223> OTHER INFORMATION: Synthetic polypeptide 1637102_VGR2E03

<400> SEQUENCE: 240

Asn Val Ser Pro Pro Arg Arg Ala Arg Val Thr Asp Ala Thr Glu Thr
1               5                   10                  15

Thr Ile Thr Ile Arg Trp Glu Arg Ala Pro Ser Glu Val Asp Gly Phe
            20                  25                  30

Gln Val Asp Ala Val Pro Ala Asn Gly Gln Thr Pro Ile Gln Arg Thr
        35                  40                  45

Ile His Ala Asp Thr Asn Ile Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 241
<211> LENGTH: 92
<212> TYPE: PRT
<213> ORGANISM: Artificial Sequence
<220> FEATURE:
<223> OTHER INFORMATION: Synthetic polypeptide 1637102_VGR2C01

<400> SEQUENCE: 241

Asn Val Ser Pro Pro Arg Arg Ala Arg Val Thr Asp Ala Thr Glu Thr
1               5                   10                  15

Thr Ile Thr Ile Arg Trp Gln Leu Pro Gly Asp Ala Asn Gly Glu Val
            20                  25                  30

Pro Gly Phe Gln Val Asp Ala Val Pro Ala Asn Gly Gln Thr Pro Ile
        35                  40                  45

Gln Arg Thr Ile Asn Ala Asp Val Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 242
<211> LENGTH: 88
<212> TYPE: PRT
<213> ORGANISM: Artificial Sequence
<220> FEATURE:
<223> OTHER INFORMATION: Synthetic polypeptide 1637102_VGR2D08

<400> SEQUENCE: 242

Asn Val Ser Pro Pro Arg Arg Ala Arg Val Thr Asp Ala Thr Glu Thr
1               5                   10                  15

Thr Ile Thr Ile Arg Trp Thr Leu Ala Gly Pro Ile Ala Gly Phe Gln
            20                  25                  30

Val Asp Ala Val Pro Ala Asn Gly Gln Thr Pro Ile Gln Arg Thr Ile
        35                  40                  45

His Ala Asp Thr Ser Thr Tyr Thr Ile Thr Gly Leu Gln Pro Gly Thr
    50                  55                  60

Asp Tyr Lys Ile Tyr Leu Tyr Thr Leu Asn Asp Asn Ala Arg Ser Ser
65                  70                  75                  80

Pro Val Val Ile Asp Ala Ser Thr
                85
```

<210> SEQ ID NO 243
<211> LENGTH: 92
<212> TYPE: PRT
<213> ORGANISM: Artificial Sequence
<220> FEATURE:
<223> OTHER INFORMATION: Synthetic polypeptide 1637102_VGR2G05

<400> SEQUENCE: 243

Asn Val Ser Pro Pro Arg Arg Ala Arg Val Thr Asp Ala Thr Glu Thr
1               5                   10                  15

Thr Ile Thr Ile Arg Trp Lys Leu Pro Ile Glu Ala Asp Gly Ile Val
            20                  25                  30

Pro Ser Phe Gln Val Asp Ala Val Pro Ala Asn Gly Gln Thr Pro Ile
        35                  40                  45

Gln Arg Thr Ile Gln Ala Asp Val Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 244
<211> LENGTH: 93
<212> TYPE: PRT
<213> ORGANISM: Artificial Sequence
<220> FEATURE:
<223> OTHER INFORMATION: Synthetic polypeptide 1637102_VGR2D04

<400> SEQUENCE: 244

Asn Val Ser Pro Pro Arg Arg Ala Arg Val Thr Asp Ala Thr Glu Thr
1               5                   10                  15

Thr Ile Thr Ile Arg Trp Arg Ala Pro Glu Ala Asn Gly Gly Ser Ala
            20                  25                  30

Val Pro Gly Phe Gln Val Asp Ala Val Pro Ala Asn Gly Gln Thr Pro
        35                  40                  45

Ile Gln Arg Thr Ile Asn Ala Asp Thr Ser Thr Tyr Thr Ile Thr Gly
    50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90

<210> SEQ ID NO 245
<211> LENGTH: 92
<212> TYPE: PRT
<213> ORGANISM: Artificial Sequence
<220> FEATURE:
<223> OTHER INFORMATION: Synthetic polypeptide 1637102_VGR2F01

<400> SEQUENCE: 245

Asn Val Ser Pro Pro Arg Arg Ala Arg Val Thr Asp Ala Thr Glu Thr
1               5                   10                  15

Thr Ile Thr Ile Arg Trp Lys Val Pro Val His Arg Asn Ser Thr Leu
            20                  25                  30

Ile Ser Phe Gln Val Asp Ala Val Pro Ala Asn Gly Gln Thr Pro Ile
        35                  40                  45

Gln Arg Thr Ile Asn Ala Thr Thr Asn Val Tyr Thr Ile Thr Gly Leu
    50                  55                  60

-continued

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 246
<211> LENGTH: 89
<212> TYPE: PRT
<213> ORGANISM: Artificial Sequence
<220> FEATURE:
<223> OTHER INFORMATION: Synthetic polypeptide 1637102_VGR2C09

<400> SEQUENCE: 246

Asn Val Ser Pro Pro Arg Arg Ala Arg Val Thr Asp Ala Thr Glu Thr
1               5                   10                  15

Thr Ile Thr Ile Arg Trp Glu Arg Ala Gln Gly Glu Val Asp Gly Phe
            20                  25                  30

Gln Val Asp Ala Val Pro Ala Asn Gly Gln Thr Pro Ile Gln Arg Thr
        35                  40                  45

Ile His Ala Asp Thr Asn Val Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 247
<211> LENGTH: 88
<212> TYPE: PRT
<213> ORGANISM: Artificial Sequence
<220> FEATURE:
<223> OTHER INFORMATION: Synthetic polypeptide 1637102_VGR2B01

<400> SEQUENCE: 247

Asn Val Ser Pro Pro Arg Arg Ala Arg Val Thr Asp Ala Thr Glu Thr
1               5                   10                  15

Thr Ile Thr Ile Arg Trp Thr Arg Ala Pro Ser Gln Asp Gly Phe Gln
            20                  25                  30

Val Asp Ala Val Pro Ala Asn Gly Gln Thr Pro Ile Gln Arg Thr Ile
        35                  40                  45

Asn Ala Asp Thr Thr Val Tyr Thr Ile Thr Gly Leu Gln Pro Gly Thr
    50                  55                  60

Asp Tyr Lys Ile Tyr Leu Tyr Thr Leu Asn Asp Asn Ala Arg Ser Ser
65                  70                  75                  80

Pro Val Val Ile Asp Ala Ser Thr
                85

<210> SEQ ID NO 248
<211> LENGTH: 92
<212> TYPE: PRT
<213> ORGANISM: Artificial Sequence
<220> FEATURE:
<223> OTHER INFORMATION: Synthetic polypeptide 1637102_VGR2H03

<400> SEQUENCE: 248

Asn Val Ser Pro Pro Arg Arg Ala Arg Val Thr Asp Ala Thr Glu Thr
1               5                   10                  15

Thr Ile Thr Ile Arg Trp Thr Leu Pro Val Gln Ala Asn Gly Ile Val
            20                  25                  30

Pro Gly Phe Gln Val Asp Ala Val Pro Ala Asn Gly Gln Thr Pro Ile 35                  40                  45

Gln Arg Thr Ile His Ala Asp Val Ser Thr Tyr Thr Ile Thr Gly Leu
 50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 249
<211> LENGTH: 93
<212> TYPE: PRT
<213> ORGANISM: Artificial Sequence
<220> FEATURE:
<223> OTHER INFORMATION: Synthetic polypeptide 1637102_VGR2E08

<400> SEQUENCE: 249

Asn Val Ser Pro Pro Arg Arg Ala Arg Val Thr Asp Ala Thr Glu Thr
1               5                   10                  15

Thr Ile Thr Ile Arg Trp Gly Ala Pro Glu Asp Asp Gly Gly Gly Thr
                20                  25                  30

Val Pro Gly Phe Gln Val Asp Ala Val Pro Ala Asn Gly Gln Thr Pro
                35                  40                  45

Ile Gln Arg Thr Ile Asn Ala Asp Thr Ser Tyr Thr Ile Thr Gly
 50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90

<210> SEQ ID NO 250
<211> LENGTH: 92
<212> TYPE: PRT
<213> ORGANISM: Artificial Sequence
<220> FEATURE:
<223> OTHER INFORMATION: Synthetic polypeptide 1637102_VGR2A09

<400> SEQUENCE: 250

Asn Val Ser Pro Pro Arg Arg Ala Arg Val Thr Asp Ala Thr Glu Thr
1               5                   10                  15

Thr Ile Thr Ile Arg Trp Glu Leu Pro Ile Lys Ala Ser Ser Ile Ile
                20                  25                  30

Pro Ser Phe Gln Val Asp Ala Val Pro Ala Asn Gly Gln Thr Pro Ile
                35                  40                  45

Gln Arg Thr Ile Gln Ala Asp Val Ser Thr Tyr Thr Ile Thr Gly Leu
 50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 251
<211> LENGTH: 93
<212> TYPE: PRT
<213> ORGANISM: Artificial Sequence
<220> FEATURE:
<223> OTHER INFORMATION: Synthetic polypeptide 1637102_VGR2A05

<400> SEQUENCE: 251

Asn Val Ser Pro Pro Arg Arg Ala Arg Val Thr Asp Ala Thr Glu Thr
1               5                   10                  15

```
Thr Ile Thr Ile Arg Trp Asn Thr Pro Glu Asn Asp Gly Gly Gly Thr
            20                  25                  30

Val Pro Gly Phe Gln Val Asp Ala Val Pro Ala Asn Gly Gln Thr Pro
        35                  40                  45

Ile Gln Arg Thr Ile Asn Ala Asp Val Ser Thr Tyr Thr Ile Thr Gly
 50                  55                  60

Leu Gln Pro Gly Thr Asp Tyr Lys Ile Tyr Leu Tyr Thr Leu Asn Asp
 65                  70                  75                  80

Asn Ala Arg Ser Ser Pro Val Val Ile Asp Ala Ser Thr
                 85                  90

<210> SEQ ID NO 252
<211> LENGTH: 92
<212> TYPE: PRT
<213> ORGANISM: Artificial Sequence
<220> FEATURE:
<223> OTHER INFORMATION: Synthetic polypeptide 1637102_VGR2F07

<400> SEQUENCE: 252

Asn Val Ser Pro Pro Arg Arg Ala Arg Val Thr Asp Ala Thr Glu Thr
 1               5                  10                  15

Thr Ile Thr Ile Arg Trp Thr Leu Gly Asp Gln Val Ser Ser Ala Ile
            20                  25                  30

Pro Gly Phe Gln Val Asp Ala Val Pro Ala Asn Gly Gln Thr Pro Ile
        35                  40                  45

Gln Arg Thr Ile Asn Ala Asp Val Ser Thr Tyr Thr Ile Thr Gly Leu
 50                  55                  60

Gln Pro Gly Thr Asp Tyr Lys Ile Tyr Leu Tyr Thr Leu Asn Asp Asn
 65                  70                  75                  80

Ala Arg Ser Ser Pro Val Val Ile Asp Ala Ser Thr
                 85                  90

<210> SEQ ID NO 253
<211> LENGTH: 93
<212> TYPE: PRT
<213> ORGANISM: Artificial Sequence
<220> FEATURE:
<223> OTHER INFORMATION: Synthetic polypeptide 1637102_VGR2D05

<400> SEQUENCE: 253

Asn Val Ser Pro Pro Arg Arg Ala Arg Val Thr Asp Ala Thr Glu Thr
 1               5                  10                  15

Thr Ile Thr Ile Arg Trp Arg Thr Pro Ala Asp Asn Gly Gly Gly Gly
            20                  25                  30

Ile Pro Ser Phe Gln Val Asp Ala Val Pro Val Asn Gly Gln Thr Pro
        35                  40                  45

Ile Gln Arg Thr Ile Asn Ala Asp Ile Ser Thr Tyr Thr Ile Thr Gly
 50                  55                  60

Leu Gln Pro Gly Thr Asp Tyr Lys Ile Tyr Leu Tyr Thr Leu Asn Asp
 65                  70                  75                  80

Asn Ala Arg Ser Ser Pro Val Val Ile Asp Ala Ser Thr
                 85                  90

<210> SEQ ID NO 254
<211> LENGTH: 89
<212> TYPE: PRT
<213> ORGANISM: Artificial Sequence
<220> FEATURE:
<223> OTHER INFORMATION: Synthetic polypeptide 1637102_VGR2G08
```

-continued

<400> SEQUENCE: 254

Asn Val Ser Pro Pro Arg Arg Ala Arg Val Thr Asp Ala Thr Glu Thr
1               5                   10                  15

Thr Ile Thr Ile Arg Trp Glu Arg Ala Ala Gly Glu Phe Ala Gly Phe
            20                  25                  30

Gln Val Asp Ala Val Pro Ala Asn Gly Gln Thr Pro Ile Gln Arg Thr
        35                  40                  45

Ile His Ala Asp Thr Asn Ile Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 255
<211> LENGTH: 93
<212> TYPE: PRT
<213> ORGANISM: Artificial Sequence
<220> FEATURE:
<223> OTHER INFORMATION: Synthetic polypeptide 1637102_VGR2C04

<400> SEQUENCE: 255

Asn Val Ser Pro Pro Arg Arg Ala Arg Val Thr Asp Ala Thr Glu Thr
1               5                   10                  15

Thr Ile Thr Ile Arg Trp Arg Thr Pro Ile Asp Ala Gly Gly Gly Gln
            20                  25                  30

Val Pro Ser Phe Gln Val Asp Ala Val Pro Ala Asn Gly Gln Thr Pro
        35                  40                  45

Ile Gln Arg Thr Ile Asn Ala Asp Val Ser Thr Tyr Thr Ile Thr Gly
    50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90

<210> SEQ ID NO 256
<211> LENGTH: 92
<212> TYPE: PRT
<213> ORGANISM: Artificial Sequence
<220> FEATURE:
<223> OTHER INFORMATION: Synthetic polypeptide 1637102_VGR2B07

<400> SEQUENCE: 256

Asn Val Ser Pro Pro Arg Arg Ala Arg Val Thr Asp Ala Thr Glu Thr
1               5                   10                  15

Thr Ile Thr Ile Arg Trp Lys Leu Pro Ile Gly Arg Gly Ser Glu Ile
            20                  25                  30

Pro Gly Phe Gln Val Asp Ala Val Pro Ala Asn Gly Gln Thr Pro Ile
        35                  40                  45

Gln Arg Thr Ile Asn Ala Asp Val Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 257

```
<211> LENGTH: 92
<212> TYPE: PRT
<213> ORGANISM: Artificial Sequence
<220> FEATURE:
<223> OTHER INFORMATION: Synthetic polypeptide 1637102_VGR2H02

<400> SEQUENCE: 257

Asn Val Ser Pro Pro Arg Arg Ala Arg Val Thr Asp Ala Thr Glu Thr
1               5                   10                  15

Thr Ile Thr Ile Arg Trp Ala Leu Gly Val Asp Ala Ser Ser Val Ile
            20                  25                  30

Pro Gly Phe Gln Val Asp Ala Val Pro Ala Asn Gly Gln Thr Pro Ile
        35                  40                  45

Gln Arg Thr Ile Asn Ala Asp Val Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 258
<211> LENGTH: 92
<212> TYPE: PRT
<213> ORGANISM: Artificial Sequence
<220> FEATURE:
<223> OTHER INFORMATION: Synthetic polypeptide 1637102_VGR2A07

<400> SEQUENCE: 258

Asn Val Ser Pro Pro Arg Arg Ala Arg Val Thr Asp Ala Thr Glu Thr
1               5                   10                  15

Thr Ile Thr Ile Arg Trp Gln Leu Pro Ile Lys Ala Ser Ser Glu Val
            20                  25                  30

Pro Gly Phe Gln Val Asp Ala Val Pro Ala Asn Gly Gln Thr Pro Ile
        35                  40                  45

Gln Arg Thr Ile Asn Ala Asp Val Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 259
<211> LENGTH: 92
<212> TYPE: PRT
<213> ORGANISM: Artificial Sequence
<220> FEATURE:
<223> OTHER INFORMATION: Synthetic polypeptide 1637102_VGR2A08

<400> SEQUENCE: 259

Asn Val Ser Pro Pro Arg Arg Ala Arg Val Thr Asp Ala Thr Glu Thr
1               5                   10                  15

Thr Ile Thr Ile Arg Trp Lys Val Pro Ile Gln Arg Asp Ser Ile Val
            20                  25                  30

Pro Gly Phe Gln Val Asp Ala Val Pro Ala Asn Gly Gln Thr Pro Ile
        35                  40                  45

Gln Arg Thr Ile Asn Ala Asp Thr Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80
```

```
Ala Arg Ser Ser Pro Val Val Ile Asp Ala Ser Thr
                85                  90
```

<210> SEQ ID NO 260
<211> LENGTH: 92
<212> TYPE: PRT
<213> ORGANISM: Artificial Sequence
<220> FEATURE:
<223> OTHER INFORMATION: Synthetic polypeptide 1637102_VGR2F05

<400> SEQUENCE: 260

```
Asn Val Ser Pro Pro Arg Arg Ala Arg Val Thr Asp Ala Thr Glu Thr
1               5                   10                  15

Thr Ile Thr Ile Arg Trp Gln Val Gly Val Asp Ala Asp Ser Pro Ile
            20                  25                  30

Pro Ser Phe Gln Val Asp Ala Val Pro Ala Asn Gly Gln Thr Pro Ile
        35                  40                  45

Gln Arg Thr Ile His Ala Asp Ile Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90
```

<210> SEQ ID NO 261
<211> LENGTH: 92
<212> TYPE: PRT
<213> ORGANISM: Artificial Sequence
<220> FEATURE:
<223> OTHER INFORMATION: Synthetic polypeptide 1637102_VGR2C03

<400> SEQUENCE: 261

```
Asn Val Ser Pro Pro Arg Arg Ala Arg Val Thr Asp Ala Thr Glu Thr
1               5                   10                  15

Thr Ile Thr Ile Arg Trp Lys Leu Pro Ile Lys Pro Asn Ser Thr Ile
            20                  25                  30

Pro Ser Phe Gln Val Asp Ala Val Pro Ala Asn Gly Gln Thr Pro Ile
        35                  40                  45

Gln Arg Thr Ile His Ala Asp Val Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90
```

<210> SEQ ID NO 262
<211> LENGTH: 92
<212> TYPE: PRT
<213> ORGANISM: Artificial Sequence
<220> FEATURE:
<223> OTHER INFORMATION: Synthetic polypeptide 1637102_VGR2C05

<400> SEQUENCE: 262

```
Asn Val Ser Pro Pro Arg Arg Ala Arg Val Thr Asp Ala Thr Glu Thr
1               5                   10                  15

Thr Ile Thr Ile Arg Trp Gln Gln Pro Ile Arg Ala Ser Gly Glu Leu
            20                  25                  30

Pro Gly Phe Gln Val Asp Ala Val Pro Ala Asn Gly Gln Thr Pro Ile
        35                  40                  45

Gln Arg Thr Ile Asn Ala Asp Thr Asn Ile Tyr Thr Ile Thr Gly Leu
```

```
                50                  55                  60
Gln Pro Gly Thr Asp Tyr Lys Ile Tyr Leu Tyr Thr Leu Asn Asp Asn
 65                  70                  75                  80

Ala Arg Ser Ser Pro Val Val Ile Asp Ala Ser Thr
                 85                  90
```

<210> SEQ ID NO 263
<211> LENGTH: 92
<212> TYPE: PRT
<213> ORGANISM: Artificial Sequence
<220> FEATURE:
<223> OTHER INFORMATION: Synthetic polypeptide 1637102_VGR2D03

<400> SEQUENCE: 263

```
Asn Val Ser Pro Pro Arg Arg Ala Arg Val Thr Asp Ala Thr Glu Thr
 1               5                  10                  15

Thr Ile Thr Ile Arg Trp Thr Val Pro Val His Arg Asp Ser Glu Ile
                 20                  25                  30

Ile Ser Phe Gln Val Asp Ala Val Pro Ala Asn Gly Gln Thr Pro Ile
             35                  40                  45

Gln Arg Thr Ile Asn Ala Thr Thr Asn Val Tyr Thr Ile Thr Gly Leu
     50                  55                  60

Gln Pro Gly Thr Asp Tyr Lys Ile Tyr Leu Tyr Thr Leu Asn Asp Asn
 65                  70                  75                  80

Ala Arg Ser Ser Pro Val Val Ile Asp Ala Ser Thr
                 85                  90
```

<210> SEQ ID NO 264
<211> LENGTH: 89
<212> TYPE: PRT
<213> ORGANISM: Artificial Sequence
<220> FEATURE:
<223> OTHER INFORMATION: Synthetic polypeptide 1637102_VGR2G09

<400> SEQUENCE: 264

```
Asn Val Ser Pro Pro Arg Arg Ala Arg Val Thr Asp Ala Thr Glu Thr
 1               5                  10                  15

Thr Ile Thr Ile Arg Trp Glu Arg Ala Pro Gly Glu Val Asp Gly Phe
                 20                  25                  30

Gln Val Asp Ala Val Pro Ala Asn Gly Gln Thr Pro Ile Gln Arg Thr
             35                  40                  45

Ile Asn Ala Asp Thr Asn Ile Tyr Thr Ile Thr Gly Leu Gln Pro Gly
     50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                 85
```

<210> SEQ ID NO 265
<211> LENGTH: 93
<212> TYPE: PRT
<213> ORGANISM: Artificial Sequence
<220> FEATURE:
<223> OTHER INFORMATION: Synthetic polypeptide 1637102_VGR2C08

<400> SEQUENCE: 265

```
Asn Val Ser Pro Pro Arg Arg Ala Arg Val Thr Asp Ala Thr Glu Thr
 1               5                  10                  15

Thr Ile Thr Ile Arg Trp Glu Thr Pro Glu Tyr Asn Gly Gly Thr Ala
                 20                  25                  30
```

```
Ile Pro Gly Phe Gln Val Asp Ala Val Pro Ala Asn Gly Gln Thr Pro
        35                  40                  45

Ile Gln Arg Thr Ile Asn Ala Asp Ile Ser Thr Tyr Thr Ile Thr Gly
 50                  55                  60

Leu Gln Pro Gly Thr Asp Tyr Lys Ile Tyr Leu Tyr Thr Leu Asn Asp
 65                  70                  75                  80

Asn Ala Arg Ser Ser Pro Val Val Ile Asp Ala Ser Thr
                 85                  90
```

<210> SEQ ID NO 266
<211> LENGTH: 89
<212> TYPE: PRT
<213> ORGANISM: Artificial Sequence
<220> FEATURE:
<223> OTHER INFORMATION: Synthetic polypeptide 1637102_VGR2E07

<400> SEQUENCE: 266

```
Asn Val Ser Pro Pro Arg Arg Ala Arg Val Thr Asp Ala Thr Glu Thr
 1               5                  10                  15

Thr Ile Thr Ile Arg Trp Ala Val Ser Gln Ser Ala Phe Asp Ser Phe
                 20                  25                  30

Gln Val Asp Ala Val Pro Ala Asn Gly Gln Thr Pro Ile Gln Arg Thr
        35                  40                  45

Ile His Ala Thr Thr Ser Thr Tyr Thr Ile Thr Gly Leu Gln Pro Gly
 50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                 85
```

<210> SEQ ID NO 267
<211> LENGTH: 92
<212> TYPE: PRT
<213> ORGANISM: Artificial Sequence
<220> FEATURE:
<223> OTHER INFORMATION: Synthetic polypeptide 1637102_VGR2E04

<400> SEQUENCE: 267

```
Asn Val Ser Pro Pro Arg Arg Ala Arg Val Thr Asp Ala Thr Glu Thr
 1               5                  10                  15

Thr Ile Thr Ile Arg Trp Glu Leu Pro Ile Glu Ala Ser Gly Leu Val
                 20                  25                  30

Pro Gly Phe Gln Val Asp Ala Val Pro Ala Asn Gly Gln Thr Pro Ile
        35                  40                  45

Gln Arg Thr Ile Asn Ala Asp Thr Ser Thr Tyr Thr Ile Thr Gly Leu
 50                  55                  60

Gln Pro Gly Thr Asp Tyr Lys Ile Tyr Leu Tyr Thr Leu Asn Asp Asn
 65                  70                  75                  80

Ala Arg Ser Ser Pro Val Val Ile Asp Ala Ser Thr
                 85                  90
```

<210> SEQ ID NO 268
<211> LENGTH: 93
<212> TYPE: PRT
<213> ORGANISM: Artificial Sequence
<220> FEATURE:
<223> OTHER INFORMATION: Synthetic polypeptide 1637102_VGR2H07

<400> SEQUENCE: 268

Asn Val Ser Pro Pro Arg Arg Ala Arg Val Thr Asp Ala Thr Glu Thr
1               5                   10                  15

Thr Ile Thr Ile Arg Trp Gly Ala Pro Glu Leu Asp Gly Gly Ser Gly
                20                  25                  30

Ile Pro Ser Phe Gln Val Asp Ala Val Pro Ala Asn Gly Gln Thr Pro
                35                  40                  45

Ile Gln Arg Thr Ile Asn Ala Asp Ile Ser Tyr Thr Ile Thr Gly
        50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90

<210> SEQ ID NO 269
<211> LENGTH: 93
<212> TYPE: PRT
<213> ORGANISM: Artificial Sequence
<220> FEATURE:
<223> OTHER INFORMATION: Synthetic polypeptide 1637102_VGR2F03

<400> SEQUENCE: 269

Asn Val Ser Pro Pro Arg Ser Ala Arg Val Thr Asp Ala Thr Glu Thr
1               5                   10                  15

Thr Ile Thr Ile Arg Trp Asp Thr Pro Gly Asp Ala Gly Gly Ser Gly
                20                  25                  30

Ile Pro Ser Phe Gln Val Asp Ala Val Pro Ala Asn Gly Gln Thr Pro
                35                  40                  45

Ile Gln Arg Thr Ile Asn Ala Asp Val Ser Thr Tyr Thr Ile Thr Gly
        50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90

<210> SEQ ID NO 270
<211> LENGTH: 89
<212> TYPE: PRT
<213> ORGANISM: Artificial Sequence
<220> FEATURE:
<223> OTHER INFORMATION: Synthetic polypeptide 1637102_VGR2F11

<400> SEQUENCE: 270

Asn Val Ser Pro Pro Arg Arg Ala Arg Val Thr Asp Ala Thr Glu Thr
1               5                   10                  15

Thr Ile Thr Ile Arg Trp Thr Arg Ala Ala Gly Glu Val Asp Gly Phe
                20                  25                  30

Gln Val Asp Ala Val Pro Ala Asn Gly Gln Thr Pro Ile Gln Arg Thr
                35                  40                  45

Ile Asn Ala Asp Thr Asn Thr Tyr Thr Ile Thr Gly Leu Gln Pro Gly
        50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 271
<211> LENGTH: 93
<212> TYPE: PRT
<213> ORGANISM: Artificial Sequence
<220> FEATURE:
<223> OTHER INFORMATION: Synthetic polypeptide 1637102_VGR2H05

<400> SEQUENCE: 271

Asn Val Ser Pro Pro Arg Arg Ala Arg Val Thr Asp Ala Thr Glu Thr
1               5                   10                  15

Thr Ile Thr Ile Arg Trp Gly Gln Pro Arg Tyr Asn Gly Gly Ser Thr
            20                  25                  30

Val Pro Ser Phe Gln Val Asp Ala Val Pro Ala Asn Gly Gln Thr Pro
        35                  40                  45

Ile Gln Arg Thr Ile Asn Ala Asp Ile Ser Tyr Thr Ile Thr Gly
    50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90

<210> SEQ ID NO 272
<211> LENGTH: 89
<212> TYPE: PRT
<213> ORGANISM: Artificial Sequence
<220> FEATURE:
<223> OTHER INFORMATION: Synthetic polypeptide 1637102_VGR2F02

<400> SEQUENCE: 272

Asn Val Ser Pro Pro Arg Ser Ala Arg Val Thr Asp Ala Thr Glu Thr
1               5                   10                  15

Thr Ile Thr Ile Arg Trp Thr Arg Ala Arg Ser Glu Val Ile Gly Phe
            20                  25                  30

Gln Val Asp Ala Val Pro Ala Asn Gly Gln Thr Pro Ile Gln Arg Thr
        35                  40                  45

Ile Asn Ala Asp Thr Asn Ile Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 273
<211> LENGTH: 89
<212> TYPE: PRT
<213> ORGANISM: Artificial Sequence
<220> FEATURE:
<223> OTHER INFORMATION: Synthetic polypeptide 1637103_VGR2H03

<400> SEQUENCE: 273

Asn Val Ser Pro Pro Arg Arg Ala Arg Val Thr Asp Ala Thr Glu Thr
1               5                   10                  15

Thr Ile Thr Ile Arg Trp Arg Val Ala Gly Ser Glu Phe Asp Ser Phe
            20                  25                  30

Gln Val Asp Ala Val Pro Ala Asn Gly Gln Thr Pro Ile Gln Arg Thr
        35                  40                  45

Ile His Ala Ala Thr Thr Thr Tyr Thr Ile Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

```
<210> SEQ ID NO 274
<211> LENGTH: 89
<212> TYPE: PRT
<213> ORGANISM: Artificial Sequence
<220> FEATURE:
<223> OTHER INFORMATION: Synthetic polypeptide 1637103_VGR2E12

<400> SEQUENCE: 274

Asn Val Ser Pro Pro Arg Arg Ala Arg Val Thr Asp Ala Thr Glu Thr
1               5                   10                  15

Thr Ile Thr Ile Arg Trp Lys Val Ala Gly Gly Thr Phe Asp Ser Phe
            20                  25                  30

Gln Val Asp Ala Val Pro Ala Asn Gly Gln Thr Pro Ile Gln Arg Thr
        35                  40                  45

Ile Asn Ala Ala Thr Thr Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 275
<211> LENGTH: 89
<212> TYPE: PRT
<213> ORGANISM: Artificial Sequence
<220> FEATURE:
<223> OTHER INFORMATION: Synthetic polypeptide 1637103_VGR2F12

<400> SEQUENCE: 275

Asn Val Ser Pro Pro Arg His Ala Arg Val Thr Asp Ala Thr Glu Thr
1               5                   10                  15

Thr Ile Thr Ile Arg Trp Arg Val Ala Gly Ser Glu Phe Asp Ser Phe
            20                  25                  30

Gln Val Asp Ala Val Pro Ala Asn Gly Gln Thr Pro Ile Gln Arg Thr
        35                  40                  45

Ile His Ala Ala Thr Thr Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 276
<211> LENGTH: 89
<212> TYPE: PRT
<213> ORGANISM: Artificial Sequence
<220> FEATURE:
<223> OTHER INFORMATION: Synthetic polypeptide 1637103_VGR2H07

<400> SEQUENCE: 276

Asn Val Ser Pro Pro Arg His Ala Arg Val Thr Asp Ala Thr Glu Thr
1               5                   10                  15

Thr Ile Thr Ile Arg Trp Lys Val Ala Gly Gly Thr Phe Asp Ser Phe
            20                  25                  30

Gln Val Asp Ala Val Pro Ala Asn Gly Gln Thr Pro Ile Gln Arg Thr
        35                  40                  45

Ile Asn Ala Ala Thr Thr Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
```

```
65                  70                  75                  80

Ser Pro Val Val Ile Asp Ala Ser Thr
                85

<210> SEQ ID NO 277
<211> LENGTH: 89
<212> TYPE: PRT
<213> ORGANISM: Artificial Sequence
<220> FEATURE:
<223> OTHER INFORMATION: Synthetic polypeptide 1637103_VGR2H11

<400> SEQUENCE: 277

Asn Val Ser Pro Pro Arg Arg Ala Arg Val Thr Asp Ala Thr Glu Thr
1               5                   10                  15

Thr Ile Thr Ile Arg Trp Lys Val Ala Gly Ser Glu Phe Asp Ser Phe
                20                  25                  30

Gln Val Asp Ala Val Pro Ala Asn Gly Gln Thr Pro Ile Gln Arg Thr
            35                  40                  45

Ile His Ala Ala Thr Thr Thr Tyr Thr Ile Thr Gly Leu Gln Pro Gly
        50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 278
<211> LENGTH: 89
<212> TYPE: PRT
<213> ORGANISM: Artificial Sequence
<220> FEATURE:
<223> OTHER INFORMATION: Synthetic polypeptide 1637103_VGR2B09

<400> SEQUENCE: 278

Asn Val Ser Pro Pro Arg Cys Ala Arg Val Thr Asp Ala Thr Glu Thr
1               5                   10                  15

Thr Ile Thr Ile Arg Trp Arg Val Ala Gly Ser Glu Phe Asp Ser Phe
                20                  25                  30

Gln Val Asp Ala Val Pro Ala Asn Gly Gln Thr Pro Ile Gln Arg Thr
            35                  40                  45

Ile His Ala Ala Thr Thr Thr Tyr Thr Ile Thr Gly Leu Gln Pro Gly
        50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 279
<211> LENGTH: 89
<212> TYPE: PRT
<213> ORGANISM: Artificial Sequence
<220> FEATURE:
<223> OTHER INFORMATION: Synthetic polypeptide 1637103_VGR2D06

<400> SEQUENCE: 279

Asn Val Ser Pro Pro Arg His Ala Arg Val Thr Asp Ala Thr Glu Thr
1               5                   10                  15

Thr Ile Thr Ile Arg Trp Thr Val Ala Glu Ser Thr Phe Asp Ser Phe
                20                  25                  30

Gln Val Asp Ala Val Pro Ala Asn Gly Gln Thr Pro Ile Gln Arg Thr
            35                  40                  45
```

```
Ile His Ala Ala Thr Thr Thr Tyr Thr Ile Thr Gly Leu Gln Pro Gly
            50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                85

<210> SEQ ID NO 280
<211> LENGTH: 89
<212> TYPE: PRT
<213> ORGANISM: Artificial Sequence
<220> FEATURE:
<223> OTHER INFORMATION: Synthetic polypeptide 1637104_VGR2G07

<400> SEQUENCE: 280

Asn Val Ser Pro Pro Arg Ser Ala Arg Val Thr Asp Ala Thr Glu Thr
 1               5                  10                  15

Thr Ile Thr Ile Arg Trp Lys Val Ala Gly Gly Thr Phe Asp Ser Phe
            20                  25                  30

Gln Val Asp Ala Val Pro Ala Asn Gly Gln Thr Pro Ile Gln Arg Thr
        35                  40                  45

Ile Asn Ala Ala Thr Thr Thr Tyr Thr Ile Thr Gly Leu Gln Pro Gly
            50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                85

<210> SEQ ID NO 281
<211> LENGTH: 89
<212> TYPE: PRT
<213> ORGANISM: Artificial Sequence
<220> FEATURE:
<223> OTHER INFORMATION: Synthetic polypeptide 1637104_VGR2G12
<220> FEATURE:
<221> NAME/KEY: misc_feature
<222> LOCATION: (80)..(80)
<223> OTHER INFORMATION: Xaa can be any naturally occurring amino acid

<400> SEQUENCE: 281

Asn Val Ser Pro Pro Arg Arg Ala Arg Val Thr Asp Ala Thr Glu Thr
 1               5                  10                  15

Thr Ile Thr Ile Arg Trp Arg Val Ala Gly Ser Glu Phe Asp Ser Phe
            20                  25                  30

Gln Val Asp Ala Val Pro Ala Asn Gly Gln Thr Pro Ile Gln Arg Thr
        35                  40                  45

Ile His Ala Ala Thr Thr Thr Tyr Thr Ile Thr Gly Leu Gln Pro Gly
            50                  55                  60

Thr Asp Tyr Lys Ile Tyr Leu Tyr Thr Leu Asn Asp Asn Ala Arg Xaa
 65                  70                  75                  80

Ser Pro Val Val Ile Asp Ala Ser Thr
                85

<210> SEQ ID NO 282
<211> LENGTH: 89
<212> TYPE: PRT
<213> ORGANISM: Artificial Sequence
<220> FEATURE:
<223> OTHER INFORMATION: Synthetic polypeptide 1637104_VGR2H12

<400> SEQUENCE: 282
```

-continued

```
Asn Val Ser Pro Pro Arg Arg Ala Arg Val Thr Asp Ala Thr Glu Thr
1               5                   10                  15

Thr Ile Thr Ile Arg Trp Arg Val Ala Gly Ser Glu Phe Asp Ser Phe
            20                  25                  30

Gln Val Asp Ala Val Pro Ala Asn Gly Gln Thr Pro Ile Gln Arg Thr
        35                  40                  45

Ile His Ala Ala Thr Thr Thr Tyr Thr Ile Thr Gly Leu Gln Pro Gly
    50                  55                  60

Thr Tyr Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 283
<211> LENGTH: 89
<212> TYPE: PRT
<213> ORGANISM: Artificial Sequence
<220> FEATURE:
<223> OTHER INFORMATION: Synthetic polypeptide 1637104_VGR2B11

<400> SEQUENCE: 283

Asn Val Ser Pro Pro Arg Arg Ala Arg Val Thr Asp Ala Thr Glu Thr
1               5                   10                  15

Thr Ile Thr Ile Arg Trp Ala Val Ala Gly Ser Glu Phe Asp Ser Phe
            20                  25                  30

Gln Val Asp Ala Val Pro Ala Asn Gly Gln Thr Pro Ile Gln Arg Thr
        35                  40                  45

Ile His Ala Ala Thr Thr Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 284
<211> LENGTH: 89
<212> TYPE: PRT
<213> ORGANISM: Artificial Sequence
<220> FEATURE:
<223> OTHER INFORMATION: Synthetic polypeptide 1637104_VGR2H04
<220> FEATURE:
<221> NAME/KEY: misc_feature
<222> LOCATION: (26)..(26)
<223> OTHER INFORMATION: Xaa can be any naturally occurring amino acid

<400> SEQUENCE: 284

Asn Val Ser Pro Pro Arg Ser Ala Arg Val Thr Asp Ala Thr Glu Thr
1               5                   10                  15

Thr Ile Thr Ile Arg Trp Glu Arg Ser Xaa Gly Gln Phe Asp Gly Phe
            20                  25                  30

Gln Val Asp Ala Val Pro Ala Asn Gly Gln Thr Pro Ile Gln Arg Thr
        35                  40                  45

Ile Asn Ala Asp Thr Asn Val Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85
```

```
<210> SEQ ID NO 285
<211> LENGTH: 89
<212> TYPE: PRT
<213> ORGANISM: Artificial Sequence
<220> FEATURE:
<223> OTHER INFORMATION: Synthetic polypeptide 1637104_VGR2H06
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid

<400> SEQUENCE: 285

Asn Val Ser Pro Pro Arg Arg Ala Arg Val Thr Asp Ala Thr Glu Thr
1               5                   10                  15

Thr Ile Thr Ile Arg Trp Xaa Gly Ala Arg Ser Glu Phe Asp Xaa Phe
            20                  25                  30

Gln Val Asp Ala Val Pro Ala Asn Gly Gln Thr Pro Ile Gln Arg Thr
        35                  40                  45

Ile His Ala Ala Thr Thr Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 286
<211> LENGTH: 89
<212> TYPE: PRT
<213> ORGANISM: Artificial Sequence
<220> FEATURE:
<223> OTHER INFORMATION: Synthetic polypeptide 1637104_VGR2C12
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid

<400> SEQUENCE: 286

Asn Val Ser Pro Pro Arg Arg Ala Arg Val Thr Asp Ala Thr Glu Thr
1               5                   10                  15

Thr Ile Thr Ile Arg Trp Arg Val Ala Gly Ser Glu Phe Asp Ser Phe
            20                  25                  30

Gln Val Asp Ala Val Pro Ala Asn Gly Gln Thr Pro Ile Gln Arg Xaa
        35                  40                  45

Ile His Ala Ala Thr Thr Thr Tyr Thr Ile Thr Gly Leu Gln Pro Gly
    50                  55                  60

Thr Asp Tyr Lys Ile Xaa Leu Tyr Thr Leu Asn Asp Asn Ala Arg Ser
65                  70                  75                  80

Xaa Pro Val Val Ile Asp Ala Ser Thr
                85

<210> SEQ ID NO 287
<211> LENGTH: 89
```

<212> TYPE: PRT
<213> ORGANISM: Artificial Sequence
<220> FEATURE:
<223> OTHER INFORMATION: Synthetic polypeptide VC09GR2

<400> SEQUENCE: 287

Asn Val Ser Pro Pro Arg Arg Ala Arg Val Thr Asp Ala Thr Glu Thr
1               5                   10                  15

Thr Ile Thr Ile Arg Trp Glu Arg Ala Arg Ser Glu Val Asp Gly Phe
            20                  25                  30

Gln Val Asp Ala Val Pro Ala Asn Gly Gln Thr Pro Ile Gln Arg Thr
        35                  40                  45

Ile Asn Ala Asp Thr Asn Val Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 288
<211> LENGTH: 90
<212> TYPE: PRT
<213> ORGANISM: Artificial Sequence
<220> FEATURE:
<223> OTHER INFORMATION: Synthetic polypeptide 1637104_VGR2A06

<400> SEQUENCE: 288

Asn Val Ser Pro Pro Arg Arg Ala Arg Val Thr Asp Ala Thr Glu Thr
1               5                   10                  15

Thr Ile Thr Ile Ser Trp Arg Leu Pro Ala Gly Ala Val Ala Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Thr Arg Gly Arg Gly Gly
65                  70                  75                  80

Ser Ser Pro Val Val Ile Asp Ala Ser Thr
                85                  90

<210> SEQ ID NO 289
<211> LENGTH: 89
<212> TYPE: PRT
<213> ORGANISM: Artificial Sequence
<220> FEATURE:
<223> OTHER INFORMATION: Synthetic polypeptide 1637104_VGR2F11

<400> SEQUENCE: 289

Asn Val Ser Pro Pro Arg Ser Ala Arg Val Thr Asp Ala Thr Glu Thr
1               5                   10                  15

Thr Ile Thr Ile Arg Trp Thr Arg Ala Ala Gly Glu Val Asp Gly Phe
            20                  25                  30

Gln Val Asp Ala Val Pro Ala Asn Gly Gln Thr Pro Ile Gln Arg Thr
        35                  40                  45

Ile Asn Ala Asp Thr Asn Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr

<210> SEQ ID NO 290
<211> LENGTH: 89
<212> TYPE: PRT
<213> ORGANISM: Artificial Sequence
<220> FEATURE:
<223> OTHER INFORMATION: Synthetic polypeptide 1637104_VGR2D07

<400> SEQUENCE: 290

Asn Val Ser Pro Pro Arg His Ala Arg Val Thr Asp Ala Thr Glu Thr
1               5                   10                  15

Thr Ile Thr Ile Arg Trp Thr Val Ser Ala Ser Glu Phe Asp Ser Phe
            20                  25                  30

Gln Val Asp Ala Val Pro Ala Asn Gly Gln Thr Pro Ile Gln Arg Thr
        35                  40                  45

Ile His Ala Thr Thr Thr Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 291
<211> LENGTH: 89
<212> TYPE: PRT
<213> ORGANISM: Artificial Sequence
<220> FEATURE:
<223> OTHER INFORMATION: Synthetic polypeptide 1637104_VGR2C05

<400> SEQUENCE: 291

Asn Val Ser Pro Pro Arg Cys Ala Arg Val Thr Asp Ala Thr Glu Thr
1               5                   10                  15

Thr Ile Thr Ile Arg Trp Thr Arg Ala Ala Gly Glu Val Asp Gly Phe
            20                  25                  30

Gln Val Asp Ala Val Pro Ala Asn Gly Gln Thr Pro Ile Gln Arg Thr
        35                  40                  45

Ile Asn Ala Asp Thr Asn Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 292
<211> LENGTH: 89
<212> TYPE: PRT
<213> ORGANISM: Artificial Sequence
<220> FEATURE:
<223> OTHER INFORMATION: Synthetic polypeptide 1637104_VGR2E02

<400> SEQUENCE: 292

Asn Val Ser Pro Pro Arg Arg Ala Arg Val Thr Asp Ala Thr Glu Thr
1               5                   10                  15

Thr Ile Thr Ile Arg Trp Lys Val Ala Gly Gly Glu Phe Asp Ser Phe
            20                  25                  30

Gln Val Asp Ala Val Pro Ala Asn Gly Gln Thr Pro Ile Gln Arg Thr
        35                  40                  45

Ile His Ala Ala Thr Thr Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 293
<211> LENGTH: 89
<212> TYPE: PRT
<213> ORGANISM: Artificial Sequence
<220> FEATURE:
<223> OTHER INFORMATION: Synthetic polypeptide 1637104_VGR2D03

<400> SEQUENCE: 293

Asn Val Ser Pro Pro Arg Arg Ala Arg Val Thr Asp Ala Thr Glu Thr
1               5                   10                  15

Thr Ile Thr Ile Arg Trp Ala Arg Ala Pro Gly Pro Phe Asp Gly Phe
            20                  25                  30

Gln Val Asp Ala Val Pro Ala Asn Gly Gln Thr Pro Ile Gln Arg Thr
        35                  40                  45

Ile Asn Ala Asp Thr Asn Ile Tyr Thr Ile Thr Gly Leu Gln Pro Gly
    50                  55                  60

Thr Asp Tyr Lys Ile Tyr Leu Tyr Thr Phe Asn Asp Asn Ala Arg Ser
65                  70                  75                  80

Ser Pro Val Val Ile Asp Ala Ser Thr
                85

<210> SEQ ID NO 294
<211> LENGTH: 93
<212> TYPE: PRT
<213> ORGANISM: Artificial Sequence
<220> FEATURE:
<223> OTHER INFORMATION: Synthetic polypeptide 1637114_VGR2G05

<400> SEQUENCE: 294

Asn Val Ser Pro Pro Arg Arg Ala Arg Val Thr Asp Ala Thr Glu Thr
1               5                   10                  15

Thr Ile Thr Ile Arg Trp Ser Thr Pro Ala Tyr Ala Gly Gly Gly Glu
            20                  25                  30

Val Pro Ser Phe Gln Val Asp Ala Val Pro Ala Asn Gly Gln Thr Pro
        35                  40                  45

Ile Gln Arg Thr Ile Asn Ala Asp Val Ser Thr Tyr Thr Ile Thr Gly
    50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90

<210> SEQ ID NO 295
<211> LENGTH: 93
<212> TYPE: PRT
<213> ORGANISM: Artificial Sequence
<220> FEATURE:
<223> OTHER INFORMATION: Synthetic polypeptide 1637114_VGR2C11

<400> SEQUENCE: 295

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

```
Gln Val Asp Ala Val Pro Ala Asn Gly Gln Thr Pro Ile Gln Arg Thr
         35                  40                  45

Ile Thr Ala Asn Glu Arg Gly Tyr Thr Ile Thr Gly Leu Gln Pro Gly
 50                  55                  60

Thr Asp Tyr Lys Ile Tyr Leu Tyr Thr Leu Asn Asp Phe Gly Asp Ser
 65                  70                  75                  80

Lys Tyr Ala Gln Leu Thr Gly Val Ile Asp Ala Ser Thr
                 85                  90

<210> SEQ ID NO 296
<211> LENGTH: 92
<212> TYPE: PRT
<213> ORGANISM: Artificial Sequence
<220> FEATURE:
<223> OTHER INFORMATION: Synthetic polypeptide B05VGR2

<400> SEQUENCE: 296

Asn Val Ser Pro Pro Arg Arg Ala Arg Val Thr Asp Ala Thr Glu Thr
 1               5                  10                  15

Thr Ile Thr Ile Arg Trp Gln Leu Pro Ile Arg Ala Asp Ser Ala Ile
                 20                  25                  30

Pro Ser Phe Gln Val Asp Ala Val Pro Ala Asn Gly Gln Thr Pro Ile
             35                  40                  45

Gln Arg Thr Ile Asn Ala Asp Ile Ser Thr Tyr Thr Ile Thr Gly Leu
 50                  55                  60

Gln Pro Gly Thr Asp Tyr Lys Ile Tyr Leu Tyr Thr Leu Asn Asp Asn
 65                  70                  75                  80

Ala Arg Ser Ser Pro Val Val Ile Asp Ala Ser Thr
                 85                  90

<210> SEQ ID NO 297
<211> LENGTH: 93
<212> TYPE: PRT
<213> ORGANISM: Artificial Sequence
<220> FEATURE:
<223> OTHER INFORMATION: Synthetic polypeptide 1637114_VGR2E04

<400> SEQUENCE: 297

Asn Val Ser Pro Pro Arg Arg Ala Arg Val Thr Asp Ala Thr Glu Thr
 1               5                  10                  15

Thr Ile Thr Ile Arg Trp Arg Thr Pro Ala Asp Thr Gly Gly Ala Gly
                 20                  25                  30

Ile Pro Ser Phe Gln Val Asp Ala Val Pro Ala Asn Gly Gln Thr Pro
             35                  40                  45

Ile Gln Arg Thr Ile His Ala Asp Val Ser Tyr Thr Ile Thr Gly
 50                  55                  60

Leu Gln Pro Gly Thr Asp Tyr Lys Ile Tyr Leu Tyr Thr Leu Asn Asp
 65                  70                  75                  80

Asn Ala Arg Ser Ser Pro Val Val Ile Asp Ala Ser Thr
                 85                  90

<210> SEQ ID NO 298
<211> LENGTH: 92
<212> TYPE: PRT
<213> ORGANISM: Artificial Sequence
<220> FEATURE:
<223> OTHER INFORMATION: Synthetic polypeptide 1637114_VGR2B01

<400> SEQUENCE: 298

Asn Val Ser Pro Pro Arg Arg Ala Arg Val Thr Asp Ala Thr Glu Thr
```

```
                 1               5                   10                  15
               Thr Ile Thr Ile Arg Trp Ala Gln Gly Gly Asn Gly Ser Gly Val Ile
                                 20                  25                  30

Pro Ser Phe Gln Val Asp Ala Val Pro Ala Asn Gly Gln Thr Pro Ile
                                 35                  40                  45

Gln Arg Thr Ile Asn Ala Asp Val Ser Thr Tyr Thr Ile Thr Gly Leu
                                 50                  55                  60

Gln Pro Gly Thr Asp Tyr Lys Ile Tyr Leu Tyr Thr Leu Asn Asp Asn
               65                  70                  75                  80

Ala Arg Ser Ser Pro Val Val Ile Asp Ala Ser Thr
                                 85                  90

<210> SEQ ID NO 299
<211> LENGTH: 92
<212> TYPE: PRT
<213> ORGANISM: Artificial Sequence
<220> FEATURE:
<223> OTHER INFORMATION: Synthetic polypeptide 1637114_VGR2B02

<400> SEQUENCE: 299

Asn Val Ser Pro Pro Arg Arg Ala Arg Val Thr Asp Ala Thr Glu Thr
1               5                   10                  15

Thr Ile Thr Ile Arg Trp Glu Leu Gly Ser Asp Arg Asp Ser Glu Val
                 20                  25                  30

Pro Ser Phe Gln Val Asp Ala Val Pro Ala Asn Gly Gln Thr Pro Ile
                 35                  40                  45

Gln Arg Thr Ile Asn Ala Asp Ile Ser Thr Tyr Thr Ile Thr Gly Leu
                 50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                 85                  90

<210> SEQ ID NO 300
<211> LENGTH: 93
<212> TYPE: PRT
<213> ORGANISM: Artificial Sequence
<220> FEATURE:
<223> OTHER INFORMATION: Synthetic polypeptide 1637114_VGR2A06

<400> SEQUENCE: 300

Asn Val Ser Pro Pro Arg Arg Ala Arg Val Thr Asp Ala Thr Glu Thr
1               5                   10                  15

Thr Ile Thr Ile Arg Trp Lys Ala Pro Ile Asp Asn Gly Gly Ser Thr
                 20                  25                  30

Val Pro Gly Phe Gln Val Asp Ala Val Pro Ala Asn Gly Gln Thr Pro
                 35                  40                  45

Ile Gln Arg Thr Ile Asn Ala Asp Thr Ser Thr Tyr Thr Ile Thr Gly
                 50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                 85                  90

<210> SEQ ID NO 301
<211> LENGTH: 92
<212> TYPE: PRT
<213> ORGANISM: Artificial Sequence
<220> FEATURE:
```

<223> OTHER INFORMATION: Synthetic polypeptide 1637114_VGR2C06

<400> SEQUENCE: 301

Asn Val Ser Pro Pro Arg Arg Ala Arg Val Thr Asp Ala Thr Glu Thr
1               5                   10                  15

Thr Ile Thr Ile Arg Trp Glu Gln Pro Val His Pro Asn Ser Leu Ile
            20                  25                  30

Pro Ser Phe Gln Val Asp Ala Val Pro Ala Asn Gly Gln Thr Pro Ile
        35                  40                  45

Gln Arg Thr Ile Asn Ala Asp Val Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 302
<211> LENGTH: 92
<212> TYPE: PRT
<213> ORGANISM: Artificial Sequence
<220> FEATURE:
<223> OTHER INFORMATION: Synthetic polypeptide 1637114_VGR2C10

<400> SEQUENCE: 302

Asn Val Ser Pro Pro Arg Arg Ala Arg Val Thr Asp Ala Thr Glu Thr
1               5                   10                  15

Thr Ile Thr Ile Arg Trp Glu Val Pro Asn Lys Gly Gly Ser Gln Leu
            20                  25                  30

Leu Ser Phe Gln Val Asp Ala Val Pro Ala Asn Gly Gln Thr Pro Ile
        35                  40                  45

Gln Arg Thr Ile Asn Ala Thr Thr Asn Val Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 303
<211> LENGTH: 92
<212> TYPE: PRT
<213> ORGANISM: Artificial Sequence
<220> FEATURE:
<223> OTHER INFORMATION: Synthetic polypeptideH02 1637114_VGR2

<400> SEQUENCE: 303

Asn Val Ser Pro Pro Arg Arg Ala Arg Val Thr Asp Ala Thr Glu Thr
1               5                   10                  15

Thr Ile Thr Ile Arg Trp Thr Val Pro Glu Gly Gly Asp Ser Ile Val
            20                  25                  30

Pro Ser Phe Gln Val Asp Ala Val Pro Ala Asn Gly Gln Thr Pro Ile
        35                  40                  45

Gln Arg Thr Ile Asn Ala Asp Val Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 304
<211> LENGTH: 92
<212> TYPE: PRT
<213> ORGANISM: Artificial Sequence
<220> FEATURE:
<223> OTHER INFORMATION: Synthetic polypeptide 1637114_VGR2G01

<400> SEQUENCE: 304

Asn Val Ser Pro Pro Arg Arg Ala Arg Val Thr Asp Ala Thr Glu Thr
1               5                   10                  15

Thr Ile Thr Ile Arg Trp Ala Pro Gly Glu Glu Arg Gly Ser Val Val
            20                  25                  30

Pro Ser Phe Gln Val Asp Ala Val Pro Ala Asn Gly Gln Thr Pro Ile
        35                  40                  45

Gln Arg Thr Ile Asn Ala Asp Thr Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 305
<211> LENGTH: 92
<212> TYPE: PRT
<213> ORGANISM: Artificial Sequence
<220> FEATURE:
<223> OTHER INFORMATION: Synthetic polypeptide 1637114_VGR2A04

<400> SEQUENCE: 305

Asn Val Ser Pro Pro Arg Arg Ala Arg Val Thr Asp Ala Thr Glu Thr
1               5                   10                  15

Thr Ile Thr Ile Arg Trp Thr Val Pro Glu Glu Arg Asp Gly Val Ile
            20                  25                  30

Pro Gly Phe Gln Val Asp Ala Val Pro Ala Asn Gly Gln Thr Pro Ile
        35                  40                  45

Gln Arg Thr Ile Asn Ala Asp Ile Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 306
<211> LENGTH: 92
<212> TYPE: PRT
<213> ORGANISM: Artificial Sequence
<220> FEATURE:
<223> OTHER INFORMATION: Synthetic polypeptide 1637114_VGR2G02

<400> SEQUENCE: 306

Asn Val Ser Pro Pro Arg Arg Ala Arg Val Thr Asp Ala Thr Glu Thr
1               5                   10                  15

Thr Ile Thr Ile Arg Trp Gln Ala Pro Asp Asp Gly Asp Gly Val Val
            20                  25                  30

Pro Gly Phe Gln Val Asp Ala Val Pro Ala Asn Gly Gln Thr Pro Ile
        35                  40                  45

Gln Arg Thr Ile Asn Ala Asp Thr Asn Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
            85                  90

<210> SEQ ID NO 307
<211> LENGTH: 92
<212> TYPE: PRT
<213> ORGANISM: Artificial Sequence
<220> FEATURE:
<223> OTHER INFORMATION: Synthetic polypeptide 1637114_VGR2H03

<400> SEQUENCE: 307

Asn Val Ser Pro Pro Arg Arg Ala Arg Val Thr Asp Ala Thr Glu Thr
1               5                   10                  15

Thr Ile Thr Ile Arg Trp Thr Val Pro Val His Gly Ser Ser Val Ile
            20                  25                  30

Pro Ser Phe Gln Val Asp Ala Val Pro Ala Asn Gly Gln Thr Pro Ile
        35                  40                  45

Gln Arg Thr Ile Asn Ala Asp Val Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
            85                  90

<210> SEQ ID NO 308
<211> LENGTH: 93
<212> TYPE: PRT
<213> ORGANISM: Artificial Sequence
<220> FEATURE:
<223> OTHER INFORMATION: Synthetic polypeptide 1637114_VGR2C07

<400> SEQUENCE: 308

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Asp Thr Ser Ala Asn Ser Tyr Thr Ile Thr Gly Leu Gln Pro Gly
    50                  55                  60

Thr Asp Tyr Lys Ile Tyr Leu Tyr Thr Leu Asn Glu Tyr Gly Asp Ser
65                  70                  75                  80

Asn Phe Thr Gln Leu Thr Gly Val Ile Asp Ala Ser Thr
            85                  90

<210> SEQ ID NO 309
<211> LENGTH: 89
<212> TYPE: PRT
<213> ORGANISM: Artificial Sequence
<220> FEATURE:
<223> OTHER INFORMATION: Synthetic polypeptide 1637114_VGR2D02

<400> SEQUENCE: 309

Asn Val Ser Pro Pro Arg Arg Ala Arg Val Thr Asp Ala Thr Glu Thr
1               5                   10                  15

Thr Ile Thr Ile Arg Trp Lys Val Ala Gly Ser Gln Phe Thr Ser Phe
            20                  25                  30

Gln Val Asp Ala Val Pro Ala Asn Gly Gln Thr Pro Ile Gln Arg Thr
        35                  40                  45

Ile Asn Ala Ala Thr Thr Thr Tyr Thr Ile Thr Gly Leu Gln Pro Gly
 50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 310
<211> LENGTH: 92
<212> TYPE: PRT
<213> ORGANISM: Artificial Sequence
<220> FEATURE:
<223> OTHER INFORMATION: Synthetic polypeptide 1637114_VGR2A05

<400> SEQUENCE: 310

Asn Val Ser Pro Pro Arg Arg Ala Arg Val Thr Asp Ala Thr Glu Thr
1               5                   10                  15

Thr Ile Thr Ile Arg Trp Lys Leu Pro Ser His Pro Ser Ser Val Val
                20                  25                  30

Leu Gly Phe Gln Val Asp Ala Val Pro Ala Asn Gly Gln Thr Pro Ile
            35                  40                  45

Gln Arg Thr Ile Asn Ala Thr Val Ser Thr Tyr Thr Ile Thr Gly Leu
 50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 311
<211> LENGTH: 92
<212> TYPE: PRT
<213> ORGANISM: Artificial Sequence
<220> FEATURE:
<223> OTHER INFORMATION: Synthetic polypeptide 1637114_VGR2F02

<400> SEQUENCE: 311

Asn Val Ser Pro Pro Arg Arg Ala Arg Val Thr Asp Ala Thr Glu Thr
1               5                   10                  15

Thr Ile Thr Ile Arg Trp Lys Gln Pro Ile His Ala Asp Ser Ile Leu
                20                  25                  30

Leu Ser Phe Gln Val Asp Ala Val Pro Ala Asn Gly Gln Thr Pro Ile
            35                  40                  45

Gln Arg Thr Ile Asn Ala Ser Thr Asn Ile Tyr Thr Ile Thr Gly Leu
 50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 312
<211> LENGTH: 93
<212> TYPE: PRT
<213> ORGANISM: Artificial Sequence
<220> FEATURE:
<223> OTHER INFORMATION: Synthetic polypeptide 1637114_VGR2H04

<400> SEQUENCE: 312

Asn Val Ser Pro Pro Arg Arg Ala Arg Val Thr Asp Ala Thr Glu Thr
1               5                   10                  15

Thr Ile Thr Ile Arg Trp Asn Thr Pro Gly Asp Ala Gly Gly Ser Thr

```
                20                  25                  30
Val Pro Gly Phe Gln Val Asp Ala Val Pro Ala Asn Gly Gln Thr Pro
            35                  40                  45

Ile Gln Arg Thr Ile Asn Ala Asp Ile Ser Tyr Thr Ile Thr Gly
 50                  55                  60

Leu Gln Pro Gly Thr Asp Tyr Lys Ile Tyr Leu Tyr Thr Leu Asn Asp
 65                  70                  75                  80

Asn Ala Arg Ser Ser Pro Val Val Ile Asp Ala Ser Thr
                85                  90

<210> SEQ ID NO 313
<211> LENGTH: 88
<212> TYPE: PRT
<213> ORGANISM: Artificial Sequence
<220> FEATURE:
<223> OTHER INFORMATION: Synthetic polypeptide 1637114_VGR2B04

<400> SEQUENCE: 313

Asn Val Ser Pro Pro Arg Arg Ala Arg Val Thr Asp Ala Thr Glu Thr
 1               5                  10                  15

Thr Ile Thr Ile Arg Trp Arg Ala Ala Arg Ser Gln Phe Gly Phe Gln
                20                  25                  30

Val Asp Ala Val Pro Ala Asn Gly Gln Thr Pro Ile Gln Arg Thr Ile
            35                  40                  45

His Ala Asp Ala Ser Thr Tyr Thr Ile Thr Gly Leu Gln Pro Gly Thr
         50                  55                  60

Asp Tyr Lys Ile Tyr Leu Tyr Thr Leu Asn Asp Asn Ala Arg Ser Ser
 65                  70                  75                  80

Pro Val Val Ile Asp Ala Ser Thr
                85

<210> SEQ ID NO 314
<211> LENGTH: 89
<212> TYPE: PRT
<213> ORGANISM: Artificial Sequence
<220> FEATURE:
<223> OTHER INFORMATION: Synthetic polypeptide 1637114_VGR2A08
<220> FEATURE:
<221> NAME/KEY: misc_feature
<222> LOCATION: (15)..(15)
<223> OTHER INFORMATION: Xaa can be any naturally occurring amino acid

<400> SEQUENCE: 314

Asn Val Ser Pro Pro Arg Arg Ala Arg Val Thr Asn Ala Thr Xaa Thr
 1               5                  10                  15

Thr Ile Thr Ile Arg Trp Glu Arg Ser Gly Gly Pro Val Asp Gly Phe
                20                  25                  30

Gln Val Asp Ala Val Pro Ala Asn Gly Gln Thr Pro Ile Gln Arg Thr
            35                  40                  45

Ile Asn Ala Asp Thr Asn Ile Tyr Thr Ile Thr Gly Leu Gln Pro Gly
         50                  55                  60

Thr Asp Tyr Lys Ile Tyr Leu Tyr Thr Leu Asn Asp Asn Ala Arg Asn
 65                  70                  75                  80

Thr Pro Val Val Ile Asp Ala Ser Thr
                85

<210> SEQ ID NO 315
<211> LENGTH: 92
<212> TYPE: PRT
<213> ORGANISM: Artificial Sequence
```

<220> FEATURE:
<223> OTHER INFORMATION: Synthetic polypeptide 1637114_VGR2D06

<400> SEQUENCE: 315

Asn Val Ser Pro Pro Arg Arg Ala Arg Val Thr Asp Ala Thr Glu Thr
1               5                   10                  15

Thr Ile Thr Ile Arg Trp Gln Leu Gly Val Gly Pro Gly Gly Thr Ile
            20                  25                  30

Pro Gly Phe Gln Val Asp Ala Val Pro Ala Asn Gly Gln Thr Pro Ile
        35                  40                  45

Gln Arg Thr Ile Asn Ala Asp Ile Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 316
<211> LENGTH: 93
<212> TYPE: PRT
<213> ORGANISM: Artificial Sequence
<220> FEATURE:
<223> OTHER INFORMATION: Synthetic polypeptide 1637114_VGR2D05

<400> SEQUENCE: 316

Asn Val Ser Pro Pro Arg Arg Ala Arg Val Thr Asp Ala Thr Glu Thr
1               5                   10                  15

Thr Ile Thr Ile Arg Trp Gly Ala Pro Glu Asp Asp Gly Gly Gly Glu
            20                  25                  30

Val Pro Gly Phe Gln Val Asp Ala Val Pro Ala Asn Gly Gln Thr Pro
        35                  40                  45

Ile Gln Arg Thr Ile Asn Ala Asp Val Ser Thr Tyr Thr Ile Thr Gly
    50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90

<210> SEQ ID NO 317
<211> LENGTH: 92
<212> TYPE: PRT
<213> ORGANISM: Artificial Sequence
<220> FEATURE:
<223> OTHER INFORMATION: Synthetic polypeptide 1637114_VGR2A02

<400> SEQUENCE: 317

Asn Val Ser Pro Pro Arg Arg Ala Arg Val Thr Asp Ala Thr Glu Thr
1               5                   10                  15

Thr Ile Thr Ile Arg Trp Glu Leu Pro Ile Gln Arg Ser Ser Leu Ile
            20                  25                  30

Pro Gly Phe Gln Val Asp Ala Val Pro Ala Asn Gly Gln Thr Pro Ile
        35                  40                  45

Gln Arg Thr Ile Asn Ala Asp Val Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 318
<211> LENGTH: 92
<212> TYPE: PRT
<213> ORGANISM: Artificial Sequence
<220> FEATURE:
<223> OTHER INFORMATION: Synthetic polypeptide 1637114_VGR2F06

<400> SEQUENCE: 318

Asn Val Ser Pro Pro Arg Arg Ala Arg Val Thr Asp Ala Thr Glu Thr
1               5                   10                  15

Thr Ile Thr Ile Arg Trp Gln Gln Gly Glu Glu Gly Gly Val Val
            20                  25                  30

Pro Gly Phe Gln Val Asp Ala Val Pro Ala Asn Gly Gln Thr Pro Ile
        35                  40                  45

Gln Arg Thr Ile Asn Ala Asp Thr Ser Thr Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 319
<211> LENGTH: 93
<212> TYPE: PRT
<213> ORGANISM: Artificial Sequence
<220> FEATURE:
<223> OTHER INFORMATION: Synthetic polypeptide 1637114_VGR2E05

<400> SEQUENCE: 319

Asn Val Ser Pro Pro Arg Arg Ala Arg Val Thr Asp Ala Thr Glu Thr
1               5                   10                  15

Thr Ile Thr Ile Arg Trp Gly Gln Pro Ala Tyr Asp Gly Gly Ser Glu
            20                  25                  30

Val Pro Gly Phe Gln Val Asp Ala Val Pro Ala Asn Gly Gln Thr Pro
        35                  40                  45

Ile Gln Arg Thr Ile Asn Ala Asp Ile Ser Thr Tyr Thr Ile Thr Gly
    50                  55                  60

Leu Gln Pro Gly Thr Asp Tyr Lys Ile Tyr Leu Tyr Thr Leu Asn Asp
65                  70                  75                  80

Asn Ala Arg Ser Ser Pro Val Val Ile Asp Ala Ser Thr
                85                  90

<210> SEQ ID NO 320
<211> LENGTH: 89
<212> TYPE: PRT
<213> ORGANISM: Artificial Sequence
<220> FEATURE:
<223> OTHER INFORMATION: Synthetic polypeptide 1637115_VGR2D10
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid

<400> SEQUENCE: 320

Asn Val Ser Pro Pro Arg Arg Ala Arg Val Thr Asp Pro Pro Asp Thr
1               5                   10                  15

Thr Ile Thr Ile Xaa Trp Thr Arg Ala Gly Gly Glu Phe Asp Gly Phe
            20                  25                  30

Gln Val Asp Ala Xaa Pro Ala Asn Gly Gln Thr Pro Ile Xaa Arg Thr
        35                  40                  45

Ile Asn Ala Asp Thr Asn Thr Tyr Thr Ile Thr Gly Leu Xaa Pro Gly
    50                  55                  60

Thr Asp Tyr Lys Ile Tyr Leu Tyr Thr Leu Asn Asp Thr Ala Arg Ser
65                  70                  75                  80

Pro Pro Val Val Ile Asp Ala Ser Thr
                85

<210> SEQ ID NO 321
<211> LENGTH: 89
<212> TYPE: PRT
<213> ORGANISM: Artificial Sequence
<220> FEATURE:
<223> OTHER INFORMATION: Synthetic polypeptide 1637115_VGR2C02

<400> SEQUENCE: 321

Asn Val Ser Pro Pro Arg Arg Ala Arg Val Thr Asp Ala Thr Glu Thr
1               5                   10                  15

Thr Ile Thr Ile Arg Trp Glu Val Ala Glu Ser Ala Phe Asp Ser Phe
            20                  25                  30

Gln Val Asp Ala Val Pro Ala Asn Gly Gln Thr Pro Ile Gln Arg Thr
        35                  40                  45

Ile Asn Ala Ala Thr Thr Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 322
<211> LENGTH: 89
<212> TYPE: PRT
<213> ORGANISM: Artificial Sequence
<220> FEATURE:
<223> OTHER INFORMATION: Synthetic polypeptide 1637115_VGR2F06

<400> SEQUENCE: 322

Asn Val Ser Pro Pro Arg Arg Ala Arg Val Thr Asp Ala Thr Glu Thr
1               5                   10                  15

Thr Ile Thr Ile Arg Trp Glu Arg Ser Gln Gly Gln Phe Asp Gly Phe
            20                  25                  30

Gln Val Asp Ala Val Pro Ala Asn Gly Gln Thr Pro Ile Gln Arg Thr
        35                  40                  45

Ile Asn Ala Asp Thr Asn Val Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 323

```
<211> LENGTH: 89
<212> TYPE: PRT
<213> ORGANISM: Artificial Sequence
<220> FEATURE:
<223> OTHER INFORMATION: Synthetic polypeptide 1637115_VGR2E01
<220> FEATURE:
<221> NAME/KEY: misc_feature
<222> LOCATION: (37)..(37)
<223> OTHER INFORMATION: Xaa can be any naturally occurring amino acid

<400> SEQUENCE: 323

Asn Val Ser Pro Pro Arg Arg Ala Arg Val Thr His Ala Thr Glu Thr
1               5                   10                  15

Thr Ile Thr Ile Arg Trp Arg Val Ala Gly Ser Glu Phe Asp Ser Phe
            20                  25                  30

Gln Val Asp Ala Xaa Pro Ala Asn Gly Gln Thr Pro Ile Gln Arg Thr
        35                  40                  45

Ile His Ala Ala Thr Thr Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Thr
65                  70                  75                  80

Ser Pro Val Val Ile Asp Ala Ser Thr
                85

<210> SEQ ID NO 324
<211> LENGTH: 89
<212> TYPE: PRT
<213> ORGANISM: Artificial Sequence
<220> FEATURE:
<223> OTHER INFORMATION: Synthetic polypeptide 1637115_VGR2C06

<400> SEQUENCE: 324

Asn Val Ser Pro Pro Arg Arg Ala Arg Val Thr Asp Ala Thr Glu Thr
1               5                   10                  15

Thr Ile Thr Ile Arg Trp Thr Val Ser Gly Ser Pro Phe Asp Gly Phe
            20                  25                  30

Gln Val Asp Ala Val Pro Ala Asn Gly Gln Thr Pro Ile Gln Arg Thr
        35                  40                  45

Ile His Ala Asp Thr Thr Val Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 325
<211> LENGTH: 89
<212> TYPE: PRT
<213> ORGANISM: Artificial Sequence
<220> FEATURE:
<223> OTHER INFORMATION: Synthetic polypeptide 1637115_VGR2F04

<400> SEQUENCE: 325

Asn Val Ser Pro Pro Arg Arg Ala Arg Val Thr Asp Ala Thr Glu Thr
1               5                   10                  15

Thr Ile Thr Ile Arg Trp Thr Val Ser Ala Ser Glu Phe Asp Ser Phe
            20                  25                  30

Gln Val Asp Ala Val Pro Ala Asn Gly Gln Thr Pro Ile Gln Arg Thr
        35                  40                  45

Ile His Ala Thr Thr Thr Thr Tyr Thr Ile Thr Gly Leu Gln Pro Gly
    50                  55                  60
```

```
Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                 85

<210> SEQ ID NO 326
<211> LENGTH: 90
<212> TYPE: PRT
<213> ORGANISM: Artificial Sequence
<220> FEATURE:
<223> OTHER INFORMATION: Synthetic polypeptide 1637115_VGR2B10

<400> SEQUENCE: 326

Asn Val Ser Pro Pro Arg Arg Ala Arg Val Thr Asp Ala Thr Glu Thr
  1               5                  10                  15

Thr Ile Thr Ile Ser Trp Arg Thr Lys Thr Lys Thr Ile Thr Gly Phe
                 20                  25                  30

Gln Val Asp Ala Val Pro Ala Asn Gly Gln Thr Pro Ile Gln Arg Thr
             35                  40                  45

Ile Glu Arg Asn Ala His Gly Tyr Thr Ile Thr Gly Leu Gln Pro Gly
         50                  55                  60

Thr Asp Tyr Lys Ile Tyr Leu Tyr Thr Leu Tyr Gly Leu Gly Glu Ala
 65                  70                  75                  80

Ser Ser Pro Val Val Ile Asp Ala Ser Thr
                 85                  90

<210> SEQ ID NO 327
<211> LENGTH: 89
<212> TYPE: PRT
<213> ORGANISM: Artificial Sequence
<220> FEATURE:
<223> OTHER INFORMATION: Synthetic polypeptide 1637115_VGR2H09

<400> SEQUENCE: 327

Asn Val Ser Pro Pro Arg Arg Ala Arg Val Thr Asp Ala Thr Glu Thr
  1               5                  10                  15

Thr Ile Thr Ile Arg Trp Arg Val Ala Gly Ser Glu Phe Asp Ser Phe
                 20                  25                  30

Gln Val Asp Ala Val Pro Ala Asn Gly Gln Thr Pro Ile Gln Arg Thr
             35                  40                  45

Ile His Ala Ala Thr Thr Thr Tyr Thr Ile Thr Gly Leu Gln Pro Gly
         50                  55                  60

Thr Asp Tyr Lys Ile Tyr Leu Tyr Thr Phe Asn Asp Asn Ala Arg Ser
 65                  70                  75                  80

Ser Pro Val Val Ile Asp Ala Ser Thr
                 85

<210> SEQ ID NO 328
<211> LENGTH: 89
<212> TYPE: PRT
<213> ORGANISM: Artificial Sequence
<220> FEATURE:
<223> OTHER INFORMATION: Synthetic polypeptide 1637115_VGR2G01

<400> SEQUENCE: 328

Asn Val Ser Pro Pro Arg Arg Ala Arg Val Thr Asp Ala Thr Glu Thr
  1               5                  10                  15

Thr Ile Thr Ile Arg Trp Lys Val Ala Gly Gly Thr Phe Asp Ser Phe
                 20                  25                  30
```

```
Gln Val Asp Ala Val Pro Ala Asn Gly Gln Thr Pro Ile Gln Arg Thr
            35                  40                  45

Ile Asn Ala Ala Thr Thr Thr Tyr Thr Ile Thr Gly Leu Gln Pro Gly
 50                  55                  60

Thr Asp Tyr Lys Ile Tyr Leu Tyr Thr Leu Asn Asp Asn Ala Arg Ser
 65                  70                  75                  80

Ile Pro Val Val Ile Asp Ala Ser Thr
                85
```

<210> SEQ ID NO 329
<211> LENGTH: 89
<212> TYPE: PRT
<213> ORGANISM: Artificial Sequence
<220> FEATURE:
<223> OTHER INFORMATION: Synthetic polypeptide 1637115_VGR2A08
<220> FEATURE:
<221> NAME/KEY: misc_feature
<222> LOCATION: (80)..(80)
<223> OTHER INFORMATION: Xaa can be any naturally occurring amino acid

<400> SEQUENCE: 329

```
Asn Val Ser Pro Pro Arg Arg Ala Arg Val Thr Asp Ala Pro Glu Thr
 1               5                  10                  15

Pro Ile Thr Ile Arg Trp Arg Val Gly Gly Ser Glu Phe Asp Ser Phe
                20                  25                  30

Gln Val Asp Ala Leu Pro Pro Asn Gly Gln Thr Pro Ile Leu Arg Thr
            35                  40                  45

Ile His Ala Ala Thr Thr Thr Tyr Thr Ile Thr Gly Leu Gln Pro Gly
 50                  55                  60

Thr Asp Tyr Lys Ile Tyr Leu Tyr Thr Leu Asn Asp Asn Ala Arg Xaa
 65                  70                  75                  80

Thr Pro Val Val Ile Asp Ala Ser Thr
                85
```

<210> SEQ ID NO 330
<211> LENGTH: 93
<212> TYPE: PRT
<213> ORGANISM: Artificial Sequence
<220> FEATURE:
<223> OTHER INFORMATION: Synthetic polypeptide 1637115_VGR2G11

<400> SEQUENCE: 330

```
Asn Val Ser Pro Pro Arg Arg Ala Arg Val Thr Asp Ala Thr Glu Thr
 1               5                  10                  15

Thr Ile Thr Ile Arg Trp Glu Arg Ser Gln Gly Gln Phe Asp Gly Phe
                20                  25                  30

Gln Val Asp Ala Val Pro Ala Asn Gly Gln Thr Pro Ile Gln Arg Thr
            35                  40                  45

Ile Asn Ala Asp Thr Asn Val Tyr Thr Ile Thr Gly Leu Gln Pro Gly
 50                  55                  60

Thr Asp Tyr Lys Ile Tyr Leu Tyr Thr Leu Thr Ala Phe Gly Ala Gly
 65                  70                  75                  80

Asp Val Thr Ser Ser Pro Val Val Ile Asp Ala Ser Thr
                85                  90
```

<210> SEQ ID NO 331
<211> LENGTH: 93
<212> TYPE: PRT
<213> ORGANISM: Artificial Sequence
<220> FEATURE:
<223> OTHER INFORMATION: Synthetic polypeptide 1637115_VGR2C03

<400> SEQUENCE: 331

Asn Val Ser Pro Pro Arg Cys Ala Arg Val Thr Asp Ala Thr Glu Thr
1               5                   10                  15

Thr Ile Thr Ile Arg Trp Gly Val Pro Glu Gly Lys Val Val Ser Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Asn Thr Gly Gly Ser
65                  70                  75                  80

Thr Tyr Thr Glu Leu Thr Val Val Ile Asp Ala Ser Thr
                85                  90

<210> SEQ ID NO 332
<211> LENGTH: 84
<212> TYPE: PRT
<213> ORGANISM: Artificial Sequence
<220> FEATURE:
<223> OTHER INFORMATION: Synthetic polypeptide 1637110_AXLC04

<400> SEQUENCE: 332

Asn Val Ser Pro Pro Arg Arg Ala Arg Val Thr Asp Ala Thr Glu Thr
1               5                   10                  15

Thr Ile Thr Ile Arg Trp Ala Val Pro Gly Phe Gln Val Asp Ala Val
            20                  25                  30

Pro Ala Asn Gly Gln Thr Pro Ile Gln Arg Thr Ile Lys Arg Asn Val
        35                  40                  45

Ser Val Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 333
<211> LENGTH: 84
<212> TYPE: PRT
<213> ORGANISM: Artificial Sequence
<220> FEATURE:
<223> OTHER INFORMATION: Synthetic polypeptide 1637110_AXLH01

<400> SEQUENCE: 333

Asn Val Ser Pro Pro Arg Arg Ala Arg Val Thr Asp Ala Thr Glu Thr
1               5                   10                  15

Thr Ile Thr Ile Arg Trp Lys Val Asp Gly Phe Gln Val Asp Ala Val
            20                  25                  30

Pro Ala Asn Gly Gln Thr Pro Ile Gln Arg Thr Ile Thr Arg Asn Thr
        35                  40                  45

Arg Thr Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 334
<211> LENGTH: 84
<212> TYPE: PRT

-continued

<213> ORGANISM: Artificial Sequence
<220> FEATURE:
<223> OTHER INFORMATION: Synthetic polypeptide 1637110_AXLA06

<400> SEQUENCE: 334

Asn Val Ser Pro Pro Arg Arg Ala Arg Val Thr Asp Ala Thr Glu Thr
1               5                   10                  15

Thr Ile Thr Ile Arg Trp Lys Val Leu Gly Phe Gln Val Asp Ala Val
            20                  25                  30

Pro Ala Asn Gly Gln Thr Pro Ile Gln Arg Thr Ile Ala Arg Gly Ala
        35                  40                  45

Arg Thr Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 335
<211> LENGTH: 84
<212> TYPE: PRT
<213> ORGANISM: Artificial Sequence
<220> FEATURE:
<223> OTHER INFORMATION: Synthetic polypeptide 1637110_AXLE06

<400> SEQUENCE: 335

Asn Val Ser Pro Pro Arg Arg Ala Arg Val Thr Asp Ala Thr Glu Thr
1               5                   10                  15

Thr Ile Thr Ile Arg Trp Lys Gly Ala Gln Phe Gln Val Asp Ala Val
            20                  25                  30

Pro Ala Asn Gly Gln Thr Pro Ile Gln Arg Thr Ile Ala Arg Gly Ala
        35                  40                  45

Asn Val Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 336
<211> LENGTH: 84
<212> TYPE: PRT
<213> ORGANISM: Artificial Sequence
<220> FEATURE:
<223> OTHER INFORMATION: Synthetic polypeptide 1637110_AXLF08

<400> SEQUENCE: 336

Asn Val Ser Pro Pro Arg Arg Ala Arg Val Thr Asp Ala Thr Glu Thr
1               5                   10                  15

Thr Ile Thr Ile Ser Trp Pro Val Pro Gly Phe Gln Val Asp Ala Val
            20                  25                  30

Pro Ala Asn Gly Gln Thr Pro Ile Gln Arg Thr Ile Lys Arg Asp Val
        35                  40                  45

Asn Ser Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 337

```
<211> LENGTH: 83
<212> TYPE: PRT
<213> ORGANISM: Artificial Sequence
<220> FEATURE:
<223> OTHER INFORMATION: Synthetic polypeptide 1637110_AXLF11

<400> SEQUENCE: 337
```

Asn Val Ser Pro Pro Arg Arg Ala Arg Val Thr Asp Ala Thr Glu Thr
1               5                   10                  15

Thr Ile Thr Ile Arg Trp Gly Thr Gly Phe Gln Val Asp Ala Val Pro
            20                  25                  30

Ala Asn Gly Gln Thr Pro Ile Gln Arg Thr Ile Lys Arg Ser Ile Thr
        35                  40                  45

Ser Tyr Thr Ile Thr Gly Leu Gln Pro Gly Thr Asp Tyr Lys Ile Tyr
    50                  55                  60

Leu Tyr Thr Leu Asn Asp Asn Ala Arg Ser Ser Pro Val Val Ile Asp
65                  70                  75                  80

Ala Ser Thr

```
<210> SEQ ID NO 338
<211> LENGTH: 89
<212> TYPE: PRT
<213> ORGANISM: Artificial Sequence
<220> FEATURE:
<223> OTHER INFORMATION: Synthetic polypeptide 1637110_AXLD03

<400> SEQUENCE: 338
```

Asn Val Ser Pro Pro Arg Arg Ala Arg Val Thr Asp Ala Thr Glu Thr
1               5                   10                  15

Thr Ile Thr Ile Arg Trp Ala Leu Pro Arg Ser Ala Phe Asp Arg Phe
            20                  25                  30

Gln Val Asp Ala Val Pro Ala Asn Gly Gln Thr Pro Ile Gln Arg Thr
        35                  40                  45

Ile Thr Thr Asn Ile Arg Ala Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

```
<210> SEQ ID NO 339
<211> LENGTH: 85
<212> TYPE: PRT
<213> ORGANISM: Artificial Sequence
<220> FEATURE:
<223> OTHER INFORMATION: Synthetic polypeptide 1637110_AXLE11

<400> SEQUENCE: 339
```

Asn Val Ser Pro Pro Arg Arg Ala Arg Val Thr Asp Ala Thr Glu Thr
1               5                   10                  15

Thr Ile Thr Ile Arg Trp Ala Gln Val Leu Ser Phe Gln Val Asp Ala
            20                  25                  30

Val Pro Ala Asn Gly Gln Thr Pro Ile Gln Arg Thr Ile Lys Arg Asp
        35                  40                  45

Val His Ser Tyr Thr Ile Thr Gly Leu Gln Pro Gly Thr Asp Tyr Lys
    50                  55                  60

Ile Tyr Leu Tyr Thr Leu Asn Asp Asn Ala Arg Ser Ser Pro Val Val
65                  70                  75                  80

Ile Asp Ala Ser Thr

<210> SEQ ID NO 340
<211> LENGTH: 92
<212> TYPE: PRT
<213> ORGANISM: Artificial Sequence
<220> FEATURE:
<223> OTHER INFORMATION: Synthetic polypeptide 1637110_AXLG07

<400> SEQUENCE: 340

Asn Val Ser Pro Pro Arg Arg Ala Arg Val Thr Asp Ala Thr Glu Thr
1               5                   10                  15

Thr Ile Thr Ile Arg Trp Thr Val Gly Gly Arg Ala Asn Ser Thr Ile
            20                  25                  30

Pro Gly Phe Gln Val Asp Ala Val Pro Ala Asn Gly Gln Thr Pro Ile
        35                  40                  45

Gln Arg Thr Ile Thr Arg Asp Ile His Ile Tyr Thr Ile Thr Gly Leu
    50                  55                  60

Gln Pro Gly Thr Asp Tyr Lys Ile Tyr Leu Tyr Thr Leu Asn Asp Asn
65                  70                  75                  80

Ala Arg Ser Ser Pro Val Val Ile Asp Ala Ser Thr
                85                  90

<210> SEQ ID NO 341
<211> LENGTH: 89
<212> TYPE: PRT
<213> ORGANISM: Artificial Sequence
<220> FEATURE:
<223> OTHER INFORMATION: Synthetic polypeptide 1637110_AXLB04

<400> SEQUENCE: 341

Asn Val Ser Pro Pro Arg Arg Ala Arg Val Thr Asp Ala Thr Glu Thr
1               5                   10                  15

Thr Ile Thr Ile Arg Trp Glu Leu Ser Arg Gly Thr Ile Thr Gly Phe
            20                  25                  30

Gln Val Asp Ala Val Pro Ala Asn Gly Gln Thr Pro Ile Gln Arg Thr
        35                  40                  45

Ile Lys Gly Ala Lys Arg Ser Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 342
<211> LENGTH: 89
<212> TYPE: PRT
<213> ORGANISM: Artificial Sequence
<220> FEATURE:
<223> OTHER INFORMATION: Synthetic polypeptide 1637110_AXLC11

<400> SEQUENCE: 342

Asn Val Ser Pro Pro Arg Arg Ala Arg Val Thr Asp Ala Thr Glu Thr
1               5                   10                  15

Thr Ile Thr Ile Arg Trp Gly Pro Ser Gln Gly Thr Val Thr Arg Phe
            20                  25                  30

Gln Val Asp Ala Val Pro Ala Asn Gly Gln Thr Pro Ile Gln Arg Thr
        35                  40                  45

Ile Lys Arg Ala Ile His Thr Tyr Thr Ile Thr Gly Leu Gln Pro Gly
    50                  55                  60

```
Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                 85

<210> SEQ ID NO 343
<211> LENGTH: 84
<212> TYPE: PRT
<213> ORGANISM: Artificial Sequence
<220> FEATURE:
<223> OTHER INFORMATION: Synthetic polypeptide 1637110_AXLB10

<400> SEQUENCE: 343

Asn Val Ser Pro Pro Arg Arg Ala Arg Val Thr Asp Ala Thr Glu Thr
  1               5                  10                  15

Thr Ile Thr Ile Arg Trp Pro Ala Pro Gly Phe Gln Val Asp Ala Val
                 20                  25                  30

Pro Ala Asn Gly Gln Thr Pro Ile Gln Arg Thr Ile Lys Arg Thr Val
             35                  40                  45

Asn Val Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 344
<211> LENGTH: 84
<212> TYPE: PRT
<213> ORGANISM: Artificial Sequence
<220> FEATURE:
<223> OTHER INFORMATION: Synthetic polypeptide 1637110_AXLD12

<400> SEQUENCE: 344

Asn Val Ser Pro Pro Arg Arg Ala Arg Val Thr Asp Ala Thr Glu Thr
  1               5                  10                  15

Thr Ile Thr Ile Thr Trp Ala Gly Pro Glu Phe Gln Val Asp Ala Val
                 20                  25                  30

Pro Ala Asn Gly Gln Thr Pro Ile Gln Arg Thr Ile His Arg Gly Ile
             35                  40                  45

Thr Ser Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 345
<211> LENGTH: 89
<212> TYPE: PRT
<213> ORGANISM: Artificial Sequence
<220> FEATURE:
<223> OTHER INFORMATION: Synthetic polypeptide 1637110_AXLA05

<400> SEQUENCE: 345

Asn Val Ser Pro Pro Arg Arg Ala Arg Val Thr Asp Ala Thr Glu Thr
  1               5                  10                  15

Thr Ile Thr Ile Arg Trp Glu Leu Pro Ala Gly Thr Val Asn Gly Phe
                 20                  25                  30

Gln Val Asp Ala Val Pro Ala Asn Gly Gln Thr Pro Ile Gln Arg Thr
             35                  40                  45
```

```
Ile Lys Gly Ala Lys Arg Gly Tyr Thr Ile Thr Gly Leu Gln Pro Gly
        50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                 85

<210> SEQ ID NO 346
<211> LENGTH: 84
<212> TYPE: PRT
<213> ORGANISM: Artificial Sequence
<220> FEATURE:
<223> OTHER INFORMATION: Synthetic polypeptide E03AXL

<400> SEQUENCE: 346

Asn Val Ser Pro Pro Arg Arg Ala Arg Val Thr Asp Ala Thr Glu Thr
  1               5                  10                  15

Thr Ile Thr Ile Arg Trp Ser Gln Pro Gly Phe Gln Val Asp Ala Val
                 20                  25                  30

Pro Ala Asn Gly Gln Thr Pro Ile Gln Arg Thr Ile Ala Arg Ala Thr
             35                  40                  45

Arg Ala Tyr Thr Ile Thr Gly Leu Gln Pro Gly Thr Asp Tyr Lys Ile
     50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 347
<211> LENGTH: 84
<212> TYPE: PRT
<213> ORGANISM: Artificial Sequence
<220> FEATURE:
<223> OTHER INFORMATION: Synthetic polypeptide 1637110_AXLH03

<400> SEQUENCE: 347

Asn Val Ser Pro Pro Arg Arg Ala Arg Val Thr Asp Ala Thr Glu Thr
  1               5                  10                  15

Thr Ile Thr Ile Arg Trp Thr Pro Pro Gly Phe Gln Val Asp Ala Val
                 20                  25                  30

Pro Ala Asn Gly Gln Thr Pro Ile Gln Arg Thr Ile Lys Arg Asn Val
             35                  40                  45

Asn Val Tyr Thr Ile Thr Gly Leu Gln Pro Gly Thr Asp Tyr Lys Ile
     50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 348
<211> LENGTH: 84
<212> TYPE: PRT
<213> ORGANISM: Artificial Sequence
<220> FEATURE:
<223> OTHER INFORMATION: Synthetic polypeptide 1637110_AXLC10

<400> SEQUENCE: 348

Asn Val Ser Pro Pro Arg Arg Ala Arg Val Thr Asp Ala Thr Glu Thr
  1               5                  10                  15

Thr Ile Thr Ile Arg Trp Pro Ile Leu Gly Phe Gln Val Asp Ala Val
                 20                  25                  30
```

Pro Ala Asn Gly Gln Thr Pro Ile Gln Arg Thr Ile Lys Arg Ser Thr
            35                  40                  45

His Ala Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 349
<211> LENGTH: 89
<212> TYPE: PRT
<213> ORGANISM: Artificial Sequence
<220> FEATURE:
<223> OTHER INFORMATION: Synthetic polypeptide 1637110_AXLE08

<400> SEQUENCE: 349

Asn Val Ser Pro Pro Arg Arg Ala Arg Val Thr Asp Ala Thr Glu Thr
1               5                   10                  15

Thr Ile Thr Ile Arg Trp Ala Leu Pro Arg Ser Glu Phe Thr Arg Phe
            20                  25                  30

Gln Val Asp Ala Val Pro Ala Asn Gly Gln Thr Pro Ile Gln Arg Thr
            35                  40                  45

Ile Thr Ser Asn Ile Arg Thr Tyr Thr Ile Gly Leu Gln Pro Gly
 50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 350
<211> LENGTH: 83
<212> TYPE: PRT
<213> ORGANISM: Artificial Sequence
<220> FEATURE:
<223> OTHER INFORMATION: Synthetic polypeptide 1637110_AXLD11

<400> SEQUENCE: 350

Asn Val Ser Pro Pro Arg Arg Ala Arg Val Thr Asp Ala Thr Glu Thr
1               5                   10                  15

Thr Ile Thr Ile Ser Trp Pro Ala Gly Phe Gln Val Asp Ala Val Pro
            20                  25                  30

Ala Asn Gly Gln Thr Pro Ile Gln Arg Thr Ile Lys Arg Gly Lys Arg
            35                  40                  45

Thr Tyr Thr Ile Thr Gly Leu Gln Pro Gly Thr Asp Tyr Lys Ile Tyr
 50                  55                  60

Leu Tyr Thr Leu Asn Asp Asn Ala Arg Ser Ser Pro Val Val Ile Asp
65                  70                  75                  80

Ala Ser Thr

<210> SEQ ID NO 351
<211> LENGTH: 84
<212> TYPE: PRT
<213> ORGANISM: Artificial Sequence
<220> FEATURE:
<223> OTHER INFORMATION: Synthetic polypeptide 1637110_AXLF09

<400> SEQUENCE: 351

Asn Val Ser Pro Pro Arg Arg Ala Arg Val Thr Asp Ala Thr Glu Thr
1               5                   10                  15

-continued

```
Thr Ile Thr Ile Arg Trp Lys Ile Ala Gly Phe Gln Val Asp Ala Val
            20                  25                  30

Pro Ala Asn Gly Gln Thr Pro Ile Gln Arg Thr Ile His Arg Gly Val
        35                  40                  45

Arg Ala Tyr Thr Ile Thr Gly Leu Gln Pro Thr Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 352
<211> LENGTH: 84
<212> TYPE: PRT
<213> ORGANISM: Artificial Sequence
<220> FEATURE:
<223> OTHER INFORMATION: Synthetic polypeptide 1637110_AXLB03

<400> SEQUENCE: 352

Asn Val Ser Pro Pro Arg Arg Ala Arg Val Thr Asp Ala Thr Glu Thr
 1               5                  10                  15

Thr Ile Thr Ile Arg Trp Lys Val Pro Gly Phe Gln Val Asp Ala Val
            20                  25                  30

Pro Ala Asn Gly Gln Thr Pro Ile Gln Arg Thr Ile His Arg Gly Ala
        35                  40                  45

Thr Val Tyr Thr Ile Thr Gly Leu Gln Pro Thr Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 353
<211> LENGTH: 85
<212> TYPE: PRT
<213> ORGANISM: Artificial Sequence
<220> FEATURE:
<223> OTHER INFORMATION: Synthetic polypeptide 1637110_AXLF07

<400> SEQUENCE: 353

Asn Val Ser Pro Pro Arg Arg Ala Arg Val Thr Asp Ala Thr Glu Thr
 1               5                  10                  15

Thr Ile Thr Ile Arg Trp Gly Gln Phe Asp Arg Phe Gln Val Asp Ala
            20                  25                  30

Val Pro Ala Asn Gly Gln Thr Pro Ile Gln Arg Thr Ile Lys Arg Thr
        35                  40                  45

Val His Ser Tyr Thr Ile Thr Gly Leu Gln Pro Gly Thr Asp Tyr Lys
 50                  55                  60

Ile Tyr Leu Tyr Thr Leu Asn Asp Asn Ala Arg Ser Ser Pro Val Val
 65                  70                  75                  80

Ile Asp Ala Ser Thr
                85

<210> SEQ ID NO 354
<211> LENGTH: 84
<212> TYPE: PRT
<213> ORGANISM: Artificial Sequence
<220> FEATURE:
<223> OTHER INFORMATION: Synthetic polypeptide 1637110_AXLA12

<400> SEQUENCE: 354
```

-continued

```
Asn Val Ser Pro Pro Arg Arg Ala Arg Val Thr Asp Ala Thr Glu Thr
1               5                   10                  15

Thr Ile Thr Ile Arg Trp Lys Val Asp Gly Phe Gln Val Asp Ala Val
            20                  25                  30

Pro Ala Asn Gly Gln Thr Pro Ile Gln Arg Thr Ile His Arg Gly Ile
        35                  40                  45

Thr Val Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr
```

<210> SEQ ID NO 355
<211> LENGTH: 84
<212> TYPE: PRT
<213> ORGANISM: Artificial Sequence
<220> FEATURE:
<223> OTHER INFORMATION: Synthetic polypeptide 1637110_AXLH08

<400> SEQUENCE: 355

```
Asn Val Ser Pro Pro Arg Arg Ala Arg Val Thr Asp Ala Thr Glu Thr
1               5                   10                  15

Thr Ile Thr Ile Arg Trp Ala Gly Ser Gly Phe Gln Val Asp Ala Val
            20                  25                  30

Pro Ala Asn Gly Gln Thr Pro Ile Gln Arg Thr Ile Asn Arg Gly Ile
        35                  40                  45

Ser Ala Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr
```

<210> SEQ ID NO 356
<211> LENGTH: 83
<212> TYPE: PRT
<213> ORGANISM: Artificial Sequence
<220> FEATURE:
<223> OTHER INFORMATION: Synthetic polypeptide 1637110_AXLE01

<400> SEQUENCE: 356

```
Asn Val Ser Pro Pro Arg Arg Ala Arg Val Thr Asp Ala Thr Glu Thr
1               5                   10                  15

Thr Ile Thr Ile Ser Trp Lys Val Arg Phe Gln Val Asp Ala Val Pro
            20                  25                  30

Ala Asn Gly Gln Thr Pro Ile Gln Arg Thr Ile Thr Ser Ser Val Arg
        35                  40                  45

Ser Tyr Thr Ile Thr Gly Leu Gln Pro Gly Thr Asp Tyr Lys Ile Tyr
    50                  55                  60

Leu Tyr Thr Leu Asn Asp Asn Ala Arg Ser Ser Pro Val Val Ile Asp
65                  70                  75                  80

Ala Ser Thr
```

<210> SEQ ID NO 357
<211> LENGTH: 85
<212> TYPE: PRT
<213> ORGANISM: Artificial Sequence
<220> FEATURE:
<223> OTHER INFORMATION: Synthetic polypeptide 1637110_AXLC08

<400> SEQUENCE: 357

| Asn | Val | Ser | Pro | Pro | Arg | Arg | Ala | Arg | Val | Thr | Asp | Ala | Thr | Glu | Thr |
|---|---|---|---|---|---|---|---|---|---|---|---|---|---|---|---|
| 1 | | | | 5 | | | | | 10 | | | | | 15 | |

| Thr | Ile | Thr | Ile | Arg | Trp | Ala | Pro | Pro | Glu | Gly | Phe | Gln | Val | Asp | Ala |
|---|---|---|---|---|---|---|---|---|---|---|---|---|---|---|---|
| | | | 20 | | | | | 25 | | | | | 30 | | |

| Val | Pro | Ala | Asn | Gly | Gln | Thr | Pro | Ile | Gln | Arg | Thr | Ile | His | Arg | Ser |
|---|---|---|---|---|---|---|---|---|---|---|---|---|---|---|---|
| | | 35 | | | | | 40 | | | | | 45 | | | |

| Ala | Arg | Ser | Tyr | Thr | Ile | Thr | Gly | Leu | Gln | Pro | Gly | Thr | Asp | Tyr | Lys |
|---|---|---|---|---|---|---|---|---|---|---|---|---|---|---|---|
| | 50 | | | | | 55 | | | | | 60 | | | | |

| Ile | Tyr | Leu | Tyr | Thr | Leu | Asn | Asp | Asn | Ala | Arg | Ser | Ser | Pro | Val | Val |
|---|---|---|---|---|---|---|---|---|---|---|---|---|---|---|---|
| 65 | | | | | 70 | | | | | 75 | | | | | 80 |

| Ile | Asp | Ala | Ser | Thr |
|---|---|---|---|---|
| | | | | 85 |

<210> SEQ ID NO 358
<211> LENGTH: 85
<212> TYPE: PRT
<213> ORGANISM: Artificial Sequence
<220> FEATURE:
<223> OTHER INFORMATION: Synthetic polypeptide 1637110_AXLA04

<400> SEQUENCE: 358

| Asn | Val | Ser | Pro | Pro | Arg | Arg | Ala | Arg | Val | Thr | Asp | Ala | Thr | Glu | Thr |
|---|---|---|---|---|---|---|---|---|---|---|---|---|---|---|---|
| 1 | | | | 5 | | | | | 10 | | | | | 15 | |

| Thr | Ile | Thr | Ile | Arg | Trp | Ser | Gln | Val | Pro | Gly | Phe | Gln | Val | Asp | Ala |
|---|---|---|---|---|---|---|---|---|---|---|---|---|---|---|---|
| | | | 20 | | | | | 25 | | | | | 30 | | |

| Val | Pro | Ala | Asn | Gly | Gln | Thr | Pro | Ile | Gln | Arg | Thr | Ile | Thr | Ser | Asp |
|---|---|---|---|---|---|---|---|---|---|---|---|---|---|---|---|
| | | 35 | | | | | 40 | | | | | 45 | | | |

| Ile | His | Ile | Tyr | Thr | Ile | Thr | Gly | Leu | Gln | Pro | Gly | Thr | Asp | Tyr | Lys |
|---|---|---|---|---|---|---|---|---|---|---|---|---|---|---|---|
| | 50 | | | | | 55 | | | | | 60 | | | | |

| Ile | Tyr | Leu | Tyr | Thr | Leu | Asn | Asp | Asn | Ala | Arg | Ser | Ser | Pro | Val | Val |
|---|---|---|---|---|---|---|---|---|---|---|---|---|---|---|---|
| 65 | | | | | 70 | | | | | 75 | | | | | 80 |

| Ile | Asp | Ala | Ser | Thr |
|---|---|---|---|---|
| | | | | 85 |

<210> SEQ ID NO 359
<211> LENGTH: 83
<212> TYPE: PRT
<213> ORGANISM: Artificial Sequence
<220> FEATURE:
<223> OTHER INFORMATION: Synthetic polypeptide 1637110_AXLB11

<400> SEQUENCE: 359

| Asn | Val | Ser | Pro | Pro | Arg | Arg | Ala | Arg | Val | Thr | Asp | Ala | Thr | Glu | Thr |
|---|---|---|---|---|---|---|---|---|---|---|---|---|---|---|---|
| 1 | | | | 5 | | | | | 10 | | | | | 15 | |

| Thr | Ile | Thr | Ile | Ser | Trp | Gln | Gln | Gly | Phe | Gln | Val | Asp | Ala | Val | Pro |
|---|---|---|---|---|---|---|---|---|---|---|---|---|---|---|---|
| | | | 20 | | | | | 25 | | | | | 30 | | |

| Ala | Asn | Gly | Gln | Thr | Pro | Ile | Gln | Arg | Thr | Ile | Lys | Arg | Ser | Ile | Ser |
|---|---|---|---|---|---|---|---|---|---|---|---|---|---|---|---|
| | | 35 | | | | | 40 | | | | | 45 | | | |

| Ser | Tyr | Thr | Ile | Thr | Gly | Leu | Gln | Pro | Gly | Thr | Asp | Tyr | Lys | Ile | Tyr |
|---|---|---|---|---|---|---|---|---|---|---|---|---|---|---|---|
| | 50 | | | | | 55 | | | | | 60 | | | | |

| Leu | Tyr | Thr | Leu | Asn | Asp | Asn | Ala | Arg | Ser | Ser | Pro | Val | Val | Ile | Asp |
|---|---|---|---|---|---|---|---|---|---|---|---|---|---|---|---|
| 65 | | | | | 70 | | | | | 75 | | | | | 80 |

| Ala | Ser | Thr |
|---|---|---|

<210> SEQ ID NO 360
<211> LENGTH: 84

```
<212> TYPE: PRT
<213> ORGANISM: Artificial Sequence
<220> FEATURE:
<223> OTHER INFORMATION: Synthetic polypeptide 1637110_AXLH10

<400> SEQUENCE: 360
```

Asn Val Ser Pro Pro Arg Arg Ala Arg Val Thr Asp Ala Thr Glu Thr
1               5                   10                  15

Thr Ile Thr Ile Thr Trp Arg Pro Pro Gly Phe Gln Val Asp Ala Val
            20                  25                  30

Pro Ala Asn Gly Gln Thr Pro Ile Gln Arg Thr Ile Lys Arg Asn Ala
        35                  40                  45

Ser Ser Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

```
<210> SEQ ID NO 361
<211> LENGTH: 85
<212> TYPE: PRT
<213> ORGANISM: Artificial Sequence
<220> FEATURE:
<223> OTHER INFORMATION: Synthetic polypeptide 1637110_AXLF04

<400> SEQUENCE: 361
```

Asn Val Ser Pro Pro Arg Arg Ala Arg Val Thr Asp Ala Thr Glu Thr
1               5                   10                  15

Thr Ile Thr Ile Arg Trp Thr Leu Gly Leu Gly Phe Gln Val Asp Ala
            20                  25                  30

Val Pro Ala Asn Gly Gln Thr Pro Ile Gln Arg Thr Ile Lys Arg Asp
        35                  40                  45

Ala His Val Tyr Thr Ile Thr Gly Leu Gln Pro Gly Thr Asp Tyr Lys
    50                  55                  60

Ile Tyr Leu Tyr Thr Leu Asn Asp Asn Ala Arg Ser Ser Pro Val Val
65                  70                  75                  80

Ile Asp Ala Ser Thr
                85

```
<210> SEQ ID NO 362
<211> LENGTH: 83
<212> TYPE: PRT
<213> ORGANISM: Artificial Sequence
<220> FEATURE:
<223> OTHER INFORMATION: Synthetic polypeptide 1637110_AXLH04

<400> SEQUENCE: 362
```

Asn Val Ser Pro Pro Arg Arg Ala Arg Val Thr Asp Ala Thr Glu Thr
1               5                   10                  15

Thr Ile Thr Ile Arg Trp Ser Ile Gly Phe Gln Val Asp Ala Val Pro
            20                  25                  30

Ala Asn Gly Gln Thr Pro Ile Gln Arg Thr Ile Lys Arg Asp Ala Pro
        35                  40                  45

Ser Tyr Thr Ile Thr Gly Leu Gln Pro Gly Thr Asp Tyr Lys Ile Tyr
    50                  55                  60

Leu Tyr Thr Leu Asn Asp Asn Ala Arg Ser Ser Pro Val Val Ile Asp
65                  70                  75                  80

Ala Ser Thr

-continued

```
<210> SEQ ID NO 363
<211> LENGTH: 89
<212> TYPE: PRT
<213> ORGANISM: Artificial Sequence
<220> FEATURE:
<223> OTHER INFORMATION: Synthetic polypeptide 1637110_AXLG03

<400> SEQUENCE: 363

Asn Val Ser Pro Pro Arg Arg Ala Arg Val Thr Asp Ala Thr Glu Thr
1               5                   10                  15

Thr Ile Thr Ile Arg Trp Ala Leu Pro Arg Ser Glu Phe Thr Arg Phe
            20                  25                  30

Gln Val Asp Ala Val Pro Ala Asn Gly Gln Thr Pro Ile Gln Arg Thr
        35                  40                  45

Ile Thr Ala Asn Ile Arg Gly Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 364
<211> LENGTH: 90
<212> TYPE: PRT
<213> ORGANISM: Artificial Sequence
<220> FEATURE:
<223> OTHER INFORMATION: Synthetic polypeptide 1637111_AXLG09

<400> SEQUENCE: 364

Asn Val Ser Pro Pro Arg Arg Ala Arg Val Thr Asp Ala Thr Glu Thr
1               5                   10                  15

Thr Ile Thr Ile Ser Trp Gly Leu Pro Arg Ser Lys Val Val Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Tyr Gly Tyr Val Ser Gly
65                  70                  75                  80

Ser Ser Pro Val Val Ile Asp Ala Ser Thr
                85                  90

<210> SEQ ID NO 365
<211> LENGTH: 93
<212> TYPE: PRT
<213> ORGANISM: Artificial Sequence
<220> FEATURE:
<223> OTHER INFORMATION: Synthetic polypeptide 1637111_AXLE12

<400> SEQUENCE: 365

Asn Val Ser Pro Pro Arg Arg Ala Arg Val Thr Asp Ala Thr Glu Thr
1               5                   10                  15

Thr Ile Thr Ile Arg Trp Lys Leu Ala Gly Ser Gln Val Val Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Thr Ile Arg Gly Gly Ser
```

```
                65                  70                  75                  80
Ala Val Gly Ser Ser Pro Val Val Ile Asp Ala Ser Thr
                85                  90

<210> SEQ ID NO 366
<211> LENGTH: 93
<212> TYPE: PRT
<213> ORGANISM: Artificial Sequence
<220> FEATURE:
<223> OTHER INFORMATION: Synthetic polypeptide 1637111_AXLB09

<400> SEQUENCE: 366

Asn Val Ser Pro Pro Arg Arg Ala Arg Val Thr Asp Ala Thr Glu Thr
1               5                   10                  15

Thr Ile Thr Ile Ser Trp Glu Arg Ser Glu Ser Thr Val Val Gly Leu
                20                  25                  30

Gln Val Asp Ala Val Pro Ala Asn Gly Gln Thr Pro Ile Gln Arg Thr
            35                  40                  45

Ile Lys Pro Asp Val Arg Ser Tyr Thr Ile Thr Gly Leu Gln Pro Gly
        50                  55                  60

Thr Asp Tyr Lys Ile Tyr Leu Tyr Thr Leu Thr Val Val Gly Lys Ser
65                  70                  75                  80

Ala His Gly Ser Ser Pro Val Val Ile Asp Ala Ser Thr
                85                  90

<210> SEQ ID NO 367
<211> LENGTH: 89
<212> TYPE: PRT
<213> ORGANISM: Artificial Sequence
<220> FEATURE:
<223> OTHER INFORMATION: Synthetic polypeptide 1637111_AXLD11

<400> SEQUENCE: 367

Asn Val Ser Pro Pro Arg Arg Ala Arg Val Thr Asp Ala Thr Glu Thr
1               5                   10                  15

Thr Ile Thr Ile Ser Trp Gly Leu Pro Arg Gly Thr Val Asn Gly Phe
                20                  25                  30

Gln Val Asp Ala Val Pro Ala Asn Gly Gln Thr Pro Ile Gln Arg Thr
            35                  40                  45

Ile Lys Gly Ala Lys Arg Val Tyr Thr Ile Thr Gly Leu Gln Pro Gly
        50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 368
<211> LENGTH: 93
<212> TYPE: PRT
<213> ORGANISM: Artificial Sequence
<220> FEATURE:
<223> OTHER INFORMATION: Synthetic polypeptide 1637111_AXLE06

<400> SEQUENCE: 368

Asn Val Ser Pro Pro Arg Arg Ala Arg Val Thr Asp Ala Thr Glu Thr
1               5                   10                  15

Thr Ile Thr Ile Arg Trp Ala Val Ser Pro Ser Thr Val Val Gly Phe
                20                  25                  30

Gln Val Asp Ala Val Pro Ala Asn Gly Gln Thr Pro Ile Gln Arg Thr
            35                  40                  45
```

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Val Lys Gly Gly Ser
65                  70                  75                  80

Ala Ser Ala Ser Ser Pro Val Val Ile Asp Ala Ser Thr
                85                  90

<210> SEQ ID NO 369
<211> LENGTH: 93
<212> TYPE: PRT
<213> ORGANISM: Artificial Sequence
<220> FEATURE:
<223> OTHER INFORMATION: Synthetic polypeptide 1637111_AXLG02

<400> SEQUENCE: 369

Asn Val Ser Pro Pro Arg Arg Ala Arg Val Thr Asp Ala Thr Glu Thr
1               5                   10                  15

Thr Ile Thr Ile Pro Trp Ala Ala Gly Ile Glu Ala Asn Gly Glu Ile
            20                  25                  30

Thr Gly Phe Gln Val Asp Ala Val Pro Ala Asn Gly Gln Thr Pro Ile
        35                  40                  45

Gln Arg Thr Ile Lys Pro Asp Val Arg Ser Tyr Thr Ile Thr Gly Leu
    50                  55                  60

Gln Pro Gly Thr Asp Tyr Lys Ile Tyr Leu Tyr Thr Leu Tyr Gly Ala
65                  70                  75                  80

Gly Lys Thr Ser Ser Pro Val Val Ile Asp Ala Ser Thr
                85                  90

<210> SEQ ID NO 370
<211> LENGTH: 97
<212> TYPE: PRT
<213> ORGANISM: Artificial Sequence
<220> FEATURE:
<223> OTHER INFORMATION: Synthetic polypeptide 1637111_AXLC01

<400> SEQUENCE: 370

Asn Val Ser Pro Pro Arg Arg Ala Arg Val Thr Asp Ala Thr Glu Thr
1               5                   10                  15

Thr Ile Thr Ile Arg Trp Lys Lys Pro Lys His Asp Gly Gly Ala Lys
            20                  25                  30

Leu Thr Gly Phe Gln Val Asp Ala Val Pro Ala Asn Gly Gln Thr Pro
        35                  40                  45

Ile Gln Arg Thr Ile Lys Pro Asp Val Arg Ser Tyr Thr Ile Thr Gly
    50                  55                  60

Leu Gln Pro Gly Thr Asp Tyr Lys Ile Tyr Leu Tyr Thr Leu Asn Thr
65                  70                  75                  80

Arg Gly Ser Gly His Val Arg Ser Ser Pro Val Val Ile Asp Ala Ser
                85                  90                  95

Thr

<210> SEQ ID NO 371
<211> LENGTH: 93
<212> TYPE: PRT
<213> ORGANISM: Artificial Sequence
<220> FEATURE:
<223> OTHER INFORMATION: Synthetic polypeptide 1637111_AXLC06

<400> SEQUENCE: 371

Asn Val Ser Pro Pro Arg Arg Ala Arg Val Thr Asp Ala Thr Glu Thr

```
1               5                   10                  15
Thr Ile Thr Ile Ser Trp Arg Arg Ala Glu Ser Thr Val Val Gly Phe
                20                  25                  30

Gln Val Asp Ala Val Pro Ala Asn Gly Gln Thr Pro Ile Gln Arg Thr
            35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Ile Arg Gly Gly Ser
65                  70                  75                  80

Ala Ala Ala Ser Ser Pro Val Val Ile Asp Ala Ser Thr
                85                  90

<210> SEQ ID NO 372
<211> LENGTH: 93
<212> TYPE: PRT
<213> ORGANISM: Artificial Sequence
<220> FEATURE:
<223> OTHER INFORMATION: Synthetic polypeptide 1637111_AXLE11

<400> SEQUENCE: 372

Asn Val Ser Pro Pro Arg Arg Ala Arg Val Thr Asp Ala Thr Glu Thr
1               5                   10                  15

Thr Ile Thr Ile Ser Trp Gly Leu Ala Pro Ser Gln Phe Ala Arg Phe
                20                  25                  30

Gln Val Asp Ala Val Pro Ala Asn Gly Gln Thr Pro Ile Gln Arg Thr
            35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Gly Tyr Gly Arg Gly
65                  70                  75                  80

Gln Val Ala Ser Ser Pro Val Val Ile Asp Ala Ser Thr
                85                  90

<210> SEQ ID NO 373
<211> LENGTH: 84
<212> TYPE: PRT
<213> ORGANISM: Artificial Sequence
<220> FEATURE:
<223> OTHER INFORMATION: Synthetic polypeptide 1637111_AXLE01

<400> SEQUENCE: 373

Asn Val Ser Pro Pro Arg Arg Ala Arg Val Thr Asp Ala Thr Glu Thr
1               5                   10                  15

Thr Ile Thr Ile Arg Trp Gly Val Pro Gly Phe Gln Val Asp Ala Val
                20                  25                  30

Pro Ala Asn Gly Gln Thr Pro Ile Gln Arg Thr Ile His Arg Ala Thr
            35                  40                  45

Asn Ile Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 374
<211> LENGTH: 93
<212> TYPE: PRT
<213> ORGANISM: Artificial Sequence
<220> FEATURE:
<223> OTHER INFORMATION: Synthetic polypeptide 1637111_AXLA09
```

<400> SEQUENCE: 374

Asn Val Ser Pro Pro Arg Arg Ala Arg Val Thr Asp Ala Thr Glu Thr
1               5                   10                  15

Thr Ile Thr Ile Ser Trp Ala Pro Ala Ala Ser Thr Val Val Gly Leu
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Thr Met Val Gly Ala Gly
65                  70                  75                  80

Ala Val Gly Ser Ser Pro Val Val Ile Asp Ala Ser Thr
                85                  90

<210> SEQ ID NO 375
<211> LENGTH: 91
<212> TYPE: PRT
<213> ORGANISM: Artificial Sequence
<220> FEATURE:
<223> OTHER INFORMATION: Synthetic polypeptide 1637111_AXLF09

<400> SEQUENCE: 375

Asn Val Ser Pro Pro Arg Arg Ala Arg Val Thr Asp Ala Thr Glu Thr
1               5                   10                  15

Thr Ile Thr Ile Arg Trp Glu Gly Arg Gly Val Ile Gly Phe Gln Val
            20                  25                  30

Asp Ala Val Pro Ala Asn Gly Gln Thr Pro Ile Gln Arg Thr Ile Lys
        35                  40                  45

Pro Asp Val Arg Ser Tyr Thr Ile Thr Gly Leu Gln Pro Gly Thr Asp
    50                  55                  60

Tyr Lys Ile Tyr Leu Tyr Thr Leu Thr Val Val Gly Asn Ser Ala Phe
65                  70                  75                  80

Ala Ser Ser Pro Val Val Ile Asp Ala Ser Thr
                85                  90

<210> SEQ ID NO 376
<211> LENGTH: 90
<212> TYPE: PRT
<213> ORGANISM: Artificial Sequence
<220> FEATURE:
<223> OTHER INFORMATION: Synthetic polypeptide 1637111_AXLC02

<400> SEQUENCE: 376

Asn Val Ser Pro Pro Arg Arg Ala Arg Val Thr Asp Ala Thr Glu Thr
1               5                   10                  15

Thr Ile Thr Ile Arg Trp Glu Arg Ala Pro Ser Lys Phe Val Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Thr Leu Tyr Gly Tyr Val Ser Gly
65                  70                  75                  80

Ser Ser Pro Val Val Ile Asp Ala Ser Thr
                85                  90

<210> SEQ ID NO 377

```
<211> LENGTH: 90
<212> TYPE: PRT
<213> ORGANISM: Artificial Sequence
<220> FEATURE:
<223> OTHER INFORMATION: Synthetic polypeptide 1637111_AXLC02

<400> SEQUENCE: 377

Asn Val Ser Pro Pro Arg Arg Ala Arg Val Thr Asp Ala Thr Glu Thr
1               5                   10                  15

Thr Ile Thr Ile Thr Trp Thr Val Pro Arg Ser Lys Phe Val Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Tyr Gly Tyr Val Ser Gly
65                  70                  75                  80

Ser Ser Pro Val Val Ile Asp Ala Ser Thr
                85                  90

<210> SEQ ID NO 378
<211> LENGTH: 94
<212> TYPE: PRT
<213> ORGANISM: Artificial Sequence
<220> FEATURE:
<223> OTHER INFORMATION: Synthetic polypeptide 1637111_AXLB01

<400> SEQUENCE: 378

Asn Val Ser Pro Pro Arg Arg Ala Arg Val Thr Asp Ala Thr Glu Thr
1               5                   10                  15

Thr Ile Thr Ile Ser Trp Lys Lys Pro Lys His Asn Gly Gly Ser Lys
            20                  25                  30

Leu Thr Gly Phe Gln Val Asp Ala Val Pro Ala Asn Gly Gln Thr Pro
        35                  40                  45

Ile Gln Arg Thr Ile Lys Pro Asp Val Arg Ser Tyr Thr Ile Thr Gly
    50                  55                  60

Leu Gln Pro Gly Thr Asp Tyr Lys Ile Tyr Leu Tyr Thr Leu Tyr Arg
65                  70                  75                  80

Arg Leu Gly Ala Ser Ser Pro Val Val Ile Asp Ala Ser Thr
                85                  90

<210> SEQ ID NO 379
<211> LENGTH: 93
<212> TYPE: PRT
<213> ORGANISM: Artificial Sequence
<220> FEATURE:
<223> OTHER INFORMATION: Synthetic polypeptide 1637111_AXLF03

<400> SEQUENCE: 379

Asn Val Ser Pro Pro Arg Arg Ala Arg Val Thr Asp Ala Thr Glu Thr
1               5                   10                  15

Thr Ile Thr Ile Thr Trp Glu Ala Pro Val Arg Ala Asn Ser Ile Leu
            20                  25                  30

Ile Ser Phe Gln Val Asp Ala Val Pro Ala Asn Gly Gln Thr Pro Ile
        35                  40                  45

Gln Arg Thr Ile Lys Pro Asp Val Arg Ser Tyr Thr Ile Thr Gly Leu
    50                  55                  60

Gln Pro Gly Thr Asp Tyr Lys Ile Tyr Leu Tyr Thr Leu Lys Asn Tyr
65                  70                  75                  80
```

```
Glu Ser Ser Ser Ser Pro Val Val Ile Asp Ala Ser Thr
                85                  90
```

```
<210> SEQ ID NO 380
<211> LENGTH: 93
<212> TYPE: PRT
<213> ORGANISM: Artificial Sequence
<220> FEATURE:
<223> OTHER INFORMATION: Synthetic polypeptide 1637111_AXLG12

<400> SEQUENCE: 380

Asn Val Ser Pro Pro Arg Arg Ala Arg Val Thr Asp Ala Thr Glu Thr
1               5                   10                  15

Thr Ile Thr Ile Arg Trp Ala Leu Pro Ala Ser Thr Val Val Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Ile Arg Gly Asn Ser
65                  70                  75                  80

Ala Ser Ala Ser Ser Pro Val Val Ile Asp Ala Ser Thr
                85                  90
```

```
<210> SEQ ID NO 381
<211> LENGTH: 90
<212> TYPE: PRT
<213> ORGANISM: Artificial Sequence
<220> FEATURE:
<223> OTHER INFORMATION: Synthetic polypeptide 1637111_AXLE04

<400> SEQUENCE: 381

Asn Val Ser Pro Pro Arg Arg Ala Arg Val Thr Asp Ala Thr Glu Thr
1               5                   10                  15

Thr Ile Thr Ile Ser Trp Glu Gly Ser Pro Ser Thr Phe Ile Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Pro Asp Ser Gly Arg Ser
65                  70                  75                  80

Ser Ser Pro Val Val Ile Asp Ala Ser Thr
                85                  90
```

```
<210> SEQ ID NO 382
<211> LENGTH: 93
<212> TYPE: PRT
<213> ORGANISM: Artificial Sequence
<220> FEATURE:
<223> OTHER INFORMATION: Synthetic polypeptide 1637111_AXLF11

<400> SEQUENCE: 382

Asn Val Ser Pro Pro Arg Arg Ala Arg Val Thr Asp Ala Thr Glu Thr
1               5                   10                  15

Thr Ile Thr Ile Thr Trp Thr Arg Ala Arg Ser Thr Val Val Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
```

```
            50                  55                  60
Thr Asp Tyr Lys Ile Tyr Leu Tyr Thr Leu Thr Val Ile Gly Asp Ser
 65                  70                  75                  80

Ala Tyr Ser Ser Ser Pro Val Val Ile Asp Ala Ser Thr
                 85                  90
```

<210> SEQ ID NO 383
<211> LENGTH: 83
<212> TYPE: PRT
<213> ORGANISM: Artificial Sequence
<220> FEATURE:
<223> OTHER INFORMATION: Synthetic polypeptide 1637111_AXLH12

<400> SEQUENCE: 383

```
Asn Val Ser Pro Pro Arg Arg Ala Arg Val Thr Asp Ala Thr Glu Thr
 1               5                  10                  15

Thr Ile Thr Ile Ser Trp Gly Val Gly Phe Gln Val Asp Ala Val Pro
                 20                  25                  30

Ala Asn Gly Gln Thr Pro Ile Gln Arg Thr Ile Lys Arg Gly Lys Thr
             35                  40                  45

Val Tyr Thr Ile Thr Gly Leu Gln Pro Gly Thr Asp Tyr Lys Ile Tyr
         50                  55                  60

Leu Tyr Thr Leu Asn Asp Asn Ala Arg Ser Ser Pro Val Val Ile Asp
 65                  70                  75                  80

Ala Ser Thr
```

<210> SEQ ID NO 384
<211> LENGTH: 93
<212> TYPE: PRT
<213> ORGANISM: Artificial Sequence
<220> FEATURE:
<223> OTHER INFORMATION: Synthetic polypeptide 1637112_AXLC05

<400> SEQUENCE: 384

```
Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
                 20                  25                  30

Gln Val Asp Ala Val Pro Ala Asn Gly Gln Thr Pro Ile Gln Arg Thr
             35                  40                  45

Ile Asn Ser Gly Ala Arg Val Tyr Thr Ile Thr Gly Leu Gln Pro Gly
         50                  55                  60

Thr Asp Tyr Lys Ile Tyr Leu Tyr Thr Leu Asn Gly Tyr Gly Val Gly
 65                  70                  75                  80

Thr His Ala Ser Ser Pro Val Val Ile Asp Ala Ser Thr
                 85                  90
```

<210> SEQ ID NO 385
<211> LENGTH: 93
<212> TYPE: PRT
<213> ORGANISM: Artificial Sequence
<220> FEATURE:
<223> OTHER INFORMATION: Synthetic polypeptide 1637112_AXLA12

<400> SEQUENCE: 385

```
Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
                 20                  25                  30
```

Gln Val Asp Ala Val Pro Ala Asn Gly Gln Thr Pro Ile Gln Arg Thr
            35                  40                  45

Ile Asp Ala Asp Ile His Thr Tyr Thr Ile Thr Gly Leu Gln Pro Gly
 50                  55                  60

Thr Asp Tyr Lys Ile Tyr Leu Tyr Thr Leu Asn Glu Ile Gly Asp Ser
65                  70                  75                  80

Lys Tyr Arg Ser Ser Pro Val Val Ile Asp Ala Ser Thr
                85                  90

<210> SEQ ID NO 386
<211> LENGTH: 90
<212> TYPE: PRT
<213> ORGANISM: Artificial Sequence
<220> FEATURE:
<223> OTHER INFORMATION: Synthetic polypeptide 1637112_AXLD06

<400> SEQUENCE: 386

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
            35                  40                  45

Ile Thr Pro Thr Ala Ser Gly Tyr Thr Ile Gly Leu Gln Pro Gly
 50                  55                  60

Thr Asp Tyr Lys Ile Tyr Leu Tyr Thr Leu Asn Asp Arg Glu Lys Ala
65                  70                  75                  80

Ser Ser Pro Val Val Ile Asp Ala Ser Thr
                85                  90

<210> SEQ ID NO 387
<211> LENGTH: 93
<212> TYPE: PRT
<213> ORGANISM: Artificial Sequence
<220> FEATURE:
<223> OTHER INFORMATION: Synthetic polypeptide 1637112_AXLG12

<400> SEQUENCE: 387

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
            35                  40                  45

Ile Thr Ala Thr Ile Ser Gly Tyr Thr Ile Gly Leu Gln Pro Gly
 50                  55                  60

Thr Asp Tyr Lys Ile Tyr Leu Tyr Thr Leu Asn Gly Tyr Gly Val Gly
65                  70                  75                  80

Thr Val Arg Ser Ser Pro Val Val Ile Asp Ala Ser Thr
                85                  90

<210> SEQ ID NO 388
<211> LENGTH: 93
<212> TYPE: PRT
<213> ORGANISM: Artificial Sequence
<220> FEATURE:
<223> OTHER INFORMATION: Synthetic polypeptide 1637112_AXLE04

<400> SEQUENCE: 388

Asn Val Ser Pro Pro Arg Arg Ala Arg Val Thr Asp Ala Thr Glu Thr

```
1               5                   10                  15
Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
                35                  40                  45

Ile Asn Ser Ala Ala His Val Tyr Thr Ile Thr Gly Leu Gln Pro Gly
                50                  55                  60

Thr Asp Tyr Lys Ile Tyr Leu Tyr Thr Leu Thr Gly Tyr Gly Val Gly
65                  70                  75                  80

Thr Asp Ala Ser Ser Pro Val Val Ile Asp Ala Ser Thr
                85                  90

<210> SEQ ID NO 389
<211> LENGTH: 93
<212> TYPE: PRT
<213> ORGANISM: Artificial Sequence
<220> FEATURE:
<223> OTHER INFORMATION: Synthetic polypeptide 1637112_AXLH07

<400> SEQUENCE: 389

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
                35                  40                  45

Ile Asn Arg Asn Ala His Ser Tyr Thr Ile Thr Gly Leu Gln Pro Gly
                50                  55                  60

Thr Asp Tyr Lys Ile Tyr Leu Tyr Thr Leu Thr Gly Tyr Gly Val Gly
65                  70                  75                  80

Thr Leu Gly Ser Ser Pro Val Val Ile Asp Ala Ser Thr
                85                  90

<210> SEQ ID NO 390
<211> LENGTH: 93
<212> TYPE: PRT
<213> ORGANISM: Artificial Sequence
<220> FEATURE:
<223> OTHER INFORMATION: Synthetic polypeptide 1637112_AXLF11

<400> SEQUENCE: 390

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
                35                  40                  45

Ile Ala Ala Ser Ile His Val Tyr Thr Ile Thr Gly Leu Gln Pro Gly
                50                  55                  60

Thr Asp Tyr Lys Ile Tyr Leu Tyr Thr Leu Asn Gly Tyr Gly Val Gly
65                  70                  75                  80

Glu Ser Arg Ser Ser Pro Val Val Ile Asp Ala Ser Thr
                85                  90

<210> SEQ ID NO 391
<211> LENGTH: 93
<212> TYPE: PRT
<213> ORGANISM: Artificial Sequence
<220> FEATURE:
```

<223> OTHER INFORMATION: Synthetic polypeptide 1637112_AXLA11

<400> SEQUENCE: 391

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Asn Ser Gly Ala Arg Ser Tyr Thr Ile Thr Gly Leu Gln Pro Gly
    50                  55                  60

Thr Asp Tyr Lys Ile Tyr Leu Tyr Thr Leu Asn Gly Tyr Gly Val Gly
65                  70                  75                  80

Thr Leu Ala Ser Ser Pro Val Val Ile Asp Ala Ser Thr
                85                  90

<210> SEQ ID NO 392
<211> LENGTH: 83
<212> TYPE: PRT
<213> ORGANISM: Artificial Sequence
<220> FEATURE:
<223> OTHER INFORMATION: Synthetic polypeptide 1637112_AXLA04

<400> SEQUENCE: 392

Asn Val Ser Pro Pro Arg Arg Ala Arg Val Thr Asp Ala Thr Glu Thr
1               5                   10                  15

Thr Ile Thr Ile Ser Trp Arg Thr Ser Phe Gln Val Asp Ala Val Pro
            20                  25                  30

Ala Asn Gly Gln Thr Pro Ile Gln Arg Thr Ile Lys Arg Gly Val Thr
        35                  40                  45

Ser Tyr Thr Ile Thr Gly Leu Gln Pro Gly Thr Asp Tyr Lys Ile Tyr
    50                  55                  60

Leu Tyr Thr Leu Asn Asp Asn Ala Arg Ser Ser Pro Val Val Ile Asp
65                  70                  75                  80

Ala Ser Thr

<210> SEQ ID NO 393
<211> LENGTH: 93
<212> TYPE: PRT
<213> ORGANISM: Artificial Sequence
<220> FEATURE:
<223> OTHER INFORMATION: Synthetic polypeptide 1637112_AXLD03

<400> SEQUENCE: 393

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Ala Ser Asn Ile His Ser Tyr Thr Ile Thr Gly Leu Gln Pro Gly
    50                  55                  60

Thr Asp Tyr Lys Ile Tyr Leu Tyr Thr Leu Asn Gly Tyr Gly Val Gly
65                  70                  75                  80

Thr Val Ser Ser Ser Pro Val Val Ile Asp Ala Ser Thr
                85                  90

<210> SEQ ID NO 394

```
<211> LENGTH: 90
<212> TYPE: PRT
<213> ORGANISM: Artificial Sequence
<220> FEATURE:
<223> OTHER INFORMATION: Synthetic polypeptide 1637112_AXLF08

<400> SEQUENCE: 394

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Ala Thr Asn Val His Ser Tyr Thr Ile Thr Gly Leu Gln Pro Gly
    50                  55                  60

Thr Asp Tyr Lys Ile Tyr Leu Tyr Thr Leu Thr Lys Arg Gly Thr Gly
65                  70                  75                  80

Ser Ser Pro Val Val Ile Asp Ala Ser Thr
                85                  90

<210> SEQ ID NO 395
<211> LENGTH: 93
<212> TYPE: PRT
<213> ORGANISM: Artificial Sequence
<220> FEATURE:
<223> OTHER INFORMATION: Synthetic polypeptide 1637112_AXLE07

<400> SEQUENCE: 395

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Ala Thr Gly Ala Arg Val Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80

Gln Ala Ala Ser Ser Pro Val Val Ile Asp Ala Ser Thr
                85                  90

<210> SEQ ID NO 396
<211> LENGTH: 90
<212> TYPE: PRT
<213> ORGANISM: Artificial Sequence
<220> FEATURE:
<223> OTHER INFORMATION: Synthetic polypeptide 1637112_AXLG06

<400> SEQUENCE: 396

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Ala Ala Ala Thr Arg Ser Tyr Thr Ile Thr Gly Leu Gln Pro Gly
    50                  55                  60

Thr Asp Tyr Lys Ile Tyr Leu Tyr Thr Leu Thr Lys Tyr Arg Ala Ala
65                  70                  75                  80
```

```
Ser Ser Pro Val Val Ile Asp Ala Ser Thr
            85                  90
```

```
<210> SEQ ID NO 397
<211> LENGTH: 84
<212> TYPE: PRT
<213> ORGANISM: Artificial Sequence
<220> FEATURE:
<223> OTHER INFORMATION: Synthetic polypeptide 1637112_AXLE12

<400> SEQUENCE: 397
```

```
Asn Val Ser Pro Pro Arg Arg Ala Arg Val Thr Asp Ala Thr Glu Thr
1               5                   10                  15

Thr Ile Thr Ile Arg Trp Ala Glu Pro Gly Phe Gln Val Asp Ala Val
            20                  25                  30

Pro Ala Asn Gly Gln Thr Pro Ile Gln Arg Thr Ile Lys Arg Thr Ala
        35                  40                  45

Arg Val Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr
```

```
<210> SEQ ID NO 398
<211> LENGTH: 93
<212> TYPE: PRT
<213> ORGANISM: Artificial Sequence
<220> FEATURE:
<223> OTHER INFORMATION: Synthetic polypeptide 1637112_AXLA10

<400> SEQUENCE: 398
```

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Ala Ser Asn Ile His Ser Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80

Thr His Gly Ser Ser Pro Val Val Ile Asp Ala Ser Thr
            85                  90
```

```
<210> SEQ ID NO 399
<211> LENGTH: 90
<212> TYPE: PRT
<213> ORGANISM: Artificial Sequence
<220> FEATURE:
<223> OTHER INFORMATION: Synthetic polypeptide 1637112_AXLF07

<400> SEQUENCE: 399
```

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Asp Pro Ser Lys Ser Gly Tyr Thr Ile Thr Gly Leu Gln Pro Gly
    50                  55                  60
```

```
Thr Asp Tyr Lys Ile Tyr Leu Tyr Thr Leu Lys Ser Gly Gly Arg Ala
 65                  70                  75                  80

Ser Ser Pro Val Val Ile Asp Ala Ser Thr
                 85                  90

<210> SEQ ID NO 400
<211> LENGTH: 93
<212> TYPE: PRT
<213> ORGANISM: Artificial Sequence
<220> FEATURE:
<223> OTHER INFORMATION: Synthetic polypeptide 1637112_AXLB11

<400> SEQUENCE: 400

Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Gly Phe
                 20                  25                  30

Gln Val Asp Ala Val Pro Ala Asn Gly Gln Thr Pro Ile Gln Arg Thr
             35                  40                  45

Ile Asn Arg Asn Ala His Thr Tyr Thr Ile Thr Gly Leu Gln Pro Gly
         50                  55                  60

Thr Asp Tyr Lys Ile Tyr Leu Tyr Thr Leu Asn Gly Tyr Gly Val Gly
 65                  70                  75                  80

Thr Val Ser Ser Ser Pro Val Val Ile Asp Ala Ser Thr
                 85                  90

<210> SEQ ID NO 401
<211> LENGTH: 93
<212> TYPE: PRT
<213> ORGANISM: Artificial Sequence
<220> FEATURE:
<223> OTHER INFORMATION: Synthetic polypeptide 1637112_AXLB09

<400> SEQUENCE: 401

Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Gly Phe
                 20                  25                  30

Gln Val Asp Ala Val Pro Ala Asn Gly Gln Thr Pro Ile Gln Arg Thr
             35                  40                  45

Ile Ala Thr Gly Ala Arg Val Tyr Thr Ile Thr Gly Leu Gln Pro Gly
         50                  55                  60

Thr Asp Tyr Lys Ile Tyr Leu Tyr Thr Leu Thr Gly Tyr Gly Val Gly
 65                  70                  75                  80

Thr His Ala Ser Ser Pro Val Val Ile Asp Ala Ser Thr
                 85                  90

<210> SEQ ID NO 402
<211> LENGTH: 90
<212> TYPE: PRT
<213> ORGANISM: Artificial Sequence
<220> FEATURE:
<223> OTHER INFORMATION: Synthetic polypeptide 1637112_AXLG05

<400> SEQUENCE: 402

Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Gly Phe
                 20                  25                  30
```

```
Gln Val Asp Ala Val Pro Ala Asn Gly Gln Thr Pro Ile Gln Arg Thr
            35                  40                  45

Ile Ala Ser Thr Val Asn Thr Tyr Thr Ile Thr Gly Leu Gln Pro Gly
 50                  55                  60

Thr Asp Tyr Lys Ile Tyr Leu Tyr Thr Leu Tyr Lys Val Arg Ala Thr
 65                  70                  75                  80

Ser Ser Pro Val Val Ile Asp Ala Ser Thr
                85                  90

<210> SEQ ID NO 403
<211> LENGTH: 93
<212> TYPE: PRT
<213> ORGANISM: Artificial Sequence
<220> FEATURE:
<223> OTHER INFORMATION: Synthetic polypeptide 1637112_AXLA05

<400> SEQUENCE: 403

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
            35                  40                  45

Ile Ala Thr Gly Ala Arg Val Tyr Thr Ile Thr Gly Leu Gln Pro Gly
 50                  55                  60

Thr Asp Tyr Lys Ile Tyr Leu Tyr Thr Leu Thr Gly Tyr Gly Val Gly
 65                  70                  75                  80

Thr Tyr Ser Ser Ser Pro Val Val Ile Asp Ala Ser Thr
                85                  90

<210> SEQ ID NO 404
<211> LENGTH: 93
<212> TYPE: PRT
<213> ORGANISM: Artificial Sequence
<220> FEATURE:
<223> OTHER INFORMATION: Synthetic polypeptide 1637112_AXLC01

<400> SEQUENCE: 404

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
            35                  40                  45

Ile Asn Ser Asn Ala His Ile Tyr Thr Ile Thr Gly Leu Gln Pro Gly
 50                  55                  60

Thr Asp Tyr Lys Ile Tyr Leu Tyr Thr Leu Asn Gly Tyr Gly Val Gly
 65                  70                  75                  80

Thr Val Thr Ser Ser Pro Val Val Ile Asp Ala Ser Thr
                85                  90

<210> SEQ ID NO 405
<211> LENGTH: 93
<212> TYPE: PRT
<213> ORGANISM: Artificial Sequence
<220> FEATURE:
<223> OTHER INFORMATION: Synthetic polypeptide 1637112_AXLE08

<400> SEQUENCE: 405

Asn Val Ser Pro Pro Arg Arg Ala Arg Val Thr Asp Ala Thr Glu Thr
```

```
                1               5                   10                  15
            Thr Ile Thr Ile Ser Trp Arg Thr Lys Thr Glu Thr Ile Thr Gly Phe
                            20                  25                  30

Gln Val Asp Ala Val Pro Ala Asn Gly Gln Thr Pro Ile Gln Arg Thr
                            35                  40                  45

Ile Asn Arg Asn Ala His Ala Tyr Thr Ile Thr Gly Leu Gln Pro Gly
                            50                  55                  60

Thr Asp Tyr Lys Ile Tyr Leu Tyr Thr Leu Thr Gly Tyr Gly Val Gly
             65                  70                  75                  80

Thr Phe Ala Ser Ser Pro Val Val Ile Asp Ala Ser Thr
                            85                  90
```

<210> SEQ ID NO 406
<211> LENGTH: 93
<212> TYPE: PRT
<213> ORGANISM: Artificial Sequence
<220> FEATURE:
<223> OTHER INFORMATION: Synthetic polypeptide 1637112_AXLE03

<400> SEQUENCE: 406

```
            Asn Val Ser Pro Pro Arg Arg Ala Arg Val Thr Asp Ala Thr Glu Thr
             1               5                   10                  15

Thr Ile Thr Ile Ser Trp Arg Thr Lys Thr Glu Thr Ile Thr Gly Phe
                            20                  25                  30

Gln Val Asp Ala Val Pro Ala Asn Gly Gln Thr Pro Ile Gln Arg Thr
                            35                  40                  45

Ile Asn Ser Gly Ala His Ser Tyr Thr Ile Thr Gly Leu Gln Pro Gly
                            50                  55                  60

Thr Asp Tyr Lys Ile Tyr Leu Tyr Thr Leu Thr Met Tyr Gly Val Gly
             65                  70                  75                  80

Glu Val Arg Ser Ser Pro Val Val Ile Asp Ala Ser Thr
                            85                  90
```

<210> SEQ ID NO 407
<211> LENGTH: 90
<212> TYPE: PRT
<213> ORGANISM: Artificial Sequence
<220> FEATURE:
<223> OTHER INFORMATION: Synthetic polypeptide 1637112_AXLE11

<400> SEQUENCE: 407

```
            Asn Val Ser Pro Pro Arg Arg Ala Arg Val Thr Asp Ala Thr Glu Thr
             1               5                   10                  15

Thr Ile Thr Ile Arg Trp Thr Leu Ala Gly Ser Gln Phe Ile Gly Phe
                            20                  25                  30

Gln Val Asp Ala Val Pro Ala Asn Gly Gln Thr Pro Ile Gln Arg Thr
                            35                  40                  45

Ile Asp Gly Ser Val His Val Tyr Thr Ile Thr Gly Leu Gln Pro Gly
                            50                  55                  60

Thr Asp Tyr Lys Ile Tyr Leu Tyr Thr Leu Ser Lys Arg Leu Glu Thr
             65                  70                  75                  80

Ser Ser Pro Val Val Ile Asp Ala Ser Thr
                            85                  90
```

<210> SEQ ID NO 408
<211> LENGTH: 93
<212> TYPE: PRT
<213> ORGANISM: Artificial Sequence
<220> FEATURE:

<223> OTHER INFORMATION: Synthetic polypeptide 1637112_AXLD08

<400> SEQUENCE: 408

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Ala Thr Ala Lys Arg Val Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80

Glu Tyr Arg Ser Ser Pro Val Val Ile Asp Ala Ser Thr
                85                  90

<210> SEQ ID NO 409
<211> LENGTH: 93
<212> TYPE: PRT
<213> ORGANISM: Artificial Sequence
<220> FEATURE:
<223> OTHER INFORMATION: Synthetic polypeptide 1637112_AXLA06

<400> SEQUENCE: 409

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Asn Ser Ala Ala His Ala Tyr Thr Ile Thr Gly Leu Gln Pro Gly
    50                  55                  60

Thr Asp Tyr Lys Ile Tyr Leu Tyr Thr Leu Asn Gly Tyr Gly Val Gly
65                  70                  75                  80

Thr Leu Ala Ser Ser Pro Val Val Ile Asp Ala Ser Thr
                85                  90

<210> SEQ ID NO 410
<211> LENGTH: 93
<212> TYPE: PRT
<213> ORGANISM: Artificial Sequence
<220> FEATURE:
<223> OTHER INFORMATION: Synthetic polypeptide 1637112_AXLH05

<400> SEQUENCE: 410

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Asn Ala Gly Ala Arg Thr Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80

Thr Phe Gly Ser Ser Pro Val Val Ile Asp Ala Ser Thr
                85                  90

<210> SEQ ID NO 411
<211> LENGTH: 93
<212> TYPE: PRT
<213> ORGANISM: Artificial Sequence
<220> FEATURE:
<223> OTHER INFORMATION: Synthetic polypeptide 1637112_AXLA08

<400> SEQUENCE: 411

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Ala Thr Gly Ala Arg Val Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80

Ala Ser Ala Ser Ser Pro Val Val Ile Asp Ala Ser Thr
                85                  90
```

<210> SEQ ID NO 412
<211> LENGTH: 93
<212> TYPE: PRT
<213> ORGANISM: Artificial Sequence
<220> FEATURE:
<223> OTHER INFORMATION: Synthetic polypeptide 1637112_AXLD02

<400> SEQUENCE: 412

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Ala Thr Ala Lys Arg Val Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80

Glu Val Arg Ser Ser Pro Val Val Ile Asp Ala Ser Thr
                85                  90
```

<210> SEQ ID NO 413
<211> LENGTH: 93
<212> TYPE: PRT
<213> ORGANISM: Artificial Sequence
<220> FEATURE:
<223> OTHER INFORMATION: Synthetic polypeptide 1637112_AXLF12

<400> SEQUENCE: 413

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Ala Ala Ala Val His Thr Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80
```

Gln Val Gly Ser Ser Pro Val Val Ile Asp Ala Ser Thr
                85                  90

<210> SEQ ID NO 414
<211> LENGTH: 93
<212> TYPE: PRT
<213> ORGANISM: Artificial Sequence
<220> FEATURE:
<223> OTHER INFORMATION: Synthetic polypeptide 1637112_AXLB10

<400> SEQUENCE: 414

Asn Val Ser Pro Pro Arg Arg Ala Arg Val Thr Asp Ala Thr Glu Thr
1               5                   10                  15

Thr Ile Thr Ile Ser Trp Leu Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile His Ala Gly Ala His Ile Tyr Thr Ile Thr Gly Leu Gln Pro Gly
    50                  55                  60

Thr Asp Tyr Lys Ile Tyr Leu Tyr Thr Leu Asn Gly Phe Gly Asn Gly
65                  70                  75                  80

Glu Phe Thr Ser Ser Pro Val Val Ile Asp Ala Ser Thr
                85                  90

<210> SEQ ID NO 415
<211> LENGTH: 84
<212> TYPE: PRT
<213> ORGANISM: Artificial Sequence
<220> FEATURE:
<223> OTHER INFORMATION: Synthetic polypeptide 1637113_AXLD11

<400> SEQUENCE: 415

Asn Val Ser Pro Pro Arg Arg Ala Arg Val Thr Asp Ala Thr Glu Thr
1               5                   10                  15

Thr Ile Thr Ile Arg Trp Lys Ile Pro Gly Phe Gln Val Asp Ala Val
            20                  25                  30

Pro Ala Asn Gly Gln Thr Pro Ile Gln Arg Thr Ile Asn Arg Gly Ile
        35                  40                  45

Thr Thr Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 416
<211> LENGTH: 84
<212> TYPE: PRT
<213> ORGANISM: Artificial Sequence
<220> FEATURE:
<223> OTHER INFORMATION: Synthetic polypeptide 1637113_AXLC05

<400> SEQUENCE: 416

Asn Val Ser Pro Pro Arg Arg Ala Arg Val Thr Asp Ala Thr Glu Thr
1               5                   10                  15

Thr Ile Thr Ile Arg Trp Thr Leu Thr Gly Phe Gln Val Asp Ala Val
            20                  25                  30

Pro Ala Asn Gly Gln Thr Pro Ile Gln Arg Thr Ile Lys Arg Ser Ala
        35                  40                  45

Asn Val Tyr Thr Ile Thr Gly Leu Gln Pro Gly Thr Asp Tyr Lys Ile

```
                  50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 417
<211> LENGTH: 86
<212> TYPE: PRT
<213> ORGANISM: Artificial Sequence
<220> FEATURE:
<223> OTHER INFORMATION: Synthetic polypeptide 1637113_AXLE10

<400> SEQUENCE: 417

Asn Val Ser Pro Pro Arg Arg Ala Arg Val Thr Asp Ala Thr Glu Thr
  1               5                  10                  15

Thr Ile Thr Ile Arg Trp Lys Ala Pro Gln Ser Asp Phe Gln Val Asp
                 20                  25                  30

Ala Val Pro Ala Asn Gly Gln Thr Pro Ile Gln Arg Thr Ile Lys Arg
             35                  40                  45

Ser Ala Thr Ile Tyr Thr Ile Thr Gly Leu Gln Pro Gly Thr Asp Tyr
         50                  55                  60

Lys Ile Tyr Leu Tyr Thr Leu Asn Asp Asn Ala Arg Ser Ser Pro Val
 65                  70                  75                  80

Val Ile Asp Ala Ser Thr
                 85

<210> SEQ ID NO 418
<211> LENGTH: 84
<212> TYPE: PRT
<213> ORGANISM: Artificial Sequence
<220> FEATURE:
<223> OTHER INFORMATION: Synthetic polypeptide 1637113_AXLG12

<400> SEQUENCE: 418

Asn Val Ser Pro Pro Arg Arg Ala Arg Val Thr Asp Ala Thr Glu Thr
  1               5                  10                  15

Thr Ile Thr Ile Arg Trp Gln Ala Leu Gly Phe Gln Val Asp Ala Val
                 20                  25                  30

Pro Ala Asn Gly Gln Thr Pro Ile Gln Arg Thr Ile Ala Arg Asn Ala
             35                  40                  45

Pro Ala Tyr Thr Ile Thr Gly Leu Gln Pro Gly Thr Asp Tyr Lys Ile
         50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 419
<211> LENGTH: 84
<212> TYPE: PRT
<213> ORGANISM: Artificial Sequence
<220> FEATURE:
<223> OTHER INFORMATION: Synthetic polypeptide 1637113_AXLA04

<400> SEQUENCE: 419

Asn Val Ser Pro Pro Arg Arg Ala Arg Val Thr Asp Ala Thr Glu Thr
  1               5                  10                  15

Thr Ile Thr Ile Arg Trp Arg Val Leu Gly Phe Gln Val Asp Ala Val
                 20                  25                  30

Pro Ala Asn Gly Gln Thr Pro Ile Gln Arg Thr Ile His Arg Gly Val
```

```
                35                  40                  45

Asn Val Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
65                   70                  75                  80

Asp Ala Ser Thr

<210> SEQ ID NO 420
<211> LENGTH: 93
<212> TYPE: PRT
<213> ORGANISM: Artificial Sequence
<220> FEATURE:
<223> OTHER INFORMATION: Synthetic polypeptide 1637113_AXLE03

<400> SEQUENCE: 420

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
            35                  40                  45

Ile Asn Ser Gly Ala Arg Ser Tyr Thr Ile Thr Gly Leu Gln Pro Gly
 50                  55                  60

Thr Asp Tyr Lys Ile Tyr Leu Tyr Thr Leu Thr Gly Tyr Gly Val Gly
65                   70                  75                  80

Gln Asp Ala Ser Ser Pro Val Val Ile Asp Ala Ser Thr
                85                  90

<210> SEQ ID NO 421
<211> LENGTH: 84
<212> TYPE: PRT
<213> ORGANISM: Artificial Sequence
<220> FEATURE:
<223> OTHER INFORMATION: Synthetic polypeptide 1637113_AXLB05

<400> SEQUENCE: 421

Asn Val Ser Pro Pro Arg Arg Ala Arg Val Thr Asp Ala Thr Glu Thr
1               5                   10                  15

Thr Ile Thr Ile Thr Trp Thr Leu Pro His Phe Gln Val Asp Ala Val
                20                  25                  30

Pro Ala Asn Gly Gln Thr Pro Ile Gln Arg Thr Ile Asp Arg Gly Thr
            35                  40                  45

Arg Ala Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
65                   70                  75                  80

Asp Ala Ser Thr

<210> SEQ ID NO 422
<211> LENGTH: 83
<212> TYPE: PRT
<213> ORGANISM: Artificial Sequence
<220> FEATURE:
<223> OTHER INFORMATION: Synthetic polypeptide 1637113_AXLB06

<400> SEQUENCE: 422

Asn Val Ser Pro Pro Arg Arg Ala Arg Val Thr Asp Ala Thr Glu Thr
1               5                   10                  15

Thr Ile Thr Ile Thr Trp Pro Leu Gly Phe Gln Val Asp Ala Val Pro
```

```
                       20                  25                  30

Ala Asn Gly Gln Thr Pro Ile Gln Arg Thr Ile Lys Arg Gly Val Ser
                35                  40                  45

Ser Tyr Thr Ile Thr Gly Leu Gln Pro Gly Thr Asp Tyr Lys Ile Tyr
 50                  55                  60

Leu Tyr Thr Leu Asn Asp Asn Ala Arg Ser Ser Pro Val Val Ile Asp
 65                  70                  75                  80

Ala Ser Thr

<210> SEQ ID NO 423
<211> LENGTH: 84
<212> TYPE: PRT
<213> ORGANISM: Artificial Sequence
<220> FEATURE:
<223> OTHER INFORMATION: Synthetic polypeptide 1637113_AXLH03

<400> SEQUENCE: 423

Asn Val Ser Pro Pro Arg Arg Ala Arg Val Thr Asp Ala Thr Glu Thr
 1               5                  10                  15

Thr Ile Thr Ile Arg Trp Arg Gly Pro Arg Phe Gln Val Asp Ala Val
                20                  25                  30

Pro Ala Asn Gly Gln Thr Pro Ile Gln Arg Thr Ile Asp Ala Gly Thr
                35                  40                  45

Arg Gly Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 424
<211> LENGTH: 84
<212> TYPE: PRT
<213> ORGANISM: Artificial Sequence
<220> FEATURE:
<223> OTHER INFORMATION: Synthetic polypeptide 1637113_AXLF01

<400> SEQUENCE: 424

Asn Val Ser Pro Pro Arg Arg Ala Arg Val Thr Asp Ala Thr Glu Thr
 1               5                  10                  15

Thr Ile Thr Ile Arg Trp Ala Ile Pro Gly Phe Gln Val Asp Ala Val
                20                  25                  30

Pro Ala Asn Gly Gln Thr Pro Ile Gln Arg Thr Ile Thr Arg Gly Ala
                35                  40                  45

Arg Ala Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 425
<211> LENGTH: 95
<212> TYPE: PRT
<213> ORGANISM: Artificial Sequence
<220> FEATURE:
<223> OTHER INFORMATION: Synthetic polypeptide 1637113_AXLF12

<400> SEQUENCE: 425

Asn Val Ser Pro Pro Arg Arg Ala Ala Ser Gln Thr Pro Pro Arg Pro
 1               5                  10                  15
```

```
Pro Ser Gln Phe Val Gly Ile His Gln Gln Thr Thr Glu Val Val Asp
            20                  25                  30

Ser Val Ser Lys Ser Thr Gln Ser Gln Pro Thr Ala Lys Leu Pro Phe
        35                  40                  45

Ser Gly Gln Ser Ser Leu Thr Phe Val Leu Ile Pro Leu Pro Gly Tyr
 50                  55                  60

Pro Gly Thr Asp Tyr Lys Ile Tyr Leu Tyr Thr Leu Thr Val Ala Gly
 65                  70                  75                  80

Ala Ser Asp Asp Arg Ser Ser Pro Val Val Ile Asp Ala Ser Thr
                85                  90                  95

<210> SEQ ID NO 426
<211> LENGTH: 84
<212> TYPE: PRT
<213> ORGANISM: Artificial Sequence
<220> FEATURE:
<223> OTHER INFORMATION: Synthetic polypeptide 1637113_AXLD08

<400> SEQUENCE: 426

Asn Val Ser Pro Pro Arg Arg Ala Arg Val Thr Asp Ala Thr Glu Thr
 1               5                  10                  15

Thr Ile Thr Ile Arg Trp Lys Val Pro Gly Phe Gln Val Asp Ala Val
            20                  25                  30

Pro Ala Asn Gly Gln Thr Pro Ile Gln Arg Thr Ile Thr Arg Gly Thr
        35                  40                  45

Arg Val Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 427
<211> LENGTH: 94
<212> TYPE: PRT
<213> ORGANISM: Artificial Sequence
<220> FEATURE:
<223> OTHER INFORMATION: Synthetic polypeptide 1637113_AXLC12

<400> SEQUENCE: 427

Asn Val Ser Pro Pro Arg Arg Ala Arg Val Thr Asp Ala Thr Glu Thr
 1               5                  10                  15

Thr Ile Thr Ile Ser Trp Lys Lys Pro Lys His Asn Gly Gly Thr Gly
            20                  25                  30

Val Thr Ser Phe Gln Val Asp Ala Val Pro Ala Asn Gly Gln Thr Pro
        35                  40                  45

Ile Gln Arg Thr Ile Lys Pro Asp Val Arg Ser Tyr Thr Ile Thr Gly
 50                  55                  60

Leu Gln Pro Gly Thr Asp Tyr Lys Ile Tyr Leu Tyr Thr Leu Asn Lys
 65                  70                  75                  80

Arg Arg Asn Ser Ser Pro Val Val Ile Asp Ala Ser Thr
                85                  90

<210> SEQ ID NO 428
<211> LENGTH: 84
<212> TYPE: PRT
<213> ORGANISM: Artificial Sequence
<220> FEATURE:
<223> OTHER INFORMATION: Synthetic polypeptide 1637113_AXLH01
```

<400> SEQUENCE: 428

Asn Val Ser Pro Pro Arg Arg Ala Arg Val Thr Asp Ala Thr Glu Thr
1               5                   10                  15

Thr Ile Thr Ile Arg Trp Ala Ala Pro Gly Phe Gln Val Asp Ala Val
            20                  25                  30

Pro Ala Asn Gly Gln Thr Pro Ile Gln Arg Thr Ile His Arg Thr Ala
        35                  40                  45

Pro Ser Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 429
<211> LENGTH: 84
<212> TYPE: PRT
<213> ORGANISM: Artificial Sequence
<220> FEATURE:
<223> OTHER INFORMATION: Synthetic polypeptide 1637113_AXLF05

<400> SEQUENCE: 429

Asn Val Ser Pro Pro Arg Arg Ala Arg Val Thr Asp Ala Thr Glu Thr
1               5                   10                  15

Thr Ile Thr Ile Arg Trp Pro Val Asn Gly Phe Gln Val Asp Ala Val
            20                  25                  30

Pro Ala Asn Gly Gln Thr Pro Ile Gln Arg Thr Ile Asn Arg Gly Val
        35                  40                  45

Arg Thr Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 430
<211> LENGTH: 84
<212> TYPE: PRT
<213> ORGANISM: Artificial Sequence
<220> FEATURE:
<223> OTHER INFORMATION: Synthetic polypeptide 1637113_AXLA08

<400> SEQUENCE: 430

Asn Val Ser Pro Pro Arg Arg Ala Arg Val Thr Asp Ala Thr Glu Thr
1               5                   10                  15

Thr Ile Thr Ile Arg Trp Gly Val Leu Gly Phe Gln Val Asp Ala Val
            20                  25                  30

Pro Ala Asn Gly Gln Thr Pro Ile Gln Arg Thr Ile Asn Arg Ser Val
        35                  40                  45

Arg Ala Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 431
<211> LENGTH: 85
<212> TYPE: PRT
<213> ORGANISM: Artificial Sequence
<220> FEATURE:

<223> OTHER INFORMATION: Synthetic polypeptide 1637113_AXLB01

<400> SEQUENCE: 431

Asn Val Ser Pro Pro Arg Arg Ala Arg Val Thr Asp Ala Thr Glu Thr
1               5                   10                  15

Thr Ile Thr Ile Arg Trp Ser Gln Ile Asp Arg Phe Gln Val Asp Ala
            20                  25                  30

Val Pro Ala Asn Gly Gln Thr Pro Ile Gln Arg Thr Ile Lys Ser Asp
        35                  40                  45

Val His Ile Tyr Thr Ile Thr Gly Leu Gln Pro Gly Thr Asp Tyr Lys
    50                  55                  60

Ile Tyr Leu Tyr Thr Leu Asn Asp Asn Ala Arg Ser Ser Pro Val Val
65                  70                  75                  80

Ile Asp Ala Ser Thr
                85

<210> SEQ ID NO 432
<211> LENGTH: 86
<212> TYPE: PRT
<213> ORGANISM: Artificial Sequence
<220> FEATURE:
<223> OTHER INFORMATION: Synthetic polypeptide 1637113_AXLE08

<400> SEQUENCE: 432

Asn Val Ser Pro Pro Arg Arg Ala Arg Val Thr Asp Ala Thr Glu Thr
1               5                   10                  15

Thr Ile Thr Ile Arg Trp Ala Ser Gln Ile Asn Gly Phe Gln Val Asp
            20                  25                  30

Ala Val Pro Ala Asn Gly Gln Thr Pro Ile Gln Arg Thr Ile Lys Arg
        35                  40                  45

Thr Ile His Val Tyr Thr Ile Thr Gly Leu Gln Pro Gly Thr Asp Tyr
    50                  55                  60

Lys Ile Tyr Leu Tyr Thr Leu Asn Asp Asn Ala Arg Ser Ser Pro Val
65                  70                  75                  80

Val Ile Asp Ala Ser Thr
                85

<210> SEQ ID NO 433
<211> LENGTH: 89
<212> TYPE: PRT
<213> ORGANISM: Artificial Sequence
<220> FEATURE:
<223> OTHER INFORMATION: Synthetic polypeptide 1637113_AXLF09

<400> SEQUENCE: 433

Asn Val Ser Pro Pro Arg Arg Ala Arg Val Thr Asp Ala Thr Glu Thr
1               5                   10                  15

Thr Ile Thr Ile Arg Trp Ala Leu Pro Arg Ser Glu Phe Thr Arg Phe
            20                  25                  30

Gln Val Asp Ala Val Pro Ala Asn Gly Gln Thr Pro Ile Gln Arg Thr
        35                  40                  45

Ile Thr Ser Asn Ile Arg Gly Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

```
<210> SEQ ID NO 434
<211> LENGTH: 86
<212> TYPE: PRT
<213> ORGANISM: Artificial Sequence
<220> FEATURE:
<223> OTHER INFORMATION: Synthetic polypeptide 1637113_AXLG07

<400> SEQUENCE: 434
```

Asn Val Ser Pro Pro Arg Arg Ala Arg Val Thr Asp Ala Thr Glu Thr
1               5                   10                  15

Thr Ile Thr Ile Arg Trp Gln Gln Tyr Ile Asn Gly Phe Gln Val Asp
            20                  25                  30

Ala Val Pro Ala Asn Gly Gln Thr Pro Ile Gln Arg Thr Ile Ala Arg
        35                  40                  45

Asp Ala Pro Thr Tyr Thr Ile Thr Gly Leu Gln Pro Gly Thr Asp Tyr
    50                  55                  60

Lys Ile Tyr Leu Tyr Thr Leu Asn Asp Asn Ala Arg Ser Ser Pro Val
65                  70                  75                  80

Val Ile Asp Ala Ser Thr
                85

```
<210> SEQ ID NO 435
<211> LENGTH: 84
<212> TYPE: PRT
<213> ORGANISM: Artificial Sequence
<220> FEATURE:
<223> OTHER INFORMATION: Synthetic polypeptide 1637113_AXLF06

<400> SEQUENCE: 435
```

Asn Val Ser Pro Pro Arg Arg Ala Arg Val Thr Asp Ala Thr Glu Thr
1               5                   10                  15

Thr Ile Thr Ile Arg Trp Gln Leu Pro Gly Phe Gln Val Asp Ala Val
            20                  25                  30

Pro Ala Asn Gly Gln Thr Pro Ile Gln Arg Thr Ile Lys Arg Ala Ala
        35                  40                  45

Asn Val Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

```
<210> SEQ ID NO 436
<211> LENGTH: 89
<212> TYPE: PRT
<213> ORGANISM: Artificial Sequence
<220> FEATURE:
<223> OTHER INFORMATION: Synthetic polypeptide 1637113_AXLC08

<400> SEQUENCE: 436
```

Asn Val Ser Pro Pro Arg Arg Ala Arg Val Thr Asp Ala Thr Glu Thr
1               5                   10                  15

Thr Ile Thr Ile Arg Trp Glu Leu Pro Ala Gly Thr Val Asn Gly Phe
            20                  25                  30

Gln Val Asp Ala Val Pro Ala Asn Gly Gln Thr Pro Ile Gln Arg Thr
        35                  40                  45

Ile Lys Gly Ala Lys Arg Gly Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

-continued

Thr Pro Val Val Ile Asp Ala Ser Thr
                85

<210> SEQ ID NO 437
<211> LENGTH: 86
<212> TYPE: PRT
<213> ORGANISM: Artificial Sequence
<220> FEATURE:
<223> OTHER INFORMATION: Synthetic polypeptide 1637113_AXLD05

<400> SEQUENCE: 437

Asn Val Ser Pro Pro Arg Arg Ala Arg Val Thr Asp Ala Thr Glu Thr
1               5                   10                  15

Thr Ile Thr Ile Arg Trp Lys Leu Pro Glu Gly Asp Phe Gln Val Asp
            20                  25                  30

Ala Val Pro Ala Asn Gly Gln Thr Pro Ile Gln Arg Thr Ile Lys Arg
        35                  40                  45

Asn Ala Ser Thr Tyr Thr Ile Thr Gly Leu Gln Pro Gly Thr Asp Tyr
    50                  55                  60

Lys Ile Tyr Leu Tyr Thr Leu Asn Asp Asn Ala Arg Ser Ser Pro Val
65                  70                  75                  80

Val Ile Asp Ala Ser Thr
                85

<210> SEQ ID NO 438
<211> LENGTH: 84
<212> TYPE: PRT
<213> ORGANISM: Artificial Sequence
<220> FEATURE:
<223> OTHER INFORMATION: Synthetic polypeptide 1637113_AXLD03

<400> SEQUENCE: 438

Asn Val Ser Pro Pro Arg Arg Ala Arg Val Thr Asp Ala Thr Glu Thr
1               5                   10                  15

Thr Ile Thr Ile Arg Trp Gly Ile Pro Gly Phe Gln Val Asp Ala Val
            20                  25                  30

Pro Ala Asn Gly Gln Thr Pro Ile Gln Arg Thr Ile Lys Arg Ala Ile
        35                  40                  45

Ser Ala Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 439
<211> LENGTH: 84
<212> TYPE: PRT
<213> ORGANISM: Artificial Sequence
<220> FEATURE:
<223> OTHER INFORMATION: Synthetic polypeptide 1637113_AXLH02

<400> SEQUENCE: 439

Asn Val Ser Pro Pro Arg Arg Ala Arg Val Thr Asp Ala Thr Glu Thr
1               5                   10                  15

Thr Ile Thr Ile Arg Trp Gly Val Leu Gly Phe Gln Val Asp Ala Val
            20                  25                  30

Pro Ala Asn Gly Gln Thr Pro Ile Gln Arg Thr Ile Lys Arg Ala Ile
        35                  40                  45

Asn Ser Tyr Thr Ile Thr Gly Leu Gln Pro Gly Thr Asp Tyr Lys Ile
    50                  55                  60

```
Tyr Leu Tyr Thr Leu Asn Asp Asn Ala Arg Ser Ser Pro Val Val Ile
 65                  70                  75                  80

Asp Ala Ser Thr

<210> SEQ ID NO 440
<211> LENGTH: 84
<212> TYPE: PRT
<213> ORGANISM: Artificial Sequence
<220> FEATURE:
<223> OTHER INFORMATION: Synthetic polypeptide 1637113_AXLA06

<400> SEQUENCE: 440

Asn Val Ser Pro Pro Arg Arg Ala Arg Val Thr Asp Ala Thr Glu Thr
  1               5                  10                  15

Thr Ile Thr Ile Arg Trp Lys Val Pro Gly Phe Gln Val Asp Ala Val
                 20                  25                  30

Pro Ala Asn Gly Gln Thr Pro Ile Gln Arg Thr Ile Thr Arg Gly Val
             35                  40                  45

Arg Gly Tyr Thr Ile Thr Gly Leu Gln Pro Gly Thr Asp Tyr Lys Ile
         50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 441
<211> LENGTH: 93
<212> TYPE: PRT
<213> ORGANISM: Artificial Sequence
<220> FEATURE:
<223> OTHER INFORMATION: Synthetic polypeptide 1637113_AXLH09

<400> SEQUENCE: 441

Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Gly Phe
                 20                  25                  30

Gln Val Asp Ala Val Pro Ala Asn Gly Gln Thr Pro Ile Gln Arg Thr
             35                  40                  45

Ile Asn Ser Ala Ala His Ser Tyr Thr Ile Gly Leu Gln Pro Gly
         50                  55                  60

Thr Asp Tyr Lys Ile Tyr Leu Tyr Thr Leu Thr Gly Tyr Gly Val Gly
 65                  70                  75                  80

Ala Val Gly Ser Ser Pro Val Val Ile Asp Ala Ser Thr
                 85                  90

<210> SEQ ID NO 442
<211> LENGTH: 93
<212> TYPE: PRT
<213> ORGANISM: Artificial Sequence
<220> FEATURE:
<223> OTHER INFORMATION: Synthetic polypeptide 1637113_AXLB04

<400> SEQUENCE: 442

Asn Val Ser Pro Pro Arg Arg Ala Arg Val Thr Asp Ala Thr Glu Thr
  1               5                  10                  15

Thr Ile Thr Ile Ser Trp Lys Val Ala Pro Ser Thr Val Val Gly Phe
                 20                  25                  30

Gln Val Asp Ala Val Pro Ala Asn Gly Gln Thr Pro Ile Gln Arg Thr
             35                  40                  45
```

```
Ile Lys Pro Asp Val Arg Ser Tyr Thr Ile Thr Gly Leu Gln Pro Gly
 50                  55                  60

Thr Asp Tyr Lys Ile Tyr Leu Tyr Thr Leu Asn Val Phe Gly Gly Ser
 65                  70                  75                  80

Ala Tyr Ser Ser Ser Pro Val Val Ile Asp Ala Ser Thr
                85                  90
```

<210> SEQ ID NO 443
<211> LENGTH: 93
<212> TYPE: PRT
<213> ORGANISM: Artificial Sequence
<220> FEATURE:
<223> OTHER INFORMATION: Synthetic polypeptide 1637113_AXLH06

<400> SEQUENCE: 443

```
Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
            35                  40                  45

Ile Asn Ser Ser Ala His Ser Tyr Thr Ile Thr Gly Leu Gln Pro Gly
 50                  55                  60

Thr Asp Tyr Lys Ile Tyr Leu Tyr Thr Leu Asn Gly Tyr Gly Val Gly
 65                  70                  75                  80

Thr Leu Ala Ser Ser Pro Val Val Ile Asp Ala Ser Thr
                85                  90
```

<210> SEQ ID NO 444
<211> LENGTH: 84
<212> TYPE: PRT
<213> ORGANISM: Artificial Sequence
<220> FEATURE:
<223> OTHER INFORMATION: Synthetic polypeptide 1637113_AXLG10

<400> SEQUENCE: 444

```
Asn Val Ser Pro Pro Arg Arg Ala Arg Val Thr Asp Ala Thr Glu Thr
 1               5                  10                  15

Thr Ile Thr Ile Arg Trp Lys Val Asp Gly Phe Gln Val Asp Ala Val
                20                  25                  30

Pro Ala Asn Gly Gln Thr Pro Ile Gln Arg Thr Ile Thr Arg Gly Val
            35                  40                  45

Arg Val Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr
```

<210> SEQ ID NO 445
<211> LENGTH: 85
<212> TYPE: PRT
<213> ORGANISM: Artificial Sequence
<220> FEATURE:
<223> OTHER INFORMATION: Synthetic polypeptide 1637113_AXLE04

<400> SEQUENCE: 445

```
Asn Val Ser Pro Pro Arg Arg Ala Arg Val Thr Asp Ala Thr Glu Thr
 1               5                  10                  15

Thr Ile Thr Ile Arg Trp Gly Ala Phe Thr Gly Phe Gln Val Asp Ala
```

```
            20                  25                  30

Val Pro Ala Asn Gly Gln Thr Pro Ile Gln Arg Thr Ile Lys Ser Asp
        35                  40                  45

Ile His Gly Tyr Thr Ile Thr Gly Leu Gln Pro Gly Thr Asp Tyr Lys
    50                  55                  60

Ile Tyr Leu Tyr Thr Leu Asn Asp Asn Ala Arg Ser Ser Pro Val Val
65                  70                  75                  80

Ile Asp Ala Ser Thr
                85

<210> SEQ ID NO 446
<211> LENGTH: 89
<212> TYPE: PRT
<213> ORGANISM: Artificial Sequence
<220> FEATURE:
<223> OTHER INFORMATION: Synthetic polypeptide 1637113_AXLG03

<400> SEQUENCE: 446

Asn Val Ser Pro Pro Arg Arg Ala Arg Val Thr Asp Ala Thr Glu Thr
1               5                   10                  15

Thr Ile Thr Ile Ser Trp Arg Arg Ser Gly Ser Glu Val Thr Arg Phe
            20                  25                  30

Gln Val Asp Ala Val Pro Ala Asn Gly Gln Thr Pro Ile Gln Arg Thr
        35                  40                  45

Ile Ala Arg Ser Ile Thr Val Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 447
<211> LENGTH: 89
<212> TYPE: PRT
<213> ORGANISM: Artificial Sequence
<220> FEATURE:
<223> OTHER INFORMATION: Synthetic polypeptide A03XL

<400> SEQUENCE: 447

Asn Val Ser Pro Pro Arg Arg Ala Arg Val Thr Asp Ala Thr Glu Thr
1               5                   10                  15

Thr Ile Thr Ile Arg Trp Ala Leu Pro Gln Ser Thr Phe Thr Arg Phe
            20                  25                  30

Gln Val Asp Ala Val Pro Ala Asn Gly Gln Thr Pro Ile Gln Arg Thr
        35                  40                  45

Ile Thr Thr Asn Ile Arg Gly Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 448
<211> LENGTH: 84
<212> TYPE: PRT
<213> ORGANISM: Artificial Sequence
<220> FEATURE:
<223> OTHER INFORMATION: Synthetic polypeptide 1637113_AXLG09

<400> SEQUENCE: 448
```

-continued

```
Asn Val Ser Pro Pro Arg Arg Ala Arg Val Thr Asp Ala Thr Glu Thr
1               5                   10                  15

Thr Ile Thr Ile Arg Trp Glu Ala Val Gly Phe Gln Val Asp Ala Val
            20                  25                  30

Pro Ala Asn Gly Gln Thr Pro Ile Gln Arg Thr Ile Lys Arg Asn Val
        35                  40                  45

Thr Val Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 449
<211> LENGTH: 90
<212> TYPE: PRT
<213> ORGANISM: Artificial Sequence
<220> FEATURE:
<223> OTHER INFORMATION: Synthetic polypeptide 1637113_AXLB11

<400> SEQUENCE: 449

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Leu Ile Gln Arg Thr
        35                  40                  45

Ile Thr Ala Ser Val Ser Ser Tyr Thr Ile Thr Gly Leu Gln Pro Gly
    50                  55                  60

Thr Asp Tyr Lys Ile Tyr Leu Tyr Thr Leu Ser Glu Tyr Glu Glu Thr
65                  70                  75                  80

Ser Ser Pro Val Val Ile Asp Ala Ser Thr
                85                  90

<210> SEQ ID NO 450
<211> LENGTH: 83
<212> TYPE: PRT
<213> ORGANISM: Artificial Sequence
<220> FEATURE:
<223> OTHER INFORMATION: Synthetic polypeptide 1637113_AXLE06

<400> SEQUENCE: 450

Asn Val Ser Pro Pro Arg Arg Ala Arg Val Thr Asp Ala Thr Glu Thr
1               5                   10                  15

Thr Ile Thr Ile Thr Trp Arg Val Ser Phe Gln Val Asp Ala Val Pro
            20                  25                  30

Ala Asn Gly Gln Thr Pro Ile Gln Arg Thr Ile Lys Arg Gly Val Ser
        35                  40                  45

Ser Tyr Thr Ile Thr Gly Leu Gln Pro Gly Thr Asp Tyr Lys Ile Tyr
    50                  55                  60

Leu Tyr Thr Leu Asn Asp Asn Ala Arg Ser Ser Pro Val Val Ile Asp
65                  70                  75                  80

Ala Ser Thr

<210> SEQ ID NO 451
<211> LENGTH: 84
<212> TYPE: PRT
<213> ORGANISM: Artificial Sequence
<220> FEATURE:
```

<223> OTHER INFORMATION: Synthetic polypeptide 1637113_AXLC02

<400> SEQUENCE: 451

Asn Val Ser Pro Pro Arg Arg Ala Arg Val Thr Asp Ala Thr Glu Thr
1               5                   10                  15

Thr Ile Thr Ile Arg Trp Gly Ala Leu Gly Phe Gln Val Asp Ala Val
            20                  25                  30

Pro Ala Asn Gly Gln Thr Pro Ile Gln Arg Thr Ile Lys Arg Ser Val
        35                  40                  45

Thr Thr Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 452
<211> LENGTH: 84
<212> TYPE: PRT
<213> ORGANISM: Artificial Sequence
<220> FEATURE:
<223> OTHER INFORMATION: Synthetic polypeptide 1637116_AXLB02

<400> SEQUENCE: 452

Asn Val Ser Pro Pro Arg Arg Ala Arg Val Thr Asp Ala Thr Glu Thr
1               5                   10                  15

Thr Ile Thr Ile Arg Trp Pro Val Pro Gly Phe Gln Val Asp Ala Val
            20                  25                  30

Pro Ala Asn Gly Gln Thr Pro Ile Gln Arg Thr Ile His Arg Ala Val
        35                  40                  45

Thr Val Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 453
<211> LENGTH: 85
<212> TYPE: PRT
<213> ORGANISM: Artificial Sequence
<220> FEATURE:
<223> OTHER INFORMATION: Synthetic polypeptide 1637116_AXLB10

<400> SEQUENCE: 453

Asn Val Ser Pro Pro Arg Arg Ala Arg Val Thr Asp Ala Thr Glu Thr
1               5                   10                  15

Thr Ile Thr Ile Arg Trp Gly Gln Val Ile Ser Phe Gln Val Asp Ala
            20                  25                  30

Val Pro Ala Asn Gly Gln Thr Pro Ile Gln Arg Thr Ile Lys Ser Asp
        35                  40                  45

Ile His Thr Tyr Thr Ile Thr Gly Leu Gln Pro Gly Thr Asp Tyr Lys
    50                  55                  60

Ile Tyr Leu Tyr Thr Leu Asn Asp Asn Ala Arg Ser Ser Pro Val Val
65                  70                  75                  80

Ile Asp Ala Ser Thr
            85

<210> SEQ ID NO 454
<211> LENGTH: 84

<212> TYPE: PRT
<213> ORGANISM: Artificial Sequence
<220> FEATURE:
<223> OTHER INFORMATION: Synthetic polypeptide 1637116_AXLB05

<400> SEQUENCE: 454

```
Asn Val Ser Pro Pro Arg Arg Ala Arg Val Thr Asp Ala Thr Glu Thr
1               5                   10                  15
Thr Ile Thr Ile Arg Trp Lys Val Asp Gly Phe Gln Val Asp Ala Val
            20                  25                  30
Pro Ala Asn Gly Gln Thr Pro Ile Gln Arg Thr Ile His Arg Ala Val
        35                  40                  45
Asn Val Tyr Thr Ile Thr Gly Leu Gln Pro Gly Thr Asp Tyr Lys Ile
    50                  55                  60
Tyr Leu Tyr Thr Leu Asn Asp Asn Ala Arg Ser Ser Pro Val Val Ile
65                  70                  75                  80
Asp Ala Ser Thr
```

<210> SEQ ID NO 455
<211> LENGTH: 84
<212> TYPE: PRT
<213> ORGANISM: Artificial Sequence
<220> FEATURE:
<223> OTHER INFORMATION: Synthetic polypeptide 1637116_AXLF09

<400> SEQUENCE: 455

```
Asn Val Ser Pro Pro Arg Arg Ala Arg Val Thr Asp Ala Thr Glu Thr
1               5                   10                  15
Thr Ile Thr Ile Arg Trp Lys Ala Ala Gly Phe Gln Val Asp Ala Val
            20                  25                  30
Pro Ala Asn Gly Gln Thr Pro Ile Gln Arg Thr Ile Lys Arg Asn Ala
        35                  40                  45
Asn Ile Tyr Thr Ile Thr Gly Leu Gln Pro Gly Thr Asp Tyr Lys Ile
    50                  55                  60
Tyr Leu Tyr Thr Leu Asn Asp Asn Ala Arg Ser Ser Pro Val Val Ile
65                  70                  75                  80
Asp Ala Ser Thr
```

<210> SEQ ID NO 456
<211> LENGTH: 93
<212> TYPE: PRT
<213> ORGANISM: Artificial Sequence
<220> FEATURE:
<223> OTHER INFORMATION: Synthetic polypeptide 1637116_AXLB12

<400> SEQUENCE: 456

```
Asn Val Ser Pro Pro Arg Arg Ala Arg Val Thr Asp Ala Thr Glu Thr
1               5                   10                  15
Thr Ile Thr Ile Pro Trp Thr Leu Gly Val Glu Ala Ser Gly Val Ile
            20                  25                  30
Thr Gly Phe Gln Val Asp Ala Val Pro Ala Asn Gly Gln Thr Pro Ile
        35                  40                  45
Gln Arg Thr Ile Lys Pro Asp Val Arg Ser Tyr Thr Ile Thr Gly Leu
    50                  55                  60
Gln Pro Gly Thr Asp Tyr Lys Ile Tyr Leu Tyr Thr Leu Tyr Gly Gly
65                  70                  75                  80
Gly Lys Thr Ser Ser Pro Val Val Ile Asp Ala Ser Thr
                85                  90
```

```
<210> SEQ ID NO 457
<211> LENGTH: 89
<212> TYPE: PRT
<213> ORGANISM: Artificial Sequence
<220> FEATURE:
<223> OTHER INFORMATION: Synthetic polypeptide 1637116_AXLE07

<400> SEQUENCE: 457

Asn Val Ser Pro Pro Arg Arg Ala Arg Val Thr Asp Ala Thr Glu Thr
1               5                   10                  15

Thr Ile Thr Ile Arg Trp Ala Leu Pro Gln Ser Ala Phe Asp Arg Phe
            20                  25                  30

Gln Val Asp Ala Val Pro Ala Asn Gly Gln Thr Pro Ile Gln Arg Thr
        35                  40                  45

Ile Thr Thr Ala Ile Arg Thr Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 458
<211> LENGTH: 84
<212> TYPE: PRT
<213> ORGANISM: Artificial Sequence
<220> FEATURE:
<223> OTHER INFORMATION: Synthetic polypeptide 1637116_AXLC06

<400> SEQUENCE: 458

Asn Val Ser Pro Pro Arg Arg Ala Arg Val Thr Asp Ala Thr Glu Thr
1               5                   10                  15

Thr Ile Thr Ile Arg Trp Pro Val Leu Gly Phe Gln Val Asp Ala Val
            20                  25                  30

Pro Ala Asn Gly Gln Thr Pro Ile Gln Arg Thr Ile Lys Arg Thr Val
        35                  40                  45

Ser Val Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 459
<211> LENGTH: 84
<212> TYPE: PRT
<213> ORGANISM: Artificial Sequence
<220> FEATURE:
<223> OTHER INFORMATION: Synthetic polypeptide 1637116_AXLA09

<400> SEQUENCE: 459

Asn Val Ser Pro Pro Arg Arg Ala Arg Val Thr Asp Ala Thr Glu Thr
1               5                   10                  15

Thr Ile Thr Ile Arg Trp Lys Val Pro Gly Phe Gln Val Asp Ala Val
            20                  25                  30

Pro Ala Asn Gly Gln Thr Pro Ile Gln Arg Thr Ile His Arg Gly Ile
        35                  40                  45

Arg Ser Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80
```

Asp Ala Ser Thr

<210> SEQ ID NO 460
<211> LENGTH: 84
<212> TYPE: PRT
<213> ORGANISM: Artificial Sequence
<220> FEATURE:
<223> OTHER INFORMATION: Synthetic polypeptide 1637116_AXLG07

<400> SEQUENCE: 460

Asn Val Ser Pro Pro Arg Arg Ala Arg Val Thr Asp Ala Thr Glu Thr
1               5                   10                  15

Thr Ile Thr Ile Arg Trp Lys Gly Ala Asp Phe Gln Val Asp Ala Val
            20                  25                  30

Pro Ala Asn Gly Gln Thr Pro Ile Gln Arg Thr Ile Thr Arg Gly Val
        35                  40                  45

Arg Thr Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 461
<211> LENGTH: 84
<212> TYPE: PRT
<213> ORGANISM: Artificial Sequence
<220> FEATURE:
<223> OTHER INFORMATION: Synthetic polypeptide 1637116_AXLG10

<400> SEQUENCE: 461

Asn Val Ser Pro Pro Arg Arg Ala Arg Val Thr Asp Ala Thr Glu Thr
1               5                   10                  15

Thr Ile Thr Ile Arg Trp Ser Leu Leu Gly Phe Gln Val Asp Ala Val
            20                  25                  30

Pro Ala Asn Gly Gln Thr Pro Ile Gln Arg Thr Ile Lys Arg Asn Val
        35                  40                  45

Asn Ala Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 462
<211> LENGTH: 84
<212> TYPE: PRT
<213> ORGANISM: Artificial Sequence
<220> FEATURE:
<223> OTHER INFORMATION: Synthetic polypeptide 1637116_AXLG05

<400> SEQUENCE: 462

Asn Val Ser Pro Pro Arg Arg Ala Arg Val Thr Asp Ala Thr Glu Thr
1               5                   10                  15

Thr Ile Thr Ile Arg Trp Lys Gly Asp Arg Phe Gln Val Asp Ala Val
            20                  25                  30

Pro Ala Asn Gly Gln Thr Pro Ile Gln Arg Thr Ile Thr Ser Gly Val
        35                  40                  45

Thr Gly Tyr Thr Ile Thr Gly Leu Gln Pro Gly Thr Asp Tyr Lys Ile
    50                  55                  60

```
Tyr Leu Tyr Thr Leu Asn Asp Asn Ala Arg Ser Ser Pro Val Val Ile
 65                  70                  75                  80

Asp Ala Ser Thr
```

<210> SEQ ID NO 463
<211> LENGTH: 84
<212> TYPE: PRT
<213> ORGANISM: Artificial Sequence
<220> FEATURE:
<223> OTHER INFORMATION: Synthetic polypeptide 1637116_AXLC09

<400> SEQUENCE: 463

```
Asn Val Ser Pro Pro Arg Arg Ala Arg Val Thr Asp Ala Thr Glu Thr
  1               5                  10                  15

Thr Ile Thr Ile Arg Trp Ser Ile Thr Gly Phe Gln Val Asp Ala Val
                 20                  25                  30

Pro Ala Asn Gly Gln Thr Pro Ile Gln Arg Thr Ile Asn Arg Gly Val
             35                  40                  45

Arg Ser Tyr Thr Ile Thr Gly Leu Gln Pro Gly Thr Asp Tyr Lys Ile
         50                  55                  60

Tyr Leu Tyr Thr Leu Asn Asp Asn Ala Arg Ser Ser Pro Val Val Ile
 65                  70                  75                  80

Asp Ala Ser Thr
```

<210> SEQ ID NO 464
<211> LENGTH: 84
<212> TYPE: PRT
<213> ORGANISM: Artificial Sequence
<220> FEATURE:
<223> OTHER INFORMATION: Synthetic polypeptide 1637116_AXLD03

<400> SEQUENCE: 464

```
Asn Val Ser Pro Pro Arg Arg Ala Arg Val Thr Asp Ala Thr Glu Thr
  1               5                  10                  15

Thr Ile Thr Ile Arg Trp Ala Val Pro Gly Phe Gln Val Asp Ala Val
                 20                  25                  30

Pro Ala Asn Gly Gln Thr Pro Ile Gln Arg Thr Ile His Arg Gly Val
             35                  40                  45

Ser Val Tyr Thr Ile Thr Gly Leu Gln Pro Gly Thr Asp Tyr Lys Ile
         50                  55                  60

Tyr Leu Tyr Thr Leu Asn Asp Asn Ala Arg Ser Ser Pro Val Val Ile
 65                  70                  75                  80

Asp Ala Ser Thr
```

<210> SEQ ID NO 465
<211> LENGTH: 93
<212> TYPE: PRT
<213> ORGANISM: Artificial Sequence
<220> FEATURE:
<223> OTHER INFORMATION: Synthetic polypeptide 1637117_AXLC11

<400> SEQUENCE: 465

```
Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Gly Phe
                 20                  25                  30

Gln Val Asp Ala Val Pro Ala Asn Gly Gln Thr Pro Ile Gln Arg Thr
             35                  40                  45

Ile Ala Thr Gly Ala Arg Val Tyr Thr Ile Thr Gly Leu Gln Pro Gly
```

```
                 50                  55                  60
Thr Asp Tyr Lys Ile Tyr Leu Tyr Thr Leu Thr Gly Tyr Gly Val Gly
 65                  70                  75                  80

Ala Val Ala Ser Ser Pro Val Val Ile Asp Ala Ser Thr
                 85                  90
```

<210> SEQ ID NO 466
<211> LENGTH: 83
<212> TYPE: PRT
<213> ORGANISM: Artificial Sequence
<220> FEATURE:
<223> OTHER INFORMATION: Synthetic polypeptide 1637117_AXLC10
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid

<400> SEQUENCE: 466

```
Asn Val Ser Pro Pro Arg Arg Ala Arg Val Thr Asp Ala Thr Glu Thr
 1               5                  10                  15

Thr Ile Thr Ile Ser Trp Arg Thr Ser Phe Gln Val Asp Ala Val Pro
                 20                  25                  30

Ala Asn Gly Gln Thr Pro Ile Gln Arg Thr Ile Lys Arg Gly Val Thr
             35                  40                  45

Ser Tyr Thr Ile Thr Gly Leu Gln Pro Gly Thr Asp Tyr Lys Ile Tyr
         50                  55                  60

Leu Tyr Xaa Leu Asn Asp Asn Ala Arg Ser Xaa Pro Val Val Ile Asp
 65                  70                  75                  80

Ala Ser Thr
```

<210> SEQ ID NO 467
<211> LENGTH: 90
<212> TYPE: PRT
<213> ORGANISM: Artificial Sequence
<220> FEATURE:
<223> OTHER INFORMATION: Synthetic polypeptide 1637117_AXLE05

<400> SEQUENCE: 467

```
Asn Val Ser Pro Pro Arg Arg Ala Arg Val Thr Asp Ala Thr Glu Thr
 1               5                  10                  15

Thr Ile Thr Ile Thr Trp Thr Gly Ser Arg Gly Lys Phe Val Gly Phe
                 20                  25                  30

Gln Val Asp Ala Val Pro Ala Asn Gly Gln Thr Pro Ile Gln Arg Thr
             35                  40                  45

Ile Lys Pro Asp Val Arg Ser Tyr Thr Ile Thr Gly Leu Gln Pro Gly
         50                  55                  60

Thr Asp Tyr Lys Ile Tyr Leu Tyr Thr Leu Tyr Gly Tyr Val Ser Gly
 65                  70                  75                  80

Ser Ser Pro Val Val Ile Asp Ala Ser Thr
                 85                  90
```

<210> SEQ ID NO 468
<211> LENGTH: 93
<212> TYPE: PRT
<213> ORGANISM: Artificial Sequence
<220> FEATURE:
<223> OTHER INFORMATION: Synthetic polypeptide 1637117_AXLE11

-continued

<400> SEQUENCE: 468

Asn Val Ser Pro Pro Arg Arg Ala Cys Val Thr Asp Ala Thr Glu Thr
1               5                   10                  15

Thr Ile Thr Ile Ser Trp Arg Leu Ala Glu Ser Lys Val Val Gly Phe
            20                  25                  30

Gln Val Asp Ala Val Pro Ala Asn Gly Gln Thr Pro Ile Gln Arg Thr
        35                  40                  45

Ile His Thr Asp Thr Ser Ser Tyr Thr Ile Thr Gly Leu Gln Pro Gly
    50                  55                  60

Thr Asp Tyr Lys Ile Tyr Leu Tyr Thr Leu Asn Thr Val Gly Lys Ser
65                  70                  75                  80

Ala Val Ala Ser Ser Pro Val Val Ile Asp Ala Ser Thr
                85                  90

<210> SEQ ID NO 469
<211> LENGTH: 89
<212> TYPE: PRT
<213> ORGANISM: Artificial Sequence
<220> FEATURE:
<223> OTHER INFORMATION: Synthetic polypeptide 1637117_AXLB08

<400> SEQUENCE: 469

Asn Val Ser Pro Pro Arg Arg Ala Arg Val Thr Asp Ala Thr Glu Thr
1               5                   10                  15

Thr Ile Thr Ile Arg Trp Glu Leu Pro Arg Gly Glu Val Thr Gly Phe
            20                  25                  30

Gln Val Asp Ala Val Pro Ala Asn Gly Gln Thr Pro Ile Gln Arg Thr
        35                  40                  45

Ile Lys Gly Ala Lys Arg Gly Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 470
<211> LENGTH: 93
<212> TYPE: PRT
<213> ORGANISM: Artificial Sequence
<220> FEATURE:
<223> OTHER INFORMATION: Synthetic polypeptide 1637117_AXLD09

<400> SEQUENCE: 470

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Ala Thr Ala Ile Arg Val Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80

Glu Ser Arg Ser Ser Pro Val Val Ile Asp Ala Ser Thr
                85                  90

<210> SEQ ID NO 471
<211> LENGTH: 83

```
<212> TYPE: PRT
<213> ORGANISM: Artificial Sequence
<220> FEATURE:
<223> OTHER INFORMATION: Synthetic polypeptide 1637117_AXLH04

<400> SEQUENCE: 471

Asn Val Ser Pro Pro Arg Arg Ala Arg Val Thr Asp Ala Thr Glu Thr
1               5                   10                  15

Thr Ile Thr Ile Arg Trp Ser Asn Gly Phe Gln Val Asp Ala Val Pro
            20                  25                  30

Ala Asn Gly Gln Thr Pro Ile Gln Arg Thr Ile Lys Arg Thr Ala Pro
        35                  40                  45

Ser Tyr Thr Ile Thr Gly Leu Gln Pro Gly Thr Asp Tyr Lys Ile Tyr
    50                  55                  60

Leu Tyr Thr Leu Asn Asp Asn Ala Arg Ser Ser Pro Val Val Ile Asp
65                  70                  75                  80

Ala Ser Thr

<210> SEQ ID NO 472
<211> LENGTH: 89
<212> TYPE: PRT
<213> ORGANISM: Artificial Sequence
<220> FEATURE:
<223> OTHER INFORMATION: Synthetic polypeptide 1637117_AXLA04

<400> SEQUENCE: 472

Asn Val Ser Pro Pro Arg Arg Ala Arg Val Thr Asp Ala Thr Glu Thr
1               5                   10                  15

Thr Ile Thr Ile Thr Trp Gly Leu Ala Glu Ser Lys Val Val Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Gly Asn Val Gly Gly
65                  70                  75                  80

Leu Thr Val Val Ile Asp Ala Ser Thr
                85

<210> SEQ ID NO 473
<211> LENGTH: 93
<212> TYPE: PRT
<213> ORGANISM: Artificial Sequence
<220> FEATURE:
<223> OTHER INFORMATION: Synthetic polypeptide 1637117_AXLE07

<400> SEQUENCE: 473

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Asn Arg Asn Ala His Ala Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80

Thr Val Ala Ser Ser Pro Val Val Ile Asp Ala Ser Thr
                85                  90
```

```
<210> SEQ ID NO 474
<211> LENGTH: 93
<212> TYPE: PRT
<213> ORGANISM: Artificial Sequence
<220> FEATURE:
<223> OTHER INFORMATION: Synthetic polypeptide 1637117_AXLC05

<400> SEQUENCE: 474
```

Asn Val Ser Pro Pro Arg Arg Ala Arg Val Thr Asp Ala Thr Glu Thr
1               5                   10                  15

Thr Ile Thr Ile Thr Trp Ala Arg Ser Gln Ser Thr Val Val Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Thr Val Val Gly Gly Ser
65                  70                  75                  80

Ala Tyr Gly Ser Ser Pro Val Val Ile Asp Ala Ser Thr
                85                  90

```
<210> SEQ ID NO 475
<211> LENGTH: 93
<212> TYPE: PRT
<213> ORGANISM: Artificial Sequence
<220> FEATURE:
<223> OTHER INFORMATION: Synthetic polypeptide 1637117_AXLH09
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid

<400> SEQUENCE: 475
```

Asn Val Ser Pro Pro Arg Arg Ala Arg Val Thr Asp Ala Thr Glu Thr
1               5                   10                  15

Thr Ile Thr Ile Ser Trp Arg Val Lys Xaa Glu Thr Ile Thr Gly Phe
            20                  25                  30

Gln Val Asp Ala Val Pro Ala Asn Gly Gln Thr Pro Ile Gln Arg Thr
        35                  40                  45

Ile Asn Arg Asn Ala His Xaa Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80

Thr Leu Gly Ser Ser Pro Val Val Ile Asp Ala Ser Thr
                85                  90

```
<210> SEQ ID NO 476
<211> LENGTH: 90
<212> TYPE: PRT
<213> ORGANISM: Artificial Sequence
<220> FEATURE:
<223> OTHER INFORMATION: Synthetic polypeptide 1637117_AXLG08

<400> SEQUENCE: 476
```

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Leu

```
                20                  25                  30

Gln Val Asp Ala Val Pro Ala Asn Gly Gln Thr Pro Ile Gln Arg Thr
            35                  40                  45

Ile Ala Thr Asn Glu Asn Ser Tyr Thr Ile Thr Gly Leu Gln Pro Gly
    50                  55                  60

Thr Asp Tyr Lys Ile Tyr Leu Tyr Thr Leu Asn Gly Arg Gly Ala Thr
65                  70                  75                  80

Ser Ser Pro Val Val Ile Asp Ala Ser Thr
                85                  90

<210> SEQ ID NO 477
<211> LENGTH: 93
<212> TYPE: PRT
<213> ORGANISM: Artificial Sequence
<220> FEATURE:
<223> OTHER INFORMATION: Synthetic polypeptide 1637117_AXLD04

<400> SEQUENCE: 477

Asn Val Ser Pro Pro Arg Arg Ala Arg Val Thr Asp Ala Thr Glu Thr
1               5                   10                  15

Thr Ile Thr Ile Ser Trp Lys Arg Ser Glu Ser Gln Val Val Gly Phe
            20                  25                  30

Gln Val Asp Ala Val Pro Ala Asn Gly Gln Thr Pro Ile Gln Arg Thr
            35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Val Val Gly Arg Ser
65                  70                  75                  80

Ala Tyr Gly Ser Ser Pro Val Val Ile Asp Ala Ser Thr
                85                  90

<210> SEQ ID NO 478
<211> LENGTH: 93
<212> TYPE: PRT
<213> ORGANISM: Artificial Sequence
<220> FEATURE:
<223> OTHER INFORMATION: Synthetic polypeptide 1637117_AXLF06

<400> SEQUENCE: 478

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
            35                  40                  45

Ile Ala Thr Gly Ile Arg Val Tyr Thr Ile Thr Gly Leu Gln Pro Gly
    50                  55                  60

Thr Asp Tyr Lys Ile Tyr Leu Tyr Thr Leu Thr Gly Tyr Gly Val Gly
65                  70                  75                  80

Thr Leu Ser Ser Ser Pro Val Val Ile Asp Ala Ser Thr
                85                  90

<210> SEQ ID NO 479
<211> LENGTH: 83
<212> TYPE: PRT
<213> ORGANISM: Artificial Sequence
<220> FEATURE:
<223> OTHER INFORMATION: Synthetic polypeptide 1637117_AXLD12
<220> FEATURE:
<221> NAME/KEY: misc_feature
```

<222> LOCATION: (49)..(49)
<223> OTHER INFORMATION: Xaa can be any naturally occurring amino acid

<400> SEQUENCE: 479

Asn Val Ser Pro Pro Arg Arg Ala Arg Val Thr Asp Ala Thr Glu Thr
1               5                   10                  15

Thr Ile Thr Ile Ser Trp Arg Thr Ser Phe Gln Val Asp Ala Val Pro
            20                  25                  30

Ala Asn Gly Gln Thr Pro Ile Gln Arg Thr Ile Lys Arg Gly Val Thr
        35                  40                  45

Xaa Tyr Thr Ile Thr Gly Leu Gln Pro Gly Thr Asp Tyr Lys Ile Tyr
    50                  55                  60

Leu Tyr Thr Leu Asn Asp Asn Ala Arg Ser Ser Pro Val Val Ile Asp
65                  70                  75                  80

Ala Ser Thr

<210> SEQ ID NO 480
<211> LENGTH: 83
<212> TYPE: PRT
<213> ORGANISM: Artificial Sequence
<220> FEATURE:
<223> OTHER INFORMATION: Synthetic polypeptide 1637118_AXLD11

<400> SEQUENCE: 480

Asn Val Ser Pro Pro Arg Arg Ala Arg Val Thr Asp Ala Thr Glu Thr
1               5                   10                  15

Thr Ile Thr Ile Ser Trp Ala Val Gly Phe Gln Val Asp Ala Val Pro
            20                  25                  30

Ala Asn Gly Gln Thr Pro Ile Gln Arg Thr Ile Lys Arg Asp Val Arg
        35                  40                  45

Ala Tyr Thr Ile Thr Gly Leu Gln Pro Gly Thr Asp Tyr Lys Ile Tyr
    50                  55                  60

Leu Tyr Thr Leu Asn Asp Asn Ala Arg Ser Ser Pro Val Val Ile Asp
65                  70                  75                  80

Ala Ser Thr

<210> SEQ ID NO 481
<211> LENGTH: 89
<212> TYPE: PRT
<213> ORGANISM: Artificial Sequence
<220> FEATURE:
<223> OTHER INFORMATION: Synthetic polypeptide 1637118_AXLF10

<400> SEQUENCE: 481

Asn Val Ser Pro Pro Arg Arg Ala Arg Val Thr Asp Ala Thr Glu Thr
1               5                   10                  15

Thr Ile Thr Ile Arg Trp Ala Leu Pro Arg Gly Thr Val Val Gly Phe
            20                  25                  30

Gln Val Asp Ala Val Pro Ala Asn Gly Gln Thr Pro Ile Gln Arg Thr
        35                  40                  45

Ile His Arg Thr Ala Thr Ser Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 482

```
<211> LENGTH: 84
<212> TYPE: PRT
<213> ORGANISM: Artificial Sequence
<220> FEATURE:
<223> OTHER INFORMATION: Synthetic polypeptide 1637118_AXLE08

<400> SEQUENCE: 482
```

Asn Val Ser Pro Pro Arg Arg Ala Arg Val Thr Asp Ala Thr Glu Thr
1               5                   10                  15

Thr Ile Thr Ile Arg Trp Lys Val Asn Gly Phe Gln Val Asp Ala Val
                20                  25                  30

Pro Ala Asn Gly Gln Thr Pro Ile Gln Arg Thr Ile His Arg Ala Val
            35                  40                  45

Arg Val Tyr Thr Ile Thr Gly Leu Gln Pro Gly Thr Asp Tyr Lys Ile
        50                  55                  60

Tyr Leu Tyr Thr Leu Asn Asp Asn Ala Arg Ser Ser Pro Val Val Ile
65                  70                  75                  80

Asp Ala Ser Thr

```
<210> SEQ ID NO 483
<211> LENGTH: 93
<212> TYPE: PRT
<213> ORGANISM: Artificial Sequence
<220> FEATURE:
<223> OTHER INFORMATION: Synthetic polypeptide 1637118_AXLA01

<400> SEQUENCE: 483
```

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
            35                  40                  45

Ile Ala Ser Asn Ile His Ser Tyr Thr Ile Thr Gly Leu Gln Pro Gly
        50                  55                  60

Thr Asp Tyr Lys Ile Tyr Leu Tyr Thr Leu Thr Gly Tyr Gly Val Gly
65                  70                  75                  80

Ala Val Gly Ser Ser Pro Val Val Ile Asp Ala Ser Thr
                85                  90

```
<210> SEQ ID NO 484
<211> LENGTH: 89
<212> TYPE: PRT
<213> ORGANISM: Artificial Sequence
<220> FEATURE:
<223> OTHER INFORMATION: Synthetic polypeptide 1637118_AXLC11

<400> SEQUENCE: 484
```

Asn Val Ser Pro Pro Arg Arg Ala Arg Val Thr Asp Ala Thr Glu Thr
1               5                   10                  15

Thr Ile Thr Ile Ser Trp Ala Val Pro Gln Ser Pro Ile Val Ser Phe
                20                  25                  30

Gln Val Asp Ala Val Pro Ala Asn Gly Gln Thr Pro Ile His Arg Thr
            35                  40                  45

Ile Asp Thr Gly Ala Ser Gly Tyr Thr Ile Thr Gly Leu Gln Pro Gly
        50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr

<210> SEQ ID NO 485
<211> LENGTH: 84
<212> TYPE: PRT
<213> ORGANISM: Artificial Sequence
<220> FEATURE:
<223> OTHER INFORMATION: Synthetic polypeptide 1637118_AXLB09

<400> SEQUENCE: 485

Asn Val Ser Pro Pro Arg Arg Ala Arg Val Thr Asp Ala Thr Glu Thr
1               5                   10                  15

Thr Ile Thr Ile Arg Trp Ala Val Pro Gly Phe Gln Val Asp Ala Val
            20                  25                  30

Pro Ala Asn Gly Gln Thr Pro Ile Gln Arg Thr Ile Gln Arg Gly Val
        35                  40                  45

Arg Ala Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr

<210> SEQ ID NO 486
<211> LENGTH: 90
<212> TYPE: PRT
<213> ORGANISM: Artificial Sequence
<220> FEATURE:
<223> OTHER INFORMATION: Synthetic polypeptide 1637118_AXLB01

<400> SEQUENCE: 486

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Ile
            20                  25                  30

Gln Val Asp Ala Val Pro Ala Asn Gly Gln Thr Pro Ile Gln Arg Thr
        35                  40                  45

Ile Ala Thr Asn Val His Val Tyr Thr Ile Thr Gly Leu Gln Pro Gly
    50                  55                  60

Thr Asp Tyr Lys Ile Tyr Leu Tyr Thr Leu Thr Gly Arg Gly Asp Ser
65                  70                  75                  80

Ser Ser Pro Val Val Ile Asp Ala Ser Thr
                85                  90

<210> SEQ ID NO 487
<211> LENGTH: 84
<212> TYPE: PRT
<213> ORGANISM: Artificial Sequence
<220> FEATURE:
<223> OTHER INFORMATION: Synthetic polypeptide 1637118_AXLA07

<400> SEQUENCE: 487

Asn Val Ser Pro Pro Arg Arg Ala Arg Val Thr Asp Ala Thr Glu Thr
1               5                   10                  15

Thr Ile Thr Ile Arg Trp Lys Val Leu Gly Phe Gln Val Asp Ala Val
            20                  25                  30

Pro Ala Asn Gly Gln Thr Pro Ile Gln Arg Thr Ile Lys Arg Asn Ile
        35                  40                  45

Ser Ser Tyr Thr Ile Thr Gly Leu Gln Pro Gly Thr Asp Tyr Lys Ile
    50                  55                  60

```
Tyr Leu Tyr Thr Leu Asn Asp Asn Ala Arg Ser Ser Pro Val Val Ile
 65                  70                  75                  80

Asp Ala Ser Thr

<210> SEQ ID NO 488
<211> LENGTH: 85
<212> TYPE: PRT
<213> ORGANISM: Artificial Sequence
<220> FEATURE:
<223> OTHER INFORMATION: Synthetic polypeptide 1637118_AXLG03

<400> SEQUENCE: 488

Asn Val Ser Pro Pro Arg Arg Ala Arg Val Thr Asp Ala Thr Glu Thr
  1               5                  10                  15

Thr Ile Thr Ile Arg Trp Ala Gln Val Leu Arg Phe Gln Val Asp Ala
                 20                  25                  30

Val Pro Ala Asn Gly Gln Thr Pro Ile Gln Arg Thr Ile Lys Arg Asp
             35                  40                  45

Val His Ser Tyr Thr Ile Thr Gly Leu Gln Pro Gly Thr Asp Tyr Lys
         50                  55                  60

Ile Tyr Leu Tyr Thr Leu Asn Asp Asn Ala Arg Ser Ser Pro Val Val
 65                  70                  75                  80

Ile Asp Ala Ser Thr
                 85

<210> SEQ ID NO 489
<211> LENGTH: 84
<212> TYPE: PRT
<213> ORGANISM: Artificial Sequence
<220> FEATURE:
<223> OTHER INFORMATION: Synthetic polypeptide 1637118_AXLB06

<400> SEQUENCE: 489

Asn Val Ser Pro Pro Arg Arg Ala Arg Val Thr Asp Ala Thr Glu Thr
  1               5                  10                  15

Thr Ile Thr Ile Arg Trp Lys Val Pro Gly Phe Gln Val Asp Ala Val
                 20                  25                  30

Pro Ala Asn Gly Gln Thr Pro Ile Gln Arg Thr Ile Ala Arg Gly Val
             35                  40                  45

Arg Val Tyr Thr Ile Thr Gly Leu Gln Pro Gly Thr Asp Tyr Lys Ile
         50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 490
<211> LENGTH: 84
<212> TYPE: PRT
<213> ORGANISM: Artificial Sequence
<220> FEATURE:
<223> OTHER INFORMATION: Synthetic polypeptide 1637119_AXLB04

<400> SEQUENCE: 490

Asn Val Ser Pro Pro Arg Arg Ala Arg Val Thr Asp Ala Thr Glu Thr
  1               5                  10                  15

Thr Ile Thr Ile Arg Trp Gly Glu Leu Gly Phe Gln Val Asp Ala Val
                 20                  25                  30

Pro Ala Asn Gly Gln Thr Pro Ile Gln Arg Thr Ile Lys Arg Ala Ala
             35                  40                  45
```

```
Asn Thr Tyr Thr Ile Thr Gly Leu Gln Pro Gly Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 491
<211> LENGTH: 84
<212> TYPE: PRT
<213> ORGANISM: Artificial Sequence
<220> FEATURE:
<223> OTHER INFORMATION: Synthetic polypeptide 1637119_AXLE06

<400> SEQUENCE: 491

Asn Val Ser Pro Pro Arg Arg Ala Arg Val Thr Asp Ala Thr Glu Thr
  1               5                  10                  15

Thr Ile Thr Ile Arg Trp Gly Val Thr Gly Phe Gln Val Asp Ala Val
                 20                  25                  30

Pro Ala Asn Gly Gln Thr Pro Ile Gln Arg Thr Ile Lys Arg Asn Ala
             35                  40                  45

Arg Ser Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 492
<211> LENGTH: 84
<212> TYPE: PRT
<213> ORGANISM: Artificial Sequence
<220> FEATURE:
<223> OTHER INFORMATION: Synthetic polypeptide 1637119_AXLF04

<400> SEQUENCE: 492

Asn Val Ser Pro Pro Arg Arg Ala Arg Val Thr Asp Ala Thr Glu Thr
  1               5                  10                  15

Thr Ile Thr Ile Arg Trp Arg Val Ala Gly Phe Gln Val Asp Ala Val
                 20                  25                  30

Pro Ala Asn Gly Gln Thr Pro Ile Gln Arg Thr Ile Ala Arg Asn Thr
             35                  40                  45

His Ser Tyr Thr Ile Thr Gly Leu Gln Pro Gly Thr Asp Tyr Lys Ile
 50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 493
<211> LENGTH: 84
<212> TYPE: PRT
<213> ORGANISM: Artificial Sequence
<220> FEATURE:
<223> OTHER INFORMATION: Synthetic polypeptide 1637119_AXLD01

<400> SEQUENCE: 493

Asn Val Ser Pro Pro Arg Arg Ala Arg Val Thr Asp Ala Thr Glu Thr
  1               5                  10                  15

Thr Ile Thr Ile Arg Trp Thr Gly Gln Arg Phe Gln Val Asp Ala Val
                 20                  25                  30

Pro Ala Asn Gly Gln Thr Pro Ile Gln Arg Thr Ile Lys Thr Thr Ile
```

```
                35                  40                  45
His Gly Tyr Thr Ile Thr Gly Leu Gln Pro Gly Thr Asp Tyr Lys Ile
         50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 494
<211> LENGTH: 84
<212> TYPE: PRT
<213> ORGANISM: Artificial Sequence
<220> FEATURE:
<223> OTHER INFORMATION: Synthetic polypeptide 1637119_AXLH10

<400> SEQUENCE: 494

Asn Val Ser Pro Pro Arg Arg Ala Arg Val Thr Asp Ala Thr Glu Thr
  1               5                  10                  15

Thr Ile Thr Ile Arg Trp Gly Gln Thr Gly Phe Gln Val Asp Ala Val
             20                  25                  30

Pro Ala Asn Gly Gln Thr Pro Ile Gln Arg Thr Ile Lys Arg Ala Ala
         35                  40                  45

Thr Ser Tyr Thr Ile Thr Gly Leu Gln Pro Gly Thr Asp Tyr Lys Ile
     50                  55                  60

Tyr Leu Tyr Thr Leu Asn Asp Asn Ala Arg Ser Ser Pro Val Val Ile
 65                  70                  75                  80

Asp Ala Ser Thr

<210> SEQ ID NO 495
<211> LENGTH: 89
<212> TYPE: PRT
<213> ORGANISM: Artificial Sequence
<220> FEATURE:
<223> OTHER INFORMATION: Synthetic polypeptide 1637119_AXLA12

<400> SEQUENCE: 495

Asn Val Ser Pro Pro Arg Arg Ala Arg Val Thr Asp Ala Thr Glu Thr
  1               5                  10                  15

Thr Ile Thr Ile Arg Trp Ala Leu Pro Arg Ser Ala Phe Asp Arg Phe
             20                  25                  30

Gln Val Asp Ala Val Pro Ala Asn Gly Gln Thr Pro Ile Gln Arg Thr
         35                  40                  45

Ile Thr Thr Ser Ile Arg Thr Tyr Thr Ile Gly Leu Gln Pro Gly
     50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                 85

<210> SEQ ID NO 496
<211> LENGTH: 84
<212> TYPE: PRT
<213> ORGANISM: Artificial Sequence
<220> FEATURE:
<223> OTHER INFORMATION: Synthetic polypeptide 1637119_AXLE11

<400> SEQUENCE: 496

Asn Val Ser Pro Pro Arg Arg Ala Arg Val Thr Asp Ala Thr Glu Thr
  1               5                  10                  15

Thr Ile Thr Ile Arg Trp Lys Val Asp Gly Phe Gln Val Asp Ala Phe
```

```
                  20                  25                  30

Pro Ala Asn Gly Gln Thr Pro Ile Gln Arg Thr Ile His Arg Ala Val
                35                  40                  45

Asn Val Tyr Thr Ile Thr Gly Leu Gln Pro Gly Thr Asp Tyr Lys Ile
             50                  55                  60

Tyr Leu Tyr Thr Leu Asn Asp Asn Ala Arg Asn Asn Pro Val Val Ile
 65                  70                  75                  80

Asp Ala Ser Thr

<210> SEQ ID NO 497
<211> LENGTH: 85
<212> TYPE: PRT
<213> ORGANISM: Artificial Sequence
<220> FEATURE:
<223> OTHER INFORMATION: Synthetic polypeptide 1637119_AXLB01
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (47)..(48)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid

<400> SEQUENCE: 497

Asn Val Ser Pro Pro Arg Arg Ala Arg Val Thr Asp Ala Thr Glu Thr
 1               5                  10                  15

Thr Ile Thr Ile Arg Trp Ala Gln Val Leu Ser Phe Gln Val Asp Xaa
                20                  25                  30

Val Pro Ala Asn Gly Gln Thr Pro Ile Gln Arg Thr Ile Lys Xaa Xaa
                35                  40                  45

Val Xaa Xaa Tyr Thr Ile Thr Gly Leu Gln Pro Gly Xaa Asp Tyr Lys
             50                  55                  60

Ile Tyr Leu Tyr Thr Leu Asn Asp Asn Ala Arg Ser Ser Pro Val Val
 65                  70                  75                  80

Ile Asp Ala Ser Thr
                85

<210> SEQ ID NO 498
<211> LENGTH: 83
<212> TYPE: PRT
<213> ORGANISM: Artificial Sequence
<220> FEATURE:
<223> OTHER INFORMATION: Synthetic polypeptide 1637119_AXLC02

<400> SEQUENCE: 498

Asn Val Ser Pro Pro Arg Arg Ala Arg Val Thr Asp Ala Thr Glu Thr
 1               5                  10                  15

Thr Ile Thr Ile Arg Trp Ala Ala Gly Phe Gln Val Asp Ala Val Pro
                20                  25                  30

Ala Asn Gly Gln Thr Pro Ile Gln Arg Thr Ile Lys Arg Asn Ile Asn
                35                  40                  45

Ser Tyr Thr Ile Thr Gly Leu Lys Pro Gly Thr Asp Tyr Lys Ile Tyr
             50                  55                  60
```

-continued

```
Leu Tyr Thr Leu Asn Asp Asn Ala Arg Ser Ser Pro Val Val Ile Asp
65                  70                  75                  80

Ala Ser Thr
```

UNIVERSAL FIBRONECTIN TYPE III BINDING-DOMAIN LIBRARIES

This patent application is a divisional of U.S. application Ser. No. 12/820,018, filed Jun. 21, 2010, which is a continuation-in-part of U.S. patent application Ser. No. 12/562,992, filed Sep. 18, 2009, which is a continuation-in-part of U.S. patent application Ser. No. 12/228,404 filed Aug. 11, 2008 which claims priority to U.S. Provisional Patent Application No. 61/075,107 filed Jun. 24, 2008 and U.S. Provisional Patent Application No. 60/955,334 filed Aug. 10, 2007, all of which are incorporated herein by reference in their entirety. The contents of any patents, patent applications, and references cited throughout this specification are hereby incorporated by reference in their entireties.

SEQUENCE LISTING

The instant application contains a Sequence Listing which has been submitted in PDF format via EFS-Web and is hereby incorporated by reference in its entirety. Said PDF copy, created on Oct. 2, 2013, is named PTI-004CP2DIV_SEQLIST.pdf and is 3,740,165 bytes in size.

BACKGROUND OF THE INVENTION

Scaffold based binding proteins are becoming legitimate alternatives to antibodies in their ability to bind specific ligand targets. These scaffold binding proteins share the quality of having a stable framework core that can tolerate multiple substitutions in the ligand binding regions. Some scaffold frameworks have immunoglobulin like protein domain architecture with loops extending from a beta sandwich core. A scaffold framework core can then be synthetically engineered from which a library of different sequence variants can be built upon. The sequence diversity is typically concentrated in the exterior surfaces of the proteins such as loop structures or other exterior surfaces that can serve as ligand binding regions.

Fibronectin Type III domain (FN3) was first identified as a one of the repeating domains in the fibronectin protein. The FN3 domain constitutes a small (~94 amino acids), monomeric β-sandwich protein made up of seven β strands with three connecting loops. The three loops near the N-terminus of FN3, are functionally analogous to the complementarity-determining regions of immunoglobulin domains. FN3 loop libraries can then be engineered to bind to a variety of targets such as cytokines, growth factors and receptor molecules and other proteins.

One potential problem in creating these synthetic libraries is the high frequency of unproductive variants leading therefore, to inefficient candidate screens. For example, creating diversity in the variants often involves in vitro techniques such as random mutagenesis, saturation mutagenesis, error-prone PCR, and gene shuffling. These strategies are inherently stochastic and often require the construction of exceedingly large libraries to comprehensively explore sufficient sequence diversity. Additionally, there is no way to enumerate the number, what type and where in the protein the mutations have occurred. Furthermore, these random strategies create indiscriminate substitutions that cause protein architecture destabilization. It has been shown that improvement in one characteristic, such as affinity optimization, usually leads to decreased thermal stability when compared to the original protein scaffold framework.

Accordingly, a need exists for a fibronectin binding domain library that is systematic in construction. By bioinformatics led design, the loop candidates are flexible for insertion into multiple FN3 scaffolds. By specific targeted loop substitutions, overall scaffold stability is maximized while concurrently, non-immunogenic substitutions are minimized. Additionally, the library can be size tailored so that the overall diversity can be readily screened in different systems. Furthermore, the representative diversity of the designed loops are still capable of binding a number of pre-defined ligand targets. Moreover, the systematic design of loop still allows subsequent affinity maturation of recovered binding clones.

SUMMARY OF THE INVENTION

In one aspect, the invention includes a natural-variant combinatorial library of fibronectin Type 3 domain polypeptides useful in screening for the presence of one or more polypeptides having a selected binding or enzymatic activity. The library polypeptides include (a) regions A, AB, B, C, CD, D, E, EF, F, and G having wildtype amino acid sequences of a selected native fibronectin Type 3 polypeptide or polypeptides, and (b) loop regions BC, DE, and FG having selected lengths. At least one selected loop region of a selected length contains a library of natural-variant combinatorial sequences expressed by a library of coding sequences that encode at each loop position, a conserved or selected semi-conserved consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents.

The library may have a given threshold is 100%, unless the loop amino acid position contains only one dominant and one variant amino, and the dominant and variant amino are chemically similar amino acids, in which case the given threshold may be 90%. In this embodiment, the library contains all natural variants or their chemical equivalents having at least some reasonable occurrence frequency, e.g., 10%, in the in the selected loop and loop position.

The natural-variant combinatorial sequences may be in a combination of loops and loop lengths selected from loops BC and DE, BC and FG, and DE and FG loops, where the BC loop is selected from one of BC/11, BC/14, and BC/15, the DE loop is DE/6, and the FG loop is selected from one of FG/8, and FG11.

The library may have at two of the loop combinations BC and DE, BC and FG, and DE and FG, beneficial mutations identified by screening a natural-variant combinatorial library containing amino acid variants in the two loop combination, and at the third loop, identified by FG, DE, and BC, respectively, a library of natural variant combinatorial sequences at a third loop and loop length identified by BC/11, BC/14, and BC/15, DE/6, or FG/8, and FG11.

In one embodiment, the library may have the wildtype amino acid sequences in regions A, AB, B, C, CD, D, E, EF, F, and G of the 14th fibronectin Type III module of human fibronectin. In another embodiment, the library may have the wildtype amino acid sequences in regions A, AB, B, C, CD, D, E, EF, F, and G of the 10th fibronectin Type III module of human fibronectin.

A natural-variant combinatorial library may have the following sequences for the indicated loops and loop lengths: (a) BC loop length of 11, and the amino acid sequence identified by SEQ ID NOS: 43 or 49; (b) BC loop length of 14, and the amino acid sequence identified by SEQ ID. NOS: 44 or 50; (c) BC loop length of 15, and the amino acid sequence identified by SEQ ID. NOS: 45 or 51; (d) DE loop length of 6, and the amino acid sequence identified by SEQ ID. NOS: 46 or 52; (e) FG loop length of 8, and the amino acid sequence identified by SEQ ID. NOS: 47, for the first N-terminal six amino acids, or SEQ ID NO:53, and (f) FG loop length of 11, and the amino acid sequence identified by SEQ ID. NO: 48, for the first N-terminal nine amino acids, or SEQ ID NO:54.

The library of polypeptides may be encoded by an expression library selected from the group consisting of a ribosome display library, a polysome display library, a phage display library, a bacterial expression library, and a yeast display library.

The libraries may be used in a method of identifying a polypeptide having a desired binding affinity, in which the natural-variant combinatorial library are screened to select for an fibronectin binding domain having a desired binding affinity. In particular, it has been found that the natural-variant combinatorial library provides high-binding polypeptides with high efficiency for a number of antigen targets, such as FNFα. VEGF, HMGB1, VEGFR2, and Axl.

The screening may involve, for example, contacting the fibronectin binding domains with a target substrate, where the fibronectin binding domains being associated with the polynucleotide encoding the fibronectin binding domain. The method may further include identifying FN3 polynucleotides that encode the selected fibronectin binding domain.

Also disclosed is an expression library of polynucleotides encoding the above library of polypeptides, and produced by synthesizing polynucleotides encoding one or more framework regions and one or more loop regions wherein the polynucleotides are predetermined, wherein the polynucleotides encoding said regions further comprise sufficient overlapping sequence whereby the polynucleotide sequences, under polymerase chain reaction (PCR) conditions, are capable of assembly into polynucleotides encoding complete fibronectin binding domains.

In another aspect, the invention includes a walk-through mutagenesis library of fibronectin Type 3 domain polypeptides useful in screening for the presence of one or more polypeptides having a selected binding or enzymatic activity. The library polypeptides include (a) regions A, AB, B, C, CD, D, E, EF, F, and G having wildtype amino acid sequences of a selected native fibronectin Type 3 polypeptide or polypeptides, and (b) loop regions BC, DE, and FG having selected lengths. At least one selected loop region of a selected length contains a library of walk through mutagenesis sequences expressed by a library of coding sequences that encode, at each loop position, a conserved or selected semi-conserved consensus amino acid and, if the consensus amino acid has a occurrence frequency equal to or less than a selected threshold frequency of at least 50%, a single common target amino acid and any co-produced amino acids.

The given threshold frequency may be 100%, or a selected frequency between 50-100%. The loops and loop lengths in the library may be selected from the group consisting of BC/11, BC/14, BC/15, DE/6, FG/8, and FG11.

The library may have a library of walk-through mutagenesis sequences formed at each of the loops and loop lengths selected from the group consisting of BC/11, BC/14, BC/15, DE/6, FG/8, and FG11, and for each common target amino selected from the group consisting of lysine, glutamine, aspartic acid, tyrosine, leucine, praline, serine, histidine, and glycine.

In one embodiment, the library may have the wildtype amino acid sequences in regions A, AB, B, C, CD, D, E, EF, F, and G of the $14^{th}$ fibronectin Type III module of human fibronectin. In another embodiment, the library may have the wildtype amino acid sequences in regions A, AB, B, C, CD, D, E, EF, F, and G of the $10^{th}$ fibronectin Type III module of human fibronectin.

In another aspect, the invention includes a method of forming a library of fibronectin Type 3 domain polypeptides useful in screening for the presence of one or more polypeptides having a selected binding or enzymatic activity. The method includes the steps of:

(i) aligning BC, DE, and FG amino acid loop sequences in a collection of native fibronectin Type 3 domain polypeptides, (ii) segregating the aligned loop sequences according to loop length, (iii) for a selected loop and loop length from step (ii), performing positional amino acid frequency analysis to determine the frequencies of amino acids at each loop position, (iv) for each loop and loop length analyzed in step (iii), identifying at each position a conserved or selected semi-conserved consensus amino acid and other natural-variant amino acids, (v) for at least one selected loop and loop length, forming:

(1) a library of walk-through mutagenesis sequences expressed by a library of coding sequences that encode, at each loop position, the consensus amino acid, and if the consensus amino acid has a occurrence frequency equal to or less than a selected threshold frequency of at least 50%, a single common target amino acid and any co-produced amino acids, or (2) a library of natural-variant combinatorial sequences expressed by a library of coding sequences that encode at each loop position, a consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents, (vi) incorporating the library of coding sequences into framework FN3 coding sequences to form an FN3 expression library, and (vi) expressing the FN3 polypeptides of the expression library.

The method may be employed in producing various type of walk-through mutagenesis and natural-variant combinatorial libraries, such as those described above.

Also disclosed is a TNF-α binding protein having a $K_d$ binding (dissociation) constant equal to or greater than 0.1 µM and having a sequence selected from SEQ ID NOS: 55-63; a VEGF binding protein having a $K_d$ binding constant equal to or greater than 0.1 µM and having a sequence selected from SEQ ID NOS: 64-67; and an HMGB1 binding protein having a $K_d$ binding constant equal to or greater than 0.1 µM and having a sequence selected from SEQ ID NOS: 67-81.

Also disclosed is a VEGFR2 (Vascular Endothelial Growth Factor Receptor 2) binding peptide having a $K_d$ dissociation constant equal to or greater than 300 nM and having a sequence selected from SEQ ID NOS: 223-331. Preferred sequences include SEQ ID NOS: 273, 226, 295, 275, 270, 274, 229, 227, 223 and 248, such as SEQ ID NOS: 273, 226, 295, 275, and 270, preferably SEQ ID NO: 273. The peptide has a preferred dissociation binding constant $K_d$ equal to or greater than 50 nM, preferably equal to or greater than 5 nM. Further disclosed is an Axl transforming receptor tyrosine kinase binding peptide having a $K_d$ dissociation constant equal to or greater than 300 nM and having a sequence selected from SEQ ID NOS: 332-498. Preferred sequences include SEQ ID NOS: 339, 366, 354, 392, 452, 454, 353, 333, 368, and 369, such as SEQ ID NOS: 339, 366, 354, 392, preferably SEQ ID NO: 339. The peptide has a preferred dissociation constant $K_d$ equal to or greater than 50 nM, preferably equal to or greater than 5 nM.

Also forming part of the invention are diagnostic and therapeutic methods and compositions that employ the 14FN3-based binding proteins, as detailed in Section III below for therapeutic applications. For example, the 14FN3 anti-VEGF peptide may be used for the treatment of certain cancers and wet age-related macular degeneration; as described in Section IIIA; the 14FN3 anti-TNF-alpha peptide, for the treatment of rheumatoid arthritis and other autoimmune disorders, as discussed in Section IIIB; and the 14FN3 anti-HMGB! peptide, in the treatment of vascular disease, rheumatoid arthritis, and sepsis, as discussed in Section IIIC. Similarly, binding peptides specific against the VEGFR2 protein may be employed in the treatment of cancer, inflammation, and conditions such as macular degeneration that respond to therapeutic anti-VEGF antibodies, and binding peptides against the Axl protein can be used in the treatment of a variety of cancers, including leukemias, colon cancer, and melanomas.

These and other objects and features of the invention will become more fully apparent when the following detailed description is read in conjunction with the accompanying drawings.

BRIEF DESCRIPTION OF THE FIGURES

FIG. 5 shows amino acid sequence alignment of the 1st-16th fibronectin type III modules of human fibronectin (SEQ ID NOS: 1-16, respectively), the location of three loops: (BC, DE, and FG), and several highly conserved residues through out the fibronectin binding domain including W22, Y/F32, V50, A57, A74, and I/L88 are indicated above the alignment. The conserved amino acid are used as landmarks to aid in alignments of the FN3 module and to introduce gaps where necessary.

FIGS. 15A-15I show the base fixed sequence and variable positions of a BC loop length size 11 and the amino acid matrix showing wild type, the WTM target positions and the extra potential diversity generated from the degenerate WTM codons for each of the selected amino acids K (15A), Q (15B), D (15C), Y (15D), L (15E), P (15F), S (15G), H (15H), and G (15I).

FIGS. 16A-16I show the base fixed sequence and variable positions of an BC loop length size 15 and the amino acid matrix showing wild type, the WTM target positions and the extra potential diversity generated from the degenerate WTM codons for each of the selected amino acids K (16A), Q (16B), D (16C), Y (16D), L (16E), P (16F), S (16G), H (16H), and G (16I).

FIGS. 17A-17I show the base fixed sequence and variable positions of an DE loop length size 6 and matrix showing wild type, the WTM target positions and the extra potential diversity generated from the degenerate WTM codons for each of the selected amino acids K (17A), Q (17B), D (17C), Y (17D), L (17E), P (17F), S (17G), H (17H), and G (17I).

FIGS. 18A-18I show the base fixed sequence and variable positions of an FG loop length size 11 amino acids and matrix showing wild type, the WTM target positions and the extra potential diversity generated from the degenerate WTM codons for each of the selected amino acids K (18A), Q (18B), D (18C), Y (18D), L (18E), P (18F), S (18G), H (18H), and G (18I).

FIG. 19 shows the degenerate and mixed base DNA oligonucleotide sequences for the fixed and variable positions of a BC loop length size 15. The amino acid matrix showing wild type, the WTM target positions and the extra potential diversity generated from the degenerate WTM codons.

FIGS. 23A-23C show the construction of the natural-variant amino acid libraries for loop BC/11 (FIG. 23A), loop DE/6 (FIG. 23B) and loop FG/11 (FIG. 23C).

FIGS. 24A-24C show ELISA with three selected anti-TNFα 14FN3 variants, A6, C10, and C5 for binding to TNFα (light bars) and VEGF (dark bars) (24A); binding specificity of anti-TNFα 14 FN3 variants with respect to TNFα (light bars), control (dark bars) and VEGF (white bars) (24B); and sequences of anti-TNFα 14FN3 variants (24C).

FIGS. 25A-25C show binding specificity of anti-VEGF 14 FN3 variants with respect to VEGF (light bars), TNFα (dark bars bars), control (white bars) (25A); sequences of three anti-VEGF 14FN3 variants (25B); and Octet analysis of variant R1D4 (25C).

FIGS. 26A-26C show sequences of anti-HMGB1 14FN3 sequences (26A); specific binding by anti-HMGB1 variants with respect to HMGB1 (light bars), TNF (dark bars), and control (white bars) (26B), and binding kinetics of HMGB1 variants (26C).

FIGS. 29A-29C show a sequence analysis of VEGFR2 binding peptides (pronectins); and FIGS. 30A-30F show a sequence analysis of Axl binding peptides (pronectins).

DETAILED DESCRIPTION OF THE INVENTION

I. Definitions

Figure 1:
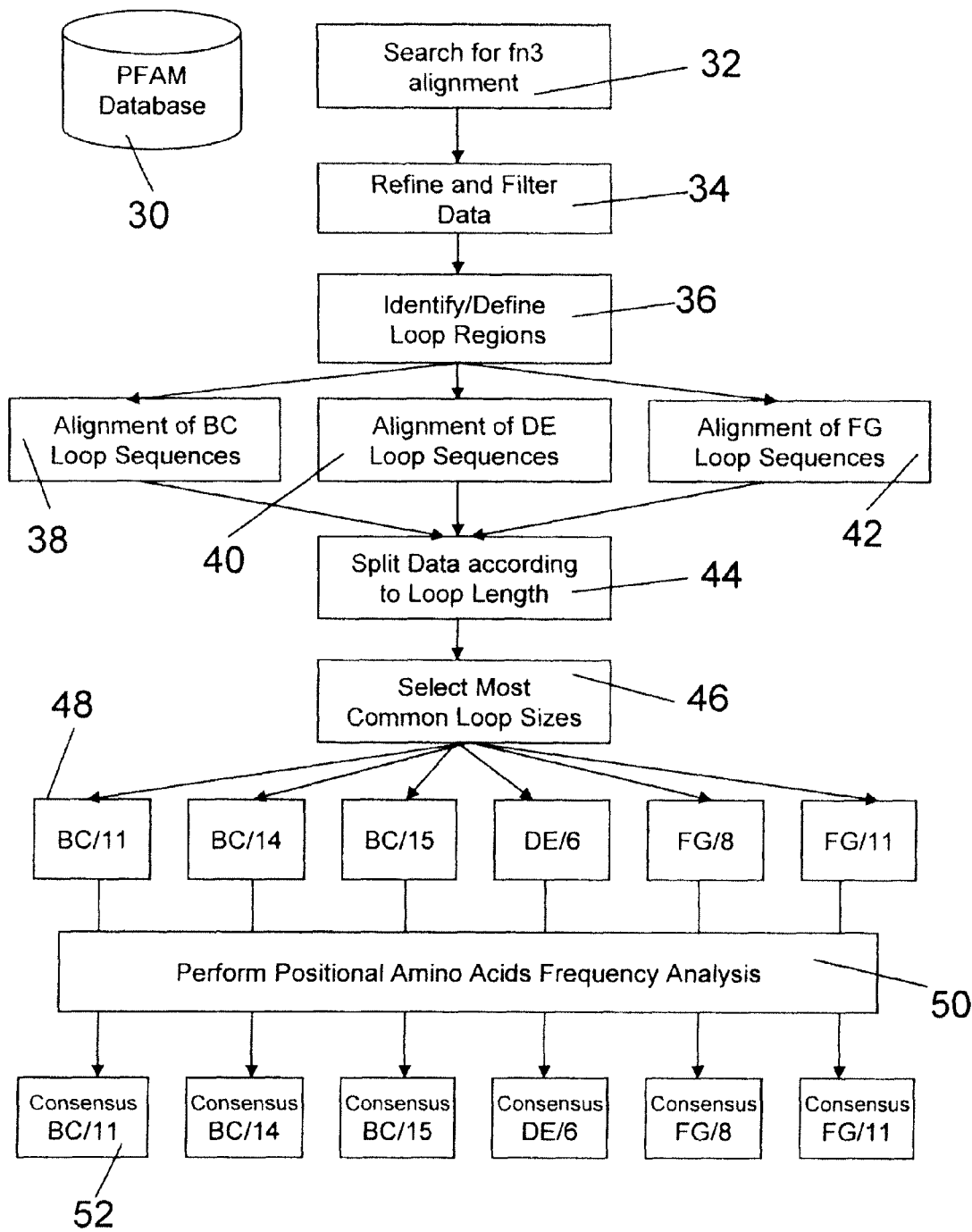
FIG. 1 is a schematic diagram illustrating the method for constructing a fibronectin binding domain libraries using computer assisted genetic database biomining and delineation of beta-scaffold and loop structures.

The terms below have the following meanings unless indicated otherwise in the specification:

"Fibronectin Type III (FN3) domain polypeptides" or "FN3 polypeptides" refer to polypeptides having the Fibronectin Type III domain or module discussed in Section II below, where one or more modules will make up a fibronectin-type protein (FN3 protein), such as the sixteen different FN3 modules making up human fibronectin (FN), and the 15 different FN3 modules making up tenascin. Individual FN3 domain polypeptides are referred to by module number and protein name, e.g., the $10^{th}$ or $14^{th}$ module of human fibronectin (10/FN or 14/FN) or the $1^{st}$ module of tenascin (1/tenascin).

A "library" of FN3 polypeptides refers to a collection of FN3 polypeptides having a selected sequence variation or diversity in at least one of the BC, DE, and FG loops of a defined length (see Section II below). The term "library" is also used to refer to the collection of amino acid sequences within a selected BC, DE, or FG loop of a selected length, and to the collection of coding sequences that encode loop or polypeptide amino acid libraries.

A "universal FN3 library" refers to a FN3 polypeptide library in which amino acid diversity in one or more of the BC, DE or FG loop regions is determined by or reflects the amino acid variants present in a collection of known FN3 sequences.

The term "conserved amino acid residue" or "fixed amino acid" refers to an amino acid residue determined to occur with a frequency that is high, typically at least 50% or more (e.g., at about 60%, 70%, 80%, 90%, 95%, or 100%), for a given residue position. When a given residue is determined to occur at such a high frequency, i.e., above a threshold of about 50%, it may be determined to be conserved and thus represented in the libraries of the invention as a "fixed" or "constant" residue, at least for that amino acid residue position in the loop region being analyzed.

The term "semi-conserved amino acid residue" refers to amino acid residues determined to occur with a frequency that is high, for 2 to 3 residues for a given residue position. When 2-3 residues, preferably 2 residues, that together, are represented at a frequency of about 40% of the time or higher (e.g., 50%, 60%, 70%, 80%, 90% or higher), the residues are determined to be semi-conserved and thus represented in the libraries of the invention as a "semi-fixed" at least for that amino acid residue position in the loop region being analyzed. Typically, an appropriate level of nucleic acid mutagenesis/variability is introduced for a semi-conserved amino acid (codon) position such that the 2 to 3 residues are properly represented. Thus, each of the 2 to 3 residues can be said to be "semi-fixed" for this position. A "selected semi-conserved amino acid residue" is a selected one of the 2 or more semi-conserved amino acid residues, typically, but not necessarily, the residue having the highest occurrence frequency at that position.

The term "variable amino acid residue" refers to amino acid residues determined to occur with a lower frequency (less than 20%) for a given residue position. When many residues appear at a given position, the residue position is determined to be variable and thus represented in the libraries of the invention as variable at least for that amino acid residue position in the loop region being analyzed. Typically, an appropriate level of nucleic acid mutagenesis/variability is introduced for a variable amino acid (codon) position such that an accurate spectrum of residues are properly represented. Of course, it is understood that, if desired, the consequences or variability of any amino acid residue position, i.e., conserved, semi-conserved, or variable, can be represented, explored or altered using, as appropriate, any of the mutagenesis methods disclosed herein, e.g., WTM and natural-variant combinatorial libraries. A lower threshold frequency of occurrence of variable amino acids may be, for example, 5-10% or lower. Below this threshold, variable amino acids may be omitted from the natural-variant amino acids at that position.

A "consensus" amino acid in a BC, DE, or FG loop of an FN3 polypeptide is a conserved amino acid or a selected one of a semi-conserved amino acids.

"Natural-variant amino acids" include conserved, semi-conserved, and variable amino acid residues observed, in accordance with their occurrence frequencies, at a given position in a selected loop of a selected length. The natural-variant amino acids may be substituted by chemically equivalent amino acids, and may exclude variable amino acid residues below a selected occurrence frequency, e.g., 5-10%, or amino acid residues that are chemically equivalent to other natural-variant amino acids.

A "library of walk through mutagenesis sequences" refers to a library of sequences within a selected FN3 loop and loop length which is expressed by a library of coding sequences that encode, at each loop position, a conserved or selected semi-conserved consensus amino acid and, if the consensus amino acid has an occurrence frequency equal to or less than a selected threshold frequency of at least 50%, a single common target amino acid and any co-produced amino acids. Thus, for each of target amino acid, the library of walk-through mutagenesis sequences within a given loop will contain the target amino acid at all combinations of one to all positions within the loop at which the consensus amino acid has an occurrence frequence equal to or less than the given threshold frequency. If this threshold frequency is set at 100%, each position in the loop will be contain the target amino acid in at least one library member. The tem "library of walk-through mutagenesis sequences" also encompasses a mixture of walk-through mutagenesis libraries, one for each target amino acids, e.g., each of nine different target amino acids.

A "library of natural-variant combinatorial sequences" refers to a library of sequences within a selected FN3 loop and loop length which is expressed by a library of coding sequences that encode at each loop position, a conserved or selected semi-conserved consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents. Thus, for each amino acid position in a selected loop and loop length, the library of natural variant combinatorial sequences will contain the consensus amino acid at that position plus other amino acid variants identified as having at least some minimum frequency at that position, e.g., at least 5-10% frequency, or chemically equivalent amino acids. In addition, natural variants may be substituted or dropped if the coding sequence for that amino acid produces a significant number of co-produced amino acids, via codon degeneracy. The average number of encoded amino acid variants in the loop region will typically between 3-5, e.g., 4, for loops having a loop length of 10 or more, e.g., BC/11, BC/14, BC/15, and may have an average number of substitutions of 6 or more for shorter loops, e.g., DE/6, FG/8 and FG/11, (where variations occurs only at six positions) such that the total diversity of a typical loop region can be maintained in the range preferably about $10^4$-$10^7$ for an FN3 BC, DE, or FG loop, and the diversity for two of the three loops can be maintained in the range of about $10^{12}$ or less. It will be appreciated from Examples 9 and 10 below that the natural variants at any loop position can be limited to the topmost frequent 3-5 variants, where natural variants that are omitted are those for which the codon change for that amino acid would also a lead to a significant number of co-produced amino acids, where the variant is already represented in the sequence by a chemically equivalent amino acid, or where the frequency of that amino acid in the sequence profile is relatively low, e.g., 10% or less.

The term "framework region" refers to the art recognized portions of a fibronectin beta-strand scaffold that exist between the more divergent loop regions. Such framework regions are typically referred to the beta strands A through G that collectively provide a scaffold for where the six defined loops can extend to form a ligand contact surface(s). In fibronectin, the seven beta-strands orient themselves as two beta-pleats to form a beta sandwich. The framework region may also include loops AB, CD, and EF between strands A and B, C and D, and E and F. Variable-sequence loops BC, DE, and FG may also be referred to a framework regions in which mutagnesis is introduced to create the desired amino acid diversity within the region.

The term "ligand" or "antigen" refers to compounds which are structurally/chemically similar in terms of their basic composition. Typical ligand classes are proteins (polypeptides), peptides, polysaccharides, polynucleotides, and small molecules. Ligand can be equivalent to "antigens" when recognized by specific antibodies.

The term "loop region" refers to a peptide sequence not assigned to the beta-strand pleats. In the fibronectin binding scaffold there are six loop regions, three of which are known to be involved in binding domains of the scaffold (BC, DE, and FG), and three of which are located on the opposite sided of the polypeptide (AB, EF, and CD). In the present invention, sequence diviersity is built into one or more of the BC, DE, and FG loops, whereas the AB, CD, and EF loops are generally assigned the wildtype amino sequences of the FN3 polypeptide from which other framework regions of the polypeptide are derived.

The term "variability profile" refers to the cataloguing of amino acids and their respective frequency rates of occurrence present at a particular loop position. The loop positions are derived from an aligned fibronectin dataset. At each loop position, ranked amino acid frequencies are added to that position's variability profile until the amino acids' combined frequencies reach a predetermined "high" threshold value.

The term "amino acid" or "amino acid residue" typically refers to an amino acid having its art recognized definition such as an amino acid selected from the group consisting of: alanine (Ala, A); arginine (Arg, R); asparagine (Asn, N); aspartic acid (Asp, D); cysteine (Cys, C); glutamine (Gln, Q); glutamic acid (Glu, E); glycine (Gly, G); histidine (His, H); isoleucine (Ile, I): leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V) although modified, synthetic, or rare amino acids may be used as desired.

"Chemically equivalent amino acids" refer to amino acids that have similar steric, charge, and solubility properties. One common scheme groups amino acids in the following way: (1) glycine, having a hydrogen side chain; (2) alanine (Ala, A), valine (Val, V), leucine (Leu, L), and isoleucine (Iso, I), having hydrogen or an unsubstituted aliphatic side chain; (3) serine (Ser, S) and threonine (Thr, T) having an aliphatic side chain bearing a hydroxyl group; (4) aspartic (Asp, D) and glutamic acid (Glu, E), having a carboxyl containing side chain; (5) asparagine (Asn, N) and glutamine (Glu, Q), having an aliphatic side chain terminating in an amide group; (6) arginine (Arg, R) lysine (Lys, L) and histidine (His, H), having an aliphatic side chain terminating in a basic amino group; (7) cysteine (Cys, C) and methionine (Met, M), having a sulfur containing aliphatic side chain; (8) tyrosine (Tyr, Y) and phenylalanine (Phe, F), having an aromatic side chain; and (9) tryptophan (Trp, W), praline (Pro, P), and histidine (His, H), having a heterocyclic side chain.

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety. Polynucleotide basis and alternative base pairs are given their usual abbreviations herein: Adenosine (A), Guanosine (G), Cytidine (C), Thymidine (T), Uridine (U), puRine (R=A/G), pyrimidine (Y=C/T or C/U), aMino (M=A/C), Keto (K=G/T or G/U), Strong (S=G/C), Weak (W=A/T or A/U), V (A or C or G, but not T), N or X, (any base).

The term "mutagenesis" refers to, unless otherwise specified, any art recognized technique for altering a polynucleotide or polypeptide sequence. Preferred types of mutagenesis include walk-through mutagenesis (WTM), natural-variant combinatorial mutageneis, and beneficial natural-variant combinatorial mutagenesis, although other mutagenesis libraries may be employed, including look-through mutagenesis (LTM), improved look-through mutagenesis (LTM2), WTM using doped nucleotides for achieving codon bias, extended WTM for holding short regions of sequence as constant or fixed within a region of greater diversity, or combinations thereof.

The term "beneficial natural-variant combinatiorial library" refers to a combination library of coding sequences that encode, in two of the three BC, DE, and FG loops of the polypeptide, beneficial mutations determined by screening natural-variant combinatorial libraries containing sequence diversity in those two loops, and natural-variant combinatorial amino acids in the third loop.

The term $K_d$ refers to the dissociation constant between a ligand (the fibronectin peptide of the invention) and a protein (the target protein), and is used to describe how tightly the peptide binds to the protein. The dissociation constant has molar units (e.g., nM), which correspond to the concentration of peptide at which the binding site on the target protein is half occupied, i.e. the concentration of peptide at which the concentration of protein with peptide bound equals the concentration of protein with no peptide bound. The smaller the dissociation constant, the more tightly bound the ligand is, or the higher the affinity between ligand and protein. For example, a ligand with a nanomolar (nM) dissociation constant binds more tightly to a particular protein than a ligand with a micromolar (μM) dissociation constant. Thus "a binding peptide having a $K_d$ dissociation constant equal to or greater than 300 nM" means that half-occupied binding between peptide and target occurs at a concentration of peptide equal to or less than 300 nM. Similarly, "a binding peptide having a $K_d$ dissociation constant equal to or greater than 50 nM" means that half-occupied binding between peptide and target occurs at a concentration of peptide equal to or less than 50 nM, and similarly for "a binding peptide having a $K_d$ dissociation constant equal to or greater than 5 nM."

II. Overview of the Method and Libraries

Artificial antibody scaffolds that bind specific ligands are becoming legitimate alternatives to antibodies. Antibodies have been useful as both diagnostic and therapeutic tools. However, obtaining specific antibodies recognizing certain ligands have been difficult. Current antibody libraries are biased against certain antigen classes only after immunological exposure. Therefore it is frequently necessary to immunize a host animal with a particular antigen before recovery of specific antibodies can occur. Furthermore, these in vivo derived antibody libraries usually do not have candidates that recognize self antigens. These are usually lost in a expressed human library because self reactive antibodies are removed by the donor's immune system by negative selection. Furthermore, antibodies are difficult and expensive to produce requiring special cell fermentation reactors and purification procedures.

The limitations of antibodies has spurred the development of alternative binding proteins based on immunoglobulin like folds or other protein topologies. These non-antibody scaffold share the general quality of having a structurally stable framework core that is tolerant to multiple substitutions in other parts of the protein.

The present invention provides a universal fibronectin binding domain library that is more comprehensive and engineered to have artificial diversity in the ligand binding loops. By creating artificial diversity, the library size can be controlled so that they can be readily screened using, for example, high throughput methods to obtain new therapeutics. The universal fibronectin library can be screened using positive physical clone selection by FACS, phage panning or selective ligand retention. These in vitro screens bypass the standard and tedious methodology inherent in generating an antibody hybridoma library and supernatant screening.

Furthermore, the universal fibronectin library has the potential to recognize any antigen as the constituent amino acids in the binding loop are created by in vitro diversity techniques. This produces the significant advantages of the library controlling diversity size and the capacity to recognize self antigens. Still further, the fibronectin binding domain library can be propagated and re-screened to discover additional fibronectin binding modules against other desired targets.

IIA. Fibronectin Review: (FN)

Figure 2A:
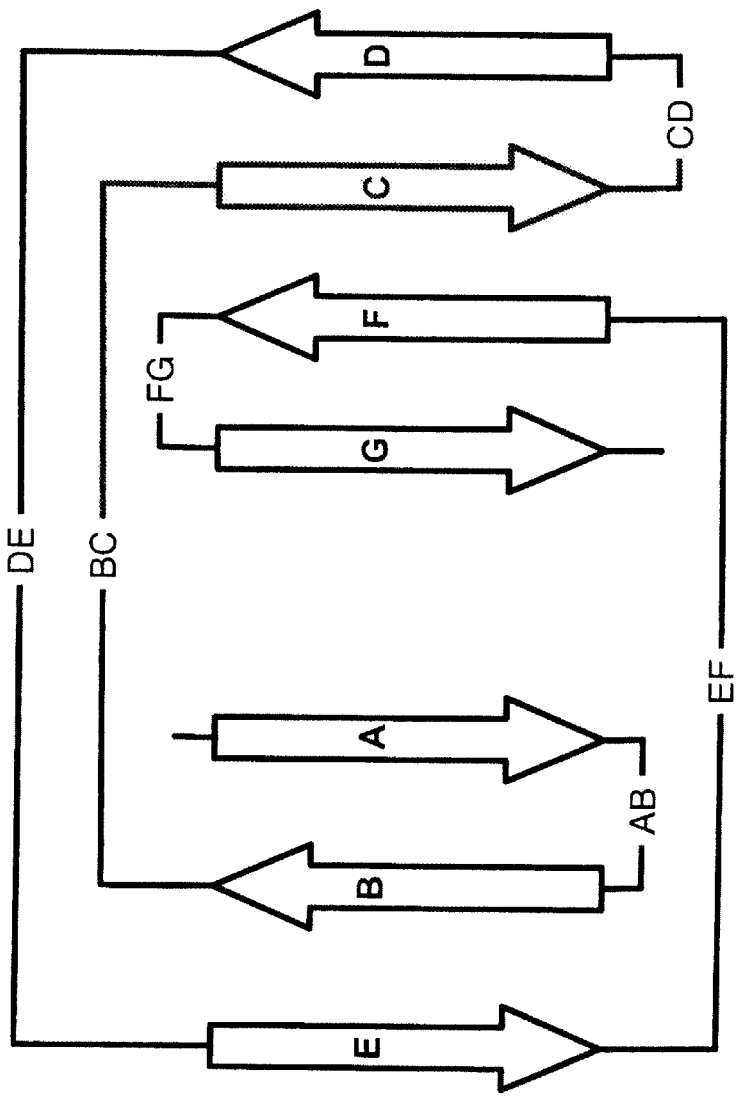
FIG. 2A is a schematic representation of the FN3 binding domain illustrating the two antiparallel beta-sheets domain. One half is composed of beta strands (ABE) and the other half is composed of (CDFG). The 6 CDR like loops are also indicated: AB, BC, CD, DE, EF, and FG. Loops BC, DE and FG (dotted lines) are present at the N-terminus of the FN3 domain and are arranged to form ligand binding surfaces. The RGD sequence is located in the FG loop.
Figure 2B:
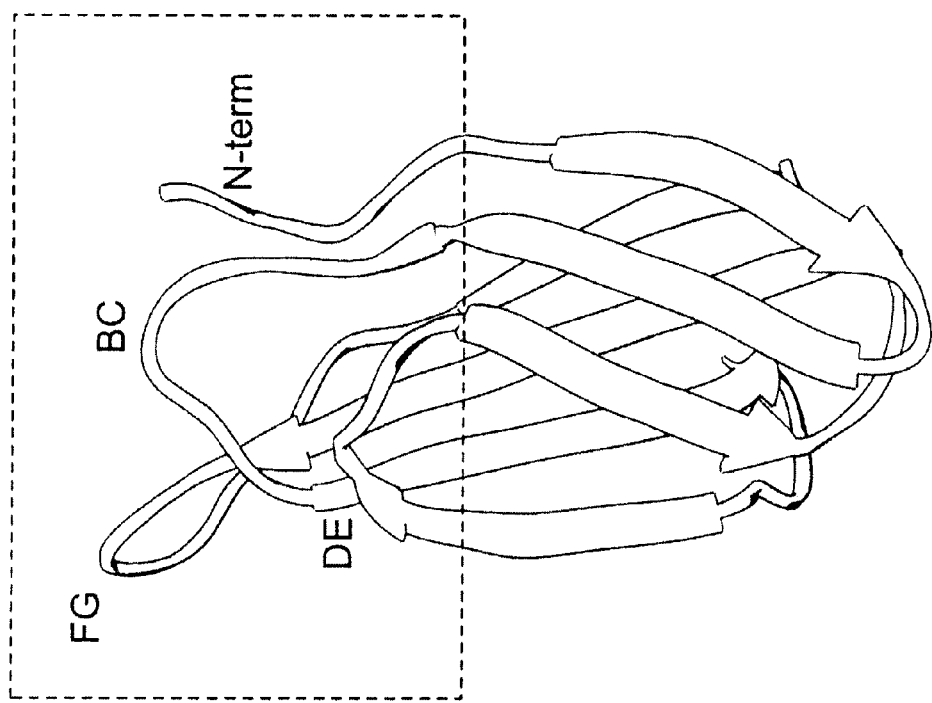
FIG. 2B shows is a ribbon diagram of the FN3 binding domain illustrating the BC, DE and FG loops (dotted lines) are present at the N-terminus of the FN3 domain and are arranged to form ligand binding surfaces

Fibronectin Type III (FN3) proteins refer to a group of proteins composed of monomeric subunits having Fibronectin Type III (FN3) structure or motif made up of seven β-strands with three connecting loops. β-strands A, B, and E form one half β-sandwich and β-strands C, D, F, and G form the other half (see FIGS. 2a and 2b), and having molecular weights of about 94 amino acids and molecular weights of about 10 Kda. The overall fold of the FN3 domain is closely related to that of the immunoglobulin domains, and the three loops near the N-terminus of FN3, named BC, DE, and FG (as illustrated in FIG. 2b), can be considered structurally analogous to the antibody variable heavy (VH) domain complementarity-determining regions, CDR1, CDR2, and CDR3, respectively. Table 1 below shows several FN3 proteins, and the number of different FN3 modules or domains associated with each protein. Thus, fibronectin itself is composed of 16 different modules or domains whose amino acid sequences are shown in aligned form in FIG. 5. A given module of an FN3 protein is identified by module number and protein name, for example, the 14$^{th}$ FN3 module of human fibronectin (14/FN or 14/FN3), the 10$^{th}$ FN3 module of human fibronectin (10/FN or 10/FN3), the 1$^{st}$ FN3 module of tenascin (1/tenascin), and so forth.

TABLE 1

Representative FN3 protins and their modules

| FN3 Protein | FN3 modules |
|---|---|
| Angiopoietin 1 receptor. | 3 |
| Contactin protein | 4 |
| Cytokine receptor common β chain | 2 |
| Down syndrome cell adhesion protein | 6 |
| *Drosophila* Sevenless protein | 7 |
| Erythropoietin receptor | 1 |
| Fibronectin | 16 |
| Growth hormone receptor | 1 |
| Insulin receptor | 2 |
| Insulin-like growth factor I receptor | 3 |
| Interferon-γ receptor β chain. | 2 |
| Interleukin-12 β chain | 1 |
| Interleukin-2 receptor β chain | 1 |
| Leptin receptor (LEP-R) | 3 |
| Leukemia inhibitory factor receptor (LIF-R) | 6 |
| Leukocyte common antigen | 2 |
| Neural cell adhesion protein L1 | 4 |
| Prolactin receptor | 2 |
| Tenascin protein | 15 |
| Thrombopoietin receptor. | 2 |
| Tyrosine-protein kinase receptor Tie-1 | 3 |

Fibronectin itself is involved in many cellular processes, including tissue repair, embryogenesis, blood clotting, by serving as a general cell adhesion molecule anchoring cells to integrin, collagen or other proteoglycan substrates. In addition, fibronectin also can serve to organize the extracellular matrix binding to different components, such as heparin, to membrane-bound receptors on cell surfaces. The amino acid sequence of fibronectin reveals three types of internally homologous repeats or modules separated by (usually) short connecting sequences. There are 12 type I, 2 type II and 16 type III modules, and referred to as FN I, FNII and FNIII respectively. Each FN module constitutes an independently folded unit, often referred to as a domain. As noted above, modules homologous to those in fibronectin are also found in other proteins, especially the FN3 motif which is one of the most ubiquitous of all modules, being found in extracellular receptor kinases, phosphatases, tenascin and others. Since its discovery, this FN3 domain has been found in many animal proteins and is estimated to occur in 2% of the proteins sequenced to date. Within fibronectin itself, there are sixteen FN3 domains and have remarkably similar tertiary structures. Interestingly, while FN3 conformation are highly conserved, the similarity between different modules of the same type within a given fibronectin protein is quite low typically less than 20%. In contrast, the amino acid sequence homology for the same FN-III modules across multiple species is notably higher, approximately 80%-90%.

Fibronectin modules fold independently and thus can exist in isolation from their neighbors. The three dimensional structures of several examples of each type of fibronectin module have been determined. As expected from the well-known relationship between amino acid sequence and 3D structure, modules of the same type have similar folds. All three types of module are composed almost exclusively of antiparallel B sheets and turns, with little or no alpha helix. In F3 modules, the top sheet contains four antiparallel beta strands and the bottom sheet is three-stranded. Disulphide bridges do not stabilize FN3 structure. Instead, this occurs solely through hydrophobic interactions in the module core.

IIB. Identifying and Selecting Fibronectin Scaffold and LOOP Components Using Bioinformatics The first step in building a universal fibronectin library of the invention is selecting sequences that meet certain predetermined criteria. PFAM, ProSite and similar databases were searched for sequences containing FN3 domains (FIG. 1). These electronic databases (box 30 in FIG. 1) contain catalogued expressed fibronectin and fibronectin-like protein sequences and can be queried for those FN3 module and similar sequences (using the BLAST search algorithm, box 32). The FN3 module sequences can then be grouped to predefined criteria such as module subclasses, sequence similarity or originating organism(s). The framework sequence selection can also be performed for scaffold proteins such as FN I, FN II or ankyrin and other proteins (box 34). Example 1 provides additional; details of the method.

Figure 3B:
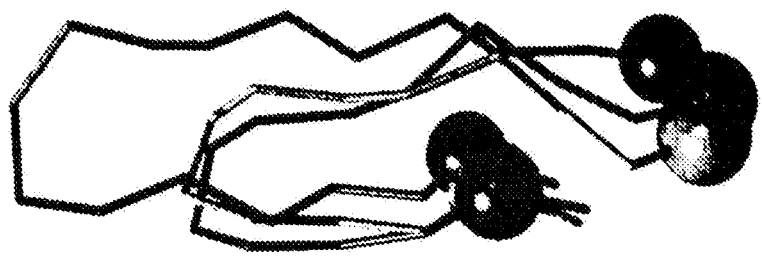
FIGS. 3A and 3B are (3A) a ribbon diagram of the structural overlay comparisons of the overall loop and beta-strand scaffolds between FN3 module 10 and module 14, and (3B) structural overlay comparisons of the FG loop and F and G beta-strand boundaries between FN3 module 10, 13, and 14 indicating that the position of the loop acceptor sites are well-conserved in the FN3 protein domain architecture even though their respective loops may be quite varied in topology.
Figure 3A:
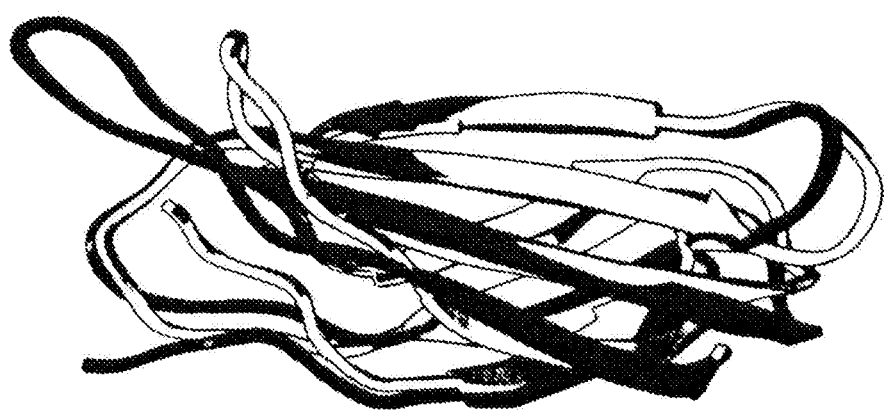
Figure 4:
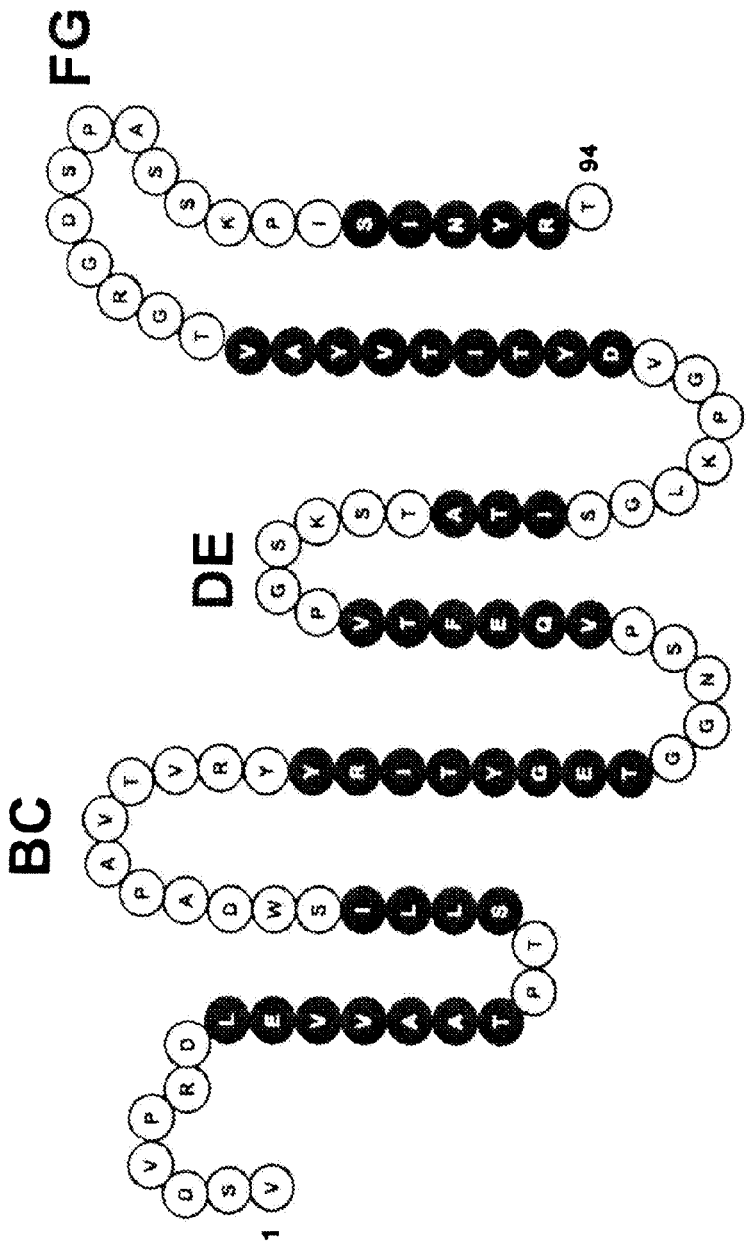
FIG. 4 (SEQ ID NO: 10) is a schematic representation of the FN3 loop and beta-strand amino acid numberings for the BC, DE and FG loop inserts (light shading).
Figure 6:
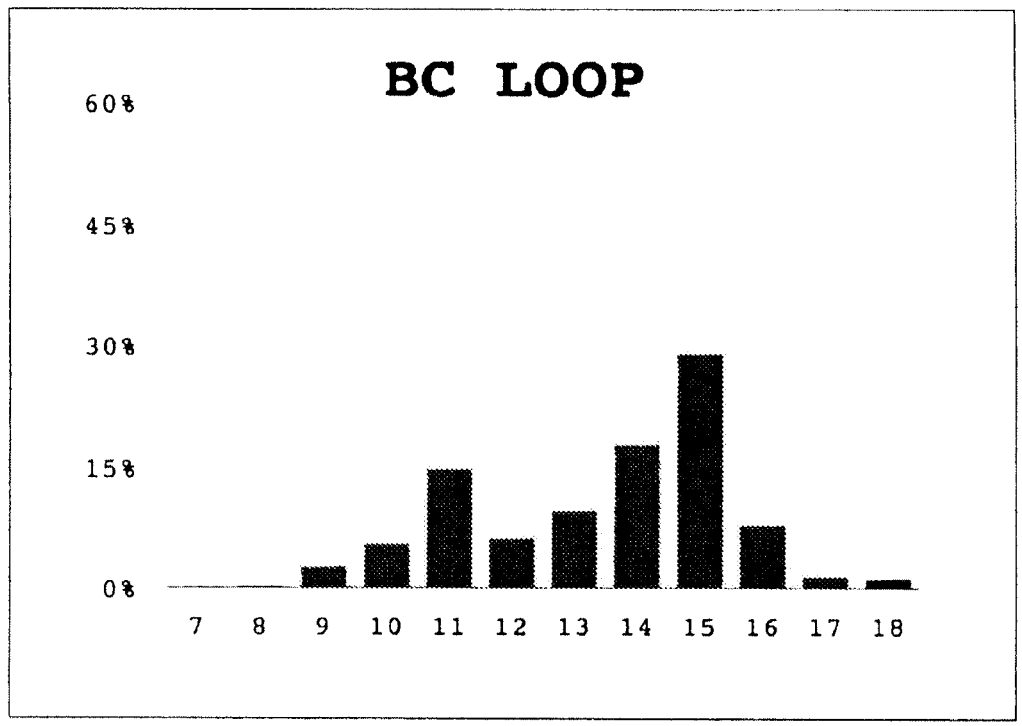
FIG. 6 is a bar graph showing BC loop length diversity derived from bioinformatics analysis of all FN3 modules. BC loop lengths 11, 14 and 15 are the predominant sizes seen in expressed FN3 sequences.
Figure 7:
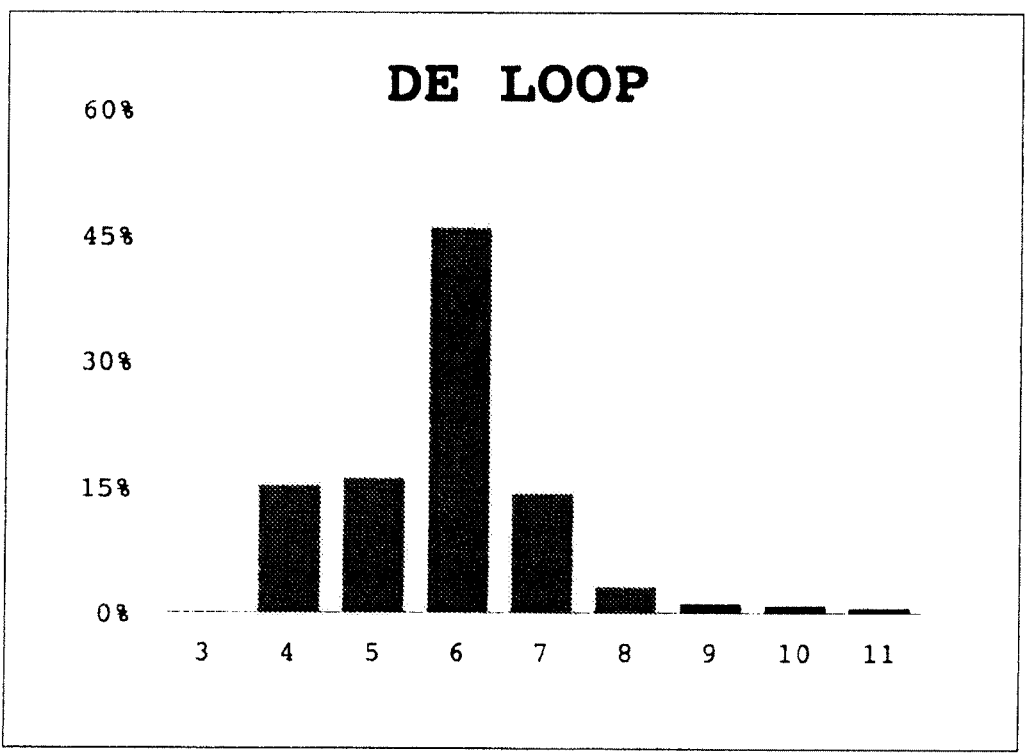
FIG. 7 is a bar graph showing DE loop length diversity derived from bioinformatics analysis of all FN3 modules. DE loop length 6 is the single most predominant size seen in expressed FN3 sequences.
Figure 8:
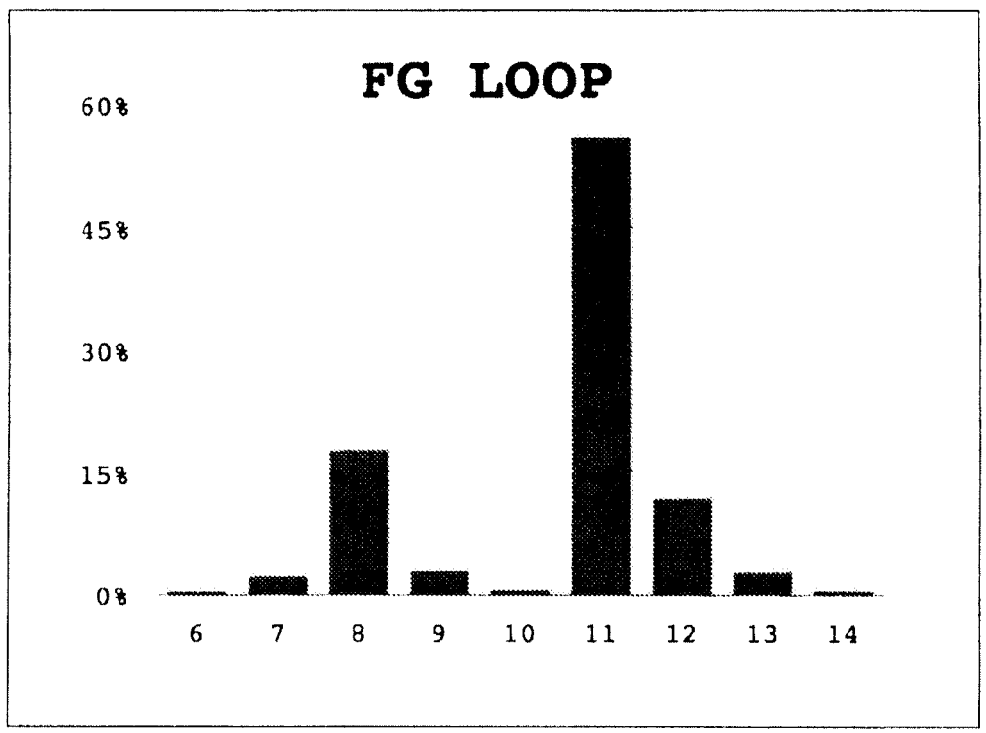
FIG. 8 is a bar graph showing FG loop length diversity derived from bioinformatics analysis of all FN3 modules. FG loop lengths 8 and 11 are the most predominant sizes seen in expressed FN3 sequences.

Candidate FN3 β-strand scaffold framework sequences are then delineated whereupon the intervening loop regions and constituent amino acids are then identified (box 36). This then determines the length of the existing loops, the amino acid profiles for each loop length and, hence the physical size and amino acid diversity that can be accommodated within these frameworks. With reference to FIG. 1, once the loop are identified, sequences within each loop are aligned, at 38, 40, and 42, and the aligned sequences are then split into groups according to loop length, as at 44. The distribution of loop lengths for the BC, DE, and FG loops are shown at FIGS. 6-8, respectively. Using this information, the most common loop sizes are selected, at 46. In a general embodiment of the invention that will be illustrated below, the selected loop lengths are BC/11, BC/14, BC15, DE/6, FG/8, and FG11, as shown at 48 for BC/11. For each β-strand, one can determine the preferred loop acceptor sites in the frameworks based on both comparative structural and sequence analysis (FIGS. 3 and 5). For example, FIG. 3*a* shows a structural overlay comparison of the overall loop and 13 strand scaffolds between the fibronectin 10/FN3 and 14/FN3. FIG. 3*b* shows the structural overlay comparison of the FG loop and F and G β strand boundaries between FN3 modules 10, 13 and 14. In identifying precise loop positions, the above step greatly minimizes necessary diversity loop mutations that would not result in functional ligand binding specificity. Additional details can be found in Example 2.

Once loop lengths are selected, a positional amino acid frequency analysis is performed at each loop position, to determine the frequency of occurrence, in a set of native FN3 modules, e.g., all human FN3 modules, at box 50. This method includes a frequency analysis and the generation of the corresponding variability profiles (VP) of existing loop sequences (See Example 2 and FIGS. 9-14). High frequency (e.g. >50%) positions are considered conserved or fixed. Moderately high frequency or "semi-conserved" amino acids or (when 2 or 3 are combined account for >40%) are chosen as "wildtype" at other positions. These wildtype amino acids are then systematically altered using, mutagenesis, e.g. walk-through mutagenesis (WTM), to generate the universal loop library (see Example 3). "Variable" positions are those where typically, no one amino acid accounts for more than 20% of the represented set.

The choice of candidate frameworks based on the criteria of the invention dictates both the loop sizes to be introduced and the initial amino acid sequence diversity.

A loop variability profile analysis of the FN3 databases allows identification of loop amino acid residue positions that fall within three categories, e.g., 1) positions that should be conserved or "fixed," and 2) semi-conserved and/or 3) variable positions that are suitable for diversity generation. A variability profile analysis is performed and a threshold frequency is used to identify the most favorable sequences to be used in designating the overall loop diversity (box 52).

The conserved or a selected semi-conserved sequence (typically the most frequent amino acid in the semi-conserved residues) is considered the "wild type" or "consensus" residue in the loop sequence. Surprisingly, this "consensus" or "frequency" approach identifies those particular amino acids under high selective pressure. Accordingly, these residue positions are typically fixed, with diversity being introduced into remaining amino acid positions (taking into account the identified preference for certain amino acids to be present at these positions). As will be seen below, the threshold for occurrence frequency at which amino acid variation will be introduced can vary between selected levels as low as 40%, preferably 50% to as high as 100%. At the 100% threshold frequency, WTM amino acids can be introduced at all positions of the loop, and the only constraints on natural-variant amino acids will be the total number of variants and whether chemical equivalents are available.

When designing the diversity for any of the above-mentioned loops, modified amino acid residues, for example, residues outside the traditional 20 amino acids used in most polypeptides, e.g., homocysteine, can be incorporated into the loops as desired. This is carried out using art recognized techniques which typically introduce stop codons into the polynucleotide where the modified amino acid residue is desired. The technique then provides a modified tRNA linked to the modified amino acid to be incorporated (a so-called suppressor tRNA of, e.g., the stop codon amber, opal, or ochre) into the polypeptide (see, e.g., Kohrer et al., Import of amber and ochre suppressors tRNAs into mammalian cells: A general approach to site-specific insertion of amino acid analogues into proteins, PNAS, 98, 14310-14315 (2001)).

The bioinformatic analysis focuses on FN3 modules genes for descriptive purposes, but it will be understood that genes for other FN modules and other scaffold protein are similarly evaluated.

IIC. Computer-Assisted Universal Fibronectin Library Construction

The universal fibronectin loop libraries of the invention and their construction is conducted with the benefit of sequence and structural information such that the potential for generating improved fibronectin binding domains is increased. Structural molecular replacement modeling information can also be used to guide the selection of amino acid diversity to be introduced into the defined loop regions. Still further, actual results obtained with the fibronectin binding domains of the invention can guide the selection (or exclusion), e.g., affinity maturation, of subsequent fibronectin binding domains to be made and screened in an iterative manner.

In the preferred embodiment, in silico modeling is used to eliminate the production of any fibronectin binding domains predicted to have poor or undesired structure and/or function. In this way, the number of fibronectin binding domains to be produced can be sharply reduced thereby increasing signal-to-noise in subsequent screening assays. In another particular embodiment, the in silico modeling is continually updated with additional modeling information, from any relevant source, e.g., from gene and protein sequence and three-dimensional databases and/or results from previously tested fibronectin binding domains, so that the in silico database becomes more precise in its predictive ability (FIG. 1).

In yet another embodiment, the in silico database is provided with the assay results, e.g., binding affinity/avidity of previously tested fibronectin binding domains and categorizes the fibronectin binding domains, based on the assay criterion or criteria, as responders or nonresponders, e.g., as fibronectin binding domain molecules that bind well or not so well. In this way, the affinity maturation of the invention can equate a range of functional responses with particular sequence and structural information and use such information to guide the production of future fibronectin binding domains to be tested. The method is especially suitable for screening fibronectin binding domains for a particular binding affinity to a target ligand using, e.g., a Biacore assay.

Accordingly, mutagenesis of noncontiguous residues within a loop region can be desirable if it is known, e.g., through in silico modeling, that certain residues in the region will not participate in the desired function. The coordinate structure and spatial interrelationship between the defined regions, e.g., the functional amino acid residues in the defined regions of the fibronectin binding domain, e.g., the diversity that has been introduced, can be considered and modeled. Such modeling criteria include, e.g., amino acid residue side group chemistry, atom distances, crystallography data, etc. Accordingly, the number fibronectin binding domains to be produced can be intelligently minimized.

In a preferred embodiment, one or more of the above steps are computer-assisted. In a particular embodiment, the computer assisted step comprises, e.g., mining the NCBI, Genbank, PFAM, and ProSite databases and, optionally, cross-referencing the results against PDB structural database, whereby certain criteria of the invention are determined and used to design the desired loop diversity (FIG. 1). The method is also amenable to being carried out, in part or in whole, by a device, e.g., a computer driven device. For example, database mining fibronectin module sequence selection, diversity design, oligonucleotide synthesis, PCR-mediated assembly of the foregoing, and expression and selection of candidate fibronectin binding domains that bind a given target, can be carried out in part or entirely, by interlaced devices. In addition, instructions for carrying out the method, in part or in whole, can be conferred to a medium suitable for use in an electronic device for carrying out the instructions. In sum, the methods of the invention are amendable to a high throughput approach comprising software (e.g., computer-readable instructions) and hardware (e.g., computers, robotics, and chips).

IID. Universal Walk-Through Mutagenesis Libraries

In one general aspect, the present invention includes a walk-through mutagenesis (WTM) library of fibronectin Type 3 domain polypeptides useful in screening for the presence of one or more polypeptides having a selected binding or enzymatic activity. The library polypeptides include (a) regions A, AB, B, C, CD, D, E, EF, F, and G having wildtype amino acid sequences of a selected native fibronectin Type 3 polypeptide or polypeptides, and (b) loop regions BC, DE, and FG having one or more selected lengths. At least one selected loop region of a selected length contains a library of WTM sequences encoded by a library of coding sequences that encode, at each loop position, a conserved or selected semi-conserved consensus amino acid and, if the consensus amino acid has a occurrence frequency equal to or less than a selected threshold frequency of at least 50%, a single common target amino acid and any co-produced amino acids (amino acids produced by the coding sequences at a given position as a result of codon degeneracy).

In constructing a WTM library within a given loop of a given loop length, the variability profile is used to define a sequence of fixed and "variable" positions, i.e., positions at which a target WTM amino acid can be introduced. The number of fixed positions (no substitutions made) will depend on the selected threshold frequency for the consensus amino acid at each position. Example 3 illustrates the design of WTM loop sequences for each of nine representative target amino acids for FG/11. Conserved or semi-conserved residues were observed for N79, G79, G/S 81 and S84 (two consensus amino acids were placed at position 81, reflecting the high frequency of both G (60%) and S (31%). These four positions (and the two terminal positions S and K) were fixed, and the WTM target amino acid was introduced at each of the other positions in the sequence. For the target amino acid lysine (K), the example shows the various WTM sequences containing a K at from one up to all substitution positions in the loop. Table 5 is the example shows the substitution sequences for all six. BC/11, BC/14, BC/15, DE/6, FG/8, and FG11 loops selected.

In an alternative embodiment, the threshold for consensus sequences is set at 100%, so that all residue positions will be selected for introduction of a WTM target amino acid. This approach in illustrated in Example 5.

Once the WTM loop sequences are selected, a library of coding-sequence oligonucleotides encoding all of the identified WTM sequences is constructed, making codon substitutions as shown that are effective to preserve the existing consensus amino acid, but also encode the selected target amino acid, and any other co-product amino acids encoded by degenerate codons, as detailed in Examples 4 and 5 for the two different WTM libraries (with and without consensus threshold constraints). FIGS. 15A-15I show the base fixed sequence and variable positions of a BC loop length size 11 and the amino acid matrix showing wild type, the WTM target positions and the extra potential diversity generated from the degenerate WTM codons for each of the selected amino acids K (15A), Q (15B), D (15C), Y (15D), L (15E), P (15F), S (15G), H (15H), and G (15I). FIGS. 16A-16I, 17A-17I, 18A-18I provide similar tables for BC loop length 15 (BC/15), DE loop length 6 (DE/6), and FG loop length 11 (FG/11), respectively.

The library of coding sequences for the WTM loops is added to the framework sequences, as detailed in the section below and in Example 6, to construct the library of coding sequences for the WTM polypeptide libraries. In one preferred embodiment, the coding library includes coding sequences for each of the six different loop and loop lengths, and for each of the nine selected "representative" WTM target amino acids (see below).

The library of polypeptides may be encoded by an expression library format that includes a ribosome display library, a polysome display library, a phage display library, a bacterial expression library, or a yeast display library.

The libraries may be used in a method of identifying a polypeptide having a desired binding affinity, in which the natural-variant combinatorial library are screened to select for an fibronectin binding domain having a desired binding affinity. The efficiency of a 14/FN WTM library constructed in accordance with the present invention, for selecting FN3 polypeptides having a high binding affinity for a selected antigen, TNFα, can be appreciated from Example 8, with respect to FIGS. 24A-24C.

FIGS. 23A-23C indicate mutations that are introduced at the indicated residue position in each of loops BC(11), DE(6), and FG(11), respectively, in forming sublibraries containing those three loops.

IIE. Universal Natural-Variant Combinatorial Mutagenesis Libraries

In another general aspect, the invention includes a natural-variant combinatorial library of fibronectin Type 3 domain polypeptides useful in screening for the presence of one or more polypeptides having a selected binding or enzymatic activity. The library polypeptides include (a) regions A, AB, B, C, CD, D, E, EF, F, and G having wildtype amino acid sequences of a selected native fibronectin Type 3 polypeptide or polypeptides, and (b) loop regions BC, DE, and FG having selected lengths. At least one selected loop region of a selected length contains a library of natural-variant combinatorial sequences expressed by a library of coding sequences that encode at each loop position, a conserved or selected semi-conserved consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents.

In constructing a natural-variant combinatorial library for a given loop and loop length, the variability profile is used to define a sequence of fixed and "variable" positions, i.e., positions at which amino acid variations can be introduced. As in the WTM libraries, the number of fixed positions (no substitutions made) will depend on the selected threshold frequency for the consensus amino acid at each position. If, for example, the selected frequency threshold was set at about 60%, the conserved or semi-conserved residues for FG/11 are N79, G79, G/S 81 and S84 (from Example 3) and natural-variant substitutions would not be made at these positions. Conversely, if the threshold frequency is set at 100%, all positions would be considered open to variation, recognizing that a single amino acid with a frequency of 100% at a loop position would not be substituted, and a position that had one very dominant amino acid, e.g., with a frequency of 90%, might be substituted only if the low-frequency variant(s) were chemically dissimilar to the dominant amino acid.

From the amino acid profile for a given loop and loop length, and knowing which of the positions will be held fixed and which will be admit variations, the amino acid substitutions at each variable position can be selected. In general, the number of variations that are selected (including co-produced amino acids) will depend on the number of variable substitution positions in the loop and the average number of variations per substituted loop position. Ideally, the number of variations selected will be such as to maintain the diversity of the loop in the range $10^5$-$10^7$ Isequences, allowing a library of two variable-sequence loops in the range of about $10^{12}$. As will be seen from Example 9 below, an FG/11 loop having amino acid variations at 10 of the 11 positions, will have an average of about 4 amino acid variations/position, whereas a shorter loop, such as DE/6 will admit up to 6 or more variations per position. Of course, if natural-variant substitutions are introduced into a single loop only, many more variations per position can be accommodated.

The particular natural variant amino acids that are selected for each position will generally include the amino acids having the highest frequencies, while limited the number of co-produced amino acids, and secondarily, preserving chemical diversity at each site. Thus, if the codon change for one variant amino acid would produce several co-produced amino acids, that variant would likely be omitted, and/or a chemically equivalent amino acid would be sought. Similarly, if one natural variant is chemically equivalent to another one, one of the two could be omitted. In summary, the natural-variant loop sequences are constructed to include the highest frequency natural variants, while minimizing co-produced amino acids and minimizing redundancy in amino acid side chain properties, and to limit the total diversity of the loop and loop length if necessary, i.e., where sequence variation is introduced into more than one loop. The application of these rules can be seen in the exemplary variant substitutions in a BC/11 loop (FIG. 25B) from the BC/11 loop profile given in FIG. 9. Similarly, the application of the rules can be seen in the exemplary variant substitutions in a DE/6 loop (FIG. 25B), from the DE loop profile in FIG. 12.

Once the natural-variant loop sequences are selected, a library of coding-sequence oligonucleotides encoding all of the identified natural-variant sequences is constructed, making codon substitutions that are effective to preserve the existing consensus amino acid, and encode the selected variant amino acids, including variants encoded encoded by degenerate codons.

The library of coding sequences for the natural-variants loops is added to the framework sequences, as detailed in the section below and in Example 6, to construct the library of coding sequences for the natural-variant polypeptide libraries. In one preferred embodiment, the coding library includes coding sequences for a pair of BC/DE, BC/FG or DE/FG loops, where each loop in the pair has one selected length, egg., BC/11 and DE/6. Such a two-loop library is described in Examples 9 and 10 below. After selecting high-affinity binding (or enzymatic) polypeptides from this library, a second "beneficial" library can be constructed that includes the beneficial mutations contained in one or both of original two-loop natural-variation library, and natural-variant amino acids in the third loop, i.e., the previously fixed-sequence loop.

Natural-variant combinatorial library may have the following sequences for the indicated loops and loop lengths: (a) BC loop length of 11, and the amino acid sequence identified by SEQ ID NOS: 43 or 49; (b) BC loop length of 14, and the amino acid sequence identified by SEQ ID. NOS: 44 or 50; (c) BC loop length of 15, and the amino acid sequence identified by SEQ ID. NOS: 45 or 51; (d) DE loop length of 6, and the amino acid sequence identified by SEQ ID. NOS: 46 or 52; (e) FG loop length of 8, and the amino acid sequence identified by SEQ ID. NOS: 47, for the first N-terminal six amino acids, or SEQ ID NO:53, and (f) FG loop length of 11, and the amino acid sequence identified by SEQ ID. NO: 48, for the first N-terminal nine amino acids, or SEQ ID NO:54.

The library of polypeptides may be encoded by an expression library that has the format of a ribosome display library, a polysome display library, a phage display library, a bacterial expression library, or a yeast display library.

The libraries may be used in a method of identifying a polypeptide having a desired binding affinity, in which the natural-variant combinatorial library are screened to select for an fibronectin binding domain having a desired binding affinity. The efficiency of a 14/FN natural-variant combinatorial library constructed in accordance with the present invention, for selecting FN3 polypeptides having a high binding affinity for each of two selected antigens, VEGF and HMGB1, can be appreciated from Example 9, with respect to FIGS. 25A-25C, and Example 10, with respect to FIGS. 26A-26C.

IIF. Synthesizing Universal Fibronectin Binding Domain Libraries

In one embodiment, the universal fibronectin binding domains of the invention are generated for screening by synthesizing individual oligonucleotides that encode the defined region of the polypeptide and have no more than one codon for the predetermined amino acid. This is accomplished by incorporating, at each codon position within the oligonucleotide either the codon required for synthesis of the wild-type polypeptide or a codon for the predetermined amino acid and is referred to as look-through mutagenesis (LTM) (see, e.g., U.S. Patent Publication No. 20050136428).

In another embodiment, when diversity at multiple amino acid positions is required, walk-through mutagenesis (WTM) can be used (see e.g., U.S. Pat. Nos. 6,649,340; 5,830,650; and 5,798,208; and U.S. Patent Publication No. 20050136428). WTM allows for multiple mutations to be made with a minimum number of oligonucleotides. The oligonucleotides can be produced individually, in batches, using, e.g., doping techniques, and then mixed or pooled as desired.

The mixture of oligonucleotides for generation of the library can be synthesized readily by known methods for DNA synthesis. The preferred method involves use of solid phase beta-cyanoethyl phosphoramidite chemistry (e.g., see U.S. Pat. No. 4,725,677). For convenience, an instrument for automated DNA synthesis can be used containing specified reagent vessels of nucleotides. The polynucleotides may also be synthesized to contain restriction sites or primer hybridization sites to facilitate the introduction or assembly of the polynucleotides representing, e.g., a defined region, into a larger gene context.

The synthesized polynucleotides can be inserted into a larger gene context, e.g., a single scaffold domain using standard genetic engineering techniques. For example, the polynucleotides can be made to contain flanking recognition sites for restriction enzymes (e.g., see U.S. Pat. No. 4,888,286). The recognition sites can be designed to correspond to recognition sites that either exist naturally or are introduced in the gene proximate to the DNA encoding the region. After conversion into double stranded form, the polynucleotides are ligated into the gene or gene vector by standard techniques. By means of an appropriate vector (including, e.g., phage vectors, plasmids) the genes can be introduced into a cell-free extract, phage, prokaryotic cell, or eukaryotic cell suitable for expression of the fibronectin binding domain molecules.

Alternatively, partially overlapping polynucleotides, typically about 20-60 nucleotides in length, are designed. The internal polynucleotides are then annealed to their complementary partner to give a double-stranded DNA molecule with single-stranded extensions useful for further annealing. The annealed pairs can then be mixed together, extended, and ligated to form full-length double-stranded molecules using SOE-PCR (see, e.g., Example 3). Convenient restriction sites can be designed near the ends of the synthetic gene for cloning into a suitable vector. The full-length molecules can then be ligated into a suitable vector.

When partially overlapping polynucleotides are used in the gene assembly, a set of degenerate nucleotides can also be directly incorporated in place of one of the polynucleotides. The appropriate complementary strand is synthesized during the extension reaction from a partially complementary polynucleotide from the other strand by enzymatic extension with a polymerase. Incorporation of the degenerate polynucleotides at the stage of synthesis also simplifies cloning where more than one domain or defined region of a gene is mutagenized or engineered to have diversity.

In another approach, the fibronectin binding domain is present on a single stranded plasmid. For example, the gene can be cloned into a phage vector or a vector with a filamentous phage origin of replication that allows propagation of single-stranded molecules with the use of a helper phage. The single-stranded template can be annealed with a set of degenerate polynucleotides representing the desired mutations and elongated and ligated, thus incorporating each analog strand into a population of molecules that can be introduced into an appropriate host (see, e.g., Sayers, J. R. et al., Nucleic Acids Res. 16: 791-802 (1988)). This approach can circumvent multiple cloning steps where multiple domains are selected for mutagenesis.

Polymerase chain reaction (PCR) methodology can also be used to incorporate polynucleotides into a gene, for example, loop diversity into β-strand framework regions. For example, the polynucleotides themselves can be used as primers for extension. In this approach, polynucleotides encoding the mutagenic cassettes corresponding to the defined region (or portion thereof) are complementary to each other, at least in part, and can be extended to form a large gene cassette (e.g., a fibronectin binding domain) using a polymerase, e.g., using PCR amplification.

The size of the library will vary depending upon the loop length and the amount of sequence diversity which needs to be represented using, e.g., WTM or L™. Preferably, the library will be designed to contain less than $10^{15}$, $10^{14}$, $10^{13}$, $10^{12}$, $10^{11}$, $10^{10}$, $10^9$, $10^8$, $10^7$ and more preferably, $10^6$ fibronectin binding domain.

The description above has centered on representing fibronectin binding domain diversity by altering the polynucleotide that encodes the corresponding polypeptide. It is understood, however, that the scope of the invention also encompasses methods of representing the fibronectin binding domain diversity disclosed herein by direct synthesis of the desired polypeptide regions using protein chemistry. In carrying out this approach, the resultant polypeptides still incorporate the features of the invention except that the use of a polynucleotide intermediate can be eliminated.

For the libraries described above, whether in the form of polynucleotides and/or corresponding polypeptides, it is understood that the libraries may be also attached to a solid support, such as a microchip, and preferably arrayed, using art recognized techniques.

The method of this invention is especially useful for modifying candidate fibronectin binding domain molecules by way of affinity maturation. Alterations can be introduced into the loops and/or into the β-strand framework (constant) region of an fibronectin binding domain. Modification of the loop regions can produce fibronectin binding domains with better ligand binding properties, and, if desired, catalytic properties. Modification of the β-strand framework region can also lead to the improvement of chemo-physical properties, such as solubility or stability, which are especially useful, for example, in commercial production, bioavailabilty, and affinity for the ligand. Typically, the mutagenesis will target the loop region(s) of the fibronectin binding domain, i.e., the structure responsible for ligand-binding activity which can be made up of the three loop regions. In a preferred embodiment, an identified candidate binding molecule is subjected to affinity maturation to increase the affinity/avidity of the binding molecule to a target ligand.

IIG. Expression and Screening Systems

Libraries of polynucleotides generated by any of the above techniques or other suitable techniques can be expressed and screened to identify fibronectin binding domain molecules having desired structure and/or activity. Expression of the fibronectin binding domain molecules can be carried out using cell-free extracts (and e.g., ribosome display), phage display, prokaryotic cells, or eukaryotic cells (e.g., yeast display).

In one embodiment, the polynucleotides are engineered to serve as templates that can be expressed in a cell free extract. Vectors and extracts as described, for example in U.S. Pat. Nos. 5,324,637; 5,492,817; 5,665,563, can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261,804; 6,258,558; and 6,214,553).

Alternatively, the polynucleotides of the invention can be expressed in a convenient E. coli expression system, such as that described by Pluckthun and Skerra. (Pluckthun, A. and Skerra, A., Meth. Enzymol. 178: 476-515 (1989); Skerra, A. et al., Biotechnology 9: 273-278 (1991)). The mutant proteins can be expressed for secretion in the medium and/or in the cytoplasm of the bacteria, as described by M. Better and A. Horwitz, Meth. Enzymol. 178: 476 (1989). In one embodiment, the fibronectin binding domain are attached to the 3' end of a sequence encoding a signal sequence, such as the ompA, phoA or pelB signal sequence (Lei, S. P. et al., J. Bacteriol. 169: 4379 (1987)). These gene fusions are assembled in a dicistronic construct, so that they can be expressed from a single vector, and secreted into the periplasmic space of E. coli where they will refold and can be recovered in active form. (Skerra, A. et al., Biotechnology 9: 273-278 (1991)).

In another embodiment, the fibronectin binding domain sequences are expressed on the membrane surface of a prokaryote, e.g., E. coli, using a secretion signal and lipidation moiety as described, e.g., in US20040072740A1; US20030100023A1; and US20030036092A1.

In still another embodiment, the polynucleotides can be expressed in eukaryotic cells such as yeast using, for example, yeast display as described, e.g., in U.S. Pat. Nos. 6,423,538; 6,331,391; and 6,300,065. In this approach, the fibronectin binding domain molecules of the library are fused to a polypeptide that is expressed and displayed on the surface of the yeast.

Higher eukaryotic cells for expression of the fibronectin binding domain molecules of the invention can also be used, such as mammalian cells, for example myeloma cells (e.g., NS/0 cells), hybridoma cells, or Chinese hamster ovary (CHO) cells. Typically, the fibronectin binding domain molecules when expressed in mammalian cells are designed to be expressed into the culture medium, or expressed on the surface of such a cell. The fibronectin binding domain can be produced, for example, as single individual module or as multimeric chains comprising dimers, trimers, that can be composed of the same module or of different module types. ($^{10}$FN3-$^{10}$FN3: homodimer, $^{10}$FN3-$^5$FN3: heterodimer)

The screening of the expressed fibronectin binding domain (or fibronectin binding domain produced by direct synthesis) can be done by any appropriate means. For example, binding activity can be evaluated by standard immunoassay and/or affinity chromatography. Screening of the fibronectin binding domain of the invention for catalytic function, e.g., proteolytic function can be accomplished using a standard hemoglobin plaque assay as described, for example, in U.S. Pat. No. 5,798,208. Determining the ability of candidate fibronectin binding domain to bind therapeutic targets can be assayed in vitro using, e.g., a Biacore instrument, which measures binding rates of a fibronectin binding domain to a given target or ligand. In vivo assays can be conducted using any of a number of animal models and then subsequently tested, as appropriate, in humans.

IIH. Analysis and Screening of FN3 WTM Libraries for Catalytic Function.

FN3 WTM libraries can also be used to screen for FN3 proteins that possess catalytic activity. The study of proteins has revealed that certain amino acids play a crucial role in their structure and function. For example, it appears that only a discrete number of amino acids participate in the catalytic event of an enzyme. Serine proteases are a family of enzymes present in virtually all organisms, which have evolved a structurally similar catalytic site characterized by the combined presence of serine, histidine and aspartic acid. These amino acids form a catalytic triad which, possibly along with other determinants, stabilizes the transition state of the substrate.

The functional role of this catalytic triad has been confirmed by individual and by multiple substitutions of serine, histidine and aspartic acid by site-directed mutagenesis of serine proteases and the importance of the interplay between these amino acid residues in catalysis is now well established. These same three amino acids are involved in the enzymatic mechanism of certain lipases as well. FIG. 26 is a schematic depiction of a "walk-through" mutagenesis of a an active site that utilizes the serine, histidine and aspartic acid triad.

Similarly, a large number of other types of enzymes are characterized by the peculiar conformation of their catalytic site and the presence of certain kinds of amino acid residues in the site that are primarily responsible for the catalytic event. For an extensive review, see Enzyme Structure and Mechanism, 1985, by A. Fersht, Freeman Ed., New York.

Though it is clear that certain amino acids are critical to the mechanism of catalysis, it is difficult, if not impossible, to predict which position (or positions) an amino acid must occupy to produce a functional site such as a catalytic site. Unfortunately, the complex spatial configuration of amino acid side chains in proteins and the interrelationship of different side chains in the catalytic pocket of enzymes are insufficiently understood to allow for such predictions. Selective site-directed mutagenesis and saturation mutagenesis are of limited utility for the study of protein structure and function in view of the enormous number of possible variations in complex proteins.

Protein libraries generated by any of the above WTM/CBM/LTM techniques or other suitable techniques can be screened to identify variants of desired structure or activity.

By comparing the properties of a wild-type protein and the variants generated, it is possible to identify individual amino acids or domains of amino acids that confer binding and/or catalytic activity. Usually, the region studied will be a functional domain of the protein such as a binding domain. For example, the region can be the external BC, DE and FG loop binding regions of FN3 domain. The screening can be done by any appropriate means. For example, catalytic activity can be ascertained by suitable assays for substrate conversion and binding activity can be evaluated by standard immunoassay and/or affinity chromatography.

From the chemical properties of the side chains, it appears that only a selected number of natural amino acids preferentially participate in a catalytic event. These amino acids belong to the group of polar and neutral amino acids such as Ser, Thr, Asn, Gln, Tyr, and Cys, the group of charged amino acids, Asp and Glu, Lys and Arg, and especially the amino acid His. Typical polar and neutral side chains are those of Cys, Ser, Thr, Asn, Gln and Tyr. Gly is also considered to be a borderline member of this group. Ser and Thr play an important role in forming hydrogen-bonds. Thr has an additional asymmetry at the beta carbon, therefore only one of the stereoisomers is used. The acid amide Gln and Asn can also form hydrogen bonds, the amido groups functioning as hydrogen donors and the carbonyl groups functioning as acceptors. Gln has one more $CH_2$ group than Asn which renders the polar group more flexible and reduces its interaction with the main chain. Tyr has a very polar hydroxyl group (phenolic OH) that can dissociate at high pH values. Tyr behaves somewhat like a charged side chain; its hydrogen bonds are rather strong.

Histidine (His) has a heterocyclic aromatic side chain with a pK value of 6.0. In the physiological pH range, its imidazole ring can be either uncharged or charged, after taking up a hydrogen ion from the solution. Since these two states are readily available, His is quite suitable for catalyzing chemical reactions. It is found in most of the active centers of enzymes.

Asp and Glu are negatively charged at physiological pH. Because of their short side chain, the carboxyl group of Asp is rather rigid with respect to the main chain. This may be the reason why the carboxyl group in many catalytic sites is provided by Asp and not by Glu. Charged acids are generally found at the surface of a protein.

Therefore, several different regions or loops of a FN3 protein domain can be mutagenized simultaneously. The same or a different amino acid can be "walked-through" each loop region. This enables the evaluation of amino acid substitutions in conformationally related regions such as the regions which, upon folding of the protein, are associated to make up a functional site such as the catalytic site of an enzyme or the binding site of an antibody. This method provides a way to create modified or completely new catalytic sites. As depicted in FIG. 26, the three loop regions of FN3, which can be engineered to confer target ligand binding, can be mutagenized simultaneously, or separately within the BC, DE and FG loops to assay for contributing catalytic functions at this binding site. Therefore, the introduction of additional "catalytically important" amino acids into a ligand binding region of a protein may result in de novo catalytic activity toward the same target ligand.

Hence, new structures can be built on the natural "scaffold" of an existing protein by mutating only relevant regions by the method of this invention. The method of this invention is suited to the design of de novo catalytic binding proteins as compared to the isolation of naturally occurring catalytic antibodies. Presently, catalytic antibodies can be prepared by an adaptation of standard somatic cell fusion techniques. In this process, an animal is immunized with an antigen that resembles the transition state of the desired substrate to induce production of an antibody that binds the transition state and catalyzes the reaction. Antibody-producing cells are harvested from the animal and fused with an immortalizing cell to produce hybrid cells. These cells are then screened for secretion of an antibody that catalyzes the reaction. This process is dependent upon the availability of analogues of the transition state of a substrate. The process may be limited because such analogues are likely to be difficult to identify or synthesize in most cases.

The method of this invention can be used to produce many different enzymes or catalytic antibodies, including oxidoreductases, transferases, hydrolases, lyases, isomerases and ligases. Among these classes, of particular importance will be the production of improved proteases, carbohydrases, lipases, dioxygenases and peroxidases. These and other enzymes that can be prepared by the method of this invention have important commercial applications for enzymatic conversions in health care, cosmetics, foods, brewing, detergents, environment (e.g., wastewater treatment), agriculture, tanning, textiles, and other chemical processes. These include, but are not limited to, diagnostic and therapeutic applications, conversions of fats, carbohydrates and protein, degradation of organic pollutants and synthesis of chemicals. For example, therapeutically effective proteases with fibrinolytic activity, or activity against viral structures necessary for infectivity, such as viral coat proteins, could be engineered. Such proteases could be useful anti-thrombotic agents or anti-viral agents against viruses such as AIDS, rhinoviruses, influenza, or hepatitis. In the case of oxygenases (e.g., dioxygenases), a class of enzymes requiring a co-factor for oxidation of aromatic rings and other double bonds, industrial applications in biopulping processes, conversion of biomass into fuels or other chemicals, conversion of waste water contaminants, bioprocessing of coal, and detoxification of hazardous organic compounds are possible applications of novel proteins.

Throughout the examples, the following materials and methods were used unless otherwise stated.

III. Applications

The 14FN3-based binding proteinc so the present invention find use in a variety of diagnostic and therapeutic applications, such as those now found for corresponding antibodies, but with the added advantages in cost, size, and possible reduced immunogenicity of the 14FN3-based binding agents.

IIIA. Applications of 14FN3 Anti-VEGF Peptides

VEGF is the dominant growth factor involved in angiogenesis and has been shown to stimulate vascular endothelial cell growth, survival, and proliferation. Across a wide range of human tumors and/or cell lines, expression of VEGF has been shown to lead to the development and maintenance of a vascular network that promotes tumor growth and metastasis. Moreover, a large and growing body of evidence indicates that both VEGF gene expression and VEGF production are associated closely with poor prognosis. VEGF has been shown to contribute to tumor growth in several important aspects: (1) Facilitates survival of existing vessels, (2) Contributes to vascular abnormalities (eg, high interstitial pressure) that may impede effective delivery of antitumor compounds, (3) Stimulates new vessel growth, and (4) May prevent immune response to tumors. Types of cancer in which 14FN3 anti-VEGF therapy may be useful include, but are not limited to, breast, lung, colorectal, renal cell carcinoma, glioblastoma, prostate, and ovarian.

The wet form of age-related macular degeneration is the most common cause of blindness among the elderly and is characterized by aberrant growth of new blood vessels mediated by VEGF. Anti-VEGF therapy has been shown to block this aberrant vascularization and improve visual acuity.

In both applications, the 14FN3 anti-VEGF peptide is formulated in a suitable pharmaceutical carrier, such as physiological saline and delivered by conventional parenteral routes, e.g., IV or intraocular injection. Suitable treatment doses can be readily determined from binding studies comparing the binding activity of the 14FN3 peptide against a known anti-VEGF antibody, to determine doses of 14FN3 anti-VEGF peptide comparable to known therapeutic doses of anti-VEGF antibody.

IIIB. Applications of 14FN3 TNF-Alpha Peptides

The anti-TNF-alpha peptides may be used for the treatment of rheumatoid arthritis. TNF-alpha is a key mediator of the inflammatory response and induces a cytokine cascade that induces inflammation and tissue damage. In rheumatoid arthritis (RA), synovial cells produce an excess of TNF-alpha and inhibition of TNF-alpha has been shown to reduce the severity and associated structural damage of RA. The 14FN3 anti-TNF-alpha peptide is used in this application.

The 14FN3 anti-TNF-alpha peptide also finds use in treating a variety of other autoimmune diseases, such as Crohn's disease, Ankylosing spondylitis, asnsd Psoriatic arthritis: The rational for anti-TNF therapy for these diseases is the same as with RA. All of these conditions are characterized by overproduction of TNF-alpha and tissue damage from the subsequent inflammatory response. Anti-TNF therapy reduces the inflammatory response and tissue damage.

As above, the 14FN3 anti-TNF-alpha peptide is formulated in a suitable pharmaceutical carrier, such as physiological saline and delivered by conventional parenteral routes, e.g., IV injections, or injections directly into the joint area, where suitable doses are determined as above.

IIIC. Applications of 14FN3 Anti-HMGB1 Peptides

HMGB1 protein (known, before 2001, as HMG; Bustin, 2001, Trends Biochem. Sci., 26, 152-153) is the archetypal protein of the HMG-box family, which is characterized by the presence of DNA binding domains, called HMG boxes. HMG1 is a small 25-kD protein, of 215 amino acids, with a highly conserved sequence among mammals. The HMGB1 molecule is organized into three domains: two DNA binding domains, HMG Box A and Box B, which are followed by an acidic COOH terminus composed of 30 glutamic and aspartic residues. The two HMG boxes, box A and box B, are 80 amino acid segments (29% identical, 65% similar), having an L-shaped tridimensional structure (Hardman et al., 1995, Biochemistry, 34: 16595-16607; Read et al., 1993, Nucleic Acids Res., 21:3427-3436; Weir et al., 1993, EMBO J., 12: 1311-1319).

HMGB1 was originally identified as a ubiquitously expressed, abundant nuclear protein. It is present in more than 1 million copies per single nucleus and binds double stranded DNA without sequence specificity. Instead, HMGB1 binds with high affinity to specific DNA structures like kinked or bent DNA and four-way junctions. However, HMGB1 can be recruited to double stranded DNA by interaction with several different DNA-binding proteins. When bound to double stranded DNA, it induces structure distortion, allowing the formation of nucleoprotein complexes where several DNA-binding proteins can contact each other while bound to their respective DNA cognate sites (Miller et al., 2001, EMBO J., 16: 4337-4340 and other references cited within). The phenotype of HMGB1 −/− mice is in agreement with this model (Calogero et al., 1999, Nat. Genet., 22:276-280).

Recently, an additional role for HMGB1 outside the cell nucleus has come into focus: HMGB1 works as a late mediator of endotoxin-induced lethality as well as acute lung inflammation in mice. In addition, the elevated serum level of HMGB1 in septic patients is a prognostic marker (international patent application No. WO00/47104). HMGB1 can be secreted by macrophages and pituicytes in culture in response to cytokines and bacterial endotoxin (Abraham et al., 2000, J. Immunol., 165: 2950-2954; Wang et al., 1999, Surgery (St. Luis), 126~389-392; Wang et al., 1999, Science, 285~248-251). The release of HMGB1 from murine erythroleukemia cells is correlated with cell differentiation and the protein can be found in a plasma membrane-associated form in these cells (Passalacqua et al., 1997, FEBS Lett., 400:275-279; Sparatore et al, 1996, Biochem. J., 320:253-256). A protein called amphoterin, identical in sequence to HMGB1, has been described in the brain, where it is found in the nucleus and cytoplasm of neuronal cells as well as in the extracellular space. If exogenously added, HMGB1 mediates outgrowth of neurites and laminin-dependent migration of neuroblastoma and qlioma cells is inhibited by antibodies against HMGB1 (Fages et al., 2000, J. Cell Sci., 113:G11-620; Merenmies et al., 1991, J. Biol. Chem., 266:16722-16729; Parkkinen et al., 1993, J. Biol. Chem., 268:19726:19738; Rauvala et al., 1988, J. Cell Biol., 107:2293-2305). Interactions between HMGB1 and the plasminogen activation system, in particular tPA (tissue-type plasminogen activator), results in enhanced plasmin formation (Parkkinen and Rauvala, 1991, J. Biol. Chem., 266: 16730-16735). Degradation of extracellular matrix proteins is an important step in the cell migration process, and HMGB1-promoted increase of extracellular protease activity might enable the cells to migrate.

HMGB1 has been identified as one of the ligands binding to the RAGE receptor (Receptor for advanced glycation end products) (Hori et al., 1995, J-Biol. Chem., 270: 25752-25761). RAGE is a multiligand receptor of the immunoglobulin superfamily and is expressed in many cell type, including endothelial cells, smooth muscle cells, mononuclear phagocytes, and neurons (Brett et al., 1993, Am. J. Pathol., 143: 1699-1712; Neeper et al., 1992, J. Biol. Chem., 267: 14998-15004). It is implicated in several different pathological processes, such as diabetes, amyloidoses, and atherosclerosis (Schmidt et al, 1999, Circ. Res., 84: 489-497). Interaction of HMGB1 and RAGE induces neurite outgrowth, and the two proteins colocalize at the leading edge of advancing neurites during embryonic development (Huttunen et al., 1999, J. Biol. Chem., 274:19919-19924). Inhibition of the HMGB1-RAGE interaction has been shown to block tumor growth and metastasis. Moreover, inhibition of this interaction suppresses activation of mitogen-activated protein (MAP) kinases and the expression of matrix metalloproteinases, molecules linked to tumor proliferation and invasion (Taguchi et al., 2000, Nature, 405: 354-360).

HMGB1 has been demonstrated to have a potent biological effect on smooth muscle cells (SMC), which express RAGE on their surface. Vascular SMC cells are the most predominant cells of the larger blood vessels; they are located in the tunica media where they are embedded in the extracellular matrix. In intact vessels, SMC cells are in a contractile state and are responsible for vessel wall rigidity, elasticity maintenance and blood pressure control. The SMC cells are also characterized by the absence of cell division and migration. When the endothelium is damaged, either after mechanical or inflammatory injuries, SMC cells switch to a proliferative phenotype and undergo cell division and cell migration. The migration of SMC cells from the tunica media to the tunica intima, resulting in intimal thickening, plays an important role in the pathophysiology of many vascular disorders, such as atherosclerosis and restenosis after coronary angioplasty. In this proliferative state, SMC cells also produce higher amounts of extracellular proteinases, growth factors, and cytokines and secrete a fibrous extracellular matrix. After vessel wall injury, the release of several growth factors and/or chemoattractants either by circulating monocytes, macrophages and platelets, or by damaged endothelial cells can induce SMC cells switch from the contractile to the proliferative phenotype and it can direct the migration of SMC cells towards the vessel intima. Among these factors, bFGF appears to be the most important, however, SMC cells can also migrate in response to angiogenic stimuli (Schwartz, 1997, J. Clin. Invest., 99:2814-2816; Van Leeuwen, 1996, Fibrinolysis, 10:59-74).

HMGB1 has been shown to be a strong chemoattractant for SMC cells and induces changes to their cell shape and cytoskeletal organization. These events are inhibited by addition of an anti-RAGE antibody and by pertussis toxin, indicating that both RAGE and a Gi/o protein may be involved in the pathway. Furthermore, the evidence that HMGB1 promotes the translocation of phosphorylated ERK1 and 2 proteins into the nucleus indicates the involvement of the MAP kinase pathway. It has been demonstrated that HMGB1 is released by damage or necrosis by a variety of cell types, including endothelial cells. Therefore, HMGB1 has all the hallmarks of a molecule that can promote atherosclerosis and restenosis after vascular damage.

Consequently, one application of the HMGB1-binding 14FN3-based antibody mimics described in Example 10 are in a pharmacological preparation to avoid, retard or inhibit atherosclerosis and restenosis after vascular epithelium damage due to angioplasty. These HMGB1-binding molecules can be injected or released by instruments used for anqioplastic surgery, or said molecules can be bound to the instruments' surface. In a preferred embodiment of the invention said molecules are released by catheters, surgical instruments or stents for angioplasty, during or after said operation.

The 14FN3 anti-TNF-alpha peptides may be used for the treatment of a variety of rheumatic diseases, such as rheumatoid arthritis (RA) and systemic lupus erythematosus (SLE). The chronic synovitis of RA is characterized by apoptosis, necrotic cell death, and macrophage activation. In this environment, release of HMGB1 by necrotic cells or activated macrophages could perpetuate and enhance the inflammatory response in the affected joint. In addition, HMGB1 may induce local tissue invasion through activation of tPA and matrix metalloproteases (Hormann et al., 2002, Genes Immun., 3:123-135; Kokkola et al., 2002, Arthritis Rheum, 46:2598-2603). High levels of HMGB1 have been found in the synovial fluid of RA patients and HMGB1 expression is enhanced in the vascular enodthelial cells and macrophages of the synovial tissue of RA patients. Synovial fluid macrophages have also been shown to have increased expression of the RAGE receptor and can be activated to release pro-inflammatory cytokines in response to HMGB1 (Taniguchi et al., 2003, Arthritis Rheum., 48:971-981).

HMGB1 has also been implicated in the pathogenesis of SLE. Skin biopsies from patients with cutaneous lupus show an increased expression of HMGB1 in the affected skin (Popovic et al., 2005, Arthritis Rheum, 52:3639-3645). In SLE, immune complexes containing DNA and RNA drive the production of IFN-alpha by plasmacytoid dentridic cells (DC). These immune complexes also contain HMGB1 and can trigger responses via RAGE. Significantly, antibodies to RAGE can block the in vitro production of IFN-alpha (Tian et al., 2007, Nat. Immunol., 8:487-496). Thus, HMGB1 may contribute to the pathogenesis of SLE through activation of RAGE, transfer of DNA into cells, and through binding to TLR9.

Inhibition of HMGB1 may be useful for the treatment of sepsis, a systemic inflammatory response syndrome resulting from a microbial infection. Sepsis is characterized by excessive release of inflammatory mediators, such as HMGB1. Extensive studies in animal models have shown that HMGB1 is a late mediator of sepsis and that inhibitors of HMGB1 are protective.

The 14Fn3 anti-TNF-alpha peptide for this application are formulated as above, and administered in a selected dose by optimal routes, e.g., IV, intra joint, or the like.

Materials and Methods

In general, the practice of the present invention employs, unless otherwise indicated, conventional techniques of chemistry, molecular biology, recombinant DNA technology, PCR technology, immunology (especially, e.g., antibody technology), expression systems (e.g., cell-free expression, phage display, ribosome display, and Profusion™), and any necessary cell culture that are within the skill of the art and are explained in the literature. See, e.g., Sambrook, Fritsch and Maniatis, *Molecular Cloning: Cold Spring Harbor Laboratory Press* (1989); *DNA Cloning*, Vols. 1 and 2, (D. N. Glover, Ed. 1985); *Oligonucleotide Synthesis* (M. J. Gait, Ed. 1984); *PCR Handbook Current Protocols in Nucleic Acid Chemistry*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis et al., Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Current Protocols in Molecular Biology*, eds. Ausubel et al., John Wiley & Sons (1992); *Large-Scale Mammalian Cell Culture Technology*, Lubiniecki, A., Ed., Marcel Dekker, Pub., (1990). *Phage Display: A Laboratory Manual*, C. Barbas (Ed.), CSHL Press, (2001); *Antibody Phage Display*, P O'Brien (Ed.), Humana Press (2001); Border et al., Yeast surface display for screening combinatorial polypeptide libraries, *Nature Biotechnology*, 15(6):553-7 (1997); Border et al., Yeast surface display for directed evolution of protein expression, affinity, and stability, *Methods Enzymol.*, 328:430-44 (2000); ribosome display as described by Pluckthun et al. in U.S. Pat. No. 6,348,315, and Profusion™ as described by Szostak et al. in U.S. Pat. Nos. 6,258,558; 6,261,804; and 6,214,553, and bacterial periplasmic expression as described in US20040058403A1.

Further details regarding fibronectin and Fn3 sequence classification, identification, and analysis may be found, e.g., in SEQHUNT. A program to screen aligned nucleotide and amino acid sequences, *Methods Mol. Biol.* 1995; 51:1-15. and Wu et al., Clustering of highly homologous sequences to reduce the size of large protein databases. Bioinformatics. 2001 March; 17(3):282-3; Databases and search and analysis programs include the PFAM database at the Sanger Institute (pfam.sanger.ac.uk); the ExPASy PROSITE database (www.expasy.ch/prosite/); SBASE web (hydra.icgeb.trieste.it/sbase/); BLAST (www.ncbi.nlm.nih.gov/BLAST/); CD-HIT (bioinformatics.ljcrf.edu/cd-hi/); EMBOSS (www.hgmp.mrc.ac.uk/Software/EMBOSS/); PHYLIP (evolution.genetics.washington.edu/phylip.html); and FASTA(fasta.bioch.virginia.edu).

Briefly, a microbial expression and display system is used which has a demonstrated reliability for expressing fibronectin binding domain libraries. Typically, the fibronectin binding domain is joined together by a linker peptide to another surface molecule creating a fusion protein. A variety of methods are available for library expression and display including ribosome, phage, *E. coli*, and yeast surface display. All combine genotype-phenotype linkage to allow selection of novel target binding clones.

Yeast:

The fibronectin binding domain library (ie. FN3) is transfected into the recipient bacterial/yeast hosts using standard techniques. Yeast can readily accommodate library sizes up to $10^7$, with $10^3$-$10^5$ copies of each FNII fusion protein being displayed on each cell surface. Yeast cells are easily screened and separated using flow cytometry and fluorescence-activated cell sorting (FACS) or magnetic beads. The yeast eukaryotic secretion system and glycosylation pathways of yeast also allows FN3 type molecules to be displayed with N and O linked sugars on the cell surface.

The yeast display system utilizes the a-agglutinin yeast adhesion receptor to display proteins on the cell surface. The proteins of interest, in this case, FN3 WTM, LTM and CBM libraries, are expressed as fusion partners with the Aga2 protein.

These fusion proteins are secreted from the cell and become disulfide linked to the Aga1 protein, which is attached to the yeast cell wall (see Invitrogen, pYD1 Yeast Display product literature). The plasmid pYD1, prepared from an *E. coli* host by plasmid purification (Qiagen), is digested with the restriction enzymes, Bam HI and Not I, terminally dephosphorylated with calf intestinal alkaline phosphatase. Ligation of the pYD1 vector and the above SOE-PCR products WTM libraries (also digested by BamHI and NotI), *E. coli* (DH5a) transformation and selection on LB-ampicillin (50 mg/ml) plates were performed using standard molecular biology protocols to amplify the WTM libraries before electroporation into yeast cell hosts.

Methods for selecting expressed FN3 library variants having substantially higher affinities for target ligands (TNF, VEGF, VEGF-R etc), relative to the reference wild type FN3 domain, will now be described.

Candidate test ligands (TNF, VEGF, VEGF-R etc), are fluorescently labeled (either directly or indirectly via a biotin-streptavidin linkage as described above). Those library clones that efficiently bind the labeled antigens are then enriched for by using FACS. This population of yeast cells is then re-grown and subjected to subsequent rounds of selection using increased levels of stringency to isolate a smaller subset of clones that recognize the target with higher specificity and affinity. The libraries are readily amenable to high-throughput formats, using, e.g., FITC labeled anti-Myc-tag FN3 binding domain molecules and FACS analysis for quick identification and confirmation. In addition, there are carboxyl terminal tags included which can be utilized to monitor expression levels and/or normalize binding affinity measurements.

To check for the display of the Aga2-FN3 fusion protein, an aliquot of yeast cells ($8\times10^5$ cells in 40 µl) from the culture medium is centrifuged for 5 minutes at 2300 rpm. The supernatant is aspirated and the cell pellet is washed with 200 µl of ice cold PBS/BSA buffer (PBS/BSA 0.5% w/v). The cells are re-pelleted and supernatant removed before re-suspending in 100 µl of buffer containing the biotinylated TNFα (200 nM). The cells were left to bind the TNFa at 20° C. for 45 minutes after which they were washed twice with PBS/BSA buffer before the addition and incubation with streptavidin-FITC (2 mg/L) for 30 minutes on ice. Another round of washing in buffer was performed before final re-suspension volume of 400 µl in PBS/BSA. The cells were then analyzed on FACScan (Becton Dickinson) using CellQuest software as per manufacturers directions.

Kinetic selections of the yeast displayed TNF-α fibronectin binding domain libraries involve initial labeling of cells with biotinylated TNF-α ligand followed by time dependent chase in the presence of large excess of un-biotinylated TNF-α ligand. Clones with slower dissociation kinetics are identified by steptavidin-PE labeling after the chase period and sorted using a high speed FACS sorter. After Aga2-FN3 induction, the cells are incubated with biotinylated TNF-α at saturating concentrations (400 nM) for 3 hours at 25 C under shaking. After washing the cells, a 40 hour cold chase using unlabelled TNF-a (1 uM) at 25° C. was performed. The cells were then washed twice with PBS/BSA buffer, labeled with Streptavidin PE (2 mg/ml) anti-HIS-FITC (25 nM) for 30 minutes on ice, washed and re-suspended and then analyzed on FACS ARIA sorter.

Ribosome Display:

Ribosome display utilizes cell free in vitro coupled transcription/translation machinery to produce protein libraries. The FN3 library genes are inserted upstream to kappa light immunoglobulin gene that does not have a termination stop codon causing the ribosome to stall, but not release, when it reaches the end of the mRNA. Additionally, the kappa domain spacer serves to physically distance the FN3 protein from the ribosome complex so that FN3 binding domain has better accessibility to recognize its cognate ligand. The mRNA library is introduced into either S30 *E. coli* ribosome extract preparations (Roche) or rabbit reticulate lysate (Promega). In either case, the 5' end of the nascent mRNA can bind to ribosomes and undergo translation. During translation, the ligand-binding protein remains non-covalently attached to the ribosome along with its mRNA progenitor in a macromolecular complex {He, 2005 #58; He, 1997 #59; He, 2007 #57}.

Figure 9:
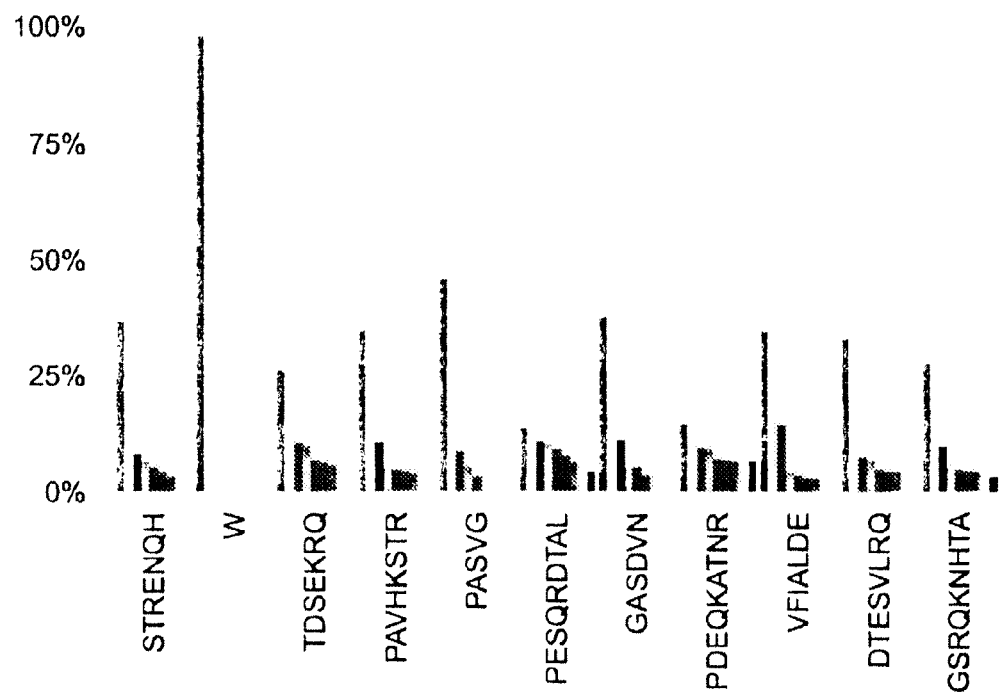
FIG. 9 shows sequence diversity of an exemplary loop region in the form of amino acid variability profile (frequency distribution) for BC loop length size 11.
Figure 10:
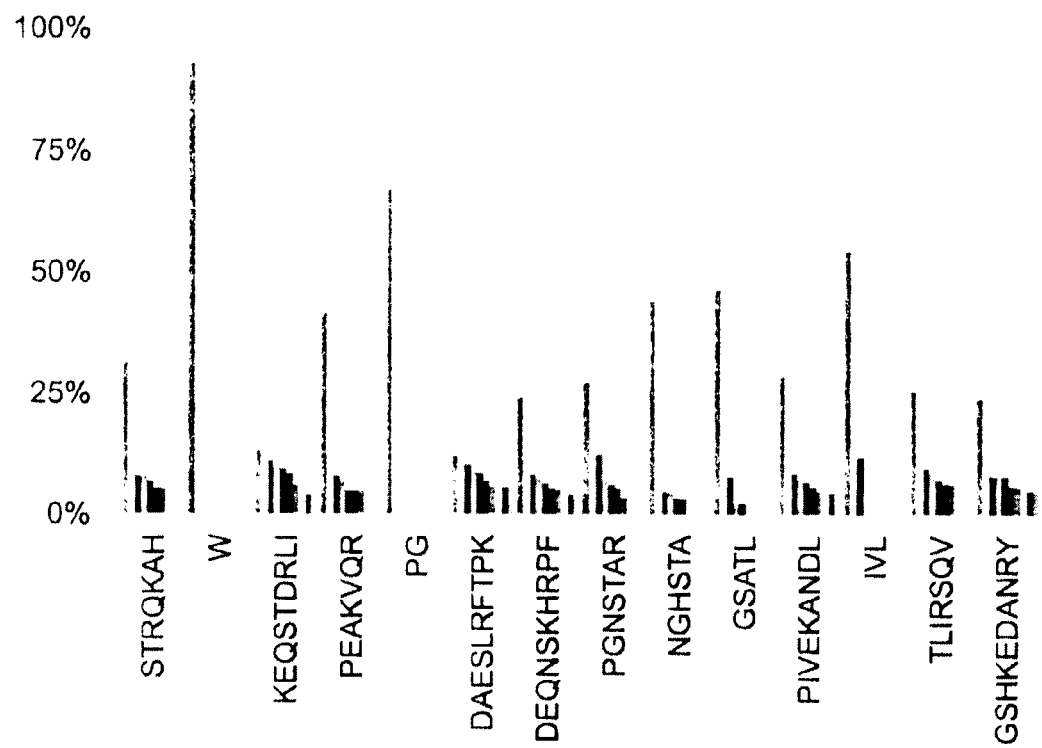
FIG. 10 shows sequence diversity of an exemplary loop region in the form of amino acid variability profile (frequency distribution) for BC loop length size 14.

The functional FN3 proteins can then bind to a specific ligand that is either attached to magnetic beads or microtiter well surface. During the enrichment process, non-specific variants are washed away before the specific FN3 binders are eluted. The bound mRNA is detected by RT-PCR using primers specific to the 5' FN3 and 3' portion of the kappa gene respectively (FIG. 9). The amplified double stranded cDNA is then cloned into an expression vector for sequence analysis and protein production.

Prokaryotic translation reactions contained 0.2 M potassium glutamate, 6.9 mM magnesium acetate, 90 mg/ml protein disulfide isomerase (Fluka), 50 mM Tris acetate (pH 7.5), 0.35 mM each amino acid, 2 mM ATP, 0.5 mM GTP, 1 mM cAMP, 30 mM acetyl phosphate, 0.5 mg/ml *E. coli* tRNA, 20 mg/ml folinic acid, 1.5% PEG 8000, 40 ml S30 *E. coli* extract and 10 mg mRNA in a total volume of 110 ml. Translation was performed at 37 C for 7 min, after which ribosome complexes were stabilized by 5-fold dilution in ice-cold selection buffer [50 mM Tris acetate (pH 7.5), 150 mM NaCl, 50 mM magnesium acetate, 0.1% Tween 20, 2.5 mg/ml heparin].

For eukaryotic ribosome display we used the Flexi Rabbit Reticulocyte Lysate

System (Promega). Eukaryotic translation reactions contained 40 mM KCl, 100 mg/ml protein disulfide isomerase (Fluke), 0.02 mM each amino acid, 66 ml rabbit reticulocyte lysate and 10 mg mRNA in a total volume of 100 ml. Translation was performed at 30 C for 20 min, after which ribosome complexes were stabilized by 2-fold dilution in ice-cold PBS.

Affinity Selection for Target Ligands.

Stabilized ribosome complexes were incubated with biotinylated hapten [50 nM fluorescein—biotin (Sigma)] or antigen [100 nM IL-13 (Peprotech) biotinylated in-house] as appropriate at 4 C for 1-2 h, followed by capture on streptavidin-coated M280 magnetic beads (Dynal). Beads were then washed to remove non-specifically bound ribosome complexes. For prokaryotic selections, five washes in ice-cold selection buffer were performed. For eukaryotic selections, three washes in PBS containing 0.1% BSA and 5 mM magnesium acetate were performed, followed by a single wash in PBS alone. Eukaryotic complexes were then incubated with 10 U DNAse I in 40 mM Tris-HCl, 6 mM MgCl2, 10 mM NaCl, 10 mM CaCl2 for 25 min at 37 C, followed by three further washes with PBS, 5 mM magnesium acetate, 1% Tween 20.

Recovery of mRNA from Selected Ribosome Complexes

For analysis of mRNA recovery without a specific disruption step, ribosome complexes bound to magnetic beads were directly processed into the reverse transcription reaction. For recovery of mRNA from prokaryotic selections by ribosome complex disruption, selected complexes were incubated in EB20 [50 mM Tris acetate (pH 7.5), 150 mM NaCl, 20 mM EDTA, 10 mg/ml *Saccharomyces cerevisae* RNA] for 10 min at 4 C. To evaluate the efficiency of the 20 mM EDTA for recovery of mRNA from eukaryotic selections, ribosome complexes were incubated in PBS20 (PBS, 20 mM EDTA, 10 mg/ml *S. cerevisae* RNA) for 10 min at 4 C. mRNA was purified using a commercial kit (High Pure RNA Isolation Kit, Roche). For prokaryotic samples, the DNAse I digestion option of the kit was performed; however, this step was not required for eukaryotic samples, as DNAse I digestion was performed during post-selection washes. Reverse transcription was performed on either 4 ml of purified RNA or 4 ml of immobilized, selected ribosome complexes (i.e. a bead suspension).

For prokaryotic samples, reactions contained 50 mM Tris-HCl (pH 8.3), 75 mM KCl, 3 mM MgCl2, 10 mM DTT, 1.25 primer, 0.5 mM PCR nucleotide mix (Amersham Pharmacia), 1 URNAsin (Promega) and 5 U SuperScript II (Invitrogen) and were performed by incubation at 50 C for 30 min. For eukaryotic samples, reactions contained 50 mM Tris-HCl (pH 8.3), 50 mM KCl, 10 mM MgCl2, 0.5 mM spermine, 10 mM DTT, 1.25 mM RT primers, 0.5 mM PCR nucleotide mix, 1 U RNasin and 5 U AMV reverse transcriptase (Promega) and were performed by incubation at 48 C for 45 min.

PCR of Selection Outputs

End-point PCR was performed to visualize amplification of the full-length construct. A 5 ml sample of each reverse transcription reaction was amplified with 2.5 UTaq polymerase (Roche) in 20 mM Tris-HCl (pH 8.4), 50 mM KCl, 1 mM MgCl2, 5% DMSO, containing 0.25 mM PCR nucleotide mix, 0.25 mM forward primer (T7B or T7KOZ for prokaryotic and or eukaryotic experiments, respectively) and 0.25 mM RT primer. Thermal cycling comprised 94 C for 3 min, then 94 C for 30 s, 50 C for 30 s and 72 C for 1.5 min for 30 cycles, with a final step at 72 C for 5 min. PCR products were visualized by electrophoresis on an ethidium bromide stained agarose gels. The isolated PCR products can then be sub-cloned into a bacterial pBAD expression vector for soluble protein production (below).

Bacterial Expression and Production:

Competent *E. coli* host cells are prepared as per manufacturer's instructions (Invitrogen pBAD expression system). Briefly, 40 µl LMG 194 competent cells and 0.5 µl pBAD FN3 constructs (approximately 1 µg DNA) is incubated together on ice for 15 minutes after which, a one minute 42° C. heat shock was applied. The cells are then allowed to recover for 10 minutes at 37° C. in SOC media before plating onto LB-Amp plates and 37° C. growth overnight. Single colonies are picked the next day for small scale liquid cultures to initially determine optimal L-arabinose induction concentrations for FN3 production. Replicates of each clone after reaching an $OD_{600}=0.5$ were test induced with serial (1:10) titrations of L-arabinose (0.2% to 0.00002% final concentration) after overnight growth at room temperature. Test cultures (1 ml) are collected, pelleted and 100 µl 1×BBS buffer (10 mM, 160 mM NaCl, 200 mM Boric acid, pH=8.0) added to resuspend the cells before the addition of 50 µl of lysozyme solution for 1 hour (37° C.). Cell supernatants from the lysozyme digestions are collected after centrifugation, and $MgSO_4$ was added to final concentration 40 mM. This solution was applied to PBS pre-equilibrated Ni-NTA columns. His-tagged bound FN3 samples are twice washed with PBS buffer upon which elution was accomplished with the addition of 250 mM imidazole. Purity of the soluble FN3 expression is then examined by SDS-PAGE.

Larger scale *E. coli* cell culture, 100 ml, pellets are collected by centrifugation after overnight growth at 25° C. The pellets are then re-suspended in PBS buffer (0.1% tween) and subjected to 5 rounds of repeated sonication (Virtis Ultrasonic cell Disrupter) to lyse the bacterial cell membrane and release the cytoplasmic contents. The suspension is first clarified by high speed centrifugation to collect the supernatant for further processing. This supernatant is then applied to PBS pre-equilibrated Ni-NTA columns. His-tagged bound FN3 samples are twice washed with PBS buffer upon which elution is accomplished with the addition of 250 mM imidazole. The pH of the supernatant is then adjusted to 5.5 with 6M HCl and before loading onto a SP Sepharose HP cation exchange column (Pharmacia). The FN3 was eluted a salt (NaCl) gradient and fraction concentrations containing the FN3 were determined by optical density at 280 nm and verified by PAGE. Fractions containing FN3s are then pooled and dialyzed with PBS.

Octet Kinetic Analysis:

Binding affinities ($KD=k_d/k_a=k_{off}/k_{on}$) of the FN3 variants are calculated from the resultant association ($k_a=k_{on}$) and dissociation ($k_d=k_{off}$) rate constants as measured using a OCTET biolayer inferometry system (ForteBio, Inc). The ligand, e.g., TNF-α, is immobilized on the OCTET streptavidin capillary sensor tip surface and, in effect, allows monitoring of the monomeric FN3 kinetic binding. OCTET streptavidin tips are activated according to manufacturer's instructions using 50 uM TNF-a. A solution of PBS/BSA is also introduced as a blocking agent.

For association kinetic measurements, FN3 variants are introduced at a concentration of 10 ug/ml. Dissociation is observed in PBS buffer without the agents. The kinetic parameters of the binding reactions were determined using ForteBio software. FIG. 25 displays OCTET results from the reference D2E7 anti-TNF-a antibodies and 9-14 TNF FN3 clone.

Candidate clones are then isolated and plasmid preparations are performed to obtain fibronectin binding domain sequence information. The approach allows for a hypothesis-driven rational replacement of codons necessary to determine and optimize amino acid functionality in the loop of the fibronectin binding domain. Comparative sequence analysis and individual clone affinity/specificity profiles then determine which clones undergo affinity

Example 1

Methods for Bioinformatic-Guided Identification of Universal Fibronectin Binding Domain Library Sequences In this example, universal BC, DE, and FG loop sequences for fibronectin binding domain library sequences are identified and selected using bioinformatics and the criteria of the invention. A generalized schematic of this process is presented in FIG. 1.

Briefly, the PFAM database was searched for a multiple sequence alignment containing only sequences belonging to the Fibronectin Type III family (FN3, PFAM ID: PF00041).

This search returned an initial dataset of 9321 protein sequences. It is noted, however, that this set of sequences can increase in number as additional sequences are cloned and entered into the database. The base dataset of ~9321 FN3 superfamily sequences included FN3 sequences from multiple sources: human fibronectin, tenascin, *drosophila* sevenless, protein tyrosine phosphatase, EPH tyrosine kinases, and cytokine receptors and Z proteins (see Table 1). It is appreciated that gene sequences related to FN1, FN2 and other protein scaffold framework domains can also be searched in these databases and identified in similar manner.

TABLE 2

Distribution of analyzed proteins in the Fibronectin module III superfamily.

| | |
|---|---|
| Base dataset: All FN module III like proteins | 9321 |
| First round filtered non redundant mammalian FN module III | 5955 |
| Non redundant human FN module III | 794 |

Within the starting FN3 sequences "base dataset", the compiled loop sequences are likely to possess vastly different characteristics. The sequences will vary with respect to: originating species, originating modules, loop lengths, and other qualities. Due to originating sequence disparity among the "base dataset" members, trying to derive a coherent analysis may require further refinement from the starting "base dataset" such that subset datasets share one or more of elected properties of interest. Therefore, from the initial ~9321 base dataset, redundant or duplicatively entered sequences were removed leaving 5955 filtered non-redundant FN3 sequences. From this second subset, another set of sequences were further parsed into a third subset made of 794 human FN3 sequences. Constituent subset members sharing those respective properties can produce a more "standardized" set of sequences for meaningful comparative and unskewed data analysis within the subgroup. This process can be iterated, resulting in the generation of smaller datasets with a higher degree of predefined relationships. Widening sequence variability may be achieved, for example, by including the datasets containing non-human modules.

The next step involved the designation of the β-scaffold framework and loop lengths and loop amino acid sequences, followed by a frequency analysis of these candidate loop sequences. Therefore, determination of variability profiles entails collection and selection of aligned amino acid sequences that shares one or more defined properties of interest to create a dataset. We developed a β-strand and loop positional classification system using the positional numbering architecture of the 10/FN3 domain as a reference point. β-strands were first identified based on the crystal structure of FN3 fibronectin-protein modules 1, 4, 7, 8, 9, 10, 12, 13, 14, and 15. We also examined their dihedral angles and hydrogen bonding patterns to assist with the assignment of β-strands. Amino acid sequence alignments were then performed to further aid in the determination of β-strands and loops. For example in Table 3, using $^{10}$FN3 as a reference sequence, the following amino acid positions for the of β-strands and loops were designated as follows:

TABLE 3

β-strands and loop amino acid positions of FN3

| β-strands | Loops |
|---|---|
| A: 8-14 | AB: 15-16 |
| B: 17-20 | BC: 21-31 |
| C: 32-39 | CD: 40-44 |
| D: 45-50 | DE: 51-56 |
| E: 57-59 | EF: 60-67 |
| F: 68-75 | FG: 76-86 |
| G: 87-94 | |

For example, the aligned analysis indicated that the tryptophan at position 22 (W22) is conserved between the different modules. Based on a crystallographic structural comparisons, W22 is located near the junction of the BC loop acceptor site and we chose position 21 as the loop starting point. There is a well conserved group of valine and isoleucine amino acids at position 20 between the FN3 domains (V20 in $^{10}$FN3) and appears to be part of the B β-strand. Immediately following W22, we found that there are structural differences between the overlayed loops before the BC loops reenter the C β-strand at a well-conserved Y/F32 found between the members. By designating position 21 and 31 as the outer boundaries of the BC loop, we then segregated the "filtered dataset" into BC loop sizes and determined their amino acid frequency compositions. Similarly, this sequence/structure comparative analysis was applied to the DE and FG loops. We designated the DE loop as bordered by a conserved group of valine, leucine and isoleucine at position 50 (V50 in $^{10}$FN3) of the D β-strand and ending at position 56 (T56 in $^{10}$FN3) of the E β-strand. Likewise, we choose positions 76 (T76 in $^{10}$FN3) and 86 (K86 in $^{10}$FN3) as the F β-strand and G β-strand junctions for the FG loop.

Based on these aligned β strand boundary definitions, the loops were found not be of one size, but to occur in differing lengths. The frequency distribution of the BC, DE and FG loop sizes were analyzed and tabulated (FIGS. 6-8). The loop size classification and description follow the nomenclature of: FN3 LOOP/LENGTH. For example BC/15 refers to FN3 BC loop length of 15 amino acids. In the BC loop definition, the scaffold loop boundaries were originally set for an eleven amino acid length. However, the BC loop ranges from nine to eighteen amino acids in length, with length fourteen (BC/14), and fifteen (BC/15) also being quite common (FIG. 6). Alignments of the loop amino acids can be performed between the differing loop lengths. For example, the proline at position 25 (P25) in BC/15 was found quite conserved within constituent BC/15 members. P25 is also observed to be quite prevalent in BC/14 and BC/11 members. The loop amino acid positions were then aligned to best approximate these equivalent positions. Hence in BC/15 the extra comprising loop amino acids given the designation 26a, 26b, 26c, and 26d, as they are located between residues 26 and 27 of the BC/15 loop. In loop BC/14 the extra comprising loop amino acids are designated from 26a, 26b, and 26c, as they are between residues 26 and 27 of the BC/14 loop. As stated above, numbering is based upon 10/FN3 (the $10^{th}$ FN3 module of human fibronectin) as a reference.

Example 2

Assessing Loop Variability Profiles Using Bioinformatics Through Filtering and Cluster Analysis of Gene Sequences The universal fibronectin binding domain libraries were designed by determining the variability profiles for the loops expressed in vivo. The variability profiles represent the cataloging of the different amino acids, and their respective rates of occurrence, present at a particular position in a dataset of aligned sequences. Size related families of loop sequences using the parameters set forth above within this starting "base dataset" can be identified and delineated. Comparative analysis of these multiple aligned loops provide variability profile information as to the existing and "tolerated" diversity for introducing amino acid changes that can lead to potential ligand binding. The designation of loops and their comprising amino acids can also be described for other scaffold like proteins using similar definitions.

The frequency distribution of the six loop sizes, shown in FIGS. 6 to 8, were generated to determine if there was preferred BC, DE and FG loop sizes for FN3 sequences (Table 2). For the BC loop (FIG. 6), a fifteen amino acid loop size was the most common accounting for 30% of the BC loop population. BC loop sizes 14 and 11 were the next common sizes occurring at 18% and 16% of the BC loop population. BC loop sizes 11, 14 and 15 were then chosen for our variability profile analysis.

Frequency size analysis of the DE loop demonstrated that loop size 6 occurred in nearly 45% of the analyzed FN3 sequences (FIG. 7). The other DE loop sizes 4, 5 and 7 accounted for no more than 16% each. DE loop size 6 accounted for 55% of the members suggesting FN3 modules have more of a preference for DE loop size 6. In this case, only DE loop size 6 was chosen for further variability profile analysis. Frequency size analysis of the FG loop demonstrated that loop size 8 and 11 were the two most common loop sizes accounting for 58% and 18% of the analyzed dataset respectively. Both FG loop sizes 8 and 11 were therefore included for further variability profile analysis. In an earlier version of the analysis, the FG loop lengths FG/8 and FG/11 were identified as FG/6 and FG/9, respectively, the difference being the addition of two C-terminal amino acids S, K to each FG loop length, as seen in Table 5 below). In some examples, where an FG/8 loop is identified by six amino acids, it is understood that these amino acids represent the six N-terminal amino acids of FG/8. Similarly, where an FG/11 loop is identified by nine amino acids, it is understood that these amino acids represent the nine N-terminal amino acids of FG/11.

TABLE 4

Lengths of FN3 BC, DE, and FG loops analyzed along with the number of sequences indicated

| LOOP | length | number of sequences |
|------|--------|---------------------|
| BC   | 11     | 885                 |
|      | 14     | 1066                |
|      | 15     | 1732                |
| DE   | 6      | 2729                |
| FG   | 8      | 1057                |
|      | 11     | 3340                |

For each of the 6 selected loops (Table 4) a separate frequency analysis was executed to determine positional amino acid usage in the context of the selected loop. A simple frequency analysis using EMBOSS/prophecy (bioinfo.nhri.org.tw/cgi-bin/emboss/prophecy) was executed generating a matrix representing the positional amino acid usage. The output matrix was then parsed and filtered in order to have relative frequency data for each position. The parser provides a very simple filter based on two thresholds (low and high). For each position the parser processes only amino acids with relative frequency above the "low" threshold until the cumulative frequency reaches the "high" threshold. If the high threshold is not reached, then the parser also evaluates the amino acids with relative frequency below the low threshold. A good low-high threshold combination was 5-50 because it provides good sensitivity for position classification. The parser therefore limits the listing of only the most frequent, and not all, amino acids that occur at each position. The parser output is visualized as frequency charts and the results are shown in FIGS. 9-14.

Example 2A

Identifying Fixed and Non-Fixed Loop Positions with Thresholds

In one embodiment, a natural-variant combinatorial library with a conserved or selected semi-conserved consensus amino acid is designed as follows.

FN3 loop datasets are enumerated as above for amino acid variability and their relative frequencies at each aligned position (FIGS. 9-14). The above analysis identified positional preferences in all FN3 module loops and are termed "variability profiles." For example, in BC loop size 11 (FIG. 9), a tryptophan (W) at position 22 is found at nearly 95% of all FN3 loop positions demonstrating high degree of selective pressure for its presence. Position 22 would be considered "conserved" for tryptophan (W22) (see below Example 3) as it occurred above a predetermined 40% threshold level and was more than twice as common as the next most frequent amino acid at that position. This "fixed" residue is seen as the dominant amino acid with respect to the other amino acids that occur at that loop position. A "fixed" position may not be subject to mutagenic diversification in first round library building. At other BC loop size 11 loop positions, it was evident that position 25 favored prolines (P) (approximately >45%) as it occurred twice as often compared to the next most frequent amino acids (<20%) in that same position. Hence, P25 position is considered "fixed" as the predominant amino acid was two fold more frequent than the next. In contrast, prolines were also the most favored amino acid at positions 24, 26 and 28, but the frequency of the other amino acids were also fairly abundant (8-19%). As positions 24, 26 and 28 have a wide range of populating amino acids with similar frequency of occurrences, and the predominant amino acid was not more than two fold more frequent, these positions would be considered "variable."

In BC loop size 14 (FIG. 10), the positional prevalence of particular amino acids was pronounced. In BC/14, the W position 22 occurs at (>95%) while position 25 has proline occurring at 70%. This indicated that W22 and P25 are heavily favored in BC/14 loops so that both positions are considered "fixed." Also fixed was isoleucine at position 29. Here in BC/14, isoleucine (I29) occurred at >52%, more than two-fold more than the next two most common amino acids, valine and leucine at 18% and 16% respectively.

For BC/15 loops (FIG. 11), W22, P25 and I29 were also found to be fixed positions similar to BC/11 and BC/14. Additionally, glycines (G) at positions 26e and 26f occur at frequencies >75% and can be also considered "fixed." By first determining these "fixed" positions and non-fixed positions (indicated by "X"), B/15 would have a starting "fixed" sequence of: X21 W22 X23 X24 P25 X26 X26a D26b G26c G26d X27 X28 I29 X30 X31 (SEQ ID NO: 45) Similarly, BC/4 and BC/1 would have starting "fixed" sequences of X21 W22 X23 X24 P25 X26 X26a X26b X26c X27 X28 I29 X30 X31 (SEQ ID NO: 44) and X21 W22 X23 X24 P25 X26 X26 X27 X28 I29 X30 X31 (SEQ ID NO: 223), respectively.

The same variability profile analysis was performed for all the other loops. Briefly, for DE loop size 6 (FIG. 12), there were no loop positions where a single amino acid accounted for more than 35% of the representative positional amino acids. There was a slight preference for glycine at position 52 (52G), threonine at position 55 (55T) and serine at position 56 (56S). In this case however, there were no predominant acids above a 40% threshold level to be considered "fixed" amino acids and all loop positions are considered "variable." For library construction, the most common amino acid in each loop position serves as the starting amino acid for first round mutagenesis. The DE/loop therefore has an all "variable" starting loop sequence of: X51 X52 X53 X54 X55 X56 (SEQ ID NO: 52.)

For FG loop size 8 (FIG. 13), the serine (S) at position 84 was "fixed" as it occurred in 75% of the populating sequences. All other remaining FG loop size 8 positions were "variable" using the most frequently occurring amino acid yielding a FG/8 starting "fixed" sequence of X76 X77 X78 X79 X80 84S (SEQ ID NO: 47) (the N-terminal six amino acids of FG/8). The FG/8 loop numbering jumps from 80 to 84 as the longer loop size nine is used as the reference size length based on 10/FN3. FG/11 contained four "fixed" amino acids with asparagine (56N), glycine (79G), serine (84S) and a "semi-fixed" glycine and serine at position 81. The three amino acids, 56N, 79G, 84S and semi-fixed 81G/S occurred at greater than 40% frequency in the populating sequences.

This analysis yielded a FG/11 starting "fixed" loop sequence of N76 X77 X78 79G X80 G/S81 X82 X83 S84 (SEQ ID NO: 48) (the N-terminal nine amino acids of FG/11).

The variability profile for each loop dataset then identifies the desired characteristics of a given loop position for further introduction of diversity representation. These above results demonstrate that the diversity of loop amino acids introduced into a library can be "fine-tuned" depending on the threshold level of frequency of occurrence. These "fixed" loop positions attempt to replicate some of the natural diversity to promote possible structural stabilization effects.

This "fixing" of positions also has the effect of "narrowing" the diversity of variable positions in starting loop sequences. However, there can be the occasion to perform the reverse, that is, to obtain larger more diverse libraries. In this case, the "widening" effect is accomplished by raising the threshold of frequency of occurrence used to designate "fixed" amino acids. In this way, the variability profile will capture fewer of the most conserved loop positions and classify them as "fixed" positions. The remaining loop positions would be part of the broader "variable" amino acids that can be diversified.

Example 2B

Identifying Fixed and Non-Fixed Loop Positions without Thresholds

In another embodiment it is possible to design natural-variation combinatorial diversity in each of the six selected loops (Table 4) without defining a variability threshold, i.e., where the selected threshold is 100%. In this embodiment each mutated loop is designed to contain amino acids that mimics its variability profile in terms of both variability and chemistry characteristics. At each specific loop position, oligonucleotide synthesis is optimized to contain a degenerate codon that would match/mimic the chemistry and the variability at that position. Positions having two or more amino acids in their variability profiles will be mutated regardless of the degree of variability of that position.

In BC loop sizes 11 (FIG. 24) and 14 only the W at position 22 will be kept fixed resulting in the following mutagenesis pattern: BC/11=X21 W22 X23 X24 X25 X26 X27 X28 X29 X30 X31 (SEO ID NO: 49); BC/14=X21 W22 X23 X24 X25 X26 X26a X26b X26c X27 X28 X29 X30 X31 (SEO ID NO: 50). In BC loop size 15 there are 3 fixed positions (W22, P25 and G26c) resulting in the following mutagenesis pattern: BC/15=X21 W22 X23 X24 P25 X26 X26a X26b G26c X26d X27 X28 X29 X30 X31) (SEQ ID NO: 51).

In DE loop size 6 all the positions are variable and therefore will have a starting sequence of DE_6=X51 X52 X53 X54 X55 X56 (SEO ID NO: 52).

The FG loop size 8 will be encoded by the starting sequence of FG/8=X76 X77 X78 X79 X80 X84 S85 S86 (SEQ ID NO: 224). Finally FG loop size 11 will be encoded as FG/11=X76 X77 X78 G79 X80 X81 X82 X83 X84 S85 S86 (SEQ ID NO: 54).

Each of the positions denoted as X will encode for the amino acids present in the related variability profile or for a subset of chemically equivalent ones. In fact in some cases two or more amino acids present at a certain position are chemically very similar. In such situations it is possible to include in the mutagenesis design only a subset of the amino acids and still preserve the natural chemistry characteristics of that position. This will both reduce the total number of mutants and give more flexibility for the optimization of the oligonucleotide synthesis.

Example 3

Methods for Designing WTM Loop Diversity for FN3 Domain Libraries with Threshold Constraints In this example, methods for optimizing the loop diversity of an FN3 binding domain library are presented. The choice of candidate frameworks, as previously noted, dictates both the loop sizes to be introduced and the initial amino acid sequence selection. The method is illustrated particularly for the FG/11 loop.

To design the FG/11 loop library for FN3 based scaffolds, the variability profile considerations are as follows: As stated above, a "fixed" amino acid residue is determined to occur with a threshold frequency that is typically at least 40% (typically at least 50%) and is twice fold more frequent than the next most frequent amino acid for a given loop position. Upon inspection of the FN3 FG/11 variability profile (FIG. 14), it can be seen that the Gly at position 79 (G79) was found to occur at nearly 85%. The next most frequently occurring amino acids, was at frequency of less than 5% and did not register on the minimum threshold value (cut off by parser). When a given residue, in this case G79, is determined to occur at such a high frequency, it is highly conserved and thus represented in the libraries of the invention as "fixed," meaning that it will not be mutated in the first round library diversification. Similarly, N76, G81 and S84 are also "highly conserved" as they occur at a frequency rate of 66%, 47%, and 61% respectively and are "fixed" in the first diversity library. In some cases, it can be that there are two semi-conserved amino acid residue at a given loop position. For example, G81 and S81 are found to occur at nearly 66% and 30% respectively. Hence, in this case, both amino acids are considered "semi-fixed" at position 81 as it appears that there is strong selective pressure to maintain G81 and S81 and no other amino acids. The 66% G81 and 30% S81 ratios can be maintained by controlled "doping" of the incoming nucleotide mixture (see Example 5). The number of WTM substitutions per loop can be readily achieved by oligonucleotide synthesis doping (see, e.g., US20040033569A1 for technical details).

Positions N76, G79, G/S81, and S84 are fixed candidate clones so that FG/11 has a starting "fixed" loop sequence of N76—77—78 79G-80 G/S81—82—83 S84 (underline indicating the fixed amino acid). The reason for not creating diversity at all sites is to restrict the initial diversity size of the library to facilitate efficient expression and display of all variants. These initially "fixed" positions indicate strong selective pressures for their preservation. However, they are still sites for look-through mutatgenesis (LTM) mutagenesis during affinity maturation. In other words, the initial "fixed" positions can be later mutated. The overall goal in "fixing" positions in the first round library diversification is two fold: 1) to maximize the number of functional clones while by incorporating most of the preferred loop residues and 2) to minimize the total library size. Subsequent LTM mapping of retrieved clones then precisely determines whether the "fixed" site is a "hot" or "cold" spot that can be mutated for further affinity maturation without losing overall binding function (see U.S. Patent Publication No. 20050136428).

The term "variable" amino acid residue refers to amino acid residues determined to occur with a lower frequency (less than the high threshold value of 20%) for a given residue position. Upon inspection of the FG/11 variability profile for example (FIG. 14), it can be seen that variable positions 77, 78, 80, 82 and 83 each have no single prevalent amino acid that occurs at higher than 40% frequency. For FG/11 positions 77, 78, 80, 82 and 83 each loop position had many different amino acids with occurring at a fairly low level frequency. Accordingly, in positions 77, 78, 80, 82 and 83 are sites for creation of initial loop sequence diversity by mutagenesis, e.g., WTM. In introducing subsequent amino acid diversity, the FG/11 sequence would then be N76 X77 X78 79G X80 G/S81 X82 X83 S84 (SEQ ID NO: 48), where X denotes the variable position for initial mutagenesis (e.g., WTM) is conducted. The X position will be consist of a starting "wild type" amino acid, the WTM replacement or a "co-product" amino acid depending on the WTM designed codon changes.

For example, to construct a WTM library within the FG/11 loop using lysine (K) as the WTM target amino acid into the starting sequence N76 X77 X78 79G X80 G/S81 X82 X83 S84 (SEQ ID NO: 48), lysine residues can be substituted in positions 77, 78, 80, 82, and 83. The FG/11 WTM(K): library variants will have resulting sequences that are comprised of single replacements:

| | |
|---|---|
| N76 K77 X78 79G X80 G/S81 X82 X83 S84 | SEQ ID NO: 225, |
| N76 X77 K78 79G X80 G/S81 X82 X83 S84 | SEQ ID NO: 226, |
| N76 X77 X78 79G K80 G/S81 X82 X83 S84 | SEQ ID NO: 227, |
| N76 X77 X78 79G X80 G/S81 K82 X83 S84 | SEQ ID NO: 228, and |
| N76 X77 X78 79G X80 G/S81 X82 K83 S84 | SEQ ID NO: 229 |

The FG/11: WTM(K): library variant sequences are additionally comprised of double replacements:

| | |
|---|---|
| N76 K77 K78 79G X80 G/S81 X82 X83 S84 | SEQ ID NO: 230, |
| N76 K77 X78 79G K 80 G/S81 X82 X83 S84 | SEQ ID NO: 231, |
| N76 K77 X78 79G X 80 G/S81 K82 X83 S84 | SEQ ID NO: 232, |
| N76 K77 X78 79G X 80 G/S81 X82 K83 S84 | SEQ ID NO: 233, |
| N76 X77 K78 79G K80 G/S81 X82 X83 S84 | SEQ ID NO: 234, |
| N76 X77 K78 79G X80 G/S81 K82 X83 S84 | SEQ ID NO: 235, |
| N76 X77 K78 79G X80 G/S81 X82 K83 S84 | SEQ ID NO: 236, |
| N76 X77 X78 79G K80 G/S81 K82 X83 S84 | SEQ ID NO: 237, |
| N76 X77 X78 79G K80 G/S81 X82 K83 S84 | SEQ ID NO: 238, |
| N76 X77 X78 79G X80 G/S81 K82 K83 S84 | SEQ ID NO: 239 |

The FG/11: WTM(K): library variant sequences could be additionally comprised of triple replacements for example:

| | |
|---|---|
| N76 K77 K78 79G K80 G/S81 X82 X83 S84 | SEQ ID NO: 240, |
| N76 K77 K78 79G X80 G/S81 K82 X83 S84 | SEQ ID NO: 241, |
| N76 K77 K78 79G X80 G/S81 X82 K83 S84 | SEQ ID NO: 242, |
| N76 K77 X78 79G K80 G/S81 K82 X83 S84 | SEQ ID NO: 243, |
| N76 K77 X78 79G K80 G/S81 X82 K83 S84 | SEQ ID NO: 244, |
| N76 X77 K78 79G K80 G/S81 X82 K83 S84 | SEQ ID NO: 245, |
| N76 X77 K78 79G X80 G/S81 K82 K83 S84 | SEQ ID NO: 246, |
| N76 X77 X78 79G K80 G/S81 K82 K83 S84 | SEQ ID NO: 247 |

The FG/11: WTM(K): library variant sequences could be additionally comprised of quadruple replacements:

| | |
|---|---|
| N76 K77 K78 79G K80 G/S81 K82 X83 S84 | SEQ ID NO: 248, |
| N76 K77 K78 79G K80 G/S81 X82 K83 S84 | SEQ ID NO: 249, |
| N76 K77 K78 79G X80 G/S81 K82 K83 S84 | SEQ ID NO: 250, |
| N76 K77 X78 79G K80 G/S81 K82 K83 S84 | SEQ ID NO: 251, |
| N76 X77 K78 79G K80 G/S81 K82 K83 S84 | SEQ ID NO: 252, |

Finally, the FG/11: WTM(K): library variant sequences could be additionally comprised of quintuple replacements:

| N76 K77 K78 79G K80 G/S81 K82 K83 S84 | SEQ ID NO: 253, |
|---|---|

For WTM™ diversity, each "X" position in the above example must have a starting "wild type" amino acid in order to perform the targeted codon changes. From the above variability profile analysis, FG/11 has a "wild type" consensus sequence of N76 A77 A78 79G V80 G/S81 P82 P83 S84 (SEQ ID NO: 254). The residues A77, A78, P82, and P83 are chosen as starting "wildtype" amino acid as the variability profile (FIG. 14) indicated that these were the most frequent amino acids at their respective positions.

In this instance, the WTM (K) effects of introducing an amine side chain are explored in ligand binding. It is appreciated that the WTM (K) amino acids will occur only in those target "variable" positions and not in the "fixed" positions. The generated WTM diversity will include any "co-product" amino acids based on the degeneracy of the "wildtype" amino acid of the target codon. For example at position 77, the "wildtype" amino acid is alanine (Ala). To perform lysine WTM at position 77 so that both Ala and Lys are present, the degenerate codon used is RMG. The "coproduct" amino acids resulting from RMG will be threonine (T) and glutamate (E). The remaining WTM amino acids (G, S, H, L, P, Y, D, and Q) are then similarly replaced into the X variable positions of FN3 FG_9 loop N76 X77 X78 79G X80 G/S81 X82 X83 S84 (SEQ ID NO: 48) sequence. It is appreciated that the WTM amino acids will occur along with their "co-product" amino acids.

WTM for FG/11 using the nine pre-chosen WTM™ amino acids produces a library diversity of approximately $2 \times 9^5$ or 59049 (which includes WTM co-products). For comparative purposes, saturation mutagenesis of five FG/11 "variable" positions with all twenty amino acids would be $20^5$ or $3.2 \times 10^6$. Accordingly, performing saturation mutagenesis at all of the FG/11 loop positions would create a library diversity of $20^9$ or $5 \times 10^{11}$ which is just at the limit of current library display and screening technology. However, it is important to note that is for an FN3 loop library with just one mutated loop, and if the other FN3 loops (e.g. BC/11 and DE/6) were diversified by saturation mutagenesis, the minimum FN3 library would then be $20^{26}$ or $6.7 \times 10^{33}$. In contrast, the minimum and maximum FN3 library based on identifying the "variable" BC, DE and FG loop positions are $6.7 \times 10^{33}$. This illustrates an advantage of the invention which, by contrast, allows for a smaller but more representative library to be constructed. Indeed, the methods of the invention provide for a manageable library for some loop positions in order to identify the first generation of binding molecules. Subsequent affinity maturation mutagenesis in the other CDR positions then optimizes those identified binding molecules.

In another approach, byproducts can be avoided by employing look-through mutagenesis (LTM) which typically requires the synthesis of an oligonucleotide for each desired change but eliminates any by-products by degenerate codons.

A summary of identified loop sequences for use in the FN3 binding domain library of the invention is set forth below in Table 5. The names of the loops, sizes, and residue positions are standardized as previously discussed. Single-letter positions are fixed positions; two-letters positions are semi-fixed positions where the synthesis is performed with a mix in order to have only 2 targeted amino acids (example: S-G); and two-letters at positions where the first is 'X' are variable positions for WTM diversity. The amino acid following the X is the most frequent amino acid based on that variability profile and considered to be "wild type" (example: X-V).

TABLE 5

In some example, where an FG/8 loop is identified by six amino acids, it is understood that these amino acids represent the six N-terminal amino acids of FG/8.

BC LOOP

| (SEQ ID NO) | 21 | 22 | 23 | 24 | 25 | 26 | 27 | 28 | 29 | 30 | 31 | | | |
|---|---|---|---|---|---|---|---|---|---|---|---|---|---|---|
| BC_11 (37) | X-S | W | X-T | X-P | P | X-P | X-G | X-P | X-V | X-D | X-G | | | |
| | 21 | 22 | 23 | 24 | 25 | 26 | 26a | 26b | 26c | 27 | 28 | 29 | 30 | 31 |
| BC_14 (38) | X-S | W | X-K | X-P | P | X-D | X-D | X-P | X-N | X-G | X-P | I | X-T | X-G |
| | 21 | 22 | 23 | 24 | 25 | 26 | 26a | 26b | 26c | 26d | 27 | 28 | 29 | 30 | 31 |
| BC_15 (39) | X-S | W | X-E | X-P | P | X-E | X-D | D | G | G | X-S | X-P | I | X-T | X-G |

DE LOOP

| | 51 | 52 | 53 | 54 | 55 | 56 |
|---|---|---|---|---|---|---|
| DE_6 (40) | X-P | X-G | X-T | X-E | X-T | X-S |

FG LOOP

| | 76 | 77 | 78 | 79 | 80 | 84 | | | |
|---|---|---|---|---|---|---|---|---|---|
| FG_6 (47) | X | X | X | X | X | S | | | |
| FG_8 | 76 | 77 | 78 | 79 | 80 | 84 | 85 | 86 | |
| FG_8 (41) | X-N | X-G | X-G | X-G | X-E | S | S | K | |
| | 76 | 77 | 78 | 79 | 80 | 81 | 82 | 83 | 84 |
| FG_9 (48) | N | X | X | G | X | G/S | X | X | S |
| FG_11 | 76 | 77 | 78 | 79 | 80 | 81 | 82 | 83 | 84 | 85 | 86 |
| FG_11 (255) | N | X-A | X-A | G | X-V | G/S | X-P | X-P | S | S | K |

Example 4

Figure 11:
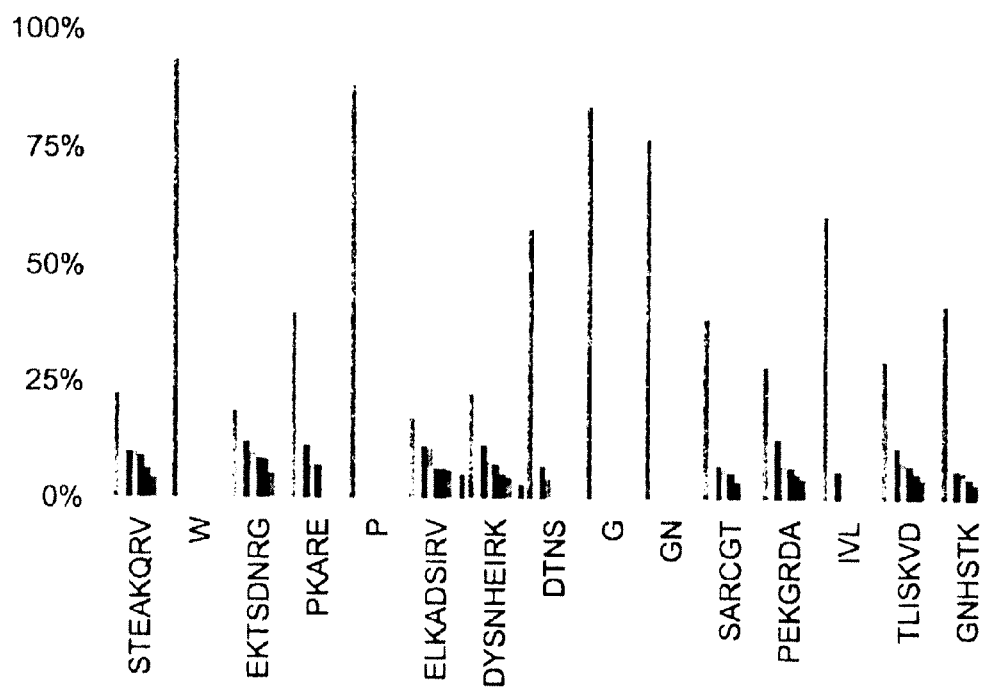
FIG. 11 shows sequence diversity of an exemplary loop region in the form of amino acid variability profile (frequency distribution) for BC loop length size 15.
Figure 12:
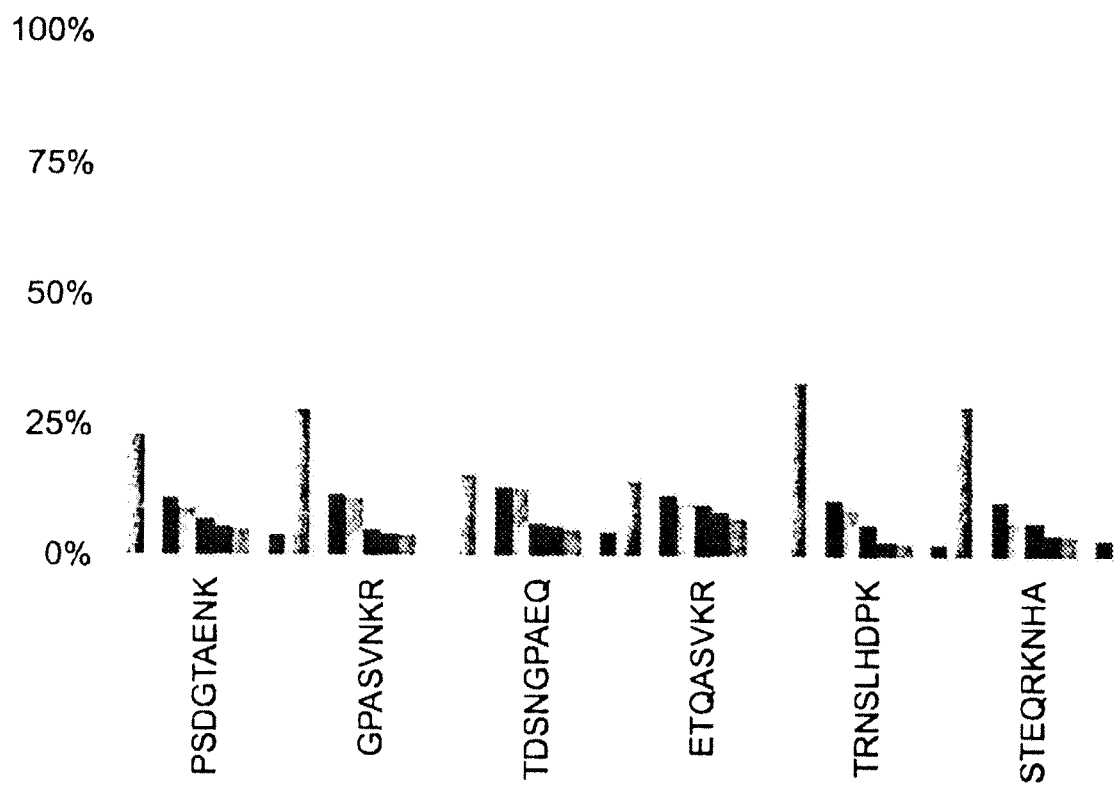
FIG. 12 shows sequence diversity of an exemplary loop region in the form of amino acid variability profile (frequency distribution). DE loop length size 6.
Figure 13:
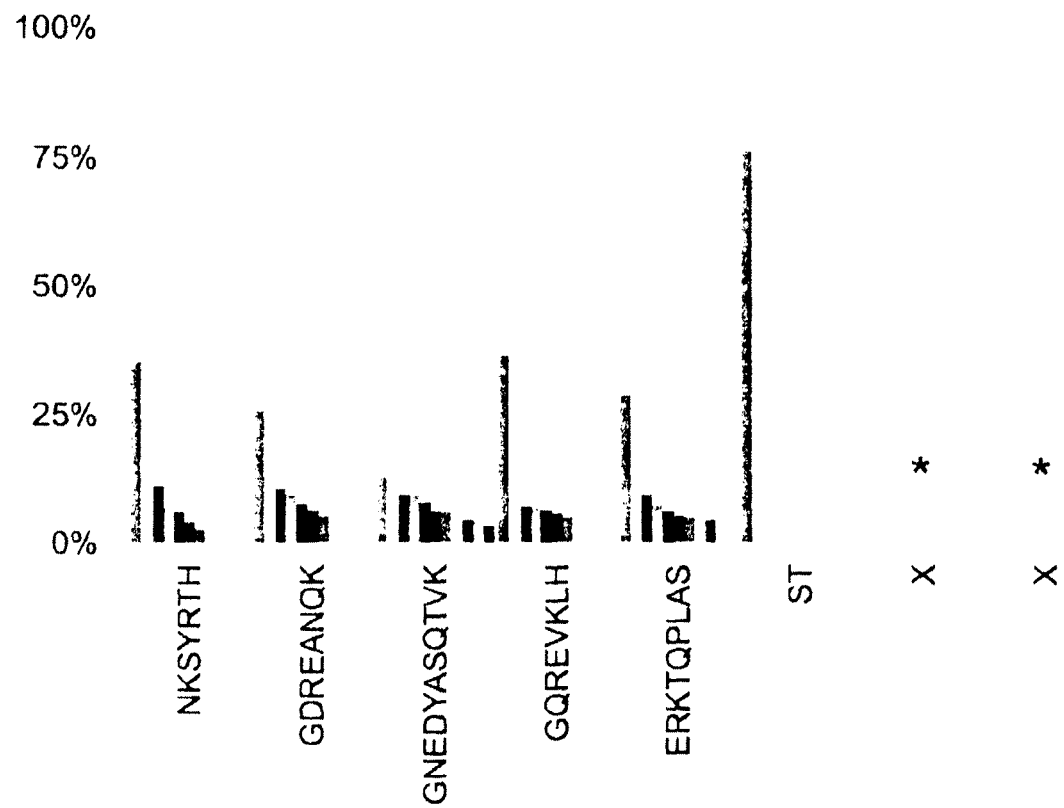
FIG. 13 shows amino acid sequence diversity of FG loop region in the form of amino acid variability profile (frequency distribution) for FG loop length size 8.
Figure 14:
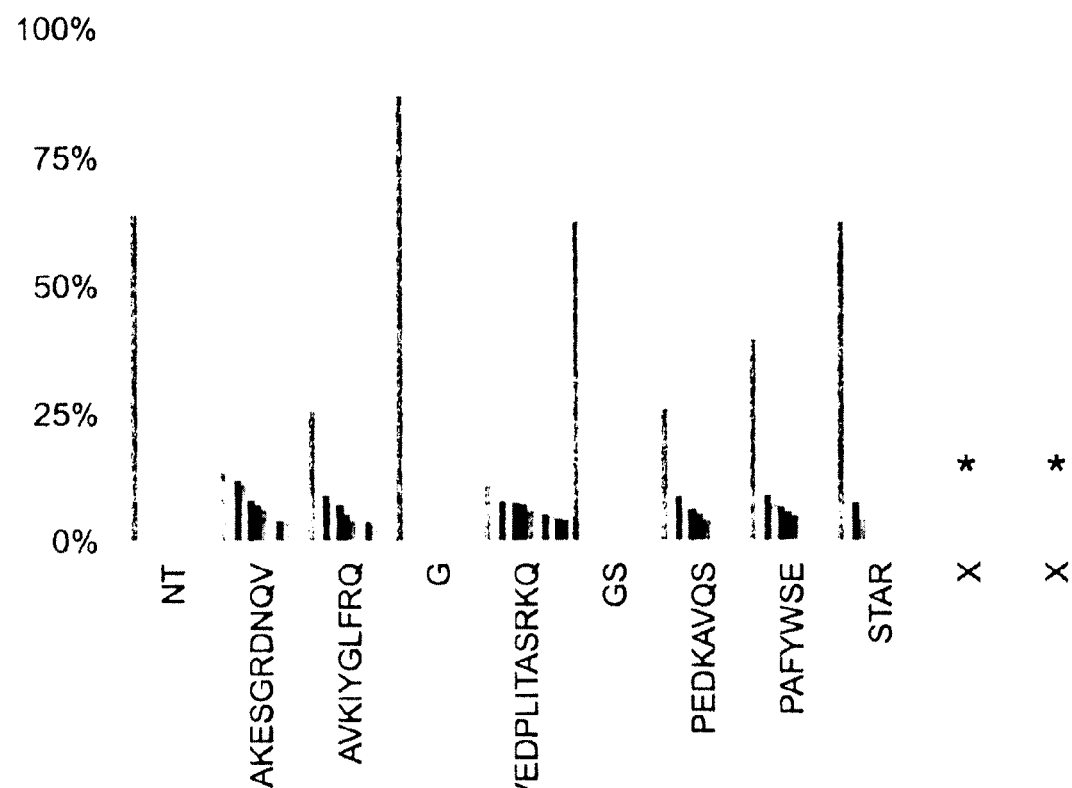
FIG. 14 shows sequence diversity of FG loop region in the form of amino acid variability profile (frequency distribution) for FG loop length size 11.

Oligonucleotide Design for Introducing Loop Diversity Using WTM and Extended WTM To design the BC/15 diversity (Table 5), a variability profile of the BC/15 loop positions from the filtered dataset was also performed using a threshold frequency of 50% (FIG. 11). The variability profile indicates that BC/15 would have a "wild type" starting sequence of: X-S21 W22 X-E23 X-P24 P25 X-E26 X-D26a D26b G26c G26d X-S27 X-P28 I29 X-T30 X-G31 (SEQ ID NO: 39).

|       | 21  | 22 | 23  | 24  | 25 | 26  | 26a | 26b | 26c | 26d | 27  | 28  | 29 | 30  | 31  |
|-------|-----|----|-----|-----|----|-----|-----|-----|-----|-----|-----|-----|----|-----|-----|
| BC/15 | X-S | W  | X-E | X-P | P  | X-E | X-D | D   | G   | G   | X-S | X-P | I  | X-T | X-G |

To perform WTM using Lys (K), one would introduce selective degenerate codons to place both the starting "wild type" amino acid and the WTM (K) amino acid in the selected "variable" position. The information presented here is also illustrated in FIGS. 16a-16i.

For position 27, or arm or (a a/g a/c) encodes R, N, K or S.
For position 28, or mma (a/c a/c a) encodes T, K, Q or P.
For position 29, or (att) encodes I.
For position 30, or ama (a a/c a) encodes T or K.
For position 31, or rra (a/g a/g a) encodes R, E, G or K.

| (SEQ ID NO) | WTM: K | 21  | 22  | 23  | 24  | 25  | 26  | 26a | 26b | 26c | 26d | 27  | 28  | 29  | 30  | 31  |
|-------------|--------|-----|-----|-----|-----|-----|-----|-----|-----|-----|-----|-----|-----|-----|-----|-----|
| 256         | BC/15  | K-S | W   | K-E | K-P | P   | K-E | K-D | D   | G   | G   | K-S | K-P | I   | K-T | K-G |
| 82          | WTM: K | arm | tgg | raa | mma | ccg | raa | raw | Gat | ggc | ggc | arm | mma | att | ama | rra |

The WTM (K) oligonucleotide sequence for BC/15 would then be: 5'(arm)(tgg)(raa)(mma)(ccg)(raa)(raw)(gat)(ggc)(ggc)(arm)(mma)(att)(ama)(rra)-3' (using degenerate base codes) (SEQ ID NO: 82), or 5'-(a a/g a/c)(tgg)(a/g a a)(a/c a/c a)(ccg)(a/g a a)(a/g a a/t)(gat)(ggc)(ggc)(a a/g a/c)(a/c a/c a)(att)(a a/c a)(a/g a/g a)-3' using standard base codes.

The oligonucleotide to be used in the subsequent PCR reaction will contain both 5' and 3' flanking regions as shown here. ACCACCATCACAATTARMTGGRAAMMAC-CGRAARAWGATGGCGGCARMMM AATTAMARRAT-TCCAAGTCGACGCA (SEQ ID NO:193)

The underlined portion encodes for the varied BC loop as described above. The 5' flanking sequence encodes the C-terminal portion of the B β strand domain and the 3' flanking sequence encodes the N-terminal portion of the C β strand domain.

For position 21, (arm) or (a a/g a/c): agc encodes S (wildtype) and aaa encodes K (WTM target). Additionally, aga encodes R and aac encodes N both of which are "co-products" from the WTM mixed base reaction.

For position 22, (tgg) encodes W.

For position 23, (raa) or (a/g a a) encodes E or K.

For position 24, (mma) or (a/c a/c a) encodes T, K, Q or P.

For position 25, (ccg) encodes P.

For position 26, (raa) or (a/g a a) encodes E or K.

For position 26a, (raw) or (a/g a a/t) encodes N, E, K or D.

For position 26b, (gat) encodes D.

For position 26c, (ggc) encodes G.

For position 26d, (ggc) encodes G.

The WTM "co-products" contribute to extra library diversity. In following this exercise through for the remaining BC_15 loop codons, we will generate a limited WTM (K) loop library of 8192 possible combination variants. We then continue applying WTM for the remaining WTM amino acids: G, S, H, L, P, Y, E, and Q (see Table 5). Overall, in completing the nine WTM amino acid series, a total BC_15 loop library size of $10^5$.

TABLE 6

WTM oligonucleotide design for BC/15

| BC_15 | | | | | | | | | | | | | | | | |
|---|---|---|---|---|---|---|---|---|---|---|---|---|---|---|---|---|
| | 21 X-S | 22 W | 23 X-E | 24 X-P | 25 P | 26 X-E | 26a X-D | 26b D | 26c G | 26d G | 27 X-S | 28 X-P | 29 I | 30 X-T | 31 X-G | SEQ ID NO: |
| WTM: K | arm | tgg | raa | mma | ccg | raa | raw | gat | ggc | ggc | arm | mma | att | ama | rra | 82 |
| WTM: G | rgc | tgg | gra | ssc | ccg | gra | grc | Gat | ggc | ggc | rgc | ssc | att | rsc | ggc | 83 |
| WTM: D | kmt | tgg | gaw | smt | ccg | gaw | gat | gat | ggc | ggc | kmt | smt | att | rmc | grt | 84 |
| WTM: Q | mrs | tgg | sag | cmg | ccg | sag | sak | gat | ggc | ggc | mrs | cmg | att | mmg | srg | 85 |
| WTM: S | agc | tgg | rrm | yct | ccg | rrm | rrc | gat | ggc | ggc | agc | yct | att | asc | rgc | 86 |
| WTM: H | ymt | tgg | saw | cmt | ccg | saw | sat | gat | ggc | ggc | ymt | cmt | att | mmc | srt | 87 |
| WTM: Y | tmt | tgg | tat gaa | ymt | ccg | tat gaa | kat | gat | ggc | ggc | tmt | ymt | att | wmc | krt | 88 |
| WTM: L | tya | tgg | swg | cyg | ccg | swg | swt | gat | ggc | ggc | tya | cyg | att | myg | skg | 89 |
| WTM: P | yct | tgg | smg | ccg | ccg | smg | smt | gat | ggc | ggc | yct | ccg | att | mcg | ssg | 90 |

Split Pool Synthesis: WTM Y Oligonucleotides

For performing tyrosine (Y) WTM where the starting "wildtype" amino acid is glutamate (E), an unwanted side effect may be the introduction of a stop codon. Tyrosine is encoded by tat and tac, glutamate is encoded by gaa and gag, the amber stop codon is tag and the ochre stop codon is taa. Substituting a tyrosine for a glutamate, therefore, requires that the first position be at for the tyrosine or g for glutamate, the second position be an a, and the third position be a t or c for tyrosine or an a or g for glutamate. Thus, a standard nucleotide mixture designed as described above may result in a taa or tag.

In this situation it can be preferable that alternate oligonucleotide synthesis procedure be utilized where pools of codons are synthesized separately then combined and split for the following round of synthesis (E A Peters, P J Schatz, S S Johnson, and W J Dower, J. Bacteriol. 1994 July; 176(14): 4296-4305.). This split pool synthesis allows for the introduction of these (Y) WTM residues without producing unwanted co-products such as the amber stop codon that occurs in regular single reaction oligonucleotide synthesis. In split pool synthesis process, two pools are utilized: the first pool utilizes the codon TAT, encoding Y, and the second pool utilizes the codon GAA, encoding E. In this split pool design, the amber stop codon is not made as each reaction pool does not code for the UAG or UAA stop codon. For BC_15 the (Y) WTM oligonucleotide reaction is made until position 26 whereupon the reaction is split into two separate columns for further synthesis.

In order to produce the defined mixture of amino acids, two columns are utilized. In the first, the fixed 3' portion of the oligonucleotides are synthesized as defined by the flanking regions and the fixed portion of the BC_15 loop shown above. For position 26 in the example sequence above, the first column synthesizes the codon TAT (TAT in the 3'-5' DNA synthesis). The second columns synthesize the codon GAA (AAG in the 3'-5' DNA synthesis). After the three nucleotides are coupled, the two columns are opened, the synthesis support is removed by washing with acetonitrile, and the resins are pooled. After mixing, the resin is placed into one column. At this point, the next position, positions 25 and 24 are synthesized. The single column synthesizes the codon CGG and YMT as described above. The resin is then split for (Y) WTM position 23 and reapportioned as described for position 26. After which, the syntheses are pooled and continued until the 5' fixed and flanking region are.

WTM oligonucleotide design for the BC/14 and BC/11 loops are the carried out in similar fashion.

In reference to FN3 BC/14 which the variability profile is described as:

| BC_14 (SEQ ID NO: 38) | 21 X-S | 22 W | 23 X-K | 24 X-P | 25 P | 26 X-D | 26a X-D | 26b X-P | 26c X-N | 27 X-G | 28 X-P | 29 I | 30 X-T | 31 X-G |
|---|---|---|---|---|---|---|---|---|---|---|---|---|---|---|

TABLE 7

WTM oligonucleotide design for BC/14

| | | | | | | BC_14 | | | | | | | | |
|---|---|---|---|---|---|---|---|---|---|---|---|---|---|---|
| | 21 X-S | 22 W | 23 X-K | 24 X-P | 25 P | 26 X-D | 26a X-D | 26b X-P | 26c X-N | 27 X-G | 28 X-P | 29 I | 30 X-T | 31 X-G | SEQ ID NO |
| WTM: K | arm | tgg | aaa | mma | ccg | raw | Raw | mma | aaw | rra | mma | att | ama | rra | 91 |
| WTM: G | rgc | tgg | rra | ssc | ccg | grc | Grc | ssc | rrc | ggc | ssc | att | rsc | ggc | 92 |
| WTM: D | kmt | tgg | raw | smt | ccg | gat | Gat | smt | rat | grt | smt | att | rmc | grt | 93 |
| WTM: Q | mrs | tgg | mag | cmg | ccg | sak | Sak | cmg | mak | srg | cmg | att | mmg | srg | 94 |
| WTM: S | agc | tgg | arm | yct | ccg | rrc | Rrc | ycy | arc | rgc | ycy | att | asc | rgc | 95 |
| WTM: H | ymt | tgg | maw | cmt | ccg | sat | Sat | cmt | mat | srt | cmt | att | mmc | srt | 96 |
| WTM: Y | tmt | tgg | aaa tat | ymt | ccg | kat | Kat | ymt | wat | krt | ymt | att | wmc | krt | 97 |
| WTM: L | tya | tgg | mwg | cyg | ccg | swt | Swt | cyg | mwt | skg | cyg | att | myg | skg | 98 |
| WTM: P | yct | tgg | mmg | ccg | ccg | smt | Smt | ccg | mmt | ssg | ccg | att | mcg | ssg | 99 |

In reference to FN3 BC_11 which the variability profile is described as:

| SEQ ID NO 37 | BC_11 | 21 X-S | 22 W | 23 X-T | 24 X-P | 25 P | 26 X-P | 27 X-C | 28 X-P | 29 X-V | 30 X-D | 31 X-G |
|---|---|---|---|---|---|---|---|---|---|---|---|---|

TABLE 8

WTM oligonucleotide design for BC/11

| | | | | BC_11 | | | | | | | |
|---|---|---|---|---|---|---|---|---|---|---|---|---|
| | 21 X-S | 22 W | 23 X-T | 24 X-P | 25 P | 26 X-P | 27 X-C | 28 X-P | 29 X-V | 30 X-D | 31 X-G | SEQ ID NO |
| WTM:K | arm | tgg | ama | mma | ccg | mma | Rra | mma | rwg | raw | rra | 100 |
| WTM:G | rgc | tgg | rsc | ssc | ccg | ssc | Ggc | ssc | gkc | grc | ggc | 101 |
| WTM:D | kmt | tgg | rmc | smt | ccg | smt | Grt | smt | gwt | gat | grt | 102 |
| WTM:Q | mrs | tgg | mmg | cmg | ccg | cmg | Srg | cmg | swg | sak | srg | 103 |
| WTM:S | agc | tgg | asc | yct | ccg | yct | Rgc | yct | rkc | rrc | rgc | 104 |
| WTM:H | ymt | tgg | mmc | cmt | ccg | cmt | Srt | cmt | swt | sat | srt | 105 |
| WTM:Y | tmt | tgg | wmc | ymt | ccg | ymt | Krt | ymt | kwt | kat | krt | 106 |
| WTM:L | Tya | tgg | myg | cyg | ccg | cyg | Skg | cyg | stg | swt | skg | 107 |
| WTM:P | yct | tgg | mcg | ccg | ccg | ccg | Ssg | ccg | syg | smt | ssg | 108 |

The co-products formed in using the above oligonucleotide design for the BC_11 loop are shown in FIGS. 15a-15i

In reference to [10]FN3 DE_6 which the variability profile is described as:

|  | DE LOOP | | | | | |
|---|---|---|---|---|---|---|
|  | 51 | 52 | 53 | 54 | 55 | 56 |
| (SEQ ID NO: 40) | X-P | X-G | X-T | X-E | X-T | X-S |

Walkthrough [10]FN3 DE/66 is performed at the appropriate variable positions and listed Table 6. As above, in the sequence denoted with an X refers to the walkthrough amino acid, and the amino acid(s) following the (dash) - refer to the starting base wild type amino acid.

TABLE 9

WTM oligonucleotide design for DE/6

| | DE_6 | | | | | |
|---|---|---|---|---|---|---|
| | 51 X-P | 52 X-G | 53 X-T | 54 X-E | 55 X-T | 56 X-S | SEQ ID NO |
| WTM:K | mma | rra | Ama | raa | ama | arm | 109 |
| WTM:G | ssc | ggc | Rsc | gra | rsc | rgc | 110 |
| WTM:D | smt | grt | Rmc | gaw | rmc | kmt | 111 |
| WTM:Q | cmg | srg | Mmg | sag | mmg | mrs | 112 |
| WTM:S | yct | rgc | Asc | rrm | asc | agc | 113 |
| WTM:H | cmt | srt | Mmc | saw | mmc | ymt | 114 |
| WTM:Y | ymt | krt | Wmc | kaw | wmc | tmt | 115 |
| WTM:L | cyg | skg | Myg | swg | myg | tya | 116 |
| WTM:P | ccg | ssg | Mcg | smg | mcg | yct | 117 |

The co-products formed in using the above oligonucleotide design for the DE/6 loop are shown in FIGS. 17a and 17b for walkthrough amino acids Q, K, H, G, S, L, P and Y in FIGS. 15a and 15b.

In reference to FN3 FG/11 which the variability profile is described as:

| SEQ ID NO | 76 | 77 | 78 | 79 | 80 | 81 | 82 | 83 | 84 |
|---|---|---|---|---|---|---|---|---|---|
| 254 | FG_9 | X-N | X-A | X-A | G | X-V | G/S | X-P | X-P | S |

TABLE 10

WTM oligonucleotide design for FG/11

| | FG_9 | | | | | | | | |
|---|---|---|---|---|---|---|---|---|---|
| | 76 X-N | 77 X-A | 78 X-A | 79 G | 80 X-V | 81 G/S | 82 X-P | 83 X-P | 84 S | SEQ ID NO |
| WTM:K | aaw | rmg | rmg | ggc | Rwg | rgc | mma | mma | Agc | 118 |
| WTM:G | rrc | gsc | gsc | ggc | Gkc | rgc | ssc | Ssc | agc | 119 |
| WTM:D | rat | gmc | gmc | ggc | Gwt | rgc | smt | Smt | agc | 120 |
| WTM:Q | mak | smg | smg | ggc | Swg | rgc | cmg | Cmg | agc | 121 |
| WTM:S | arc | kct | kct | ggc | Rkc | rgc | yct | yct | agc | 122 |
| WTM:H | mat | smc | smc | ggc | Swt | rgc | cmt | cmt | agc | 123 |
| WTM:Y | wat | kmc | kmc | ggc | Kwt | rgc | ymt | ymt | agc | 124 |
| WTM:L | mwt | syg | syg | ggc | Stg | rgc | cyg | cyg | agc | 125 |
| WTM:P | mmt | scg | scg | ggc | Syg | rgc | ccg | ccg | agc | 126 |

The co-products formed in using the above oligonucleotide design for the FG_9 loop are shown in FIGS. 18a-18c.

In reference to FN3 6 which the variability profile is described as:

| SEQ ID NO | | 76 | 77 | 78 | 79 | 80 | 84 |
|---|---|---|---|---|---|---|---|
| 257 | FG_6 | X-N | X-G | X-G | X-G | X-E | S |

TABLE 11

WTM oligonucleotide design for FG_6

| | FG_6 | | | | | | |
|---|---|---|---|---|---|---|---|
| | 76 X-N | 77 X-G | 78 X-G | 79 X-G | 80 X-E | 84 S | SEQ ID NO |
| WTM:K | aaw | rra | rra | rra | Raa | arm | 127 |
| WTM:G | rrc | ggc | ggc | ggc | Gra | rgc | 128 |
| WTM:D | rat | grt | grt | grt | Gaw | kmt | 129 |
| WTM:Q | mak | srg | srg | srg | Sag | mrs | 130 |
| WTM:S | arc | rgc | rgc | rgc | Rrm | agc | 131 |
| WTM:H | mat | srt | srt | srt | Saw | ymt | 132 |
| WTM:Y | wat | krt | krt | krt | tat gaa | tmt | 133 |
| WTM:L | mwt | skg | skg | skg | Swg | tya | 134 |
| WTM:P | mmt | ssg | ssg | ssg | Smg | yct | 135 |

All 20 amino acids and unnatural amino acids utilizing the amber codon can potentially be walked through at the appropriate shaded positions.

Oligo Construction using Table 11, was carried out using extended walkthrough and doping as follows.

Extended walkthrough (for loop) can also be performed at the appropriate loop positions where noted in the sequence denoted with an X. The X refers to the walkthrough amino acid, and the amino acid(s) following the (dash) - refer to the base wild-type amino acid and any required co-products denoted after a (slash)/. Extended walkthrough is another example of WTM codon design where the co-product can be predetermined to occur. For example, the variability profiles have illustrated that G and P are frequent amino acids in the loop positions. The frequency of some G and P amino acids do not characterize them as either "fixed" or "wild-type" amino acids in the starting WTM sequence. However, by extended walkthrough, the degenerate WTM codons can be biased to that either G or P can be a WTM co-product.

TABLE 12

| | | | | | | | BC_14 | | | | | | | | |
|---|---|---|---|---|---|---|---|---|---|---|---|---|---|---|---|
| | 21 | 22 | 23 | 24 | 25 | 26 | 26a | 26b | 26c | 27 | 28 | 29 | 30 | 31 | SEQ ID NO |
| Regular WTM | X-S | W | X-K | X-P | P | X-D | X-D | X-P | X-N | X-G | X-P | I | X-T | X-G | 38 |
| Extended WTM | X-S | W | X-K | X-P | P | X-D | X-D | X-P/G | X-N/G | X-G | X-P | I | X-T | X-G | 258 |
| WTM:K | arm | tgg | aaa | maa | ccg | raa | Raw | gat | Ggc | arm | mma | att | ama | rra | 136 |
| Extended WTM:K | arm | tgg | aaa | maa | ccg | raa | Raw | mca | Rrm | arm | mma | att | ama | rra | 137 |

Here, a second BC/14 loop variation is given to exemplify the use of extended walkthrough mutagenesis with required co-products. The regular WTM and extended WTM design in Table 11 for BC_14 is shown above. In this case, regular WTM has P and N as the starting "wildtype" amino acid at positions 26b and 26c respectively. For WTM using K as the target amino acid, the required co-products are G at both positions.

For position 26b, we use the degenerate codon v(acg)ca. The codon aca codes for the WTM K amino acid, the codon cca codes P, the wildtype amino acid, and gca codes for G the required coproduct amino acid. Therefore a, c, and g are in the first position, c is in the second position, and a is in the third codon position.

Similarly, the degenerate codon rrm is used at position 26c. The codon aaa codes for K, aac codes for N, and gga codes for G. Therefore a, and g are in the first position, a and g are in the second position, and c and a are in the third codon position.

These extended WTM (K) results are summarized below and the 5' and 3' flanking codons are the same as the regular WTM (K) oligonucleotides. This principle would be applied to the remaining WTM amino acids (G, S, H, L, P, Y, D, and Q) so that degenerate codons are designed to incorporate the WTM, wildtype and any required co-products.

Doping of the incoming base mixture can be performed to achieve predetermined amino acid ratios.

In position 26 of this example, it is desired that the WTM K (lysine) be incorporated into the loop 70% of the time as compared to the 30% of starting D (aspartic acid) wildtype amino acid. The usage of lysine is defined by the percentage of "a" utilized in the first codon position. Therefore, to achieve 70% lysine incorporation, the percentage of "a" in the mixture was introduced at 70% while "g" was introduced at 30% to achieve 30% aspartic acid.

In position 26a of this example, it is desired that the WTM K (lysine) be incorporated into the loop in equal 50% with 50% of starting D (aspartic acid) wildtype amino acid. Therefore, to achieve 50% lysine incorporation and 50% aspartic acid, the percentage of "a" and "g" were both adjusted to be introduced at 50% for oligonucleotide incorporation.

Similarly, in positions 96-99, the level of glycine incorporation was tuned to achieve an approximately 25% level of glycine incorporation while decreasing the level of co-product incorporation.

In the preferred usage, flanking regions are added to the 5' and 3' oligonucleotide regions to facilitate incorporation of the BC, DE and FG loops into the β-scaffold FN3 domain. The flanking regions have complementary base pairing with the oligonucleotides encoding other β-strands so that SOE-

| | | | | | | | BC_14 | | | | | | | |
|---|---|---|---|---|---|---|---|---|---|---|---|---|---|---|
| | 21 | 22 | 23 | 24 | 25 | 26 | 26a | 26b | 26c | 27 | 28 | 29 | 30 | 31 |
| Regular WTM | X-S | W | X-K | X-P | P | X-D | X-D | X-P | X-N | X-G | X-P | I | X-T | X-G |
| Extended WTM | X-S | W | X-K | X-P | P | X-D | X-D | X-P/G | X-N/G | X-G | X-P | I | X-T | X-G |
| WTM:K | arm | tgg | Aaa | maa | ccg | raa | Raa | gat | | arm | mma | att | ama | rra |

50

TABLE 13

Doping of base mixture incorporation of extended BC_14 WTM (K) oligonucleotide (SEQ ID NO: 138).

| | 25 | | 26 | | | 26a | | | 26b | | | 26c | | | 27 | | |
|---|---|---|---|---|---|---|---|---|---|---|---|---|---|---|---|---|---|
| 5'- c | c | g | a | a | a | a | a | a | a | c | a | a | a | c | a | a | a -3' |
| | | | g | | | g | | | c | | | g | g | a | | g | c |
| | | | | | | | | | g | | | | | | | | |
| | | | 70 | | | 50 | | | 50 | 50 | | 40 | 40 | 40 | | 50 | 50 |
| | | | 30 | | | 50 | | | 50 | 25 | | 60 | 60 | 60 | | 50 | 50 |
| | | | | | | | | | | 25 | | | | | | | |

Figure 20:
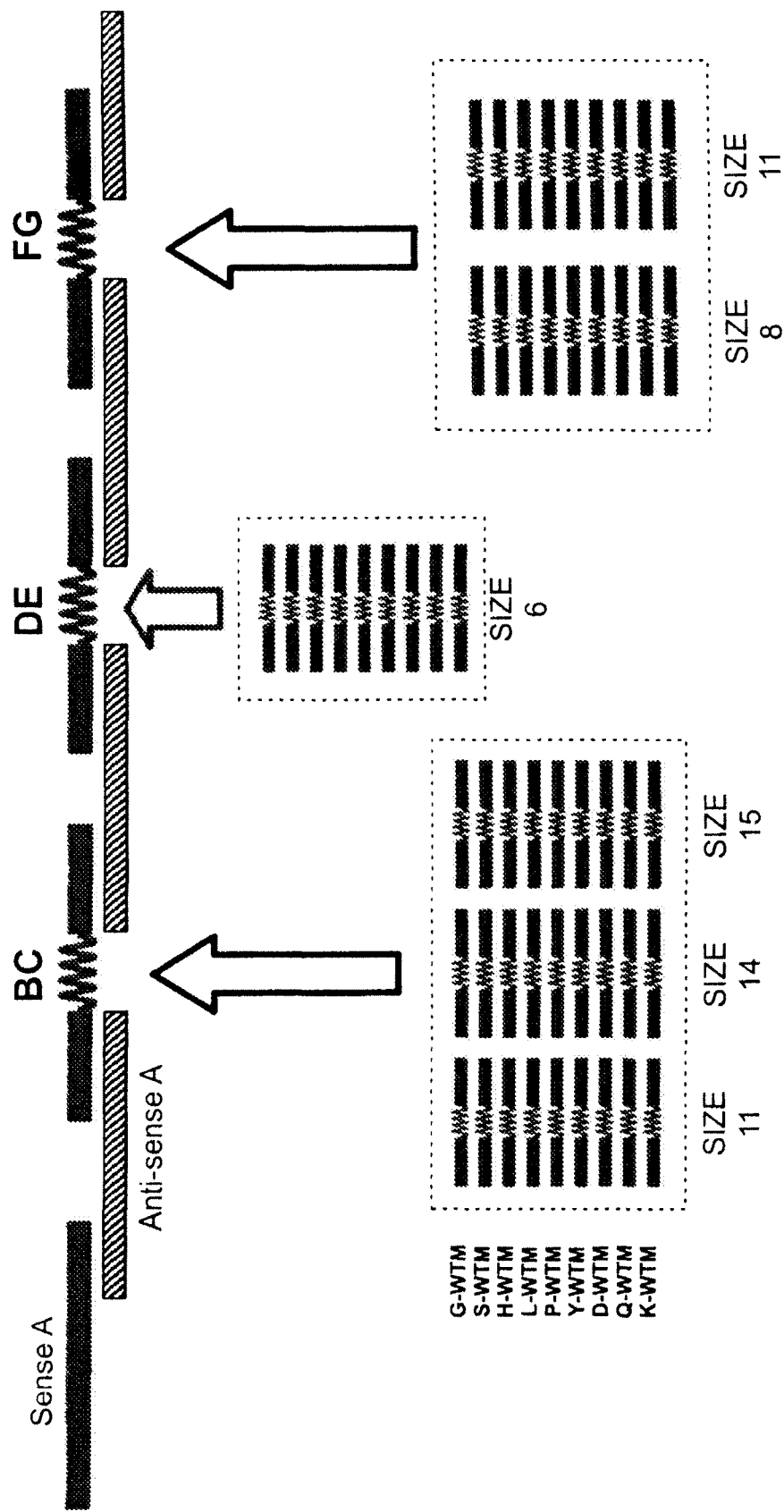
FIG. 20 shows construction of the FN3 binding domain library using a combination of overlapping nondegenerate and degenerate oligonucleotides that can be converted to double-stranded nucleic acids using the single overlap extension polymerase chain reaction (SOE-PCR). Eight oligonucleotides are required for the entire gene. Each loop (BC, DE, and FG) is encoded by a separate series of degenerate oligonucleotides.

PCR can be performed (see FIG. 20). The following flanking scaffold 5' and 3' sequences are used for the BC, DE and FG loops:

| B' β-strand | 16 | 17 | 18 | 19 | 20 | BC loop | 31 | 32 | 33 | 34 | 35 | C' β-strand |
|---|---|---|---|---|---|---|---|---|---|---|---|---|
|  | ACC | TCT | TTG | CTT | ATA |  | TCG | GAT | CAC | GTA | C | (SEQ ID NO: 194) |
| D' β-strand | 46 | 47 | 48 | 49 | 50 | DE loop | 56 | 57 | 58 | 59 | 60 | E' β-strand |
| F' β-strand | 71 | 72 | 73 | 74 | 75 | FG loop | 85 | 86 | 87 | 88 | 89 | G' β-strand |

Example 5

WTM Oligonucleotide Design (No Threshold)

In another embodiment it is possible to execute WTM mutagenesis for the entire length of each loop, all the positions in the loops were considered as variable (threshold=100%). Therefore this library is a superset of the one in the previous example. In addition, because of how WTM works, the most abundant amino acid at each position is encoded at each and every position in the loops with a frequency between 25% and 50%. Thus, the libraries will cover a much larger sequence space, yet still be biased towards the amino acid pattern found in the database.

Positions at the strand-loop boundary require special handling. In fact residues at this positions might very important for the stability of the framework. Therefore if such positions are highly conserved in the related variability profile, they will be kept fixed (see S21, W22 and G31 in loop BC_11; S21 and W22 in loops BC_14 and BC_15; N76 in loops FG_8 and FG_11).

TABLE 14

Summary of loop sequences for the universal Fibronectin III binding domains library

BC LOOP

| (SEQ ID NO) | 21 | 22 | 23 | 24 | 25 | 26 | 26a | 26b | 26c | 26d | 27 | 28 | 29 | 30 | 31 |
|---|---|---|---|---|---|---|---|---|---|---|---|---|---|---|---|
| BC_11 (37) | S | W | X-T | X-P | X-P | X-P |  |  |  |  | X-G | X-P | X-V | X-D | G |
| BC_14 (38) | S | W | X-K | X-P | X-P | X-D | X-D | X-P | X-N | | X-G | X-P | X-I | X-T | X-G |
| BC_15 (39) | S | W | X-E | X-P | X-P | X-E | X-D | X-D | X-G | X-G | X-S | X-P | X-I | X-T | X-G |

DE LOOP

| | 51 | 52 | 53 | 54 | 55 | 56 |
|---|---|---|---|---|---|---|
| DE_6 (40) | X-P | X-G | X-T | X-E | X-T | X-S |

FG LOOP

| | 76 | 77 | 78 | 79 | 80 | 81 | 82 | 83 | 84 | 85 | 86 |
|---|---|---|---|---|---|---|---|---|---|---|---|
| FG_8 (41) | N | X-G | X-G | X-G | X-E |  |  |  | X-S | X-S | X-K |
| FG_11 (259) | N | X-A | X-A | X-G | X-V | X-G | X-P | X-P | X-S | X-S | X-K |

By following Table 14, the design of loop BC_15 will be as described here below:

| SEQ ID NO | | 21 | 22 | 23 | 24 | 25 | 26 | 26a | 26b | 26c | 26d | 27 | 28 | 29 | 30 | 31 |
|---|---|---|---|---|---|---|---|---|---|---|---|---|---|---|---|---|
| 39 | BC_15 | S | W | X-E | X-P | X-P | X-E | X-D | X-D | X-G | X-G | X-S | X-P | X-I | X-T | X-G |

To perform WTM using Lys (K), one would introduce selective degenerate codons to place both the starting "wild type" amino acid and the WTM (K) amino acid in the selected "variable" position.

| SEQ ID NO | | 21 | 22 | 23 | 24 | 25 | 26 | 26a | 26b | 26c | 26d | 27 | 28 | 29 | 30 | 31 |
|---|---|---|---|---|---|---|---|---|---|---|---|---|---|---|---|---|
| 39 | BC_15 | S | W | X-E | X-P | X-P | X-E | X-D | X-D | X-G | X-G | X-S | X-P | X-I | X-T | X-G |
| 139 | WTM: K | agc | tgg | raa | mma | mma | raa | raw | Raw | rra | rra | arm | mma | awa | ama | rra |

The WTM (K) oligonucleotide sequence for BC_15 would then be: 5'-(agc)(tgg)(raa)(mma)(mma)(raa)(raw)(raw)(rra)(rra)(arm)(mma)(awa)(ama)(rra)-3' (SEQ ID NO:82) (using degenerate base codes) or
5'-(agc)(tgg)(a/g a a)(a/c a/c a)(a/c a/c a aya/g a a)(a/g a a/t)(a/g a a/t)(a/g a/g a)(a/ga/ga)(a a/g a/c)(a/c a/c a)(aa/ta)(a a/c a)(a/g a/g a)-3' using standard base codes.

The oligonucleotide to be used in the subsequent PCR reaction will contain both 5' and 3' flanking regions as shown here. ACCACCATCACAATTAGCTGGRAAMMAMMARAARAWRAWRRARRAARMMMAAWAAMARRATTCCAAGTCGACGCA
(SEQ ID NO:195)

The underlined portion encodes for the varied BC loop as described above. The 5' flanking sequence encodes the C-terminal portion of the B β strand domain and the 3' flanking sequence encodes the N-terminal portion of the C β strand domain.

For position 21, (agc) encodes S.
For position 22, (tgg) encodes W.
For position 23, (raa) or (a/g a a) encodes E or K.
For position 24, (mma) or (a/c a/c a) encodes P, K, Q or T.
For position 25, (mma) or (a/c a/c a) encodes P, K, Q or T.
For position 26, (raa) or (a/g a a) encodes E or K.
For position 26a, (raw) or (a/g a a/t) encodes D, E, K or N.
For position 26b, (raw) or (a/g a a/t) encodes D, E, K or N.
For position 26c, (rra) or (a/g a/g a) encodes G, R, E or K.
For position 26c, (rra) or (a/g a/g a) encodes G, R, E or K.
For position 27, or arm or (a a/g a/c) encodes S, N, K or R.
For position 28, or mma (a/c a/c a) encodes P, K, Q or T.
For position 29, or (awa) or (a a/t a) encodes I or K.
For position 30, or ama (a a/c a) encodes T or K.
For position 31, or rra (a/g a/g a) encodes G, R, E or K.

This approach would be continued for the remaining WTM amino acids: G, S, H, L, P, Y, E, and Q (see Table 5).

TABLE 15

WTM oligonucleotide design for BC/15

BC_15

| | 21 | 22 | 23 | 24 | 25 | 26 | 26a | 26b | 26c | 26d | 27 | 28 | 29 | 30 | 31 | |
|---|---|---|---|---|---|---|---|---|---|---|---|---|---|---|---|---|
| | S | W | X-E | X-P | X-P | X-E | X-D | X-D | X-G | X-G | X-S | X-P | X-I | X-T | X-G | SEQ ID NO |
| WTM: K | agc | tgg | raa | mma | mma | raa | Raw | Raw | rra | rra | arm | mma | awa | ama | rra | 139 |
| WTM: G | agc | tgg | gra | ssc | ssc | gra | Grc | Grc | ggc | ggc | rgc | ssc | rkc | rsc | ggc | 140 |
| WTM: D | agc | tgg | gaw | smt | smt | gaw | Gat | Gat | grt | grt | kmt | smt | rwt | rmc | grt | 141 |
| WTM: Q | agc | tgg | sag | cmg | cmg | sag | Sak | Sak | srg | srg | mrs | cmg | mwa | mmg | srg | 142 |
| WTM: S | agc | tgg | rrm | yct | yct | rrm | Rrc | Rrc | rgc | rgc | agc | yct | akc | asc | rgc | 143 |
| WTM: H | agc | tgg | saw | cmt | cmt | saw | Sat | Sat | srt | srt | ymt | cmt | mwt | mmc | srt | 144 |
| WTM: Y | agc | tgg | tat gaa | ymt | ymt | tat gaa | Kat | Kat | krt | krt | tmt | ymt | wwt | wmc | krt | 145 |
| WTM: L | agc | tgg | swg | cyg | cyg | swg | Swt | Swt | skg | skg | tya | cyg | wta | myg | skg | 146 |
| WTM: P | agc | tgg | smg | ccg | ccg | smg | smt | Smt | ssg | ssg | yct | ccg | myt | mcg | ssg | 147 |

WTM oligonucleotide design for the BC_14 and BC_11 loops are the carried out in similar fashion.

In reference to FN3 BC_14 which the variability profile is described as:

| SEQ ID NO | | 21 | 22 | 23 | 24 | 25 | 26 | 26a | 26b | 26c | 27 | 28 | 29 | 30 | 31 |
|---|---|---|---|---|---|---|---|---|---|---|---|---|---|---|---|
| 38 | BC_14 | S | W | X-K | X-P | X-P | X-D | X-D | X-P | X-N | X-G | X-P | X-I | X-T | X-G |

TABLE 16

WTM oligonucleotide design for BC/14

| BC_14 | 21 | 22 | 23 | 24 | 25 | 26 | 26a | 26b | 26c | 27 | 28 | 29 | 30 | 31 | |
|---|---|---|---|---|---|---|---|---|---|---|---|---|---|---|---|
| | S | W | X-K | X-P | X-P | X-D | X-D | X-P | X-N | X-G | X-P | X-I | X-T | X-G | SEQ ID NO |
| WTM: K | agc | tgg | aaa | mma | mma | raw | raw | mma | aas | rra | mma | awa | ama | rra | 148 |
| WTM: G | agc | tgg | rra | ssc | ssc | grc | grc | ssc | rrt | ggc | ssc | rkc | rsc | ggc | 149 |
| WTM: D | agc | tgg | raw | smt | smt | gat | gat | smt | rat | grt | smt | rwt | rmc | grt | 150 |
| WTM: Q | agc | tgg | mag | cmg | cmg | sak | sak | cmg | mcw | srg | cmg | mwa | mmg | srg | 151 |
| WTM: S | agc | tgg | arm | yct | yct | rrc | rrc | yct | arc | rgc | yct | akc | asc | rgc | 152 |
| WTM: H | agc | tgg | maw | cmt | cmt | sat | sat | cmt | mat | srt | cmt | mwt | mmc | srt | 153 |
| WTM: Y | agc | tgg | aaa tat | ymt | ymt | kat | kat | ymt | wat | krt | ymt | wwt | wmc | krt | 154 |
| WTM: L | agc | tgg | mwg | cyg | cyg | swt | swt | cyg | mwc | skg | cyg | wta | myg | skg | 155 |
| WTM: P | agc | tgg | mmg | ccg | ccg | smt | smt | ccg | mmt | ssg | ccg | myt | mcg | ssg | 156 |

In reference to FN3 BC_11 which the variability profile is described as:

| SEQ ID NO | | 21 | 22 | 23 | 24 | 25 | 26 | 27 | 28 | 29 | 30 | 31 |
|---|---|---|---|---|---|---|---|---|---|---|---|---|
| 37 | BC_11 | S | W | X-T | X-P | X-P | X-P | X-G | X-P | X-V | X-D | G |

TABLE 17

| WTM oligonucleotide design for BC/11 | | | | | | | | | | | | |
|---|---|---|---|---|---|---|---|---|---|---|---|---|
| | BC_11 | | | | | | | | | | | |
| | 21 S | 22 W | 23 X-T | 24 X-P | 25 X-P | 26 X-P | 27 X-G | 28 X-P | 29 X-V | 30 X-D | 31 G | SEQ ID NO |
| WTM: K | agc | tgg | ama | mma | mma | mma | rra | mma | rwg | raw | ggc | 157 |
| WTM: G | agc | tgg | rsc | ssc | ssc | ssc | ggc | ssc | gkc | grc | ggc | 158 |
| WTM: D | agc | tgg | rmc | smt | smt | smt | grt | smt | gwt | gat | ggc | 159 |
| WTM: Q | agc | tgg | mmg | cmg | cmg | cmg | srg | cmg | swg | sak | ggc | 160 |
| WTM: S | agc | tgg | asc | yct | yct | yct | rgc | yct | rkc | rrc | ggc | 161 |
| WTM: H | agc | tgg | mmc | cmt | cmt | cmt | srt | cmt | swt | sat | ggc | 162 |
| WTM: Y | agc | tgg | wmc | ymt | ymt | ymt | krt | ymt | kwt | kat | ggc | 163 |
| WTM: L | agc | tgg | myg | cyg | cyg | cyg | skg | cyg | stg | swt | ggc | 164 |
| WTM: P | agc | tgg | mcg | ccg | ccg | ccg | ssg | ccg | syg | smt | ggc | 165 |

The co-products formed in using the above oligonucleotide design for the BC_11 loop are shown in FIGS. 15*a* and 15*b*.

In reference to DE_6 the variability profile is described as:**

| SEQ ID NO | | 51 | 52 | 53 | 54 | 55 | 56 |
|---|---|---|---|---|---|---|---|
| 40 | DE/6 | X-P | X-G | X-T | X-E | X-T | X-S |

Walkthrough DE/6 is performed at the appropriate variable positions and listed Table 6. As above, in the sequence denoted with an X refers to the walkthrough amino acid, and the amino acid(s) following the (dash) - refer to the starting base wild type amino acid.

TABLE 18

| WTM oligonucleotide design for DE/6 | | | | | | | |
|---|---|---|---|---|---|---|---|
| | DE/6 | | | | | | |
| | 51 X-P | 52 X-G | 53 X-T | 54 X-E | 55 X-T | 56 X-S | SEQ ID NO |
| WTM: K | mma | Rra | Ama | raa | ama | arm | 166 |
| WTM: G | ssc | Ggc | Rsc | gra | <u>rsc</u> | rgc | 167 |
| WTM: D | smt | Grt | Rmc | gaw | <u>rmc</u> | kmt | 168 |
| WTM: Q | cmg | Srg | Mmg | sag | <u>mmg</u> | mrs | 169 |
| WTM: S | yct | Rgc | Asc | rrm | <u>asc</u> | agc | 170 |
| WTM: H | cmt | Srt | Mmc | saw | <u>mmc</u> | ymt | 171 |
| WTM: Y | ymt | Krt | Wmc | kaw | <u>wmc</u> | tmt | 172 |
| WTM: L | cyg | Skg | Myg | swg | <u>myg</u> | tya | 173 |
| WTM: P | ccg | Ssg | mcg | smg | <u>mcg</u> | yct | 174 |

The co-products formed in using the above oligonucleotide design for the DE/6 loop are shown in FIGS. 17*a* and 17*b*.

In reference to the FG/11 loop the variability profile is described as:

| SEQ ID NO | | 76 | 77 | 78 | 79 | 80 | 81 | 82 | 83 | 84 | 85 | 86 |
|---|---|---|---|---|---|---|---|---|---|---|---|---|
| 259 | FG/11 | N | X-A | X-A | X-G | X-V | X-G | X-P | X-P | X-S | X-S | X-K |

TABLE 19

WTM oligonucleotide design for FG/11

| FG/11 | 76 N | 77 X-A | 78 X-A | 79 X-G | 80 X-V | 81 X-G | 82 X-P | 83 X-P | 84 X-S | 85 X-S | 86 X-K | SEQ ID NO |
|---|---|---|---|---|---|---|---|---|---|---|---|---|
| WTM: K | aat | rmg | rmg | Rra | Rwg | Rra | mma | mma | arm | arm | aaa | 175 |
| WTM: G | aat | gsc | gsc | Ggc | Gkc | Ggc | ssc | ssc | rgc | rgc | rra | 176 |
| WTM: D | aat | gmc | gmc | Grt | Gwt | Grt | smt | smt | kmt | kmt | raw | 177 |
| WTM: Q | aat | smg | smg | Srg | Swg | Srg | cmg | cmg | mrs | mrs | mag | 178 |
| WTM: S | aat | kct | kct | Rgc | Rkc | Rgc | yct | yct | agc | agc | arm | 179 |
| WTM: H | aat | smc | smc | Srt | Swt | Srt | cmt | cmt | ymt | ymt | maw | 180 |
| WTM: Y | aat | kmc | kmc | Krt | Kwt | krt | ymt | ymt | tmt | tmt | aaa tat | 181 |
| WTM: L | aat | syg | syg | Skg | Stg | Skg | cyg | cyg | tya | tya | mwg | 182 |
| WTM: P | aat | scg | scg | Ssg | Syg | Ssg | ccg | ccg | yct | yct | mmg | 183 |

The co-products formed in using the above oligonucleotide design for the FG/9 loop are shown in FIGS. 18a-18c.

In reference to the FG/8 loop the variability profile is described as:

| SEQ ID NO | | 76 | 77 | 78 | 79 | 80 | 84 | 85 | 86 |
|---|---|---|---|---|---|---|---|---|---|
| 41 | FG/8 | N | X-G | X-G | X-G | X-E | X-S | X-S | X-K |

TABLE 20

WTM oligonucleotide design for FG/8

| | 76 N | 77 X-G | 78 X-G | 79 X-G | 80 X-E | 84 X-S | 85 X-S | 86 X-K | SEQ ID NO |
|---|---|---|---|---|---|---|---|---|---|
| WTM: K | aat | rra | rra | rra | raa | arm | arm | aaa | 184 |
| WTM: G | aat | ggc | ggc | ggc | gra | rgc | rgc | rra | 185 |
| WTM: D | aat | grt | grt | grt | gaw | kmt | kmt | raw | 186 |
| WTM: Q | aat | srg | srg | srg | sag | mrs | mrs | mag | 187 |
| WTM: S | aat | rgc | rgc | rgc | rrm | agc | agc | arm | 188 |
| WTM: H | aat | srt | srt | srt | saw | ymt | ymt | maw | 189 |
| WTM: Y | aat | krt | krt | krt | tat gaa | tmt | tmt | aaa tat | 190 |
| WTM: L | aat | skg | skg | skg | swg | tya | tya | mwg | 191 |
| WTM: P | aat | ssg | ssg | ssg | smg | yct | yct | mmg | 192 |

Example 6

Methods for Genetically Engineering a Fibronectin Binding Domain Library

In this example, the steps for making and assembling a universal fibronectin binding domain library using genetic engineering techniques are described. The approach in making the WTM FN3 libraries is summarized below and in FIG. 20.

Figure 21A:
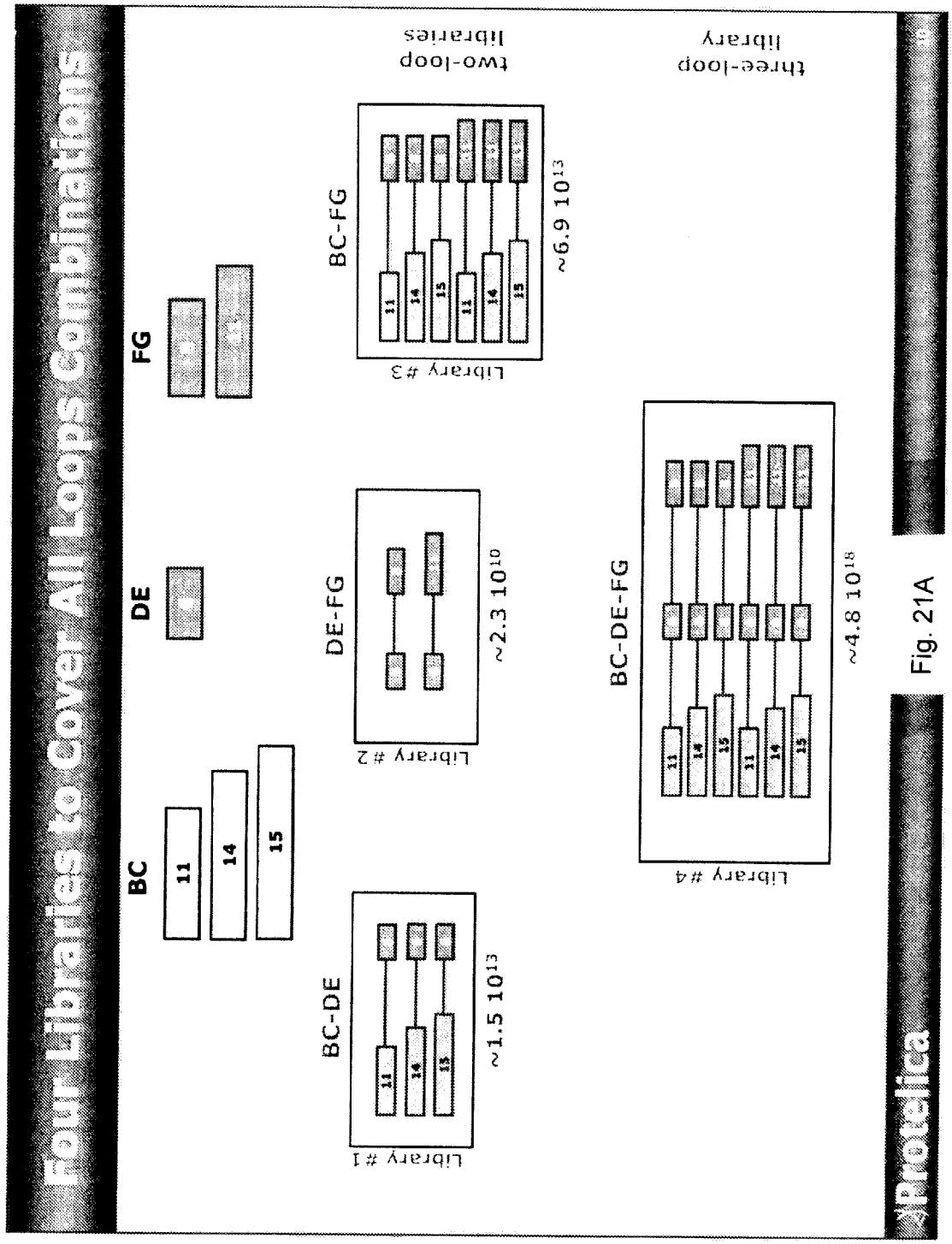
FIGS. 21A and 21B show different combinations of fibronectin loop libraries constructed for use in the invention (FIG. 21A), and diversity by WTM in the BC, DE, and FG variable positions and total fibronectin binding domain library size when combining the different FN3 loops (FIG. 21B).

FIG. 21A shows various combinations of variable loop sequences in various combinations of BC, DE, and FG loops. As seen, there are three separate two-loop libraries designated #1-3 for the BC-DE, DE-FG, and BC-FG libraries, respectively. Library #1 contains three sublibraries of BC-DE loop sequences, one for each of the three different BC loop lengths (11, 14, or 15); library #2, two sublibraries of DE-FG loop sequences, one for each of the two FG loop lengths (8 and 11); and library #3, the six sublibraries of BC-FG loop sequences, one for each of thew three BC lengths and two FG lengths. In the studies reported below, the libraries screened contained all three libraries, i.e., all eight sublibraries. The value below each library indicates the total number of sifferent-sequences peptides contained in each of the three libraries. A fourth library containing sequence varioations in all three loops is also shown.

In preparing the sublibraries, the fibronectin modules are cloned using standard molecular biology techniques. The oligonucleotides encoding the beta-strand scaffold framework and diversity loops of the variable regions are assembled by the single overlap extension polymerase chain reaction (SOE-PCR) as illustrated in FIG. 20. The full-length molecules are then amplified using flanking 5' and 3' primers containing restriction sites that facilitate cloning into the expression-display vector(s). The total diversity of the libraries generated depends on the number of framework sequences and number of positions in the loops chosen for mutagenesis, e.g., using WTM.

Figure 21B:
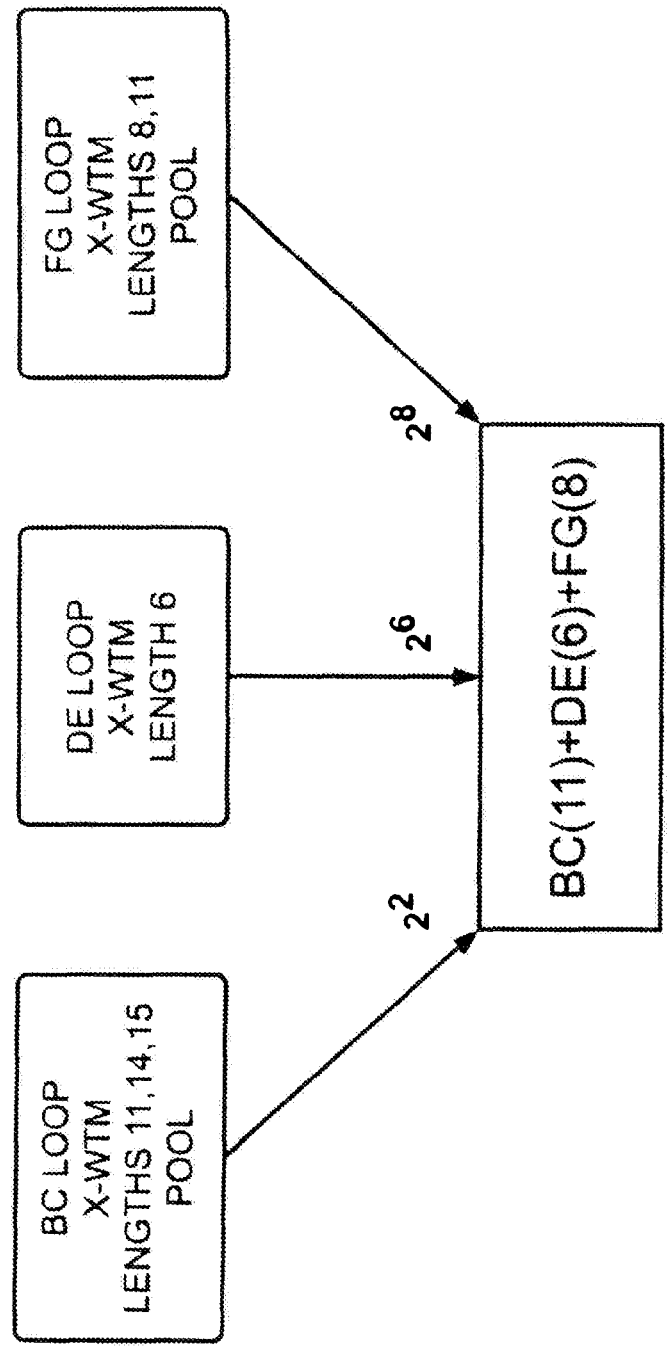
Figure 22:
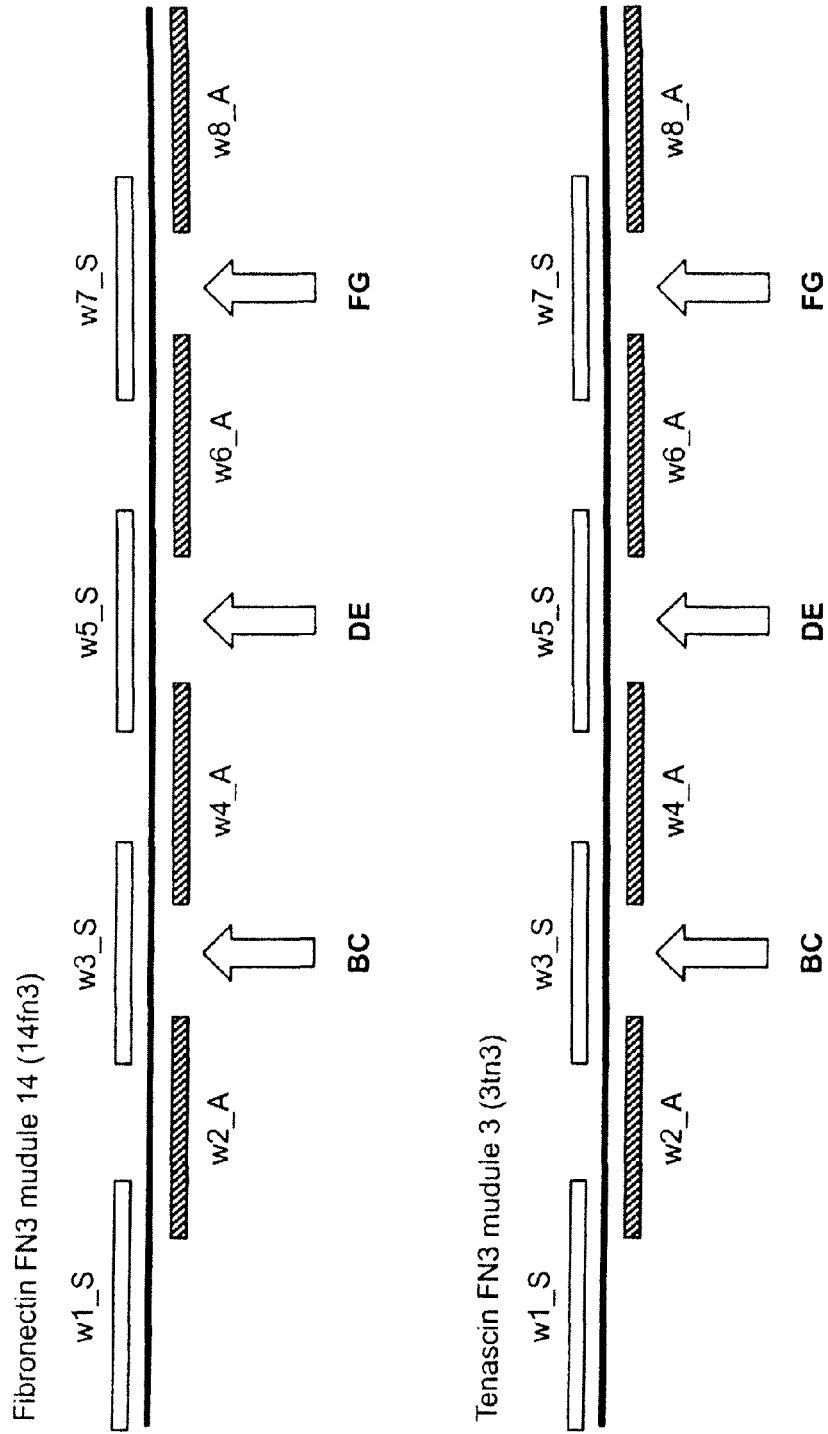
FIG. 22 shows the modular construction using different FN III binding domains of module 14 and Tenascin using their respective set of overlapping non-degenerate and degenerate oligonucleotides. The same BC, DE and FG loop diversity library can be placed into their respective module 14 and Tenascin loop positions.

For example, the diversity of the FN3 BC/11, FN3 DE/6 and FN3 FG/11 library, using 9 amino acids to conduct WTM™, is $3.5 \times 10^6$ ($2^2$ for FN3 BC/11 $\times 2^6$ for FN3 DE/6 $\times 2^8$ for the 13 amino acids FN3 FG/9) (see FIG. 21). The diversity of the is an upper limit and the diversity library from $10^{10}$ to $10^{11}$ which is within the range of the transformation efficiencies of bacterial systems.

Accordingly, 5 oligonucleotides are synthesized to encompass the β-strand frameworks (strands A, B, C, D, E, F, and G) for the fibronectin module libraries. To build a library based on the module $^{10}$FN3 scaffold, the β-strand oligonucleotides are listed below:

A' beta-strand (sense strand encoding the N-terminus of A beta strand with flanking region containing a BamHI restriction site):

```
                                        (SEQ ID NO: 196)
5'-CATATTGCTGGTACTCAGGGATCCGTTAGTGACGTCCCA-3'
```

B'-beta-strand (antisense strand that spans the AB loop):

```
                                        (SEQ ID NO: 197)
TATAAGCAAAGAGGTAGGAGTCGCTGCAACCACTTCCAGATCCCGTGGGAC

GTCACTAAC-3'
```

C'-beta-strand (antisense strand that spans the CD loop):

```
                                        (SEQ ID NO: 198)
5'-AACTGTGAATTCTTGAACTGGTGAGTTGCCACCTGTCTCTCCGTACGT

GATCCGATA-3'
```

D'-beta-strand (antisense strand that spans the EF loop):

```
                                        (SEQ ID NO: 199)
5'-CACTGCATAGACAGTAATGGTATAGTCGACACCGGGCTTAAGTCCAGA

GATAGTTGC-3'
```

F' beta-strand (antisense strand that encodes the C-terminus of the F beta-strand, with flanking region containing an XhoI restriction site):

```
                                        (SEQ ID NO: 200)
5'-ATGAACTGGGTATACTCTCTCGAGCGTCCGATAGTTGATGGA-3'
```

The B', C', D', and F' oligonucleotides described above are depicted in FIG. 20.

In addition, there are two flanking oligonucleotides that code for the N-terminal linker region and a C-terminal linker that have His and Myc immunotags respectively. In addition, a subset of 30-60 degenerate oligonucleotides in FN3 BC/11, FN3 DE/6 and FN3 FG/9 loops are synthesized (total 90-180). These oligonucleotides are assembled by the SOE-PCR method to generate the libraries that include the necessary FN3 BC/11, FN3 DE/6 and FN3 FG/9 combinations.

In the SOE-PCR reactions, the oligonucleotides for β-strands and the designed combinations of the BC, DE and FG loop libraries are added. PCR reactions used: 5 µl of 10 µM oligonucleotide mix, 0.5 µl Pfx DNA polymerase (2.5 U/µl), 5 µl Pfx buffer (Invitrogen), 1 µl 10 mM dNTP, 1 µl 50 mM MgSO4 and 37.5 µl dH20 at 94C for 2 min, followed by 24 cycles of 30 sec at 94C, 30 sec at 50C, and 1 min at 68 C and then incubated for a 68 C for 5 min. The reactions were performed using a programmable thermocycler (MJ Research). An aliquot of the above SOE-PCR reaction is then taken to which the 5' and 3' primer pairs are added to a new PCR reaction.

Random clones from each library are then chosen for sequence verification and assessment of library quality with respect to desired mutational diversity, unintended point mutations, deletions, and insertions. This efficiency contrasts with random/stochastic mutagenesis strategies where uncontrolled introduction of various bases produces higher levels of undesired base change effects leading to low expression or fibronectin binding domains functionality due to unfavorable amino acid usage and inadvertent stop codons.

Individual FN3 modules can then be subsequently linked with together with natural FN linking sequences or use of synthetic poly-Gly-Ser linker (typically GGGGSGGGGSGGGGS) (SEQ ID NO:201) to generate multimeric binding domains.

Example 7

Methods for Performing High-Throughput Affinity Maturation of Candidates from a Universal Fibronectin Binding Domain Library In this example, the steps for identifying and improving a candidate fibronectin binding domain using CBM (combinatorial beneficial mutations)/WTM/LTM affinity maturation is described.

Briefly, a known 9-14 TNFα fibronectin binding domain can be designated as a test clone and mutagenized (using, e.g., CBMWTMLTMtechnology), expressed, displayed, and improved according to the methods of the invention. Regarding loop diversity, LTM is used to explore small perturbations within the loops (e.g., one change per loop). For further improvement, combinatorial beneficial mutagenesis (CBM), is subsequently used to exhaustively incorporate the individual LTM changes into the loop landscape(s).

The test lysozyme fibronectin binding domain was expressed and displayed using phage display, although any of the above-mentioned yeast/bacterial display systems can also be used.

Example 8

Screening and Analysis of WTM 14/FN3 Libraries for Anti-Tnfα Binding Activity

WTM Library Construction

The WTM fibronectin libraries were assembled by polymerase cycling assembly (PCA) and cloned into a phagemid vector. The oligonucleotides share fifteen base pair homology with its reverse orientated neighboring oligonucleotide. The complete fibronectin gene was assembled using eight oligonucleotides. Oligo 3 contains the eleven amino acid BC loop, Oligo 5 encodes the six amino acid DE loop and Oligo 7 contains the 9 amino acid FG loop.

The 8 framework oligos for wildtype 14FN3 are:

```
Oligo 1: 14FN3_FMK_1_S
                                        (SEQ ID NO: 202)
CATATTGCTGGTACTCAGGGATCCAACGTTAGTCCGCCT Oligo 2: 14FN3_FMK_2_S
                                        (SEQ ID NO: 203)
AATTGTGATGGTGGTCTCGGTGGCGTCTGTGACGCGGGCACGCCGAGGCG
GACTAACGTT Oligo 3: 14FN3_FMK_3_S
                                        (SEQ ID NO: 204)
ACCACCATCACAATTAGCTGGCGCACTAAAACGGAAACAATCACCGGTTTC
CAAGTCGACGCA Oligo 4: 14FN3_FMK_4_A
                                        (SEQ ID NO: 205)
GATTGTCCGCTGAATGGGAGTTTGGCCGTTGGCTGGGACTGCGTCGACTTG
GAA
```

```
Oligo 5: 14FN3_FMK_5_S
                                      (SEQ ID NO: 206)
ATTCAGCGGACAATCAAGCCTGACGTTCGTTCTTATACCATTACCGGG Oligo 6: 14FN3_FMK_6_A
                                      (SEQ ID NO: 207)
CAAAGTATACAGGTAGATTTTATAATCAGTTCCTGGCTGTAACCCGGTAAT
GGTATA Oligo 7: 14FN3_FMK_7_S
                                      (SEQ ID NO: 208)
TACCTGTATACTTTGAATGACAACGCGCGTAGCAGTCCGGTGGTTATAGAT
GCCAGC Oligo 8: 14FN3_FMK_8_A
                                      (SEQ ID NO: 209)
TGAACTGGGTATACTCTCGAGCGTGCTGGCATCTATAAC
```

The UF3L-WTM-TYR construction use Oligo 1, Oligo 2, Oligo 4, Oligo 6, and Oligo 8 of the wildtype 14FN3 framework sequence. Oligo 3, Oligo 5A/Oligo 5B, and Oligo 7A/Oligo 7B are replace with the following:

```
Oligo 3: 14FN3UL_w3_S_WTM-TYR
                                      (SEQ ID NO: 210)
ACCACCATCACAATTAGCTGGWMCYMTYMTYMTKRTYMTKWTKATGGCTTC
CAAGTCGACGCA Oligo 5A: 14FN3UL_w5_S_WTM_TYR1
                                      (SEQ ID NO: 211)
ATTCAGCGGACAATCYMTKRTWMCTATWMCTMTTATACCATTACCGGG Oligo 5B: 14FN3UL_w5_S_WTM_TYR2
                                      (SEQ ID NO: 212)
ATTCAGCGGACAATCYMTKRTWMCGAAWMCTMTTATACCATTACCGGG Oligo 7A: 14FN3UL_w7_S_WTM_TYR1
                                      (SEQ ID NO: 213)
TACCTGTATACTTTGAATKMCKMCKRTKWTKRTYMTYMTTMTTMTAAACCG
GTGGTTATAGATGCCAGC Oligo 7B: 14FN3UL_w7_S_WTM_TYR2
                                      (SEQ ID NO: 214)
TACCTGTATACTTTGAATKMCKMCKRTKWTKRTYMTYMTTMTTMTTATCCG
GTGGTTATAGATGCCAGC
```

The 14 amino acid extended BC loop library, UF3L-WTM-TYR-BC_extended, construction use Oligo 1, Oligo 2, Oligo 4, Oligo 6, and Oligo 8 of the wildtype 14FN3 framework sequence. Oligo 3A, Oligo 3B, Oligo 3C, Oligo 3D, Oligo 5A/Oligo 5B, and Oligo 7A/Oligo 7B are the same as in the UF3L-WTM-TYR library.

```
Oligo 3A BC ext: 14FN3UL_w3_15_S_WTM_TYR1
                                      (SEQ ID NO: 215)
ACCACCATCACAATTAGCTGGTATYMTYMTTATKATKATKRTKRTTMTYMT
WWTWMCKRTTTCCAAGTCGACGCA Oligo 3B BC ext: 14FN3UL_w3_15_S_WTM_TYR2
                                      (SEQ ID NO: 216)
ACCACCATCACAATTAGCTGGTATYMTYMTGAAKATKATKRTKRTTMTYMT
WWTWMCKRTTTCCAAGTCGACGCA Oligo 3C BC ext: 14FN3UL_w3_15_S_WTM_TYR3
                                      (SEQ ID NO: 217)
ACCACCATCACAATTAGCTGGGAAYMTYMTTATKATKATKRTKRTTMTYMT
WWTWMCKRTTTCCAAGTCGACGCA Oligo 3D BC ext: 14FN3UL_w3_15_S_WTM_TYR4
                                      (SEQ ID NO: 218)
ACCACCATCACAATTAGCTGGGAAYMTYMTGAGKATKATKRTKRTTMTYMT
WWTWMCKRTTTCCAAGTCGACGCA
```

All eight oligos are mixed together at 10 μM to assemble the fibronectin gene by PCA. The 50 μl Assembly PCR 1 mixture contains 5 μl pooled oligos (10 μM), 10 μl 5× Buffer (Finnzymes), 1 μl 10 mM dNTPs, 0.5 μl Phusion Polymerase (Finnzymes), 33.5 μl diH$_2$O. The PCR protocol is one cycle of 98° C. for 30 sec, followed by 30 cycles of 98° C. for 7 sec, 50° C. for 20 sec, and 72° C. for 15 sec. The final cycle is 72° C. for 1 min.

The 100 μl Rescue PCR mixture contains 2.5 μl of the PCR 1 reaction, 2.5 μl of Oligo 1: 14FN3_FMK_1_S, 2.5 μl of Oligo 8: 14FN3_FMK_8_A, 2 μl 10 mM dNTPs, 20 μl 5× Buffer (Finnzymes), 1 μl Phusion Polymerase (Finnzymes), 69.5 μl diH$_2$O. The PCR protocol is one cycle of 98° C. for 30 sec, followed by 30 cycles of 98° C. for 7 sec, 50° C. for 20 sec, and 72° C. for 15 sec. The final cycle is 72° C. for 1 min.

The PCR amplicons were purified using the Qiagen Qiaquick PCR Clean-up Kit by manufacturer's protocol and eluted off the spin column with 80 μl diH$_2$O. The PCR fragment was digested at 37° C. with the restriction enzymes BamHI (NEB) and XhoI (NEB), gel purified on a 1.2% agarose gel and the DNA band was purified using the Qiagen Gel Extraction Kit.

The backbone DNA for the phage display libraries is a pBluescript-based phagemid vector. This vector features: (1) a N-terminal signal sequence from the *E. Coli* DsbA gene for periplasmic export, (2) a multiple cloning site to insert the FN3-based scaffolds, (3) a c-myc epitope tag for monitoring protein expression, (4) a hexahistidine tag for protein purification, (5) the C-terminal domain (aa250-406) of the M13 p3 protein for display of the FN3 on the phage surface, and (6) an amber stop codon (TAG) inserted between the FN3 and the M13 p3 CTD which allows switching between expression of membrane anchored FN3-p3 fusion proteins and soluble FN3 proteins simply by using different *E. Coli* strains. Expression of fusion proteins is under the control of an inducible lac promoter.

The 20 μg of phagemid vector was digested at 37° C. with the restriction enzymes BamHI (NEB), XhoI (NEB), and Calf Intestinal Alkaline Phosphatase (CIP from NEB) until completion. The backbone DNA was gel purified on a 1.2% agarose gel and the DNA band was purified using the Qiagen Gel Extraction Kit. Overnight ligations were set-up with the phagemid backbone DNA and the gene synthesized PCR fragment. The ligations were purified by phenol/chloroform extraction and ethanol precipitated and electroporated into *E. Coli* XL-1 Blue cells (Stratagene). Library transformation efficiency was determined by serial dilution tittering.

The effective library sizes for UF3L-WTM-TYR-BC extended was 8.0e$^7$ variants and for UF3L-WTM-TYR was 1.2e$^8$ variants.

Phage Display

Phage particle library stocks were produced by starting with an initial inoculum of library TG1 cells at ten times the size of the library (media=2YT, 1% glucose, 50 ug/ml ampicillin). When cells reached an OD$_{600}$=0.5, an MOI=20 of M13K07 helper phage (Invitrogen) is added and the cells are incubated at 37° C. for 30 minutes. Next the cells shake for an additional 30 minutes at 37° C. The cells are spun down and resuspended in induction media (2YT, 50 ug/ml ampicillin, 25 ug/ml kanamycin, and 0.1 mM IPTG) and shaked overnight at 30° C. Phage is purified from the supernatant by standard 20% PEG/2.5M NaCl precipitation protocol and tittered by serial dilution in TG1 cells.

The following conditions were used for the panning of the library against the target TNF-α by phage display. The first three rounds of panning were preformed on Reacti-Bind™ NeutrAvidin™ Coated High Binding Capacity (HBC) Clear 8-well Strips with Superblock® Blocking Buffer (Pierce) and round 4 was done on a MaxiSorp plate (Nunc). This will eliminate any nuetravidin binding phage and phage that only recognize the biotintylated TNF-α target protein. TNF-Negative controls were carried out with no biotintylated-TNFα (R&D Systems) added. Different blocking reagents will be used including BSA, ovalbumin, and instant milk for each round of panning.

For Round 1, 0.25 ug of biotintylated TNF-α in 0.5% BSA blocking solution (100 ul) bound to the plate for two hours and then washed with PBS-0.05% Tween-20. Next the overnight binding buffer was added which contains $1e10^{13}$ library phage particles, 1 uM biotin, and 0.2% BSA, 0.1% Tween-20 in PBS. The next day the wells were washed 5 times with 0.2% BSA, 0.1% Tween-20 in PBS and five more times with 0.05% Tween-20 in PBS. The phage was eluted with 100 ul 100 mM HCL and neutralized in 1 ml of 1.0 M Tris-HCl, pH 8.0. The phage was tittered on TG1 cells. For round 1, the output phage was $1.7e^7$ phage/ml and the negative control was at $2.4e^6$ phage/ml. This is a 7.1 fold increase in enrichment.

For Round 2, 0.25 ug of biotintylated TNF-α in 0.5% ovalbumin blocking solution (100 ul) bound to the plate for two hours and then washed with PBS-0.05% Tween-20. Next the overnight binding buffer was added which contains $1e10^{13}$ Round 1 phage particles, 1 uM biotin, 0.1 mg/ml streptavidin, and 0.2% ovalbumin, 0.1% Tween-20 in PBS. The next day the wells were washed 5 times with 0.2% ovalbumin, 0.1% Tween-20 in PBS and five more times with 0.05% Tween-20 in PBS. The phage was eluted with 100 ul 100 mM HCl and neutralized in 1 ml of 1.0 M Tris-HCl, pH 8.0. The phage was tittered on TG1 cells. For round 2, the output phage was $3.0e^6$ phage/ml and the negative control was at $1.36e^6$ phage/ml. This is a 2.2 fold increase in enrichment.

For Round 3, 0.25 ug of biotintylated TNF-α in 0.5% instant milk blocking solution (100 ul) bound to the plate for two hours and then washed with PBS-0.05% Tween-20. Next the overnight binding buffer was added which contains $1e10^{13}$ Round 2 phage particles, 1 uM biotin, 0.1 mg/ml streptavidin, and 0.2% instant milk, 0.1% Tween-20 in PBS. The next day the wells were washed 5 times with 0.2% instant milk, 0.1% Tween-20 in PBS and five more times with 0.05% Tween-20 in PBS. The phage was eluted with 100 ul 100 mM HCl and neutralized in 1 ml of 1.0 M Tris-HCl, pH 8.0. The phage was tittered on TG1 cells. For round 3, the output phage was $5.66e^7$ phage/ml and the negative control was at $4.16e^7$ phage/ml. This is a 1.4 fold increase in enrichment.

For Round 4, 0.25 ug of biotintylated TNF-α in 0.5% instant milk blocking solution (100 ul) was bound to a MaxiSorp plate for two hours and then washed with PBS-0.05% Tween-20. Next the overnight binding buffer was added which contains $1e10^{13}$ Round 3 phage particles and 0.2% instant milk, 0.1% Tween-20 in PBS. The next day the wells were washed 5 times with 0.2% instant milk, 0.1% Tween-20 in PBS and five more times with 0.05% Tween-20 in PBS. The phage was eluted with 100 ul 100 mM HCl and neutralized in 1 ml of 1.0 M Tris-HCl, pH 8.0. The phage was tittered on TG1 cells. For round 4, the output phage was $1.0e^6$ phage/ml and the negative control was at $3.56e^5$ phage/ml. This is a 2.8 fold increase in enrichment.

Elisa Screening

After the third and fourth rounds of selection, a total of 373 clones were analyzed for TNF-α binding using phage ELISA. Briefly, phage from individual clones was produced by co-infection with M13K07 helper phage in 1 ml cultures in 96-deep well blocks. Phage-containing culture supernatants were then added to microtiter plates coated with the target protein. Following washes with PBS-0.1% Tween-20, bound phage was detected with a mouse anti-M13 antibody horseradish peroxidase conjugate (GE Biosciences) and TMB substrate (Pierce). Positive variants were then screened for binding specificity against VEG-F and nuetravidin plate only.

Figure 24A:
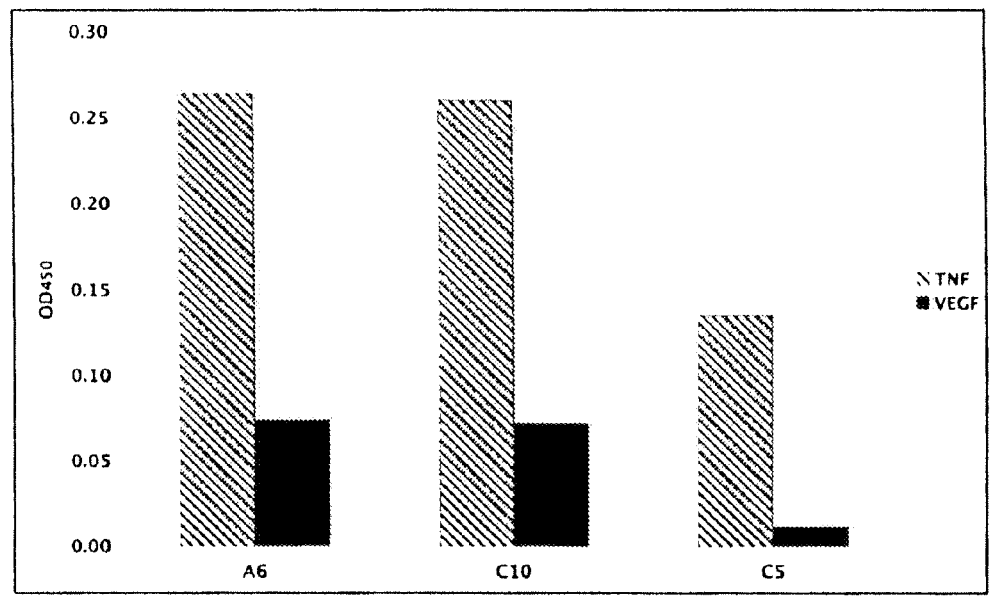
Figure 24B:
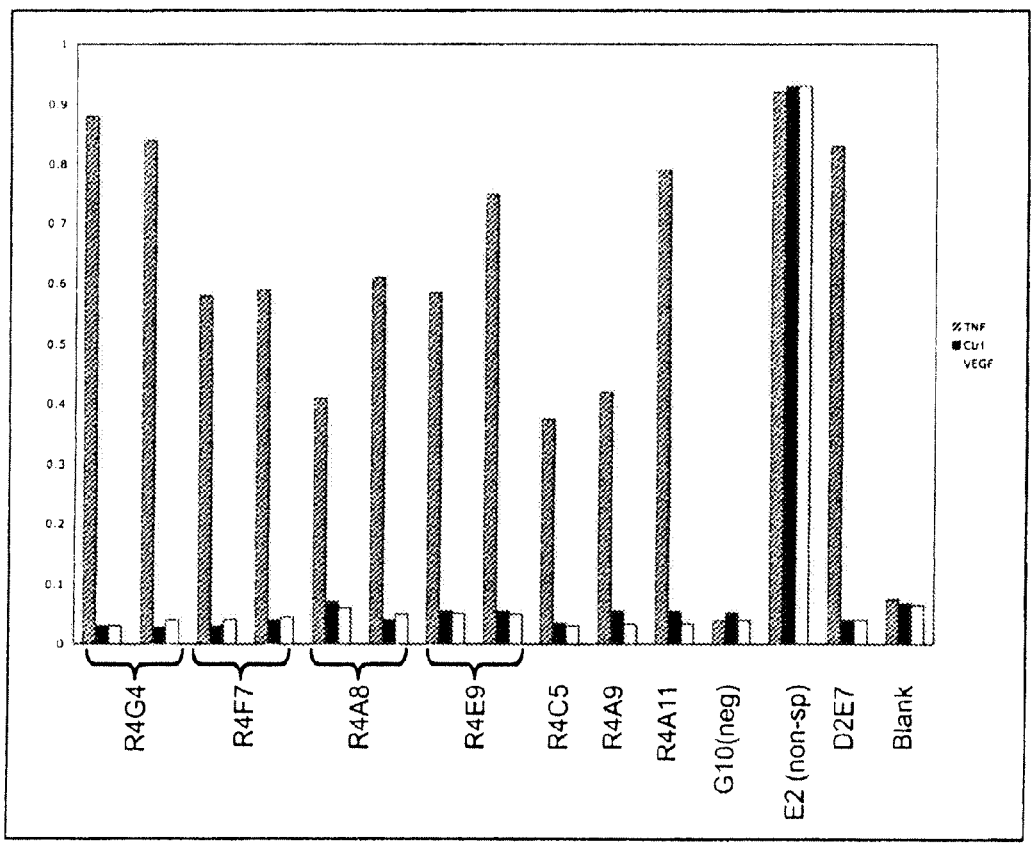

From these assays, 48 positive clones were identified. As shown in FIG. 24b, these clones bound TNF-α but not VEGF or a blank well, indicating specific binding to TNF-α.

Three of these clones were screened for further analysis. The variants were expressed as soluble protein. Transforming the phagemid clone into the non-suppressing TOP10 E. Coli strain produced soluble protein. Protein expression was induced with 1 mM IPTG for 4 hours at 30° C. and the 6×His-tagged protein was purified by Ni-NTA spin columns (Qiagen). ELISA determined the binding specificity of these variants. As seen in FIG. 24a, all three variants bound TNFα, but did not cross-react with VEGF, indicating specific binding to TNFα. The results of this screen demonstrated that the 14FN3 scaffold is suitable to generate specific binding proteins.

Sequencing

After sequencing the 48 positive clones, 9 unique variants were identified. Sequencing of the anti-TNFα variants revealed significant convergence of the sequences, particularly in the BC and FG loops, as several of the clones contained the same FG loop. Interestingly, all the variants recovered were from the tyrosine WTM libraries, with a clear preference for a BC loop length of 14 amino acids. In addition, all of the variants contained cysteine residues in the BC and FG loops, with a definite selection for cysteines at positions 26C in the extended BC loop and 82 in the FG loop. The presence of these cysteines suggests that a disulfide bond may form between the BC and FG loop in these variants. Formation of a disulfide bridge between the BC and FG loops could serve to stabilize the 14FN3 structure and bring the loops closer together, resulting in a larger contact surface with TNFα and a higher binding affinity.

Figure 24C:
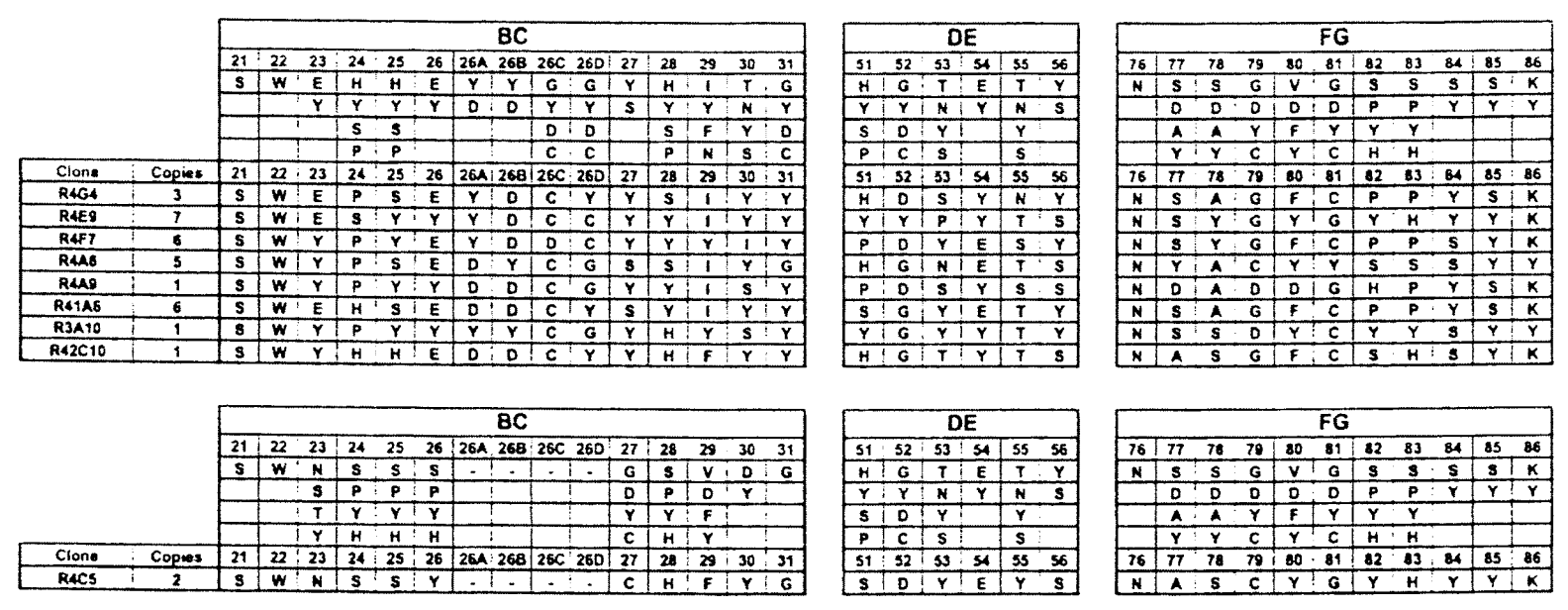

The sequences of 8 high-affinity binders are shown in FIG. 24C, and the nine high-affinity binders are identified as SEQ ID NOS: 55-63.

Cloning 14FN3 TNFα Binder as Fc Construct

To examine the properties of a 14FN3-Fc fusion, the best anti-TNFα variant, R41A6, was expressed as an Fc fusion protein. The template DNA for the Fc was from clone MGC: 39273 IMAGE:5440834 9 (Ref ID: BC024289). The following oligonucleotides were used to PCR amplify the R41A6 gene with NcoI and XhoI restriction sites and the Fc region of human IgG, with XhoI ends.

```
14FN3 NcoI For:
                                    (SEQ ID NO: 219)
ATCGCCATGGAAAACGTTAGTCCGCCTCGGCGT

14FN3 FMK 8 A:
                                    (SEQ ID NO: 220)
ATGAACTGGGTATACTCTCTCGAGCGTGCTGGCATCTATAAC

Fc XhoI For:
                                    (SEQ ID NO: 221)
ATCGCTCGAGCCCAAATCTTGTGACAAAAC

Fc XhoI Rev:
                                    (SEQ ID NO: 222)
CGATCTCGAGTTTACCCGGAGACAGGGAGA
```

The PCR reaction for A6 amplification contained 2 ul phagemid R41A6 mini-prep DNA (100 ng), 1 ul of 14FN3 NcoI For primer (20 uM), 1 ul of 14FN3 FMK 8 A primer (20 uM), 1 ul 10 mM dNTPs (NEB), 5 ul 10× Standard Taq Reaction Buffer (NEB), 1 ul Taq DNA Polymerase (NEB), and 39 ul $diH_2O$. The PCR reaction for Fc amplification contained 2 ul Origene clone BC024289.1 mini-prep DNA (100 ng), 1 ul of Fc XhoI For primer (20 uM), 1 ul of Fc XhoI Rev primer (20 uM), 1 ul 10 mM dNTPs, 5 ul 10× Standard Taq Reaction Buffer (NEB), 1 ul Taq DNA Polymerase (NEB), and 39 ul diH$_2$O.

The PCR protocol is one cycle of 94° C. for 2 min., followed by 25 cycles of 94° C. for 30 sec, 60° C. for 30 sec, and 75° C. for 4 min. The final cycle is 75° C. for 3 min.

First the TNF-α binder R41A6 gene was cloned into the pET-20b expression vector (Novagen). This vector contains the pelB signal sequence for periplasmic targeting of the protein and also a C-terminal hexahistidine tag for purification. The 20 µg of pET-20b vector was digested at 37° C. with the restriction enzymes NcoI (NEB), XhoI (NEB), and Calf Intestinal Alkaline Phosphatase (CIP from NEB) until completion. The backbone DNA was gel purified on a 1.2% agarose gel, and the DNA band was purified using the Qiagen Gel Extraction Kit. The PCR amplicons were purified using the Qiagen Qiaquick PCR Clean-up Kit by manufacturer's protocol and eluted off the spin column with 80 µl diH$_2$O. The R41A6 PCR fragment was digested at 37° C. with the restriction enzymes NcoI (NEB) and XhoI (NEB), gel purified on a 1.2% agarose gel and the DNA band was purified using the Qiagen Gel Extraction Kit. Overnight ligations were set-up with the digested pET-20b backbone DNA and R41A6 PCR fragment. The ligation DNA (1 ul) was electroporated into TOP10 cells (Invitrogen) and clones selected on LB-AMP plates. Clone pET-20b+TNF A6 #27 was recovered after screening mini-prep DNA by restriction digest and sequencing.

Next the Fc fragment is cloned into the XhoI site of the vector pET-20b+TNF A6 #27. The 20 µg of pET-20b+TNF A6 vector was digested at 37° C. with the restriction enzymes XhoI (NEB), and Calf Intestinal Alkaline Phosphatase (CIP from NEB) until completion. The backbone DNA was gel purified on a 1.2% agarose gel, and the DNA band was purified using the Qiagen Gel Extraction Kit. The PCR amplicons were purified using the Qiagen Qiaquick PCR Clean-up Kit by manufacturer's protocol and eluted off the spin column with 80 µl diH$_2$O. The Fc PCR fragment was digested at 37° C. with the restriction enzymes XhoI (NEB), gel purified on a 1.2% agarose gel and the DNA band was purified using the Qiagen Gel Extraction Kit. Overnight ligations were set-up with the digested pET-20b+TNF A6 #27 (A6) backbone DNA and Fc PCR fragment. The ligation DNA (1 ul) was electroporated into TOP10 cells (Invitrogen) and clones selected on LB-AMP plates. Clone pET-20b+TNF A6+Fc #39 (A6+Fc) was recovered after screening mini-prep DNA for the correct orientation by restriction digest and sequencing.

The A6 and A6+Fc clones were expressed in BL-21(DE3) cells (Invitrogen) and purified using Talon Magnetic beads (Invitrogen). The A6 and A6+Fc clones in BL-21 were grown to a density of OD$_{600}$=0.6 in LB media with 100 ug/ml ampicillin. At this density, IPTG was added to a final concentration of 1 mM, and the cells were put in the shaker at 30° C. for 4 hours. Cell pellets were frozen overnight at −80° C.

Thawed cell pellets were resuspended in lysis buffer (50 mM Sodium phosphate, pH 8, 500 mM NaCl, 40 mM Imidazole, 5% glycerol, 1× Bugbuster detergent (EMD), 1× protease inhibitors (Sigma), and 1 ul Lysonase (EMD)) and mix for 20 minutes at 4° C. Lysate is spun down at 14,000 rpm for 20 minutes at 4° C. and mixed with Talon magnetic beads for 1 hour at 4° C. Beads were pelleted on a magnet and washed five times with wash buffer (50 mM Sodium phosphate, pH 8, 500 mM NaCl, 40 mM Imidazole, 5% glycerol, and 0.01% Tween-20). Protein was eluted two times with 350 ul elution buffer (50 mM Sodium phosphate, pH 8, 500 mM NaCl, 150 mM Imidazole, 5% glycerol, and 0.01% Tween-20) and buffer exchanged into PBS using a 2 ml Zeba desalting column (Pierce). Protein concentration was quantified using the CBQCA Protein Quantification Kit (Invitrogen).

The $K_a$, $K_{dis}$, and $K_D$ values for soluble protein A6 and A6+Fc were determined using an Octet instrument (ForteBio), which measures refracted surface light interference. The target protein was biotintylated TNF-α soluble protein (R&D Systems) and is at a concentration of 0.25 ug/ml for loading onto the streptavidin sensor tips. The A6 protein was loaded at 290 nM and the A6+Fc protein was loaded a 370 nM. The Octet was run using the manufacturers protocol for Basic Kinetic Assay. The $K_D$ for A6 is between 20-100 nM and the $K_D$ for A6+Fc is between 12-25 nM. The $K_{off}$ for A6+Fc was improved 2 fold as compared to the monomeric A6 protein. These results demonstrate that adding the Fc region to a 14FN3 binder can improve its binding properties.

| Kinetic Binding Summary | | | |
|---|---|---|---|
| | Kon [1/Ms] | Koff [1/s] | KD |
| A6 + Fc | 9.12E+03 | 2.26E−04 | 24.8 nM |
| A6 + Fc | 1.49E+04 | 2.20E−04 | 14.9 nM |
| A6 + Fc | 1.95E+04 | 2.29E−04 | 11.7 nM |
| A6 | 2.37E+04 | 4.38E−04 | 18.4 nM |
| A6 | 2.74E+03 | 2.67E−04 | 97.4 nM |

Example 9

Screening and Analysis of Fn3 Libraries for Anti-VEGF Binding

In order to test the functionality of our combinatorial library design, a 14FN3 library with 2 natual-variant combinatorial loops (BC/11 andf DE/6) for binders designed. The library was constructed to contain the natural-variant amino acids or chemical equivalents shown at the top in FIG. 25B for the BC loop. A comparison of the natural amino acid variants given in FIG. 9 and those incorporated into the BC loop (FIG. 25A) shows that in general, the highest occurring 1-6 amino acid variants or their chemical equivalents were selected for at each position, where the number selected depended on the frequency distribution of the variants, minimizing where necessary codon changes leading to co-produced amino acids, such that the average number of variants per residue was somewhat greater than 4, yielding a total diversity of about $10^6$. Similarly, the DE/6 loop was constructed to contain the natural-variant amino acids or chemical equivalents shown at the top in FIG. 25B for the BC loop. A comparison of the natural amino acid variants given in FIG. 12 and those incorporated into the DE loop (FIG. 25A) shows that in general, the highest occurring 6 amino acid variants or their chemical equivalents were used at each position, except for position 1 where all nine variants were used. The greater average number of variants at each position was guided, in part, on the fewer number of residue positions, allowing more residues at each position while still retaining a total diversity of less than about $10^5$.

The library was constructed in the phagemid vector as described above. To screen the library, phage were incubated with biotinylated VEGF(121) that had been pre-bound to streptavidin-coated magnetic beads for 1 hr at room temperature in PBS-2.5% nonfat dry milk. Following washes with PBS-0.1% Tween-20, bound phage were eluted with 0.1 N HCl and propagated in TG1 cells for the next round of selection. In round 1 the VEGF concentration used was 1 µM and this was reduced 5-fold per round such that the final round of selection contained 20 nM VEGF. To measure relative enrichment, phage prepared from a non-displaying control phagemid (pBC), which confers chloramphenicol resistance, were also included in the selection reactions. In each round a 2 to 5-fold enrichment of library phage as compared to the non-displaying control phage was observed (Table 20).

TABLE 20

VEGF 14FN3 Combinatorial Library Selection

| Round | [VEGF] | Phage Titer | Enrichment |
|---|---|---|---|
| 1 | 1 µM | $1.6 \times 10^5$ | ND |
| 2 | 0.2 µM | $1.9 \times 10^5$ | 5 |
| 3 | 40 nM | $4.0 \times 10^5$ | 2 |
| 4 | 20 nM | $4.2 \times 10^5$ | 3 |

Figure 25A:
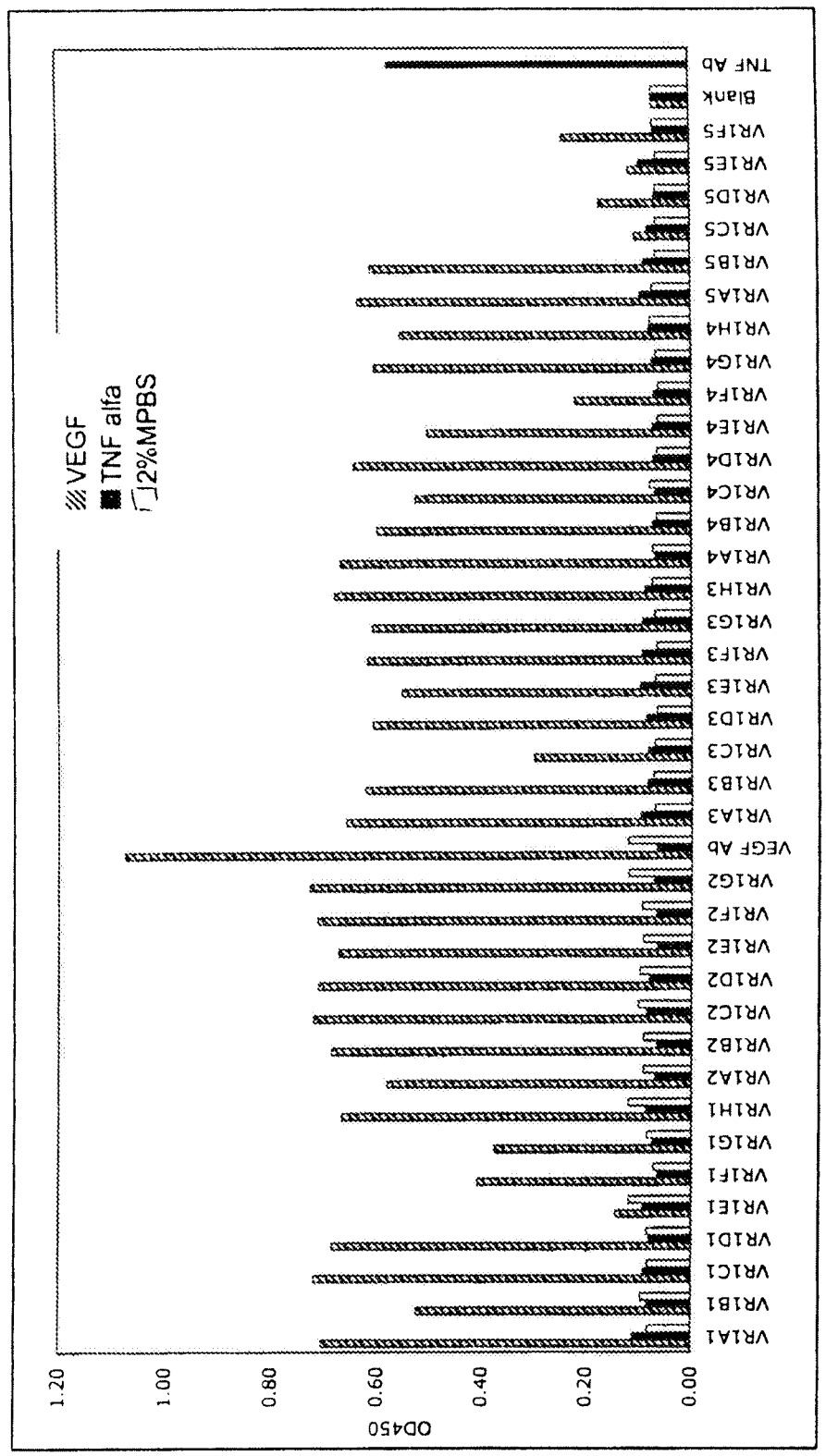
Figure 26B:
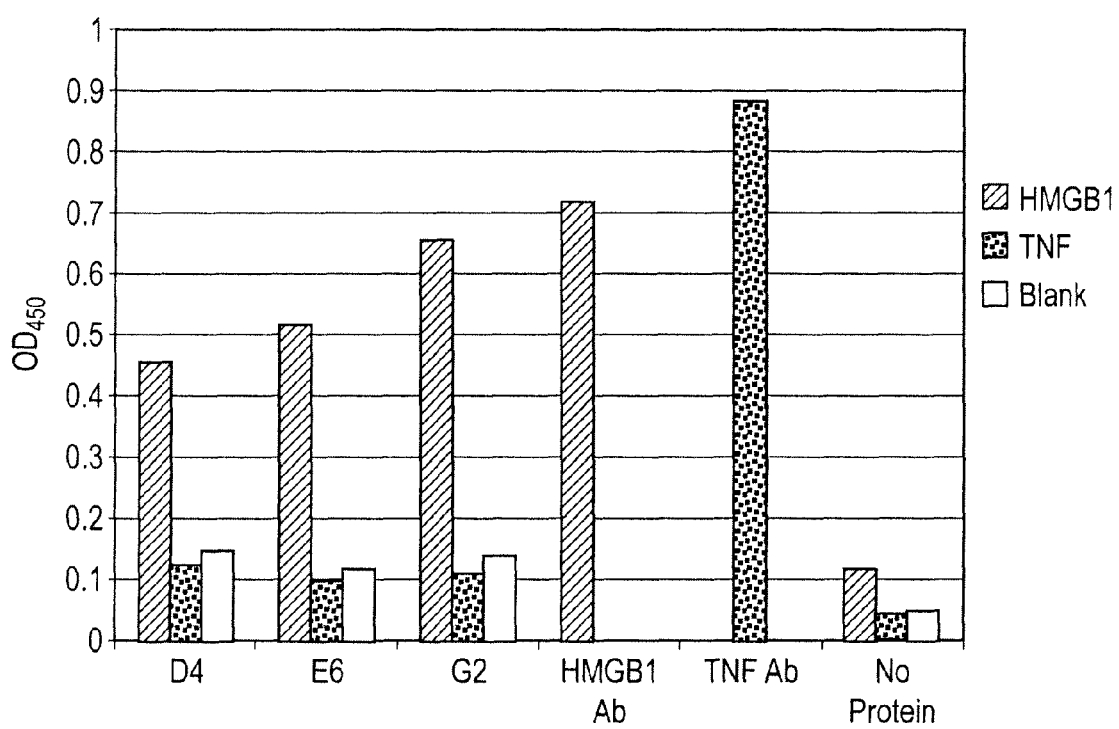

After the selections, individual clones were screened for binding to VEGF by phage ELISA. A total of 380 clones were screened from rounds 3 and 4, identifying 37 positive clones (FIG. 25a). These positive clones were rescreened by phage ELISA for binding specificity against VEGF, TNFα or a blank plate Of these 37 clones, 35 specifically bound VEGF. Sequencing of these clones identified 3 unique variants (FIG. 25b). One variant, R1D4, was found in 29/35 clones, while the other two were seen only once. This indicates significant convergence on a single sequence from the combinatorial library.

Figure 25C:
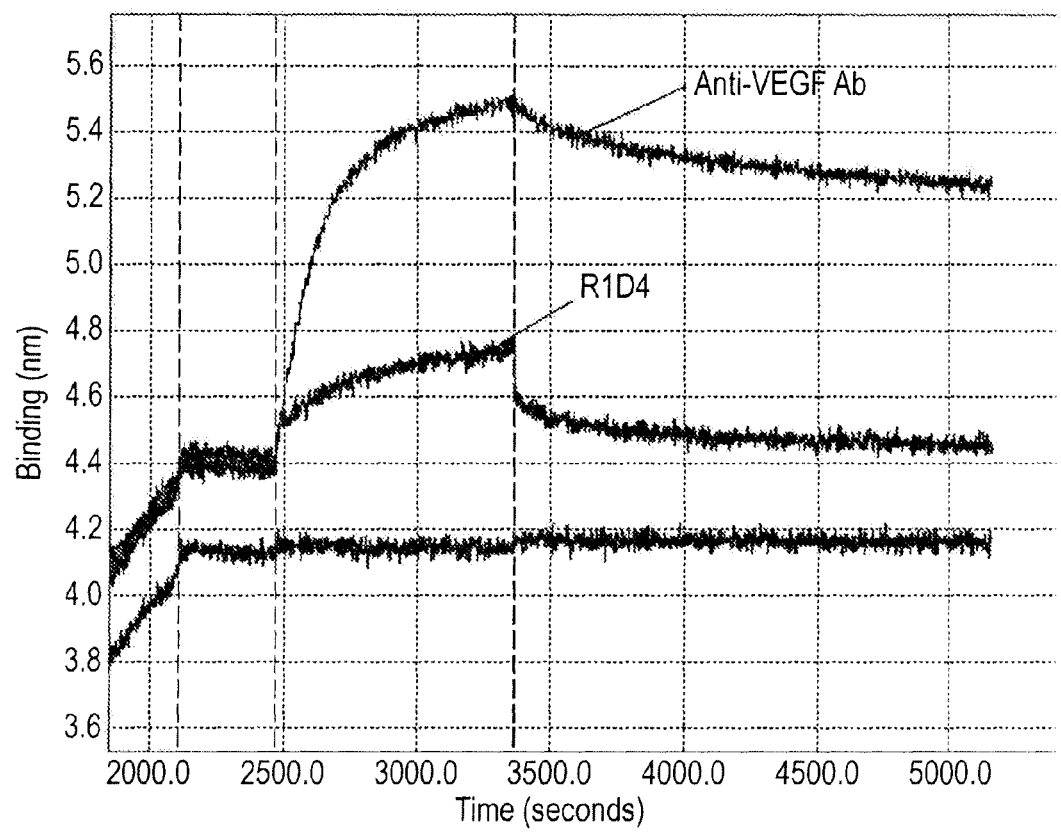

The most abundant clone, R1D4, was selected for further analysis. R1D4 was expressed as a soluble protein and purified using a Ni-chelating column. Using the Octet, the dissociation rate for binding to VEGF was measured as $1.7 \times 10^{-4}$ (FIG. 25c). This is comparable to an anti-VEGF antibody which had a Koff value of $1.1 \times 10^{-4}$. These findings validate the combination of combinatorial library design and 14FN3 scaffold as able to generate binders with significant affinity to their target.

Example 10

Screening and Analysis of FN3 Libraries for Anti-HMGB1 Binding Activity

HMGB1 Screen of 14FN3 Combinatorial Universal Library.

The 14FN3 natural-variant combinatorial library from Example 9 was also against another therapeutic target, HMGB1. (FIG. 26A shows the sequence variation at each position of the BC/11 and DE/6 loops). HMGB1 was initially described as a ubiquitous DNA-binding protein critical for chromatin stabilization and transcriptional regulation. More recently, extracellular HMGB1, when released by either necrotic cells or activated immune cells, has been shown to be an important pro-inflammatory cytokine. To identify 14FN3-based antibody mimics against HMGB1, the 14FN3 2 loop (BC/DE) combinatorial library for HMGB1 binders. Three rounds of phage display selection were performed as described above for VEGF. In round 1, either 0.5 or 0.1 µM HMGB1 was used. This was reduced 2.5-fold each round such that the final round selections contained either 80 or 16 nM HMGB1. In the final round of selection a 900 to 1300-fold enrichment of library phage over a non-displaying control phage was observed (Table 21).

TABLE 21

HMGB1 14FN3 Combinatorial Library Selection

|  | [HMGB1] | Phage Titer | Enrichment |
|---|---|---|---|
| Round 1 | 0.5 µM | $6.3 \times 10^4$ | ND |
|  | 0.1 µM | $1.2 \times 10^5$ |  |
| Round 2 | 0.2 µM | $5.4 \times 10^5$ | 16 |
|  | 40 nM | $5.6 \times 10^5$ | 7 |
| Round 3 | 80 nM | $2.6 \times 10^7$ | 1300 |
|  | 16 nM | $4.4 \times 10^7$ | 898 |

Following the selections, 439 individual clones from rounds 2 and 3 were screened by phage ELISA for binding to HMGB1. This screen resulted in 143 positive clones. Sequencing of 50 of these clones identified 15 unique 14FN3 variants (FIG. 26B, having sequences identified by SEQ ID NOS: 67-81. The most common variant was found in 22/50 clones, while 4 other sequences were also isolated multiple times. Interestingly, we observed significant similarity between the sequences, indicating convergence on a common set of traits. There was a clear selection for basic amino acids in the DE loop, in particular a KR(S/T)-H motif. The BC loop also contains several conserved residues: such as the valine or isoleucine at positions 24 and 29 and the arginine at positions 21 and 31. The similarities between the variants suggest that they may recognize a common epitope in HMGB1.

To analyze these variants effectively, a small-scale expression system to produce soluble protein was developed. Each clone was transformed into the non-suppressing E. coli strain NEB Express lq. Next, a 2 ml culture was induced with 1 mM IPTG for 6 hrs at 30° C. The 6xHis-tagged 14FN3 variants were then purified using Talon magnetic beads (Invitrogen). This procedure yielded from 5 to 10 µg of each soluble protein.

Figure 26C:
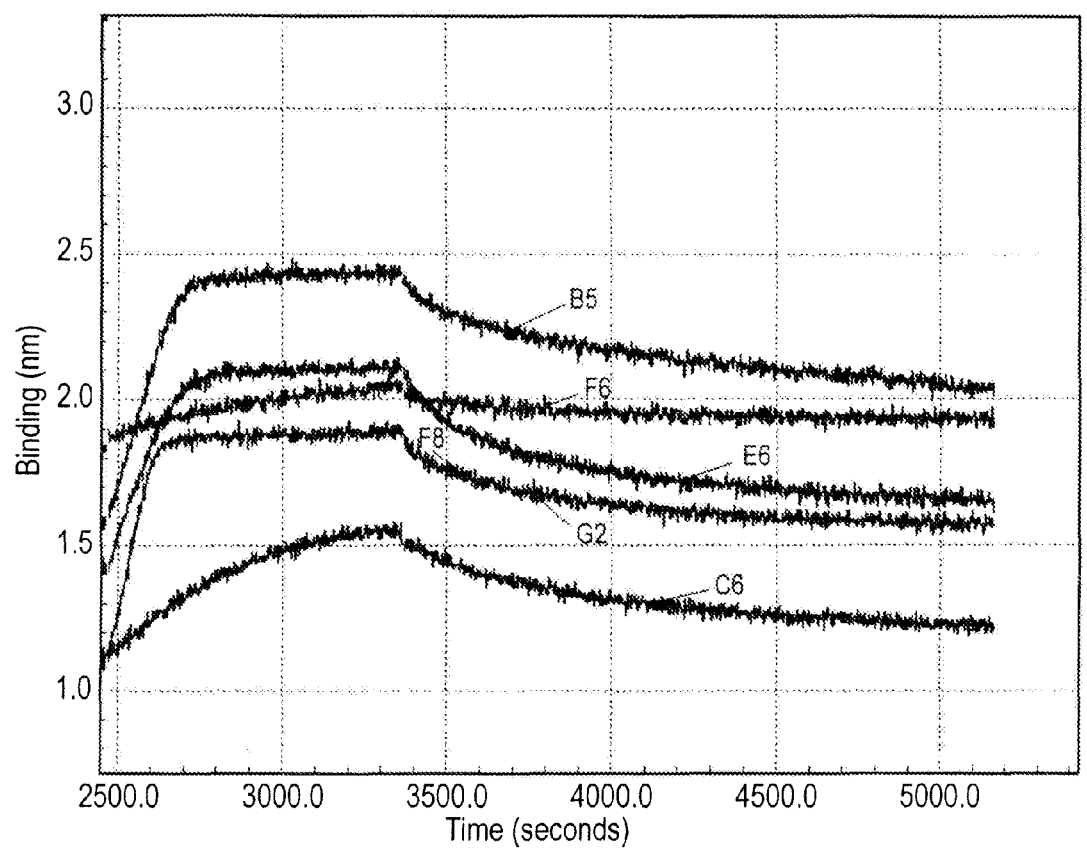

To determine the relative affinities of the variants, the dissociation rates of the individual proteins were measured using the Octet. Since the dissociation rate is the largest contributor to binding affinity and is not dependent on protein concentration, this analysis allowed us to quickly screen the variants and select the best proteins for further characterization. The clones displayed a range of dissociation rates from $1.4 \times 10^{-2}$ to $1.0 \times 10^{-6}$, with the majority between 1.5 to $2.0 \times 10^{-4}$. Dissociation rates in this range suggest that these binders have a high affinity for HMGB1. We then selected six candidates for further investigation. We measured association and disassociation rates using the Octet (FIG. 26C). Table 22 below shows that the obtained $K_d$ values are in the low-nanomolar range.

Figure 27A:
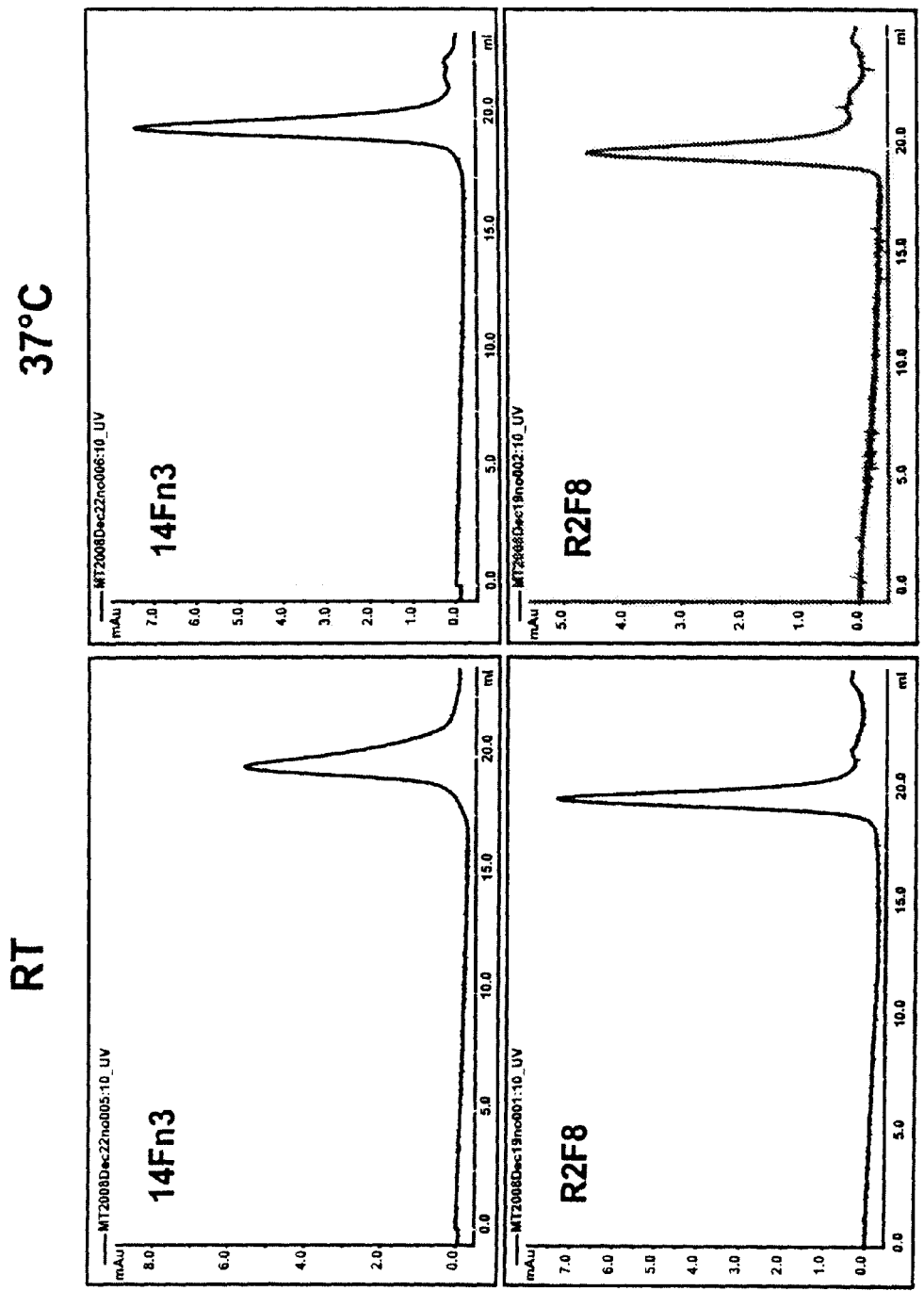
FIGS. 27A and 27B show (FIG. 27A) elution profiles by size exclusion chromatography of R2F8 and wild-type 14FN3 that had been incubated in PBS at the indicated temperature for 18 hrs, showing in both cases a single major peak of the correct size, and (FIG. 27B) the in vitro serum stability of R2F8 and wild-type 14FN3 after incubation in human serum at 37° C. for the indicated times, and detection by immunoblot.
Figure 27B:
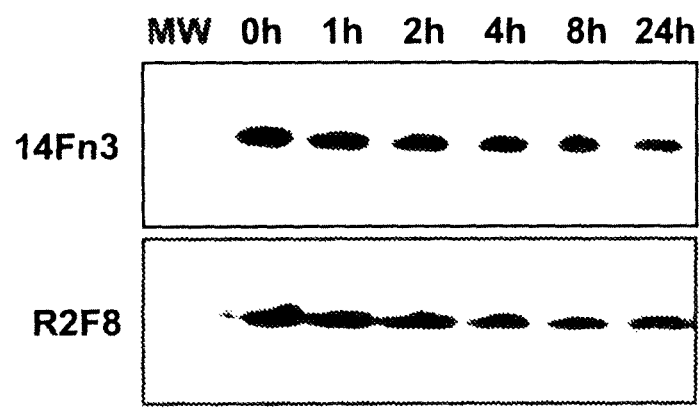

FIG. 27A shows size-exclusion elution profiles for the R2F8 HMGB1 FN3 and wild-type peptides after incubation at the indicated temperature for 18 hours. The profiles show a single peak at the correct monomer size for both peptides. FIG. 27B shows immunoblots for the R2F8 HMGB1 FN3 and wild-type peptides after incubation in human serum at 37° C. for the indicated times, demonstrating serum stability of the binding agent for up to 24 hours.

Figure 28:
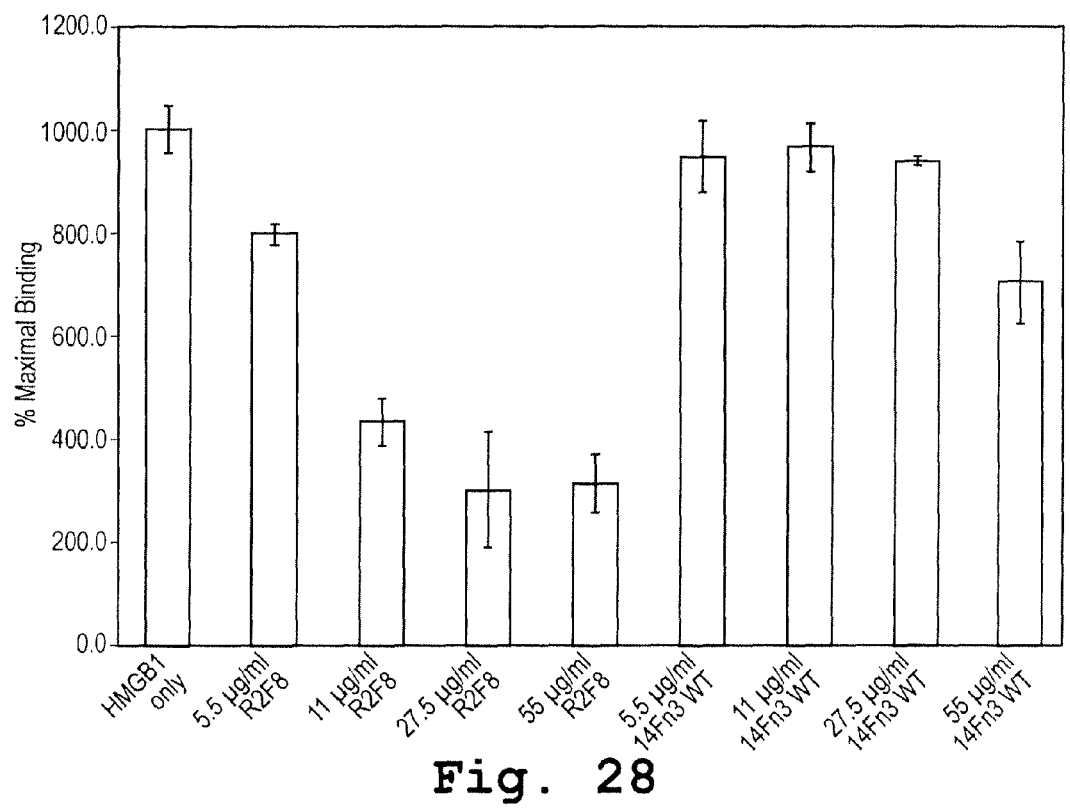
FIG. 28 plots the % HMGB1 binding to RAGE, when biotinylated HMGB1 was pre-incubated with the indicated molar ratios of R2F8 or wild-type 14FNN3 protein prior to binding to immobilized RAGE.

FIG. 28 shows that the R2F8 peptide blocks binding of HMGB1 to the RAGE receptor in a dose dependent manner. In this study, biotinylated HMGB1 was pre-incubated with the indicated molar ratios of R2F8 or wild-type 14FN3 peptide prior to binding to immobilized RAGE, and binding of HMGB1 was detected with streptavidin-HRP with TMB substrate. R2F8 blocked HMGB1 binding to the receptor in a dose dependent manner, while wild-type 14FN3 had essentially no effect.

TABLE 22

| Clone | Tm | Kon/$10^3$($M^{-1} s^{-1}$) | Koff/$10^{-4}$($M^{-1}$ ($s^-$ | KD (nM) |
|---|---|---|---|---|
| R2B5 | — | 4.35 | 2.87 | 65.8 |
| P2C6 | — | 9.54 | 9.91 | 104 |
| R2E6 | — | 5.04 | 9.55 | 189 |
| R2F8 | 48.9 | 7.58 | 2.67 | 35.3 |
| R2G2 | — | 1.84 | 4.90 | 266 |
| P2F3 | 52.7 | 97.9 | 2.71 | 277 |
| P1E8 | — | 1.69 | 3.25 | 192 |
| R2D4 | 57.0 | 1.30 | 2.06 | 159 |
| 14Fn3 WT | 74.9 | — | — | — |

Example 11

Screening and Analysis of FN3 Libraries for Catalytic Function

Protease Activity Plate Assays

In the case where the activity to be assayed is a proteolytic activity, substrate-containing nutrient plates can be used for screening for colonies which secrete a protease. Protease substrates such as denatured hemoglobin can be incorporated into nutrient plates (Schumacher, G. F. B. and Schill, W. B., Anal. Biochem., 48: 9-26 (1972); Benyon and Bond, Proteolytic Enzymes, 1989 (IRL Press, Oxford) p. 50). FN3 variant libraries can be displayed on the yeast cell surfaces or bacterial cell surfaces {Rutherford, 2006 #60} {Varadarajan, 2005 #61} as fusion proteins.

Alternatively, when bacterial colonies capable of secreting a protease are grown on these plates, the colonies are surrounded by a clear zone, indicative of digestion of the protein substrate present in the medium. A protease must meet several criteria to be detected by this assay. First, the protease must be secreted into the medium where it can interact with the substrate. Second, the protease must cleave several peptide bonds in the substrate so that the resulting products are soluble, and a zone of clearing results. Third, the cells must secrete enough protease activity to be detectable above the threshold of the assay. As the specific activity of the protease decreases, the threshold amount required for detection in the assay will increase. Proteases that are produced as phage p3 fusion proteins are also capable of enzymatic function (REF).

One or more protease substrates may be used. For example, hemoglobin (0.05-0.1%), casein (0.2%), or dry milk powder (3%) can be incorporated into appropriate nutrient plates. Colonies can be transferred from a master plate using and inoculating manifold, by replica-plating or other suitable method, onto one or more assay plates containing a protease substrate. Following growth at 37° C. (or the appropriate temperature), zones of clearing are observed around the colonies secreting a protease capable of digesting the substrate. Four proteases of different specificities and reaction mechanisms were tested to determine the range of activities detectable in the plate assay. The enzymes included elastase, subtilisin, trypsin, and chymotrypsin. Specific activities (elastase, 81 U/mg powder; subtilisin, 7.8 U/mg powder; trypsin, 8600 U/mg powder; chymotrypsin, 53 U/mg powder) were determined by the manufacturer. A dilution of each enzyme, elastase, subtilisin, trypsin, and chymotrypsin, was prepared and 5 µl aliquots were pipetted into separate wells on each of three different assay plates.

Plates containing casein, dry milk powder, or hemoglobin in a 1% Difco bacto agar matrix (10 ml per plate) in 50 mM Tris, pH 7.5, 10 mM CaCl.sub.2 buffer were prepared. On casein plates (0.2%), at the lowest quantity tested (0.75 ng of protein), all four enzymes gave detectable clearing zones under the conditions used. On plates containing powdered milk (3%), elastase and trypsin were detectable down to 3 ng of protein, chymotrypsin was detectable to 1.5 ng, and subtilisin was detectable at a level of 25 ng of protein spotted. On hemoglobin plates, at concentrations of hemoglobin ranging from 0.05 and 0.1 percent, 1.5. ng of elastase, trypsin and chymotrypsin gave detectable clearing zones. On hemoglobin plates, under the conditions used, subtilisin did not yield a visible clearing zone below 6 ng of protein.

Example 12

Screening and Analysis of FN3 Libraries for Anti-VEGFR2 Binding Activity

VEGFR2Screen of 14FN3 Combinatorial Universal Library.

The 14FN3 natural-variant combinatorial library from Example 9 and FIGS. 23A-23C was screened against VEGFR2. VEGF-2 appears to mediate almost all of the known cellular responses to VEGF, and thus a peptide capable of binding to VEGFR2 would function to block such responses. In particular, a VEGFR2 inhibitor has the potential to block the growth of new blood vessles that tumors need for growth and thus can function as an anti-cancer agaent. A VEGFR2 bbinding peptide could also be used in the treatment of other vascular proliferation conditions, such as macular degeneration.

To identify 14FN3-based antibody mimics against VEGFR2, the 14FN3 2 loop (BC/DE) (DE-FG), and (BC-FG) combinatorial libraries described above were used to select fibronectin peptides that had a binding dissociation constant $K_d$ of greater than 300 nM, i.e., produced half-occupied binding with the VEGFR2 target at concentrations of peptide no higher than 300 nM. As noted above, each two-loop library consisted of sublibraries of the three BC loops (11, 14, and 15), the one DE loop and the two FG loops (8 and 11). One or more rounds of phage display selection were performed as described above for VEGF. In round 1, either 0.5 or 0.1 µM VEGFR2 was used. A total of 480 peptide sequences that showed elevated binding were analyzed, yielding 109 unique sequences, identified as SEQ ID NOS: 223-331. A sequence analysis showing the amino acid variations in the identified peptides is shown in FIGS. 30A-30F, illustrating the variability in sequences seen among the peptides, particularly in the BC loop.

The 10 most common variants for the VEGFR2 binding peptides are shown in the Table 23 below, where each peptide is identified by its 15-digit code number, SEQ ID NO, the number of peptides having that sequence present in the original 480 identified peptides (shown in parenthesis) and the actual aminod acid sequence of the peptide. Thus, for example, the first entry in the table represents peptide 1637103_VGR2H03 identified by SEQ ID N: 273, occurring in 167 of the 480 high-binding peptides screened, and having the amino acid sequence shown. Peptides that have the highest occurrences numbers among the 480 peptides identified are assumed to have the highest binding affinities for VEGFR2.

TABLE 23

1. 1637103_VGR2H03, SEQ ID NO: 273 (167)
NVSPPRRARVTDATETTITIRWRVAGSEFDSFQVDAVPANGQTPIQRTIH
AATTTYTITG LQPGTDYKIYLYTLNDNARSSPVVIDAST

TABLE 23-continued

```
2. 1637102_VGR2D12, SEQ ID NO: 226 (22)
NVSPPRRARVTDATETTITIRWERSGGPVDGFQVDAVPANGQTPIQRTIN
ADTNIYTITGLQPGTDYKIYLYTLNDNARSSPVVIDAST 3. 1637102_VGR2E11, SEQ ID NO: 295 (20)
NVSPPRRARVTDATETTITISWRTKTETITGFQVDAVPANGQTPIQRTIE
TGARGYTITGLQPGTDYKIYLYTLNEDGGSAYTELTGVIDAST 4. 1637103_VGR2F12, SEQ ID NO: 275 (20)
NVSPPRHARVTDATETTITIRWRVAGSEFDSFQVDAVPANGQTPIQRTIH
AATTTYTITGLQPGTDYKIYLYTLNDNARSSPVVIDAST 5. 1637102_VGR2F11, SEQ ID NO: 270 (16)
NVSPPRRARVTDATETTITIRWTRAAGEVDGFQVDAVPANGQTPIQRTIN
ADTNTYTITGLQPGTDYKIYLYTLNDNARSSPVVIDAST 6. 1637103_VGR2E12, SEQ ID NO: 274 (13)
NVSPPRRARVTDATETTITIRWKVAGGTFDSFQVDAVPANGQTPIQRTIN
AATTTYTITGLQPGTDYKIYLYTLNDNARSSPVVIDAST 7. 1637102_VGR2F04, SEQ ID NO: 229 (9)
NVSPPRRARVTDATETTITIRWKAPEYTGGAEVLGFQVDAVPANGQTPIQ
RTINADTSTYTITGLQPGTDYKIYLYTLNDNARSSPVVIDAST 8. 1637102_VGR2B05, SEQ ID NO: 227 (7)
NVSPPRRARVTDATETTITIRWKQPKEADSQVLSFQVDAVPANGQTPIQR
TINASTNVYTITGLQPGTDYKIYLYTLNDNARSSPVVIDAST 9. 1637102_VGR2C10, SEQ ID NO: 223 (5)
NVSPPRRARVTDATETTITIRWKLPVSADGVVPGFQVDAVPANGQTPIQR
TINADISTYTITGLQPGTDYKIYLYTLNDNARSSPVVIDAST 10. 1637102_VGR2H03, SEQ ID NO: 248 (3)
NVSPPRRARVTDATETTITIRWTLPVQANGIVPGFQVDAVPANGQTPIQR
TIHADVSTYTITGLQPGTDYKIYLYTLNDNARSSPVVIDAST
```

Example 13

Screening and Analysis of FN3 Libraries for Anti-Axl Binding Activity

Axl Screen of 14FN3 Combinatorial Universal Library.

The 14FN3 natural-variant combinatorial library from Example 9 and FIGS. 23A-23C was screened against Axl. Tyrosine-protein kinase receptor UFO is an enzyme that in humans is encoded by the AXL gene. The protein encoded by this gene is a member of the receptor tyrosine kinase subfamily. Although it is similar to other receptor tyrosine kinases, the Axl protein represents a unique structure of the extracellular region that juxtaposes IgL and FNIII repeats. It transduce signals from the extracellular matrix into the cytoplasm by binding growth factors like vitamin K-dependent protein growth-arrest-specific gene 6. It is involved in the stimulation of cell proliferation. This receptor can also mediate cell aggregation by homophilic binding. Axl is a chronic myelogenous leukemia-associated oncogene and also associated with colon cancer and melanoma. Thus, a peptide capable of binding to Axl protein would be useful in the treatment of cancers, including leukemias, colon cancer and melanomas.

To identify 14FN3-based antibody mimics against Axl, the 4FN3 2-loop (BC/DE) (DE-FG), and (BC-FG) combinatorial libraries described above were used to select fibronectin peptides that had a binding dissociation constant $K_d$ of greater than 300 nM, i.e., produced half-occupied binding with the Axl target at concentrations of peptide no higher than 300 nM. As noted above, each two-loop library consisted of sublibraries of the three BC loops (11, 14, and 15), the one DE loop and the two FG loops (8 and 11). One or more rounds of phage display selection were performed as described above for VEGF. In round 1, a total of 768 peptide sequences that showed elevated binding were analyzed, yielding 166 unique sequences that are identified as SEQ ID NOS: 332-498. A sequence analysis showing the amino acid variations in the identified peptides is shown in FIGS. 30A-30C, illustrating the variable in sequence seen among the peptides, particularly in the BC loop.

The 10 most common variants for the Axl binding peptides are shown in the Table 24 below, where each peptide is identified by its 15-digit code number, SEQ ID NO, the number of peptides having that sequence present in the original 768 identified peptides (shown in parenthesis) and the actual amino acid sequence of the peptide. Thus, for example, the first entry in the table represents peptide 1637110_AXLE11 identified by SEQ ID N: 339, occurring in 119 of the 768 high-binding peptides screened, and having the amino acid sequence shown. Peptides that have the highest occurrences numbers among the 768 peptides identified are assumed to have the highest binding affinities for Axl.

TABLE 24

```
1. 1637110_AXLE11, SEQ ID NO: 339 (119)
NVSPPRRARVTDATETTITIRWAQVLSFQVDAVPANGQTPIQRTIKRDVH
SYTITGLQPGTDYKIYLYTLNDNARSSPVVIDAST 2. 1637111_AXLB09, SEQ ID NO: 366 (53)
NVSPPRRARVTDATETTITISWERSESTVVGLQVDAVPANGQTPIQRTIK
PDVRSYTITGLQPGTDYKIYLYTLTVVGKSAHGSSPVVIDAST 3. 1637110_AXLA12, SEQ ID NO: 354 (25)
NVSPPRRARVTDATETTITIRWKVDGFQVDAVPANGQTPIQRTIHRGITV
YTITGLQPGTDYKIYLYTLNDNARSSPVVIDAST 4. 1637112_AXLA04, SEQ ID NO: 392 (31)
NVSPPRRARVTDATETTITISWRTSFQVDAVPANGQTPIQRTIKRGVTSY
TITGLQPGTDYKIYLYTLNDNARSSPVVIDAST 5. 1637116_AXLB02, SEQ ID NO: 452 (16)
NVSPPRRARVTDATETTITIRWPVPGFQVDAVPANGQTPIQRTIHRAVTV
YTITGLQPGTDYKIYLYTLNDNARSSPVVIDAST 6. 1637116_AXLB05, SEQ ID NO: 454 (15)
NVSPPRRARVTDATETTITIRWKVDGFQVDAVPANGQTPIQRTIHRAVNV
YTITGLQPGTDYKIYLYTLNDNARSSPVVIDAST 7. 1637110_AXLF07, SEQ ID NO: 353 (13)
NVSPPRRARVTDATETTITIRWGQFDRFQVDAVPANGQTPIQRTIKRTVH
SYTITGLQPGTDYKIYLYTLNDNARSSPVVIDAST 8. 1637110_AXLH01, SEQ ID NO: 333 (913)
NVSPPRRARVTDATETTITIRWKVDGFQVDAVPANGQTPIQRTITRNTRT
YTITGLQPGTDYKIYLYTLNDNARSSPVVIDAST 9. 1637111_AXLE06, SEQ ID NO: 368 (12)
NVSPPRRARVTDATETTITIRWAVSPSTVVGFQVDAVPANGQTPIQRTIK
PDVRSYTITGLQPGTDYKIYLYTLNVKGGSASASSPVVIDAST 10. 1637111_AXLG02, SEQ ID NO: 369 (12)
NVSPPRRARVTDATETTITIPWAAGIEANGEITGFQVDAVPANGQTPIQR
TIKPDVRSYTITGLQPGTDYKIYLYTLYGAGKTSSPVVIDAST
```

Although the invention has been described with respect to specific embodiments and applications, it will be appreciated that the invention encompasses other embodiments and modifications that are within the scope of the claims.

```
Sequence Listing for SEQ ID NOS: 1-81
SEQ ID NO: 1 (Fn3 module 1)
SGPVEVFITETPSQPNSHPIQWNAPQPSHISKYILRWRPKNSVGRWKEAT

IPGHLNSYTIKGLKPGVVYEGQLISIQQYGHQEVTRFDFTTT

SEQ ID NO: 2 (Fn3 module 2)
SPLVATSESVTEITASSFVVSWVSASDTVSGFRVEYELSEEGDEPQYLDL
```

-continued

PSTATSVNIPDLLPG RKYIVNVYQISEDGEQSLILSTSQTT

SEQ ID NO: 3 (Fn3 module 3)
APDAPPDPTVDQVDDTSIVVRWSRPQAPITGYRIVYSPSVEGSSTELNLP

ETANSVTLSDLQPGVQYNITIYAVEENQESTPVVIQQETTGTPR

SEQ ID NO: 4 (Fn3 module 4)
TVPSPRDLQFVEVTDVKVTIMWTPPESAVTGYRVDVIPVNLPGEHGQRLP

ISRNTFAEVTGLSPGVTYYFKVFAVSHGRESKPLTAQQTT

SEQ ID NO: 5 (Fn3 module 5)
KLDAPTNLQFVNETDSTVLVRWTPPRAQITGYRLTVGLTRRGQPRQYNVG

PSVSKYPLRNLQPASEYTVSLVAIKGNQESPKATGVFTTL

SEQ ID NO: 6 (Fn3 module 6)
QPGSSIPPYNTEVTETTIVITWTPAPRIGFKLGVRPSQGGEAPREVTSDS

GSIVVSGLTPGVEYVYTIQVLRDGQERDAPIVNKVVT

SEQ ID NO: 7 (Fn3 module 7)
PLSPPTNLHLEANPDTGVLTVSWERSTTPDITGYRITTTPTNGQQGNSLE

EVVHADQSSCTFDNLSPGLEYNVSVYTVKDDKESVPISDTIIP

SEQ ID NO: 8 (Fn3 module 8)
AVPPPTDLRFTNIGPDTMRVTWAPPPSIDLTNFLVRYSPVKNEEDVAELS

ISPSDNAVVLTNLLPGTEYVVSVSSVYEQHESTPLRGRQKT

SEQ ID NO: 9 (Fn3 module 9)
GLDSPTGIDFSDITANSFTVHWIAPRATITGYRIRHHPEHFSGRPREDRV

PHSRNSITLTNLTPGTEYVVSIVALNGREESPLLIGQQST

SEQ ID NO: 10 (Fn3 module 10)
VSDVPRDLEVVAATPTSLLISWDAPAVTVRYYRITYGETGGNSPVQEFTV

PGSKSTATISGLKPGVDYTITVYAVTGRGDSPASSKPISINYRT

SEQ ID NO: 11 (Fn3 module 11)
EIDKPSQMQVTDVQDNSISVKWLPSSSPVTGYRVTTTPKNGPGPTKTKTA

GPDQTEMTIEGLQPTVEYVVSVYAQNPSGESQPLVQTAVT

SEQ ID NO: 12 (Fn3 module 12)
NIDRPKGLAFTDVDVDSIKIAWESPQGQVSRYRVTYSSPEDGIHELFPAP

DGEEDTAELQGLRPGSEYTVSVVALHDDMESQPLIGTQST

SEQ ID NO: 13 (Fn3 module 13)
AIPAPTDLKFTQVTPTSLSAQWTPPNVQLTGYRVRVTPKEKTGPMKEINL

APDSSSVVVSGLMVATKYEVSVYALKDTLTSRPAQGVVTTLE

SEQ ID NO: 14 (Fn3 module 14)
NVSPPRRARVTDATETTITISWRTKTETITGFQVDAVPANGQTPIQRTIK

PDVRSYTITGLQPGTDYKIYLYTLNDNARSSPVVIDAST

SEQ ID NO: 15 (Fn3 module 15)
AIDAPSNLRFLATTPNSLLVSWQPPRARITGYIIKYEKPGSPPREVVPRP

RPGVTEATITGLEPGTEYTIYVIALKNNQKSEPLIGRKKT

SEQ ID NO: 16 (Fn3 module 16)
PGLNPNASTGQEALSQTTISWAPFQDTSEYIISCHPVGTDEEPLQFRVPG

TSTSATLTGLTRGATYNIIVEALKDQQRHKVREEVVTV

SEQ ID NO: 17 (Fn3/10, A strand)
VSDVPRDLEVVAAT

SEQ ID NO: 18 (Fn3/10, AB strand)
PT

SEQ ID NO: 19 (Fn3/10, B strand)
SLLI

SEQ ID NO: 20 (Fn3/10, C strand)
YRITYGET

SEQ ID NO: 21 (Fn3/10, CD strand)
GGNSP

SEQ ID NO: 22 (Fn3/10, D strand)
VQEFTV

SEQ ID NO: 23 (Fn3/10, E strand)
ATI

SEQ ID NO: 24 (Fn3/10, EF strand)
SGLKPGVD

SEQ ID NO: 25 (Fn3/10, F strand)
YTITVYAV

SEQ ID NO: 26 (Fn3/10, G strand)
PISINYRT

SEQ ID NO: 27 (Fn3/14, A strand)
NVSPPRRARVTDAT

SEQ ID NO: 28 (Fn3/14, AB strand)
ET

SEQ ID NO: 29 (Fn3/14, B strand)
TITI

SEQ ID NO: 30 (Fn3/14, C strand)
FQVDAVPA

SEQ ID NO: 31 (Fn3/14, CD strand)
NGQTP

SEQ ID NO: 32 (Fn3/14, D strand)
IQRTI

SEQ ID NO: 33 (Fn3/14, E strand)
YTI

SEQ ID NO: 34 (Fn3/14, EF strand)
TGLQPGTD

SEQ ID NO: 35 (Fn3/14, F strand)
YKIYLYTL

SEQ ID NO: 36 (Fn3/14, G strand)
PVVIDAST

SEQ ID NO: 37 (BC/11 consensus)
SWTPPPGPVDG

SEQ ID NO: 38 (BC/14 consensus)
SWKPPDDPNGPITG

SEQ ID NO: 39 (BC/15 consensus)
SWEPPEDDGGSPITG

SEQ ID NO: 40 (DE/6 consensus)
PGTETS

SEQ ID NO: 41 (FG/8 consensus)
NGGGESsk

SEQ ID NO: 42 (FG/11 consensus)
NAAGVGPPSss

SEQ ID NO: 43 (BC/11 original universal)
$X_1WX_2X_3PX_4X_5X_6X_7X_8X_9$ where $X_1$ = R, N, K, S, $X_2$ = T, K, $X_3$ = T, K, Q, P, $X_4$ = T, K, Q, P, $X_5$ = R, E, K, G, $X_6$ = T, K, Q, P, $X_7$ = E, N, D, M, $X_8$ = E, N, K, D, $X_9$ = R, E, K, G, SEQ ID NO: 44 (BC/14 original universal)
$X_1WX_2X_3PX_4X_5X_6X_7X_8X_9IX_{10}X_{11}$ where $X_1$ = R, N, K, S, $X_2$ = Q, K, E, P, T, A, -continued $X_3$ = T, K, Q, P $X_4$ = E, N, K, D, $X_5$ = E, N, K, D, $X_6$ = T, K, Q, P, $X_7$ = N, K, $X_8$ = R, E, K, G, $X_9$ = T, K, Q, P, $X_{10}$ = K, T, Xii = R, E, K, G, SEQ ID NO: 45 (BC/15 original universal)
$X_1WX_2X_3PX_4X_5DGGX_6X_7IX_8X_9$ where $X_1$ = R, N, K, S, $X_2$ = E, K, $X_3$ = T, K, Q, P, $X_4$ = E, K, $X_5$ = E, N, K, D, $X_6$ = R, N, K, S, $X_7$ = T, K, Q, P, $X_8$ = K, T, $X_9$ = R, E, K, G, SEQ ID NO: 46 (DE/6 original universal)
$X_1X_2X_3X_4X_5$ where $X_1$ = T, K, Q, P, $X_2$ = R, E, K, G, $X_3$ = T, K, $X_4$ = E, K, $X_5$ = T, K, $X_6$ = R, N, K, S, SEQ ID NO: 47 (FG/8 original universal)
$X_1X_2X_3X_4X_5S$ where $X_1$ = N, K, $X_2$ = R, E, K, G, $X_3$ = R, E, K, G, $X_4$ = R, E, K, G, $X_5$ = E, K, SEQ ID NO: 48 (FG/11 original universal)
$NX_1X_2GX_3X_4X_5X_6S$ where $X_1$ = A, T, E, K, $X_2$ = A, T, $X_3$ = E, K, V, M, $X_4$ = G, S, $X_5$ = T, K, Q, P, $X_6$ = T, K, Q, P, SEQ ID NO: 49 (BC/11 new universal)
$X_1WX_2X_3X_4X_5X_6X_7X_8X_9X_{10}$ where $X_1$ = S, T, R, P, $X_2$ = T, K, R, A, E, G, $X_3$ = P, A, V, L, R, G, $X_4$ = P, A, S, $X_5$ = P, E, Q, R, A, G, $X_6$ = G, S, $X_7$ = P, E, Q, A, T, K, $X_8$ = F, I, V, $X_9$ = T, I, N, V, A, D, $X_{10}$ = G, S, R, SEQ ID NO: 50 (BC/14 new universal)
$X_1WX_2X_3X_4X_5X_6X_7X_8X_9X_{10}X_{11}X_{12}X_{13}$ where $X_1$ = S, T, R, P, $X_2$ = Q, K, E, P, T, A, $X_3$ = P, E, A, Q, $X_4$ = P, G, $X_5$ = T, K, R, A, E, G, $X_6$ = D, E, K, N, $X_7$ = P, T, A, R, S, G, $X_8$ = N, G, S, D, $X_9$ = G, S, A, T, $X_{10}$ = P, T, A, L, I, V, $X_{11}$ = I, V, L, $X_{12}$ = T, L, P, I, $X_{13}$ = G, S, H, R, N, D, SEQ ID NO: 51 (BC/15 new universal)
$X_1WX_2X_3PX_4X_5X_6GX_7X_8X_9X_{10}X_{11}X_{12}$ where $X_1$ = S, T, R, P, $X_2$ =, Q, K, E, P, T, A $X_3$ = P, E, A, Q, $X_4$ = Q, K, E, L, I, V $X_5$ = Y, N, D, S, T, A, $X_6$ = D, N, S, G, $X_7$ = G, N, $X_8$ = S, R, G, P, T, A, $X_9$ = P, Q, A, E, $X_{10}$ = I, V, L, $X_{11}$ = I, T, L, P, $X_{12}$ = G, N, S, D, SEQ ID NO: 52 (DE/6 new universal)
$X_1X_2X_3X_4X_5X_6$ where $X_1$ = P, T, A, H, N, D, Q, K, E, $X_2$ = G, P, A, S, R, T, $X_3$ = T, D, S, N, G, A, $X_4$ = E, K, T, A, V, I, $X_5$ = T, R, N, S, H, P, $X_6$ = S, T, I, V, A, G, SEQ ID NO: 53 (FG/8 new universal)
$X_1X_2X_3X_4X_5X_6SK$ where $X_1$ = N, K, S, R, $X_2$ = N, S, D, G, R, K, E, $X_3$ = N, S, D, G, R, K, E,, $X_4$ = G, Q, R, E, $X_5$ = E, K, Q, P, T, A, $X_6$ = S, T SEQ ID NO: 54 (FG/11 new universal)
$X_1X_2X_3GX_4X_5X_6X_7X_8SS$ where $X_1$ = N, T, $X_2$ = T, A, I, V, K, E, N, D, $X_3$ = T, A, I, V, K, E, N, D, $X_4$ = T, A, I, V, K, E, N, D, $X_5$ = G, S, $X_6$ = P, E, K, A, Q, T, $X_7$ = P, F, V, S, L, A, $X_8$ = S, T, A SEQ ID NO: 55 TNF-α binder R41A6
NVSPPRRARVTDATETTITISWEHSEDDCYSYIYYFQVDAVPANGQTPIQ

RTISGYETYYTITGLQPGTDYKIYLYTLNSAGFCPPYSKPVVIDAST

SEQ ID NO: 56: TNF-α binder R4G4
NVSPPRRARVTDATETTITISWEPSEYDCYYSIYYFQVDAVPANGQTPIQ

RTIHDSYNYYTITGLQPGTDYKIYLYTLNSAGFCPPYSKPVVIDAST

SEQ ID NO: 57: TNF-α binder R4E9
NVSPPRRARVTDATETTITISWESYYYDCCYYIYYFQVDAVPANGQTPIQ

RTIYYPYTSYTITGLQPGTDYKIYLYTLNSYGYGYHYYKPVVIDAST

SEQ IG NO: 58 TNF-α binder R4F7
NVSPPRRARVTDATETTITISWYPYEYDDCYYYIYYFQVDAVPANGQTPI

QRTIPDYESYYTITGLQPGTDYKIYLYTLNSYGFCPPSYKPVVIDAST

SEQ ID NO: 59 TNF-α binder R4A8
NVSPPRRARVTDATETTITISWYPSEDYCGSSIYGFQVDAVPANGQTPIQ

RTIHGNETSYTITGLQPGTDYKIYLYTLNSAGFCPPYSKPVVIDAST

SEQ ID NO: 60: TNF-α binder A4A9
NVSPPRRARVTDATETTITISWYPYYDDCGYYISYFQVDAVPANGQTPIQ

RTIPDSYSSYTITGLQPGTDYKIYLYTLNDADDGHPYSKPVVIDAST

SEQ ID NO: 61 TNF-α binder R3A10
NVSPPRRARVTDATETTITISWYPYYYYCGYHYSYFQVDAVPANGQTPIQ

RTIYGYYTYYTITGLQPGTDYKIYLYTLNSSDYCYYSYYPVVIDAST

SEQ ID NO: 62 TNF-α binder R42C10
NVSPPRRARVTDATETTITISWYHHEDDCYYHFYYFQVDAVPANGQTPIQ

RTILHGTYTSYTITGLQPGTDYKIYLYTLNASGFCSHSYKPVVIDAST

SEQ ID NO: 63 TNF-α binder R4C5
NVSPPRRARVTDATETTITISWNSSYCHFYGFQVDAVPANGQTPIQRTIS

DYEYSYTITGLQPGTDYKIYLYTLNASCYGYHYYKPVVIDAST

SEQ ID NO: 64 (R1 D4 anti-VEGF)
NVSPPRRARVTDATETTITIPWEVAGGPIISFQVDAVPANGQTPIQRTIT

PDATGYTITGLQPGTDYKIYLYTLNDNARSSPVVIDAST

SEQ ID NO: 65 (R1 F1 anti-VEGF)
NVSPPRRARVTDATETTITIPWALAGGPIISFQVDAVPANGQTPIQRTIT

PDIRGYTITGLQPGTDYKIYLYTLNDNARSSPVVIDAST

SEQ ID NO: 66 (R1G1 anti-VEGF)
NVSPPRRARVTDATETTITIRWAGSPGPVDSFQVDAVPANGQTPIQRTIQ

TSETGYTITGLQPGTDYKIYLYTLNDNARSSPVVIDAST

SEQ ID NO: 67 (R2E6 anti-HMGB1)
NVSPPRRARVTDATETTITIRWGVAQSQVARFQVDAVPANGQTPIQRTIK

RSVHTYTITGLQPGTDYKIYLYTLNDNARSSPVVIDAST

SEQ ID NO: 68 (P2F3 anti-HMGB1)
NVSPPRRARVTDATETTITIRWGVPHSFQVDAVPANGQTPIQRTIKRGVR

SYTITGLQPGTDYKIYLYTLNDNARSSPVVIDAST

SEQ ID NO: 69 (R2G2 anti-HMGB1)
NVSPPRRARVTDATETTITISWRAAESAIARFQVDAVPANGQTPIQRTIK

RTKHTYTITGLQPGTDYKIYLYTLNDNARSSPVVIDAST

SEQ ID NO: 70 (R2D4 anti-HMGB1)
NVSPPRRARVTDATETTITISWGVAESEVTRFQVDAVPANGQTPIQRTIK

RSKHAYTITGLQPGTDYKIYLYTLNDNARSSPVVIDAST

SEQ ID NO: 71 (P1E8 anti-HMGB1)
NVSPPRRARVTDATETTITISWRAAESAIARFQVDAVPANGQTPIQRTIK

RTKHTYTITGLQPGTDYKIYLYTLNDNARSSPVVIDAST

SEQ ID NO: 72 (R2F8 anti-HMGB1)
NVSPPRRARVTDATETTITIRWARSASEIARFQVDAVPANGQTPIQRTIK
RSANIYTITGLQPGTDYKIYLYTLNDNARSSPVVIDAST SEQ ID NO: 73 (R2G9 anti-HMGB1)
NVSPPRRARVTDATETTITIRWGVSESEVIRFQVDAVPANGQTPIQRTIK
RSKHAYTITGLQPGTDYKIYLYTLNDNARSSPVVIDAST SEQ ID NO: 74 (R2F4 anti-HMGB1)
NVSPPRRARVTDATETTITIRWGVSPSEVVRFQVDAVPANGQTPIQRTIK
RSVHGYTITGLQPGTDYKIYLYTLNDNARSSPVVIDAST SEQ ID NO: 75 (R2B5 anti-HMGB1)
NVSPPRRARVTDATETTITIRWTVAESKIARFQVDAVPANGQTPIQRTIK
RSKHSYTITGLQPGTDYKIYLYTLNDNARSSPVVIDAST SEQ ID NO: 76 (R2E5 anti-HMGB1)
NVSPPRRARVTDATETTITISWGVAPSEINRFQVDAVPANGQTPIQRTIK
RSKHAYTITGLQPGTDYKIYLYTLNDNARSSPVVIDAST SEQ ID NO: 77 (R2F5 anti-HMGB1)
NVSPPRRARVTDATETTITIRWGVSEGQIVRFQVDAVPANGQTPIQRTIK
RSKHAYTITGLQPGTDYKIYLYTLNDNARSSPVVIDAST SEQ ID NO: 78 (P2F6 anti-HMGB1)
NVSPPRRARVTDATETTITIRWTVPASPIARFQVDAVPANGQTPIQRTIK
RTTRTYTITGLQPGTDYKIYLYTLNDNARSSPVVIDAST SEQ ID NO: 79 (P2C6 anti-HMGB1)
NVSPPRRARVTDATETTITIRWGVAPSQVIRFQVDAVPANGQTPIQRTIK
RSVHAYTITGLQPGTDYKIYLYTLNDNARSSPVVIDAST SEQ ID NO: 80 (P2F5 anti-HMGB1)
NVSPPRRARVTDATETTITIRWGVPGSPVVRFQVDAVPANGQTPIQRTIK
RGARIYTITGLQPGTDYKIYLYTLNDNARSSPVVIDAST SEQ ID NO: 81 (P2F7 anti-HMGB1)
NVSPPRRARVTDATETTITIRWGAPASEIIRFQVDAVPANGQTPIQRTIK
RTIHTYTITGLQPGTDYKIYLYTLNDNARSSPVVIDAST

---

It is claimed:

1. An Axl transforming receptor tyrosine kinase binding peptide having a Kd dissociation constant equal to or greater than 300 nM and having a sequence selected from SEQ ID NOS: 332-498.

2. The Axl binding peptide of claim 1, which has a sequence selected from the group consisting of SEQ ID NOS: 339, 366, 354, 392, 452, 454, 353, 333, 368, and 369.

3. The Axl binding peptide of claim 2, wherein the dissociation constant Kd is equal to or greater than 50 nM.

4. The Axl binding peptide of claim 3, wherein the dissociation constant Kd is equal to or greater than 5 nM.

5. The Axl binding peptide of claim 2, which has the sequence a sequence selected from the group consisting of SEQ ID NOS: 339, 366, 354, and 392.

6. The Axl binding protein of claim 5, which has the sequence SEQ ID NOS: 339.

* * * * *